US012279999B2

(12) United States Patent
Williams et al.

(10) Patent No.: US 12,279,999 B2
(45) Date of Patent: Apr. 22, 2025

(54) WIRELESS CONFIGURATION AND AUTHORIZATION OF A WALL UNIT THAT PAIRS WITH A MEDICAL DEVICE

(71) Applicant: Hill-Rom Services, Inc., Batesville, IN (US)

(72) Inventors: Jason M. Williams, Cary, NC (US); Vijay Aditya Tadipatri, Madeira, OH (US); Steven V. McCaig, Greensburg, IN (US); John V. Harmeyer, Cleves, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 381 days.

(21) Appl. No.: 17/846,170

(22) Filed: Jun. 22, 2022

(65) Prior Publication Data

US 2022/0313515 A1 Oct. 6, 2022

Related U.S. Application Data

(63) Continuation-in-part of application No. 17/577,496, filed on Jan. 18, 2022.

(Continued)

(51) Int. Cl.
*A61G 7/05* (2006.01)
*A61G 7/018* (2006.01)
(Continued)

(52) U.S. Cl.
CPC ............. *A61G 7/05* (2013.01); *A61G 7/018* (2013.01); *G16H 40/20* (2018.01); *G08B 5/222* (2013.01)

(58) Field of Classification Search
CPC .......... A61G 7/05; A61G 7/018; G16H 40/20; G16H 40/40; G16H 40/63; G16H 40/67;
(Continued)

(56) References Cited

U.S. PATENT DOCUMENTS 2,330,356 A 9/1943 Belliveau
2,335,524 A 11/1943 Lomax
(Continued)

FOREIGN PATENT DOCUMENTS

CN 104639213 A 5/2015
CN 206424245 U 8/2017
(Continued)

OTHER PUBLICATIONS

Ayoub, Michael Atef; "The Use of Bluetooth Low Energy for Continuous Monitoring of Body Sensor Networks;" Thesis; University of California, Irvine; 2019 (70 pages).
(Continued)

*Primary Examiner* — Joseph H Feild
*Assistant Examiner* — Sharmin Akhter
(74) *Attorney, Agent, or Firm* — Barnes & Thornburg LLP

(57) ABSTRACT

A time-based wireless pairing operation between a medical device, such as a patient bed, and a wall module in a patient room is initiated in response to a power plug of the medical device being plugged into a power receptacle carried by the wall module. Times determined by timers of the medical device and the wall module are compared by the wall module or by the medical device so that wireless pairing occurs only with the medical device that was plugged into the wall module. Different types of plug detectors used in the wall module to detect connection of the power plug include optical detectors, mechanical switches, and current sensors.

20 Claims, 61 Drawing Sheets

Related U.S. Application Data

(60) Provisional application No. 63/344,723, filed on May 23, 2022, provisional application No. 63/232,737, filed on Aug. 13, 2021, provisional application No. 63/193,680, filed on May 27, 2021, provisional application No. 63/168,371, filed on Mar. 31, 2021, provisional application No. 63/140,601, filed on Jan. 22, 2021.

(51) Int. Cl.
*G16H 40/20* (2018.01)
*G08B 5/22* (2006.01)

(58) Field of Classification Search
CPC ........ G16H 10/60; G08B 5/222; G08B 5/221; G08B 21/0461; G08B 21/22
See application file for complete search history.

(56) References Cited

U.S. PATENT DOCUMENTS

| | | |
|---|---|---|
| 2,736,888 A | 2/1956 | Mclain |
| 2,740,873 A | 4/1956 | Cronk |
| 2,858,421 A | 10/1958 | Achille |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,953,933 A | 5/1976 | Goldstein |
| 3,973,200 A | 8/1976 | Akerberg |
| 3,987,928 A | 10/1976 | Mori |
| 4,067,005 A | 1/1978 | Levy et al. |
| 4,150,284 A | 4/1979 | Trenkler et al. |
| 4,151,407 A | 4/1979 | Delagi et al. |
| 4,183,015 A | 1/1980 | Drew et al. |
| 4,216,462 A | 8/1980 | Digiacomo et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,343,411 A | 8/1982 | Chesnut et al. |
| 4,356,475 A | 10/1982 | Neumann et al. |
| 4,363,137 A | 12/1982 | Salisbury |
| 4,418,334 A | 11/1983 | Burnett |
| 4,455,548 A | 6/1984 | Burnett |
| 4,465,333 A | 8/1984 | Caserta et al. |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,633,237 A | 12/1986 | Tucknott et al. |
| 4,649,385 A | 3/1987 | Aires et al. |
| 4,677,599 A | 6/1987 | Obayashi et al. |
| 4,678,264 A | 7/1987 | Bowen et al. |
| 4,680,790 A | 7/1987 | Packard et al. |
| 4,688,026 A | 8/1987 | Scribner et al. |
| 4,709,330 A | 11/1987 | Yokoi et al. |
| 4,721,358 A | 1/1988 | Faber et al. |
| 4,740,788 A | 4/1988 | Konneker |
| 4,752,951 A | 6/1988 | Konneker |
| 4,767,168 A | 8/1988 | Grandy |
| 4,767,181 A | 8/1988 | Mceowen |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,835,343 A | 5/1989 | Graef et al. |
| 4,837,568 A | 6/1989 | Snaper |
| 4,844,582 A | 7/1989 | Giannini |
| 4,850,040 A | 7/1989 | Teich et al. |
| 4,853,692 A | 8/1989 | Wolk et al. |
| 4,882,566 A | 11/1989 | Koerber, Sr. et al. |
| 4,899,135 A | 2/1990 | Ghahariiran |
| 4,903,340 A | 2/1990 | Sorensen |
| 4,924,349 A | 5/1990 | Buehler et al. |
| 4,934,468 A | 6/1990 | Koerber, Sr. et al. |
| 4,947,152 A | 8/1990 | Hodges |
| 4,955,000 A | 9/1990 | Nastrom |
| 4,958,645 A | 9/1990 | Cadell et al. |
| 4,967,195 A | 10/1990 | Shipley |
| 4,977,619 A | 12/1990 | Crimmins |
| 4,984,297 A | 1/1991 | Manome |
| 4,990,892 A | 2/1991 | Guest et al. |
| 4,998,095 A | 3/1991 | Shields |
| 4,998,939 A | 3/1991 | Potthast et al. |
| 5,003,984 A | 4/1991 | Muraki et al. |
| 5,006,830 A | 4/1991 | Merritt |
| 5,027,314 A | 6/1991 | Linwood et al. |
| 5,033,112 A | 7/1991 | Bowling et al. |
| 5,036,852 A | 8/1991 | Leishman |
| 5,041,086 A | 8/1991 | Koenig et al. |
| 5,049,876 A | 9/1991 | Kahle et al. |
| 5,060,303 A | 10/1991 | Wilmoth |
| 5,062,151 A | 10/1991 | Shipley |
| 5,065,154 A | 11/1991 | Kaiser et al. |
| 5,073,681 A | 12/1991 | Hubben et al. |
| 5,086,290 A | 2/1992 | Murray et al. |
| 5,089,974 A | 2/1992 | Demeyer et al. |
| 5,099,346 A | 3/1992 | Lee et al. |
| 5,103,108 A | 4/1992 | Crimmins |
| 5,109,452 A | 4/1992 | Selvin et al. |
| 5,124,991 A | 6/1992 | Allen |
| 5,137,033 A | 8/1992 | Norton |
| 5,140,659 A | 8/1992 | Minds et al. |
| 5,146,528 A | 9/1992 | Gleim et al. |
| 5,153,584 A | 10/1992 | Engira |
| 5,180,886 A | 1/1993 | Dierenbach et al. |
| 5,212,760 A | 5/1993 | Goetz |
| 5,214,526 A | 5/1993 | Tonomura |
| 5,228,449 A | 7/1993 | Christ et al. |
| 5,242,315 A | 9/1993 | O'Dea |
| 5,247,380 A | 9/1993 | Lee et al. |
| 5,266,944 A | 11/1993 | Carroll et al. |
| 5,274,490 A | 12/1993 | Tsushima et al. |
| 5,278,536 A | 1/1994 | Furtaw et al. |
| 5,291,399 A | 3/1994 | Chaco |
| 5,305,132 A | 4/1994 | Fasen et al. |
| 5,305,133 A | 4/1994 | Cooper et al. |
| 5,319,355 A | 6/1994 | Russek |
| 5,319,363 A | 6/1994 | Welch et al. |
| 5,321,542 A | 6/1994 | Freitas et al. |
| 5,357,254 A | 10/1994 | Kah, Jr. |
| 5,375,604 A | 12/1994 | Kelly et al. |
| 5,394,882 A | 3/1995 | Mawhinney |
| 5,396,224 A | 3/1995 | Dukes et al. |
| 5,396,227 A | 3/1995 | Carroll et al. |
| 5,415,167 A | 5/1995 | Wilk |
| 5,416,627 A | 5/1995 | Wilmoth |
| 5,416,695 A | 5/1995 | Stutman et al. |
| 5,417,222 A | 5/1995 | Dempsey et al. |
| 5,434,775 A | 7/1995 | Sims et al. |
| 5,446,678 A | 8/1995 | Saltzstein et al. |
| 5,455,560 A | 10/1995 | Owen |
| 5,455,851 A | 10/1995 | Chaco et al. |
| 5,456,373 A | 10/1995 | Ford |
| 5,458,123 A | 10/1995 | Unger |

(56) References Cited

U.S. PATENT DOCUMENTS

| | | |
|---|---|---|
| 5,461,390 A | 10/1995 | Hoshen |
| 5,475,367 A | 12/1995 | Prevost |
| 5,477,010 A | 12/1995 | Buckshaw et al. |
| 5,508,836 A | 4/1996 | Decaro et al. |
| 5,511,553 A | 4/1996 | Segalowitz |
| 5,515,426 A | 5/1996 | Yacenda et al. |
| 5,534,851 A | 7/1996 | Russek |
| 5,537,459 A | 7/1996 | Price et al. |
| 5,544,661 A | 8/1996 | Davis et al. |
| 5,548,637 A | 8/1996 | Heller et al. |
| 5,548,654 A | 8/1996 | Fast |
| 5,549,113 A | 8/1996 | Halleck et al. |
| 5,561,412 A | 10/1996 | Novak et al. |
| 5,568,119 A | 10/1996 | Schipper et al. |
| 5,576,452 A | 11/1996 | Dever et al. |
| 5,576,952 A | 11/1996 | Stutman et al. |
| 5,579,001 A | 11/1996 | Dempsey et al. |
| 5,579,775 A | 12/1996 | Dempsey et al. |
| 5,588,005 A | 12/1996 | Ali et al. |
| 5,594,786 A | 1/1997 | Chaco et al. |
| 5,596,648 A | 1/1997 | Fast |
| 5,617,236 A | 4/1997 | Wang et al. |
| 5,621,388 A | 4/1997 | Sherburne et al. |
| 5,628,324 A | 5/1997 | Sarbach |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,657,201 A | 8/1997 | Kochis |
| 5,664,270 A | 9/1997 | Bell et al. |
| 5,675,125 A | 10/1997 | Hollinger |
| 5,678,562 A | 10/1997 | Sellers |
| 5,682,139 A | 10/1997 | Pradeep et al. |
| 5,682,142 A | 10/1997 | Loosmore et al. |
| 5,686,888 A | 11/1997 | Welles et al. |
| 5,686,902 A | 11/1997 | Reis et al. |
| 5,687,717 A | 11/1997 | Halpern et al. |
| 5,687,734 A | 11/1997 | Dempsey et al. |
| 5,689,229 A | 11/1997 | Chaco et al. |
| 5,691,980 A | 11/1997 | Welles, II et al. |
| 5,696,861 A | 12/1997 | Schimmeyer et al. |
| 5,699,038 A | 12/1997 | Ulrich et al. |
| 5,705,980 A | 1/1998 | Shapiro |
| 5,706,110 A | 1/1998 | Nykanen |
| 5,708,421 A | 1/1998 | Boyd |
| 5,712,795 A | 1/1998 | Layman et al. |
| 5,713,856 A | 2/1998 | Eggers et al. |
| 5,719,761 A | 2/1998 | Gatti et al. |
| 5,723,817 A | 3/1998 | Arenas et al. |
| 5,724,025 A | 3/1998 | Tavori |
| 5,731,757 A | 3/1998 | Layson, Jr. |
| 5,738,102 A | 4/1998 | Lemelson |
| 5,742,237 A | 4/1998 | Bledsoe |
| 5,742,238 A | 4/1998 | Fox |
| 5,751,246 A | 5/1998 | Hertel |
| 5,752,917 A | 5/1998 | Fuchs |
| 5,760,704 A | 6/1998 | Barton et al. |
| 5,764,162 A | 6/1998 | Ehrlich |
| 5,767,791 A | 6/1998 | Stoop et al. |
| 5,772,599 A | 6/1998 | Nevo et al. |
| 5,781,442 A | 7/1998 | Engleson et al. |
| 5,793,290 A | 8/1998 | Eagleson et al. |
| 5,800,387 A | 9/1998 | Duffy et al. |
| 5,808,564 A | 9/1998 | Simms et al. |
| 5,811,729 A | 9/1998 | Rintz |
| 5,811,730 A | 9/1998 | Rintz |
| 5,812,056 A | 9/1998 | Law |
| 5,813,873 A | 9/1998 | Mcbain et al. |
| 5,822,418 A | 10/1998 | Yacenda et al. |
| 5,822,544 A | 10/1998 | Chaco et al. |
| 5,825,283 A | 10/1998 | Camhi |
| 5,836,910 A | 11/1998 | Duffy et al. |
| 5,838,223 A | 11/1998 | Gallant et al. |
| 5,838,471 A | 11/1998 | Beard |
| 5,844,488 A | 12/1998 | Musick |
| 5,862,803 A | 1/1999 | Besson et al. |
| 5,867,821 A | 2/1999 | Ballantyne et al. |
| 5,873,369 A | 2/1999 | Aniado et al. |
| 5,874,693 A | 2/1999 | Rintz |
| 5,877,675 A | 3/1999 | Rebstock et al. |
| 5,877,820 A | 3/1999 | Yamamuro et al. |
| 5,895,888 A | 4/1999 | Arenas et al. |
| 5,907,419 A | 5/1999 | Martnelli et al. |
| 5,910,776 A | 6/1999 | Black |
| 5,919,141 A | 7/1999 | Money et al. |
| 5,933,488 A | 8/1999 | Marcus et al. |
| 5,936,539 A | 8/1999 | Fuchs |
| 5,941,846 A | 8/1999 | Duffy et al. |
| 5,942,986 A | 8/1999 | Shabot et al. |
| 5,944,659 A | 8/1999 | Flach et al. |
| 5,949,567 A | 9/1999 | Jebens |
| 5,957,854 A | 9/1999 | Besson et al. |
| 5,963,133 A | 10/1999 | Monjo |
| 5,963,137 A | 10/1999 | Waters, Sr. |
| 5,967,840 A | 10/1999 | Rose et al. |
| 5,974,389 A | 10/1999 | Clark et al. |
| 5,982,519 A | 11/1999 | Martnelli et al. |
| 5,990,866 A | 11/1999 | Yollin |
| 5,991,728 A | 11/1999 | Debusk et al. |
| 5,994,998 A | 11/1999 | Fisher et al. |
| 5,995,253 A | 11/1999 | Flaherty |
| 5,995,937 A | 11/1999 | Debusk et al. |
| 5,998,735 A | 12/1999 | Patterson |
| 6,009,333 A | 12/1999 | Chaco |
| 6,014,346 A | 1/2000 | Malone |
| 6,014,633 A | 1/2000 | Debusk et al. |
| 6,027,367 A | 2/2000 | Woertz et al. |
| 6,028,519 A | 2/2000 | Dessureau et al. |
| 6,038,469 A | 3/2000 | Karlsson et al. |
| 6,044,283 A | 3/2000 | Fein et al. |
| 6,044,382 A | 3/2000 | Martino |
| 6,047,203 A | 4/2000 | Sackner et al. |
| 6,051,787 A | 4/2000 | Rintz |
| 6,057,758 A | 5/2000 | Dempsey et al. |
| 6,057,782 A | 5/2000 | Koenig |
| 6,067,019 A | 5/2000 | Scott |
| 6,071,015 A | 6/2000 | Erbse et al. |
| 6,074,345 A | 6/2000 | Van Oostrom et al. |
| 6,076,166 A | 6/2000 | Moshfeghi et al. |
| 6,078,261 A | 6/2000 | Davsko |
| 6,080,106 A | 6/2000 | Lloyd et al. |
| 6,085,493 A | 7/2000 | Debusk et al. |
| 6,088,362 A | 7/2000 | Turnbull et al. |
| 6,092,102 A | 7/2000 | Wagner |
| 6,093,146 A | 7/2000 | Filangeri |
| 6,097,308 A | 8/2000 | Albert et al. |
| 6,111,509 A | 8/2000 | Holmes |
| 6,117,076 A | 9/2000 | Cassidy |
| 6,125,350 A | 9/2000 | Dirbas |
| 6,132,371 A | 10/2000 | Dempsey et al. |
| 6,133,837 A | 10/2000 | Riley |
| 6,135,949 A | 10/2000 | Russo et al. |
| 6,140,911 A | 10/2000 | Fisher et al. |
| 6,147,592 A | 11/2000 | Ulrich et al. |
| 6,147,618 A | 11/2000 | Halleck et al. |
| 6,150,951 A | 11/2000 | Olejniczak |
| 6,159,147 A | 12/2000 | Lichter et al. |
| 6,160,478 A | 12/2000 | Jacobsen et al. |
| 6,167,258 A | 12/2000 | Schmidt et al. |
| 6,171,264 B1 | 1/2001 | Bader |
| 6,183,101 B1 | 2/2001 | Chien |
| 6,183,417 B1 | 2/2001 | Geheb et al. |
| 6,186,962 B1 | 2/2001 | Lloyd et al. |
| 6,198,394 B1 | 3/2001 | Jacobsen et al. |
| 6,208,250 B1 | 3/2001 | Dixon et al. |
| 6,213,942 B1 | 4/2001 | Flach et al. |
| 6,241,668 B1 | 6/2001 | Herzog |
| 6,259,355 B1 | 7/2001 | Chaco et al. |
| 6,264,614 B1 | 7/2001 | Albert et al. |
| 6,270,457 B1 | 8/2001 | Bardy |
| 6,272,347 B1 | 8/2001 | Griffith et al. |
| 6,277,080 B1 | 8/2001 | Nissil et al. |
| 6,279,183 B1 | 8/2001 | Kummer et al. |

(56) References Cited

U.S. PATENT DOCUMENTS

| | | |
|---|---|---|
| 6,281,440 B1 | 8/2001 | Baldwin et al. |
| 6,287,253 B1 | 9/2001 | Ortega et al. |
| 6,289,238 B1 | 9/2001 | Besson et al. |
| 6,293,699 B1 | 9/2001 | Bailey et al. |
| 6,302,844 B1 | 10/2001 | Walker et al. |
| 6,304,600 B1 | 10/2001 | Chiba |
| 6,304,774 B1 | 10/2001 | Gorman |
| 6,314,556 B1 | 11/2001 | Debusk et al. |
| 6,320,510 B2 | 11/2001 | Menkedick et al. |
| 6,329,906 B1 | 12/2001 | Fisher et al. |
| 6,336,900 B1 | 1/2002 | Alleckson et al. |
| 6,336,903 B1 | 1/2002 | Bardy |
| 6,344,794 B1 | 2/2002 | Ulrich et al. |
| 6,348,777 B1 | 2/2002 | Brown et al. |
| 6,355,885 B1 | 3/2002 | Rintz et al. |
| 6,362,725 B1 | 3/2002 | Ulrich et al. |
| 6,364,834 B1 | 4/2002 | Reuss et al. |
| 6,368,284 B1 | 4/2002 | Bardy |
| 6,398,727 B1 | 6/2002 | Bui et al. |
| 6,398,728 B1 | 6/2002 | Bardy |
| 6,402,691 B1 | 6/2002 | Peddicord et al. |
| 6,406,426 B1 | 6/2002 | Reuss et al. |
| 6,407,335 B1 | 6/2002 | Franklin-Lees et al. |
| 6,411,840 B1 | 6/2002 | Bardy |
| 6,412,980 B1 | 7/2002 | Lounsberry et al. |
| 6,416,471 B1 | 7/2002 | Kumar et al. |
| 6,421,649 B1 | 7/2002 | Rattner |
| 6,434,187 B1 | 8/2002 | Beard et al. |
| 6,437,692 B1 | 8/2002 | Petite et al. |
| 6,439,769 B1 | 8/2002 | Polkus et al. |
| 6,441,742 B1 | 8/2002 | Lovely et al. |
| 6,441,747 B1 | 8/2002 | Khair et al. |
| 6,442,145 B1 | 8/2002 | De Lange et al. |
| 6,442,290 B1 | 8/2002 | Ellis et al. |
| 6,443,890 B1 | 9/2002 | Schulze et al. |
| 6,445,299 B1 | 9/2002 | Rojas |
| 6,450,953 B1 | 9/2002 | Place et al. |
| 6,450,956 B1 | 9/2002 | Rappaport et al. |
| 6,457,874 B1 | 10/2002 | Clapp et al. |
| 6,462,656 B2 | 10/2002 | Ulrich et al. |
| 6,475,153 B1 | 11/2002 | Khair et al. |
| 6,486,792 B1 | 11/2002 | Moster et al. |
| 6,493,121 B1 | 12/2002 | Althaus |
| 6,493,568 B1 | 12/2002 | Bell et al. |
| 6,493,747 B2 | 12/2002 | Simmon et al. |
| 6,494,829 B1 | 12/2002 | New et al. |
| 6,494,831 B1 | 12/2002 | Koritzinsky |
| 6,496,105 B2 | 12/2002 | Fisher et al. |
| 6,496,705 B1 | 12/2002 | Ng et al. |
| 6,497,656 B1 | 12/2002 | Evans et al. |
| 6,500,026 B2 | 12/2002 | Yamaguchi |
| 6,504,633 B1 | 1/2003 | Hovorka et al. |
| 6,504,635 B1 | 1/2003 | Nakashima |
| 6,510,344 B1 | 1/2003 | Halpern |
| 6,514,652 B2 | 2/2003 | Cash |
| 6,516,324 B1 | 2/2003 | Jones et al. |
| 6,517,497 B2 | 2/2003 | Rymut et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,533,466 B1 | 3/2003 | Smith |
| 6,533,729 B1 | 3/2003 | Khair et al. |
| 6,535,576 B2 | 3/2003 | Vafi et al. |
| 6,539,393 B1 | 3/2003 | Kabala |
| 6,540,686 B2 | 4/2003 | Heikkil et al. |
| 6,544,173 B2 | 4/2003 | West et al. |
| 6,544,174 B2 | 4/2003 | West et al. |
| 6,544,200 B1 | 4/2003 | Smith et al. |
| 6,545,218 B1 | 4/2003 | Blaess |
| 6,551,243 B2 | 4/2003 | Bocionek et al. |
| 6,551,252 B2 | 4/2003 | Sackner et al. |
| 6,552,888 B2 | 4/2003 | Weinberger |
| 6,553,106 B1 | 4/2003 | Gould et al. |
| 6,554,174 B1 | 4/2003 | Aceves |
| 6,556,630 B1 | 4/2003 | Brinsfield et al. |
| 6,558,045 B2 | 5/2003 | Yamaguchi |
| 6,559,620 B2 | 5/2003 | Zhou et al. |
| 6,560,274 B1 | 5/2003 | Leitgeb et al. |
| 6,563,618 B1 | 5/2003 | Morrow et al. |
| 6,569,094 B2 | 5/2003 | Suzuki et al. |
| 6,572,556 B2 | 6/2003 | Stoycos et al. |
| 6,575,901 B2 | 6/2003 | Stoycos et al. |
| 6,575,902 B1 | 6/2003 | Burton |
| 6,577,893 B1 | 6/2003 | Besson et al. |
| 6,579,231 B1 | 6/2003 | Phipps |
| 6,581,204 B2 | 6/2003 | Debusk et al. |
| 6,584,182 B2 | 6/2003 | Brodnick |
| 6,584,454 B1 | 6/2003 | Hummel et al. |
| 6,585,431 B1 | 7/2003 | Okamoto |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,593,845 B1 | 7/2003 | Friedman et al. |
| 6,594,146 B2 | 7/2003 | Frangesch et al. |
| 6,594,511 B2 | 7/2003 | Stone et al. |
| 6,594,519 B2 | 7/2003 | Stoycos et al. |
| 6,595,929 B2 | 7/2003 | Stivoric et al. |
| 6,599,025 B1 | 7/2003 | Deutsch |
| 6,600,421 B2 | 7/2003 | Freeman |
| 6,602,191 B2 | 8/2003 | Quy |
| 6,603,401 B1 | 8/2003 | Ueyama |
| 6,603,494 B1 | 8/2003 | Banks et al. |
| 6,605,038 B1 | 8/2003 | Teller et al. |
| 6,608,253 B1 | 8/2003 | Rintz |
| 6,609,115 B1 | 8/2003 | Mehring et al. |
| 6,609,166 B1 | 8/2003 | Nakashima |
| 6,611,705 B2 | 8/2003 | Hopman et al. |
| 6,612,984 B1 | 9/2003 | Kerr |
| 6,616,606 B1 | 9/2003 | Petersen et al. |
| 6,622,088 B2 | 9/2003 | Hood |
| 6,640,246 B1 | 10/2003 | Gary et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,668,328 B1 | 12/2003 | Bell |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,674,367 B2 | 1/2004 | Sweatte |
| 6,685,633 B2 | 2/2004 | Albert et al. |
| 6,688,779 B2 | 2/2004 | Nishita |
| 6,689,091 B2 | 2/2004 | Bui et al. |
| 6,693,514 B2 | 2/2004 | Perea et al. |
| 6,694,180 B1 | 2/2004 | Boesen |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,710,704 B2 | 3/2004 | Fisher et al. |
| 6,714,913 B2 | 3/2004 | Brandt et al. |
| 6,721,818 B2 | 4/2004 | Nakamura |
| 6,723,046 B2 | 4/2004 | Lichtenstein et al. |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,736,759 B1 | 5/2004 | Stubbs et al. |
| 6,740,033 B1 | 5/2004 | Olejniczak et al. |
| 6,748,250 B1 | 6/2004 | Berman et al. |
| 6,749,566 B2 | 6/2004 | Russ |
| 6,751,630 B1 | 6/2004 | Franks et al. |
| 6,753,761 B2 | 6/2004 | Fisher et al. |
| 6,754,545 B2 | 6/2004 | Haeuser et al. |
| 6,754,883 B2 | 6/2004 | Debusk et al. |
| 6,758,812 B2 | 7/2004 | Lang |
| 6,759,959 B2 | 7/2004 | Wildman |
| 6,763,195 B1 | 7/2004 | Willebrand et al. |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |

(56) References Cited

U.S. PATENT DOCUMENTS

| | | |
|---|---|---|
| 6,784,797 B2 | 8/2004 | Smith et al. |
| 6,791,460 B2 | 9/2004 | Dixon et al. |
| 6,792,396 B2 | 9/2004 | Inda et al. |
| 6,793,524 B2 | 9/2004 | Clark et al. |
| 6,798,352 B2 | 9/2004 | Holowick |
| 6,801,227 B2 | 10/2004 | Bocionek et al. |
| 6,807,543 B2 | 10/2004 | Muthya |
| 6,810,435 B2 | 10/2004 | Palmer et al. |
| 6,817,979 B2 | 11/2004 | Nihtil |
| 6,819,247 B2 | 11/2004 | Birnbach et al. |
| 6,822,555 B2 | 11/2004 | Mansfield et al. |
| 6,822,571 B2 | 11/2004 | Conway |
| 6,823,036 B1 | 11/2004 | Chen |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,840,904 B2 | 1/2005 | Goldberg |
| 6,847,435 B2 | 1/2005 | Honda et al. |
| 6,847,814 B1 | 1/2005 | Vogeleisen |
| 6,868,256 B2 | 3/2005 | Dooley et al. |
| 6,870,466 B2 | 3/2005 | Rust et al. |
| 6,870,477 B2 | 3/2005 | Gruteser et al. |
| 6,871,211 B2 | 3/2005 | Labounty et al. |
| 6,873,884 B2 | 3/2005 | Brackett et al. |
| 6,875,174 B2 | 4/2005 | Braun et al. |
| 6,876,303 B2 | 4/2005 | Reeder et al. |
| 6,876,985 B2 | 4/2005 | Kawanaka |
| 6,885,288 B2 | 4/2005 | Pincus |
| 6,885,796 B2 | 4/2005 | Lubkert et al. |
| 6,891,909 B2 | 5/2005 | Hurley et al. |
| 6,893,346 B2 | 5/2005 | Small et al. |
| 6,893,396 B2 | 5/2005 | Schulze et al. |
| 6,897,780 B2 | 5/2005 | Ulrich et al. |
| 6,897,788 B2 | 5/2005 | Khair et al. |
| 6,904,161 B1 | 6/2005 | Matsui et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,937,150 B2 | 8/2005 | Medema et al. |
| 6,942,616 B2 | 9/2005 | Kerr, II |
| 6,954,148 B2 | 10/2005 | Pulkkinen et al. |
| 6,958,706 B2 | 10/2005 | Chaco et al. |
| 6,970,097 B2 | 11/2005 | Welles, II et al. |
| 6,982,639 B2 | 1/2006 | Brackett et al. |
| 6,984,297 B2 | 1/2006 | Nisch et al. |
| 6,987,965 B2 | 1/2006 | Ng et al. |
| 6,988,989 B2 | 1/2006 | Weiner et al. |
| 6,998,986 B2 | 2/2006 | Smith |
| 7,002,468 B2 | 2/2006 | Eveland et al. |
| 7,004,907 B2 | 2/2006 | Banet et al. |
| 7,010,337 B2 | 3/2006 | Furnary et al. |
| 7,020,508 B2 | 3/2006 | Stivoric et al. |
| 7,029,455 B2 | 4/2006 | Flaherty |
| 7,034,690 B2 | 4/2006 | Chaco |
| 7,038,584 B2 | 5/2006 | Carter |
| 7,038,588 B2 | 5/2006 | Boone et al. |
| 7,039,456 B2 | 5/2006 | Chen |
| 7,043,573 B2 | 5/2006 | Ito |
| 7,049,524 B2 | 5/2006 | Belli et al. |
| 7,053,767 B2 | 5/2006 | Petite et al. |
| 7,053,831 B2 | 5/2006 | Dempsey et al. |
| 7,068,143 B2 | 6/2006 | Doering et al. |
| 7,068,670 B2 | 6/2006 | Gancarcik et al. |
| 7,071,820 B2 | 7/2006 | Callaway |
| 7,079,036 B2 | 7/2006 | Cooper et al. |
| RE39,233 E | 8/2006 | McGrath |
| 7,088,233 B2 | 8/2006 | Menard |
| 7,088,235 B1 | 8/2006 | Carricut |
| 7,092,376 B2 | 8/2006 | Schuman |
| 7,099,895 B2 | 8/2006 | Dempsey |
| 7,103,407 B2 | 9/2006 | Djelt et al. |
| 7,103,511 B2 | 9/2006 | Petite |
| 7,104,955 B2 | 9/2006 | Bardy |
| 7,107,106 B2 | 9/2006 | Engleson et al. |
| 7,117,027 B2 | 10/2006 | Zheng et al. |
| 7,117,041 B2 | 10/2006 | Engleson et al. |
| 7,123,149 B2 | 10/2006 | Nowak et al. |
| 7,127,261 B2 | 10/2006 | Van Erlach |
| 7,127,738 B1 | 10/2006 | Jackson |
| 7,129,836 B2 | 10/2006 | Lawson et al. |
| 7,130,396 B2 | 10/2006 | Rogers et al. |
| 7,138,902 B2 | 11/2006 | Menard |
| 7,150,655 B2 | 12/2006 | Mastrototaro et al. |
| 7,153,262 B2 | 12/2006 | Stivoric et al. |
| 7,153,263 B2 | 12/2006 | Carter et al. |
| 7,154,397 B2 | 12/2006 | Zerhusen et al. |
| 7,154,398 B2 | 12/2006 | Chen et al. |
| 7,156,807 B2 | 1/2007 | Carter et al. |
| 7,171,166 B2 | 1/2007 | Ng et al. |
| 7,177,673 B2 | 2/2007 | Matsumura et al. |
| 7,197,357 B2 | 3/2007 | Istvan et al. |
| 7,197,492 B2 | 3/2007 | Sullivan |
| 7,215,991 B2 | 5/2007 | Besson et al. |
| 7,222,054 B2 | 5/2007 | Geva |
| 7,231,258 B2 | 6/2007 | Moore et al. |
| 7,242,306 B2 | 7/2007 | Wildman et al. |
| 7,242,308 B2 | 7/2007 | Ulrich et al. |
| 7,244,150 B1 | 7/2007 | Brase et al. |
| 7,245,625 B2 | 7/2007 | Manis et al. |
| 7,248,933 B2 | 7/2007 | Wildman |
| 7,256,708 B2 | 8/2007 | Rosenfeld et al. |
| 7,272,428 B2 | 9/2007 | Hopman et al. |
| 7,277,758 B2 | 10/2007 | Dilorenzo |
| 7,283,423 B2 | 10/2007 | Holm et al. |
| 7,289,761 B2 | 10/2007 | Mazar |
| 7,292,135 B2 | 11/2007 | Bixler et al. |
| 7,292,139 B2 | 11/2007 | Mazar et al. |
| 7,294,105 B1 | 11/2007 | Islam |
| 7,295,132 B2 | 11/2007 | Steiner |
| 7,298,359 B2 | 11/2007 | Kim et al. |
| 7,301,451 B2 | 11/2007 | Hastings |
| 7,304,580 B2 | 12/2007 | Sullivan et al. |
| 7,316,648 B2 | 1/2008 | Kelly et al. |
| 7,319,386 B2 | 1/2008 | Collins, Jr. et al. |
| 7,324,824 B2 | 1/2008 | Smith et al. |
| 7,333,002 B2 | 2/2008 | Bixler et al. |
| 7,336,187 B2 | 2/2008 | Hubbard, Jr. et al. |
| 7,336,563 B2 | 2/2008 | Holm |
| 7,352,652 B2 | 4/2008 | Holm et al. |
| 7,362,656 B2 | 4/2008 | Holm |
| 7,382,247 B2 | 6/2008 | Welch et al. |
| 7,384,110 B2 | 6/2008 | Hoshiyama et al. |
| 7,390,299 B2 | 6/2008 | Weiner et al. |
| 7,394,385 B2 | 7/2008 | Franco, Jr. et al. |
| 7,399,205 B2 | 7/2008 | Mcneely et al. |
| 7,403,111 B2 | 7/2008 | Tessier et al. |
| 7,403,808 B2 | 7/2008 | Istvan et al. |
| 7,413,471 B2 | 8/2008 | Chan |
| 7,415,212 B2 | 8/2008 | Matsushita et al. |
| 7,439,856 B2 | 10/2008 | Weiner et al. |
| 7,443,300 B2 | 10/2008 | Tessier |
| 7,443,302 B2 | 10/2008 | Reeder et al. |
| 7,454,885 B2 | 11/2008 | Lin et al. |
| 7,468,661 B2 | 12/2008 | Petite et al. |
| 7,480,951 B2 | 1/2009 | Ulrich et al. |
| 7,508,307 B2 | 3/2009 | Albert |
| 7,512,380 B2 | 3/2009 | Mcgowan |
| 7,515,043 B2 | 4/2009 | Welch et al. |
| 7,520,006 B2 | 4/2009 | Vanderpohl, III et al. |
| 7,526,582 B2 | 4/2009 | Best et al. |
| 7,533,429 B2 | 5/2009 | Stolpmann et al. |
| 7,535,796 B2 | 5/2009 | Holm et al. |
| 7,538,659 B2 | 5/2009 | Ulrich et al. |
| 7,567,794 B2 | 7/2009 | Dempsey |
| 7,568,211 B2 | 7/2009 | Mai et al. |
| 7,580,420 B2 | 8/2009 | Schweidler et al. |
| 7,598,853 B2 | 10/2009 | Becker et al. |
| 7,636,549 B2 | 12/2009 | Ma et al. |

(56) References Cited

U.S. PATENT DOCUMENTS

| | | |
|---|---|---|
| 7,649,449 B2 | 1/2010 | Fenske et al. |
| 7,671,733 B2 | 3/2010 | Mcneal et al. |
| 7,676,380 B2 | 3/2010 | Graves et al. |
| 7,697,492 B2 | 4/2010 | Petite |
| 7,706,896 B2 | 4/2010 | Music et al. |
| 7,715,354 B2 | 5/2010 | Arunan et al. |
| 7,724,147 B2 | 5/2010 | Brown |
| 7,733,224 B2 | 6/2010 | Tran |
| 7,734,476 B2 | 6/2010 | Wildman et al. |
| 7,737,827 B2 | 6/2010 | Perkins et al. |
| 7,741,966 B2 | 6/2010 | Bonnefin et al. |
| 7,746,218 B2 | 6/2010 | Collins, Jr. et al. |
| 7,751,375 B2 | 7/2010 | Perkins et al. |
| 7,756,723 B2 | 7/2010 | Rosow et al. |
| 7,761,164 B2 | 7/2010 | Verhoef et al. |
| 7,761,555 B1 | 7/2010 | Bishel |
| 7,768,949 B2 | 8/2010 | Perkins et al. |
| 7,771,385 B2 | 8/2010 | Eggers et al. |
| 7,771,386 B2 | 8/2010 | Eggers et al. |
| 7,786,874 B2 | 8/2010 | Rodgers |
| 7,796,045 B2 | 9/2010 | Spear et al. |
| 7,831,152 B2 | 11/2010 | Tatum et al. |
| 7,836,307 B2 | 11/2010 | Aihara et al. |
| 7,852,208 B2 | 12/2010 | Collins, Jr. et al. |
| 7,860,557 B2 | 12/2010 | Istvan et al. |
| 7,868,740 B2 | 1/2011 | Mcneely et al. |
| 7,884,703 B2 | 2/2011 | Sowada et al. |
| 7,889,069 B2 | 2/2011 | Fifolt et al. |
| 7,890,181 B2 | 2/2011 | Denzene et al. |
| 7,898,407 B2 | 3/2011 | Hufton et al. |
| 7,921,235 B2 | 4/2011 | Best et al. |
| 7,924,163 B1 | 4/2011 | Long et al. |
| 7,942,844 B2 | 5/2011 | Moberg et al. |
| 7,962,544 B2 | 6/2011 | Torok et al. |
| 7,991,446 B2 | 8/2011 | Ali et al. |
| 8,001,235 B2 | 8/2011 | Russ et al. |
| 8,026,821 B2 | 9/2011 | Reeder et al. |
| 8,031,057 B2 | 10/2011 | Mcneely et al. |
| 8,036,911 B2 | 10/2011 | Bellon et al. |
| 8,046,225 B2 | 10/2011 | Masuko et al. |
| 8,073,008 B2 | 12/2011 | Mehta et al. |
| 8,082,160 B2 | 12/2011 | Collins, Jr. et al. |
| 8,096,813 B2 | 1/2012 | Biggs |
| 8,102,254 B2 | 1/2012 | Bhimavarapu et al. |
| 8,104,117 B2 | 1/2012 | Heimbrock et al. |
| 8,120,471 B2 | 2/2012 | Collins, Jr. et al. |
| 8,125,318 B2 | 2/2012 | Heimbrock et al. |
| 8,130,083 B2 | 3/2012 | Dorney |
| 8,140,943 B1 | 3/2012 | Wu et al. |
| 8,169,304 B2 | 5/2012 | Schuman, Sr. et al. |
| 8,170,888 B2 | 5/2012 | Silverman |
| 8,174,148 B2 | 5/2012 | Crucs |
| 8,175,533 B2 | 5/2012 | Schubert |
| 8,180,650 B2 | 5/2012 | Graves et al. |
| 8,181,233 B2 | 5/2012 | Wyld |
| 8,216,135 B2 | 7/2012 | Goscha et al. |
| 8,237,613 B2 | 8/2012 | Sohn |
| 8,258,973 B2 | 9/2012 | Newkirk |
| 8,266,742 B2 | 9/2012 | Andrienko |
| 8,272,892 B2 | 9/2012 | Mcneely et al. |
| 8,284,047 B2 | 10/2012 | Collins, Jr. et al. |
| 8,289,716 B2 | 10/2012 | Patel et al. |
| 8,319,633 B2 | 11/2012 | Bhimavarapu et al. |
| 8,334,777 B2 | 12/2012 | Wilson et al. |
| 8,344,860 B2 | 1/2013 | Collins, Jr. et al. |
| 8,353,605 B2 | 1/2013 | Huang et al. |
| 8,364,221 B2 | 1/2013 | Mannheimer et al. |
| 8,384,526 B2 | 2/2013 | Schuman, Sr. et al. |
| 8,408,457 B2 | 4/2013 | Overhultz et al. |
| 8,416,084 B2 | 4/2013 | Beltmann et al. |
| 8,417,215 B2 | 4/2013 | Baldus et al. |
| 8,421,606 B2 | 4/2013 | Collins, Jr. et al. |
| 8,427,296 B2 | 4/2013 | Pance et al. |
| 8,432,287 B2 | 4/2013 | O'Keefe et al. |
| 8,437,824 B2 | 5/2013 | Moon et al. |
| 8,439,032 B2 | 5/2013 | Andrieux et al. |
| 8,446,254 B2 | 5/2013 | Carrick et al. |
| 8,449,471 B2 | 5/2013 | Tran |
| 8,451,101 B2 | 5/2013 | Somasundaram et al. |
| 8,456,286 B2 | 6/2013 | Schuman et al. |
| 8,456,346 B2 | 6/2013 | Zhang et al. |
| 8,461,968 B2 | 6/2013 | Ball et al. |
| 8,461,982 B2 | 6/2013 | Becker et al. |
| 8,467,734 B2 | 6/2013 | Schubert |
| 8,485,501 B1 | 7/2013 | Hard |
| 8,527,038 B2 | 9/2013 | Moon et al. |
| 8,536,990 B2 | 9/2013 | Collins, Jr. et al. |
| 8,545,417 B2 | 10/2013 | Banet et al. |
| 8,554,297 B2 | 10/2013 | Moon et al. |
| 8,564,445 B2 | 10/2013 | Dring et al. |
| 8,591,411 B2 | 11/2013 | Banet et al. |
| 8,594,776 B2 | 11/2013 | Mccombie et al. |
| 8,598,995 B2 | 12/2013 | Schuman et al. |
| 8,602,997 B2 | 12/2013 | Banet et al. |
| 8,604,916 B2 | 12/2013 | Mcneely et al. |
| 8,604,917 B2 | 12/2013 | Collins et al. |
| 8,608,505 B2 | 12/2013 | Mantay et al. |
| 8,610,562 B2 | 12/2013 | Weiner et al. |
| 8,622,922 B2 | 1/2014 | Banet et al. |
| 8,624,740 B2 | 1/2014 | Sweeney |
| 8,639,521 B2 | 1/2014 | Eggers et al. |
| 8,645,154 B2 | 2/2014 | Eggers et al. |
| 8,650,045 B2 | 2/2014 | Baldock et al. |
| 8,672,854 B2 | 3/2014 | Mccombie et al. |
| 8,674,826 B2 | 3/2014 | Bhimavarapu et al. |
| 8,674,840 B2 | 3/2014 | Snodgrass |
| 8,723,639 B2 | 5/2014 | Butler et al. |
| 8,723,677 B1 | 5/2014 | Kiani |
| 8,727,216 B2 | 5/2014 | Graves et al. |
| 8,727,804 B2 | 5/2014 | Mcneely et al. |
| 8,727,977 B2 | 5/2014 | Banet et al. |
| 8,738,118 B2 | 5/2014 | Moon et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,756,078 B2 | 6/2014 | Collins, Jr. et al. |
| 8,771,184 B2 | 7/2014 | Besson et al. |
| 8,779,924 B2 | 7/2014 | Pesot et al. |
| 8,786,402 B2 | 7/2014 | Barnes |
| 8,799,011 B2 | 8/2014 | Wilson et al. |
| 8,806,347 B2 | 8/2014 | Simister |
| 8,808,188 B2 | 8/2014 | Banet et al. |
| 8,818,260 B2 | 8/2014 | Gaines et al. |
| 8,837,683 B2 | 9/2014 | Conroy |
| 8,857,716 B1 | 10/2014 | Giobbi et al. |
| 8,872,665 B2 | 10/2014 | Snodgrass |
| 8,874,819 B2 | 10/2014 | Chen |
| 8,888,700 B2 | 11/2014 | Banet et al. |
| 8,909,330 B2 | 12/2014 | Mccombie et al. |
| 8,920,332 B2 | 12/2014 | Hong et al. |
| 8,937,930 B2 | 1/2015 | Sprigg et al. |
| 8,944,826 B1 | 2/2015 | Wilkolaski et al. |
| 8,954,336 B2 | 2/2015 | Blomquist |
| 8,954,762 B2 | 2/2015 | Boss et al. |
| 8,956,293 B2 | 2/2015 | Mccombie et al. |
| 8,956,294 B2 | 2/2015 | Mccombie et al. |
| 8,979,765 B2 | 3/2015 | Banet et al. |
| 8,992,260 B2 | 3/2015 | Coffey et al. |
| 8,992,261 B2 | 3/2015 | Mattson |
| 9,013,283 B1 | 4/2015 | Tackaberry |
| 9,020,419 B2 | 4/2015 | Gaines et al. |
| 9,054,440 B2 | 6/2015 | Taylor et al. |
| 9,064,022 B2 | 6/2015 | Smith et al. |
| 9,078,126 B2 | 7/2015 | Yi et al. |
| 9,130,400 B2 | 9/2015 | Terlizzi et al. |
| 9,136,676 B2 | 9/2015 | Yang et al. |
| 9,138,190 B2 | 9/2015 | Liu et al. |
| 9,142,923 B2 | 9/2015 | Mcneely et al. |
| 9,144,688 B2 | 9/2015 | Baumgartner et al. |
| 9,144,746 B2 | 9/2015 | Cannon |
| 9,161,700 B2 | 10/2015 | Banet et al. |
| 9,171,543 B2 | 10/2015 | Emerick et al. |
| 9,172,199 B2 | 10/2015 | Birdwell et al. |
| 9,173,593 B2 | 11/2015 | Banet et al. |

(56) References Cited

U.S. PATENT DOCUMENTS

| | | |
|---|---|---|
| 9,173,594 B2 | 11/2015 | Banet et al. |
| 9,177,465 B2 | 11/2015 | Vanderpohl, III |
| 9,192,022 B2 | 11/2015 | Gillies et al. |
| 9,204,232 B2 | 12/2015 | Klemmensen |
| 9,204,794 B2 | 12/2015 | Lisogurski et al. |
| 9,211,065 B2 | 12/2015 | Marsh et al. |
| 9,215,986 B2 | 12/2015 | Banet et al. |
| 9,265,450 B1 | 2/2016 | Giobbi |
| 9,298,881 B2 | 3/2016 | Wildman |
| 9,306,322 B2 | 4/2016 | Bhimavarapu et al. |
| 9,317,817 B2 | 4/2016 | Barsky |
| 9,320,444 B2 | 4/2016 | Hayes et al. |
| 9,320,662 B2 | 4/2016 | Hayes et al. |
| 9,339,209 B2 | 5/2016 | Banet et al. |
| 9,350,113 B2 | 5/2016 | Garner et al. |
| 9,364,158 B2 | 6/2016 | Banet et al. |
| 9,370,457 B2 | 6/2016 | Nunn et al. |
| 9,380,952 B2 | 7/2016 | Banet et al. |
| 9,392,879 B2 | 7/2016 | Nunn et al. |
| 9,401,552 B2 | 7/2016 | Coffey et al. |
| 9,411,934 B2 | 8/2016 | Robinson et al. |
| 9,439,574 B2 | 9/2016 | Mccombie et al. |
| 9,445,719 B2 | 9/2016 | Libbus et al. |
| 9,445,751 B2 | 9/2016 | Young et al. |
| 9,449,496 B2 | 9/2016 | Meredith et al. |
| 9,463,126 B2 | 10/2016 | Zerhusen et al. |
| 9,466,877 B2 | 10/2016 | Dixon et al. |
| 9,489,818 B2 | 11/2016 | Vanderpohl, III |
| 9,492,092 B2 | 11/2016 | Mccombie et al. |
| 9,492,341 B2 | 11/2016 | Huster et al. |
| 9,504,416 B2 | 11/2016 | Young et al. |
| 9,510,688 B2 | 12/2016 | Nunn et al. |
| 9,526,920 B2 | 12/2016 | Tanis et al. |
| 9,539,155 B2 | 1/2017 | Johannigman et al. |
| 9,539,156 B2 | 1/2017 | Mayoras, Jr. et al. |
| 9,572,737 B2 | 2/2017 | Mcneely et al. |
| 9,578,668 B2 | 2/2017 | Sim |
| 9,585,577 B2 | 3/2017 | Banet et al. |
| 9,595,797 B2 | 3/2017 | Taylor et al. |
| 9,596,098 B1 | 3/2017 | Djakovic et al. |
| 9,596,999 B2 | 3/2017 | Moon et al. |
| 9,635,953 B2 | 5/2017 | Nunn et al. |
| 9,642,967 B2 | 5/2017 | Ribble et al. |
| 9,668,656 B2 | 6/2017 | Banet et al. |
| 9,717,466 B2 | 8/2017 | Meredith et al. |
| 9,724,255 B2 | 8/2017 | Hollyoak et al. |
| 9,734,293 B2 | 8/2017 | Collins, Jr. et al. |
| 9,737,649 B2 | 8/2017 | Miller et al. |
| 9,740,826 B2 | 8/2017 | Raghavan et al. |
| 9,760,140 B1 | 9/2017 | Krummey et al. |
| 9,769,939 B2 | 9/2017 | Coffey et al. |
| 9,770,114 B2 | 9/2017 | Brosnan et al. |
| 9,775,529 B2 | 10/2017 | Moon et al. |
| 9,793,697 B1 | 10/2017 | Colao et al. |
| 9,804,210 B2 | 10/2017 | Haebler et al. |
| 9,820,658 B2 | 11/2017 | Tran |
| 9,825,411 B2 | 11/2017 | Wu et al. |
| 9,830,424 B2 | 11/2017 | Schuman, Sr. et al. |
| 9,833,194 B2 | 12/2017 | Hayes et al. |
| 9,838,836 B2 | 12/2017 | Hayes et al. |
| 9,844,275 B2 | 12/2017 | Nunn et al. |
| 9,861,824 B2 | 1/2018 | Baumgartner et al. |
| 9,866,016 B2 | 1/2018 | Terlizzi et al. |
| 9,872,150 B2 | 1/2018 | Priness et al. |
| 9,882,610 B1 | 1/2018 | Baker et al. |
| 9,901,503 B2 | 2/2018 | Christensen et al. |
| 9,904,816 B1 | 2/2018 | Giobbi et al. |
| 9,905,976 B1 | 2/2018 | Birdwell et al. |
| 9,925,104 B2 | 3/2018 | Mcneely et al. |
| 9,928,712 B1 | 3/2018 | Clark |
| 9,931,085 B2 | 4/2018 | Young et al. |
| 9,937,090 B2 | 4/2018 | Hayes et al. |
| 9,949,083 B1 | 4/2018 | Kirby et al. |
| 9,954,995 B2 | 4/2018 | Sulaiman et al. |
| 9,961,186 B2 | 5/2018 | Li et al. |
| 9,966,997 B2 | 5/2018 | Hayes et al. |
| 9,967,983 B2 | 5/2018 | Coffey et al. |
| 9,985,387 B2 | 5/2018 | Calange |
| 9,993,207 B2 | 6/2018 | Al-Ali et al. |
| 9,993,210 B2 | 6/2018 | Meredith et al. |
| 9,999,375 B2 | 6/2018 | Hayes et al. |
| 10,004,447 B2 | 6/2018 | Shen et al. |
| 10,007,758 B2 | 6/2018 | Al-Ali et al. |
| 10,013,847 B2 | 7/2018 | Chun |
| 10,016,117 B2 | 7/2018 | Lisogurski et al. |
| 10,016,325 B2 | 7/2018 | Ribble et al. |
| 10,020,075 B2 | 7/2018 | Perlman et al. |
| 10,021,239 B2 | 7/2018 | Ledingham et al. |
| 10,022,277 B2 | 7/2018 | Heil et al. |
| 10,034,351 B2 | 7/2018 | Kim et al. |
| 10,057,732 B2 | 8/2018 | Soomro |
| 10,058,467 B2 | 8/2018 | Stusynski et al. |
| 10,058,768 B2 | 8/2018 | Chun |
| 10,061,899 B2 | 8/2018 | Kunzeman et al. |
| 10,068,061 B2 | 9/2018 | Kunzeman et al. |
| 10,085,657 B2 | 10/2018 | Moon et al. |
| 10,085,905 B2 | 10/2018 | Bhimavarapu et al. |
| 10,086,216 B2 | 10/2018 | Tanis et al. |
| 10,087,572 B2 | 10/2018 | Bilionis et al. |
| 10,089,439 B2 | 10/2018 | Hunn |
| 10,089,443 B2 | 10/2018 | Kunzeman et al. |
| 10,092,242 B2 | 10/2018 | Nunn et al. |
| 10,095,840 B2 | 10/2018 | Kunzeman et al. |
| 10,102,923 B1 | 10/2018 | Laborde |
| 10,115,291 B2 | 10/2018 | Tallent et al. |
| 10,123,722 B2 | 11/2018 | Banet et al. |
| 10,140,837 B2 | 11/2018 | Shen et al. |
| 10,149,549 B2 | 12/2018 | Erko et al. |
| 10,155,070 B2 | 12/2018 | Childress et al. |
| 10,159,607 B2 | 12/2018 | Voll et al. |
| 10,172,565 B1 | 1/2019 | Laborde |
| 10,176,700 B2 | 1/2019 | Dixon et al. |
| 10,177,514 B2 | 1/2019 | Taylor et al. |
| 10,179,064 B2 | 1/2019 | Connor |
| 10,182,661 B2 | 1/2019 | Nunn et al. |
| 10,192,395 B2 | 1/2019 | Chun |
| 10,201,234 B2 | 2/2019 | Nunn et al. |
| 10,204,498 B2 | 2/2019 | Trishaun |
| 10,206,837 B2 | 2/2019 | Mcneely et al. |
| 10,212,032 B2 | 2/2019 | Sobie |
| 10,213,159 B2 | 2/2019 | Moon et al. |
| 10,217,339 B1 | 2/2019 | Giobbi |
| 10,222,449 B2 | 3/2019 | Doescher et al. |
| 10,224,117 B2 | 3/2019 | Kunzeman et al. |
| 10,229,294 B1 | 3/2019 | Giobbi et al. |
| 10,230,783 B2 | 3/2019 | Rajan et al. |
| 10,248,176 B2 | 4/2019 | Boss et al. |
| 10,251,490 B2 | 4/2019 | Nunn et al. |
| 10,257,063 B2 | 4/2019 | Bhimavarapu et al. |
| 10,258,258 B2 | 4/2019 | Larson et al. |
| 10,278,645 B2 | 5/2019 | Moon |
| 10,283,952 B2 | 5/2019 | Dombrowski et al. |
| 10,285,297 B2 | 5/2019 | Bratcher et al. |
| 10,290,071 B2 | 5/2019 | Robinson et al. |
| 10,292,661 B1 | 5/2019 | Laborde |
| 10,299,968 B2 | 5/2019 | Heil et al. |
| 10,300,288 B2 | 5/2019 | Baumgartner et al. |
| 10,304,068 B2 | 5/2019 | Hyde et al. |
| 10,328,188 B2 | 6/2019 | Deutsch et al. |
| 10,338,113 B2 | 7/2019 | Haebler et al. |
| 10,339,789 B1 | 7/2019 | Macdonald |
| 10,350,116 B2 | 7/2019 | Monson et al. |
| 10,357,187 B2 | 7/2019 | Mccombie et al. |
| 10,360,787 B2 | 7/2019 | Smith et al. |
| 10,363,182 B2 | 7/2019 | Zerhusen et al. |
| 10,363,183 B2 | 7/2019 | Ribble et al. |
| 10,376,214 B2 | 8/2019 | Hayes et al. |
| 10,383,518 B2 | 8/2019 | Abu-Tarif et al. |
| 10,389,546 B2 | 8/2019 | Djakovic et al. |
| 10,395,769 B2 | 8/2019 | Ribble et al. |
| 10,417,384 B2 | 9/2019 | Auchard et al. |
| 10,420,476 B2 | 9/2019 | Moon et al. |
| 10,426,685 B2 | 10/2019 | Christensen et al. |
| 10,431,220 B2 | 10/2019 | Emerick et al. |

(56) References Cited

U.S. PATENT DOCUMENTS

| | | |
|---|---|---|
| 10,437,960 B2 | 10/2019 | Sheldon et al. |
| 10,441,086 B2 | 10/2019 | Nunn et al. |
| 10,441,483 B2 | 10/2019 | Puvogel et al. |
| 10,445,467 B2 | 10/2019 | Contolini et al. |
| 10,446,004 B2 | 10/2019 | Trishaun |
| 10,448,749 B2 | 10/2019 | Palashewski et al. |
| 10,454,229 B2 | 10/2019 | Wolff |
| 10,460,555 B2 | 10/2019 | Chun |
| 10,470,320 B2 | 11/2019 | Coffey et al. |
| 10,471,231 B2 | 11/2019 | Moore-Ede et al. |
| 10,474,808 B2 | 11/2019 | Huster |
| 10,492,969 B2 | 12/2019 | Stusynski et al. |
| 10,497,474 B2 | 12/2019 | Perlman et al. |
| 10,500,105 B2 | 12/2019 | Voll et al. |
| 10,500,401 B2 | 12/2019 | Hayes |
| 10,504,353 B2 | 12/2019 | Wiggermann et al. |
| 10,512,422 B2 | 12/2019 | Hayes et al. |
| 10,512,573 B2 | 12/2019 | Johannigman et al. |
| 10,517,784 B2 | 12/2019 | Zerhusen et al. |
| 10,529,168 B2 | 1/2020 | Chun |
| 10,529,211 B2 | 1/2020 | Freeman et al. |
| 10,530,102 B2 | 1/2020 | Zhang et al. |
| 10,535,432 B2 | 1/2020 | Perlman et al. |
| 10,537,252 B2 | 1/2020 | Soro |
| 10,543,137 B2 | 1/2020 | Hayes et al. |
| 10,546,357 B2 | 1/2020 | Herbst et al. |
| 10,555,676 B2 | 2/2020 | Mccombie et al. |
| 10,559,187 B2 | 2/2020 | Flanagan et al. |
| 10,566,088 B2 | 2/2020 | Mcneely et al. |
| 10,574,008 B2 | 2/2020 | Taylor et al. |
| 10,582,981 B2 | 3/2020 | Childs et al. |
| 10,586,020 B2 | 3/2020 | Madhavan et al. |
| 10,588,565 B2 | 3/2020 | Larson et al. |
| 10,593,427 B2 | 3/2020 | Herbst et al. |
| 10,595,746 B2 | 3/2020 | Banet et al. |
| 10,601,971 B2 | 3/2020 | Hatch et al. |
| 10,610,624 B2 | 4/2020 | Deutsch et al. |
| 10,616,742 B2 | 4/2020 | Tetreault et al. |
| 10,621,305 B2 | 4/2020 | Raghavan et al. |
| 10,631,732 B2 | 4/2020 | Larson et al. |
| 10,632,032 B1 | 4/2020 | Stusynski et al. |
| 10,639,502 B2 | 5/2020 | Tanis et al. |
| 10,646,050 B2 | 5/2020 | Nunn et al. |
| 10,646,379 B2 | 5/2020 | Heil et al. |
| 10,648,659 B2 | 5/2020 | Jnsson et al. |
| 10,653,567 B2 | 5/2020 | Weidman et al. |
| 10,674,832 B2 | 6/2020 | Brosnan et al. |
| 10,679,489 B2 | 6/2020 | Bodurka et al. |
| 10,682,076 B2 | 6/2020 | Larson et al. |
| 10,682,263 B2 | 6/2020 | Heil et al. |
| 10,688,383 B2 | 6/2020 | Chun |
| 10,689,792 B2 | 6/2020 | Bilionis et al. |
| 10,698,989 B2 | 6/2020 | Giobbi |
| 10,702,298 B2 | 7/2020 | Tilstra |
| 10,709,624 B2 | 7/2020 | Bhimavarapu et al. |
| 10,716,474 B2 | 7/2020 | Bodurka et al. |
| 10,716,512 B2 | 7/2020 | Nunn et al. |
| 10,716,715 B2 | 7/2020 | Ribble et al. |
| 10,722,130 B2 | 7/2020 | Banet et al. |
| 10,722,131 B2 | 7/2020 | Banet et al. |
| 10,722,132 B2 | 7/2020 | Banet et al. |
| 10,729,255 B2 | 8/2020 | Erko et al. |
| 10,729,357 B2 | 8/2020 | Larson et al. |
| 10,735,052 B2 | 8/2020 | Hayes et al. |
| 10,740,691 B2 | 8/2020 | Choueiter et al. |
| 10,741,284 B2 | 8/2020 | Brosnan et al. |
| 10,757,228 B1 | 8/2020 | Bhimavarapu et al. |
| 10,758,162 B2 | 9/2020 | Shen et al. |
| 10,764,044 B1 | 9/2020 | Giobbi et al. |
| 10,765,326 B2 | 9/2020 | Banet et al. |
| 10,769,939 B2 | 9/2020 | Brown et al. |
| 10,786,408 B2 | 9/2020 | Sidhu et al. |
| 10,789,825 B2 | 9/2020 | Freeman et al. |
| 10,796,801 B2 | 10/2020 | Silverman |
| 10,806,351 B2 | 10/2020 | Moon et al. |
| 10,811,136 B2 | 10/2020 | Bhimavarapu et al. |
| 10,813,806 B2 | 10/2020 | Paul |
| 10,817,964 B2 | 10/2020 | Guillama et al. |
| 10,820,369 B2 | 10/2020 | Liu |
| 10,841,304 B2 | 11/2020 | Kim et al. |
| 10,856,752 B2 | 12/2020 | Banet et al. |
| 10,857,050 B2 | 12/2020 | Huster et al. |
| 10,859,613 B2 | 12/2020 | Haebler et al. |
| 10,863,012 B2 | 12/2020 | Hatch et al. |
| 10,868,694 B2 | 12/2020 | Djakovic et al. |
| 10,872,537 B1 * | 12/2020 | Frist, Jr. ................. G16H 50/30 |
| 10,874,330 B2 | 12/2020 | Larson et al. |
| 10,881,219 B2 | 1/2021 | Nunn et al. |
| 10,886,024 B2 | 1/2021 | Mcneely et al. |
| 10,888,251 B2 | 1/2021 | Larson et al. |
| 10,898,398 B2 | 1/2021 | Hayes et al. |
| 10,918,545 B2 | 2/2021 | Bhimavarapu et al. |
| 10,950,117 B2 | 3/2021 | Bodurka et al. |
| 10,958,311 B2 | 3/2021 | Ayers et al. |
| 10,978,191 B2 | 4/2021 | Collins, Jr. et al. |
| 11,011,267 B2 | 5/2021 | Schuman, Sr. et al. |
| 11,013,418 B2 | 5/2021 | Ayers et al. |
| 11,031,130 B2 | 6/2021 | Collins, Jr. et al. |
| 11,062,585 B2 | 7/2021 | Durlach et al. |
| 11,110,020 B2 | 9/2021 | Bodurka |
| 11,113,935 B2 | 9/2021 | Bodurka et al. |
| 11,178,487 B2 | 10/2021 | Nelson et al. |
| 11,164,674 B2 | 11/2021 | Lange |
| 11,229,564 B2 | 1/2022 | Bhimavarapu et al. |
| 2001/0034475 A1 | 10/2001 | Flach et al. |
| 2001/0050610 A1 | 12/2001 | Gelston |
| 2001/0051765 A1 | 12/2001 | Walker et al. |
| 2002/0012329 A1 | 1/2002 | Atkinson et al. |
| 2002/0014951 A1 | 2/2002 | Kramer et al. |
| 2002/0023121 A1 | 2/2002 | Sugiyama et al. |
| 2002/0044059 A1 | 4/2002 | Reeder et al. |
| 2002/0060624 A1 | 5/2002 | Zhang |
| 2002/0067273 A1 | 6/2002 | Jaques et al. |
| 2002/0067282 A1 | 6/2002 | Moskowitz et al. |
| 2002/0070867 A1 | 6/2002 | Conway et al. |
| 2002/0091843 A1 | 7/2002 | Vaid |
| 2002/0149822 A1 | 10/2002 | Stroud |
| 2002/0165731 A1 | 11/2002 | Dempsey |
| 2002/0173991 A1 | 11/2002 | Avitall |
| 2002/0179092 A1 | 12/2002 | Swennen et al. |
| 2002/0198986 A1 | 12/2002 | Dempsey |
| 2003/0006881 A1 | 1/2003 | Reyes |
| 2003/0010345 A1 | 1/2003 | Koblasz et al. |
| 2003/0028449 A1 | 2/2003 | Heinen et al. |
| 2003/0062990 A1 | 4/2003 | Schaeffer, Jr. et al. |
| 2003/0141981 A1 | 7/2003 | Bui et al. |
| 2003/0149598 A1 | 8/2003 | Santoso et al. |
| 2003/0176798 A1 | 9/2003 | Simon |
| 2003/0227900 A1 | 12/2003 | Watanabe |
| 2004/0072475 A1 | 4/2004 | Istvan |
| 2004/0073127 A1 | 4/2004 | Istvan et al. |
| 2004/0091270 A1 | 5/2004 | Choi et al. |
| 2004/0106854 A1 | 6/2004 | Muraki |
| 2004/0121767 A1 | 6/2004 | Simpson et al. |
| 2004/0127802 A1 | 7/2004 | Istvan et al. |
| 2004/0147818 A1 | 7/2004 | Levy et al. |
| 2004/0167465 A1 | 8/2004 | Mihai et al. |
| 2004/0176667 A1 | 9/2004 | Mihai et al. |
| 2004/0186358 A1 | 9/2004 | Chernow et al. |
| 2004/0193449 A1 | 9/2004 | Wildman et al. |
| 2005/0035871 A1 | 2/2005 | Dixon et al. |
| 2005/0065817 A1 | 3/2005 | Mihai et al. |
| 2005/0102167 A1 | 5/2005 | Kapoor |
| 2005/0114177 A1 | 5/2005 | Sweeney |
| 2005/0119866 A1 | 6/2005 | Zaleski |
| 2005/0122119 A1 | 6/2005 | Barlow |
| 2005/0144042 A1 | 6/2005 | Joffe et al. |
| 2005/0197545 A1 | 9/2005 | Hoggle |
| 2005/0251002 A1 | 11/2005 | Istvan et al. |
| 2005/0251003 A1 | 11/2005 | Istvan et al. |
| 2006/0002340 A1 | 1/2006 | Criss et al. |
| 2006/0058587 A1 | 3/2006 | Heimbrock et al. |
| 2006/0089539 A1 | 4/2006 | Miodownik et al. |
| 2006/0095234 A1 | 5/2006 | Brignone et al. |

(56) References Cited

U.S. PATENT DOCUMENTS

| | | |
|---|---|---|
| 2006/0135083 A1 | 6/2006 | Leinonen et al. |
| 2006/0155589 A1 | 7/2006 | Lane et al. |
| 2006/0190302 A1 | 8/2006 | Eggers et al. |
| 2006/0239195 A1 | 10/2006 | Camins et al. |
| 2006/0248221 A1 | 11/2006 | Hottel et al. |
| 2006/0253281 A1 | 11/2006 | Letzt et al. |
| 2006/0277202 A1 | 12/2006 | Dempsey |
| 2007/0004971 A1 | 1/2007 | Riley et al. |
| 2007/0010719 A1 | 1/2007 | Huster et al. |
| 2007/0037614 A1 | 2/2007 | Rosenberg |
| 2007/0054641 A1 | 3/2007 | Goedicke et al. |
| 2007/0110097 A1 | 5/2007 | Hsieh |
| 2007/0135866 A1 | 6/2007 | Baker et al. |
| 2007/0142716 A1 | 6/2007 | Biondi |
| 2007/0156456 A1 | 7/2007 | Mcgillin et al. |
| 2007/0156707 A1 | 7/2007 | Fuchs et al. |
| 2007/0180140 A1 | 8/2007 | Welch et al. |
| 2007/0233199 A1 | 10/2007 | Moore et al. |
| 2007/0255348 A1 | 11/2007 | Holtzclaw |
| 2007/0258395 A1 | 11/2007 | Jollota et al. |
| 2007/0288263 A1 | 12/2007 | Rodgers |
| 2008/0009694 A1 | 1/2008 | Hopman et al. |
| 2008/0057868 A1 | 3/2008 | Chang |
| 2008/0114689 A1 | 5/2008 | Psynik et al. |
| 2008/0120784 A1 | 5/2008 | Warner et al. |
| 2008/0122616 A1 | 5/2008 | Warner et al. |
| 2008/0126122 A1 | 5/2008 | Warner et al. |
| 2008/0126132 A1 | 5/2008 | Warner et al. |
| 2008/0147442 A1 | 6/2008 | Warner et al. |
| 2008/0164998 A1 | 7/2008 | Scherpbier et al. |
| 2008/0224861 A1 | 9/2008 | Mcneely et al. |
| 2009/0056027 A1 | 3/2009 | Ball et al. |
| 2009/0243833 A1 | 10/2009 | Huang et al. |
| 2010/0001838 A1 | 1/2010 | Miodownik et al. |
| 2010/0217618 A1 | 8/2010 | Piccirillo et al. |
| 2011/0021142 A1 | 1/2011 | Desai et al. |
| 2011/0025915 A1 | 2/2011 | Daban |
| 2011/0054936 A1 | 3/2011 | Cowan et al. |
| 2011/0205061 A1 | 8/2011 | Wilson et al. |
| 2011/0210833 A1 | 9/2011 | Mcneely et al. |
| 2012/0028488 A1 | 2/2012 | Puschnigg et al. |
| 2012/0072238 A1 | 3/2012 | Collins, Jr. et al. |
| 2012/0246088 A1 | 9/2012 | Steinbarth et al. |
| 2012/0316892 A1 | 12/2012 | Huster et al. |
| 2013/0069771 A1 | 3/2013 | Frondorf |
| 2013/0109315 A1 | 5/2013 | Polo et al. |
| 2013/0127620 A1 | 5/2013 | Siebers et al. |
| 2013/0253291 A1 | 9/2013 | Dixon et al. |
| 2014/0236629 A1 | 8/2014 | Kim et al. |
| 2014/0370811 A1 | 12/2014 | Kang et al. |
| 2015/0019250 A1 | 1/2015 | Goodman et al. |
| 2016/0027289 A1 | 1/2016 | Hargis |
| 2016/0073949 A1 | 3/2016 | Grant |
| 2016/0094953 A1 | 3/2016 | Russ et al. |
| 2016/0212194 A1 | 7/2016 | Palin et al. |
| 2016/0321418 A1* | 11/2016 | Reid ...................... G16H 10/65 |
| 2017/0155523 A1 | 6/2017 | Fu et al. |
| 2017/0303076 A1 | 10/2017 | Song et al. |
| 2017/0324195 A1 | 11/2017 | Eriksen et al. |
| 2018/0085051 A1 | 3/2018 | Kawashima et al. |
| 2018/0152979 A1 | 5/2018 | Lee et al. |
| 2018/0333317 A1 | 11/2018 | Zerhusen et al. |
| 2019/0008709 A1 | 1/2019 | Bhimavarapu et al. |
| 2019/0183705 A1* | 6/2019 | Bodurka ................. H04B 5/48 |
| 2019/0188992 A1 | 6/2019 | Bodurka et al. |
| 2019/0287381 A1 | 9/2019 | Enzinna et al. |
| 2020/0066415 A1 | 2/2020 | Hettig et al. |
| 2020/0082937 A1 | 3/2020 | Bodurka et al. |
| 2020/0121226 A1 | 4/2020 | Hayes et al. |
| 2020/0170516 A1 | 6/2020 | Ayers et al. |
| 2020/0203010 A1 | 6/2020 | Durlach et al. |
| 2020/0342986 A1 | 10/2020 | Raghavan et al. |
| 2020/0345568 A1 | 11/2020 | Heimbrock et al. |
| 2020/0396295 A1 | 12/2020 | Martin et al. |
| 2020/0411179 A1 | 12/2020 | Frye et al. |
| 2021/0006915 A1 | 1/2021 | Hegde |
| 2021/0118561 A1* | 4/2021 | Löser ................... H04L 9/0872 |
| 2021/0145677 A1 | 5/2021 | Bhimavarapu et al. |
| 2022/0054337 A1 | 2/2022 | Tallent et al. |
| 2022/0233382 A1 | 7/2022 | Williams et al. |

FOREIGN PATENT DOCUMENTS

| | | |
|---|---|---|
| CN | 206962160 U | 2/2018 |
| CN | 108616853 A | 10/2018 |
| CN | 108986898 A | 12/2018 |
| CN | 109286840 A | 1/2019 |
| CN | 110944316 A | 3/2020 |
| CN | 210575132 U | 5/2020 |
| EP | 3121930 A1 | 1/2017 |
| JP | 2001211259 A | 8/2001 |
| JP | 2009042822 A | 2/2009 |
| JP | 2019140645 A | 8/2019 |
| JP | 6774839 B2 | 10/2020 |
| JP | 6851215 B2 | 3/2021 |
| WO | 2015009315 A1 | 1/2015 |
| WO | 2019066520 A2 | 4/2019 |
| WO | 2019223919 A1 | 11/2019 |
| WO | 2020087542 A1 | 5/2020 |
| WO | 2021046171 A1 | 3/2021 |
| WO | 2021074895 A1 | 4/2021 |
| WO | 2022081400 A1 | 4/2022 |

OTHER PUBLICATIONS

Touati, Farid et al., "A Real-time BLE Enabled ECG System for Remote Monitoring," ICBET 2013: May 19-20, 2013; Copenhagen, Denmark (8 pages).

\* cited by examiner

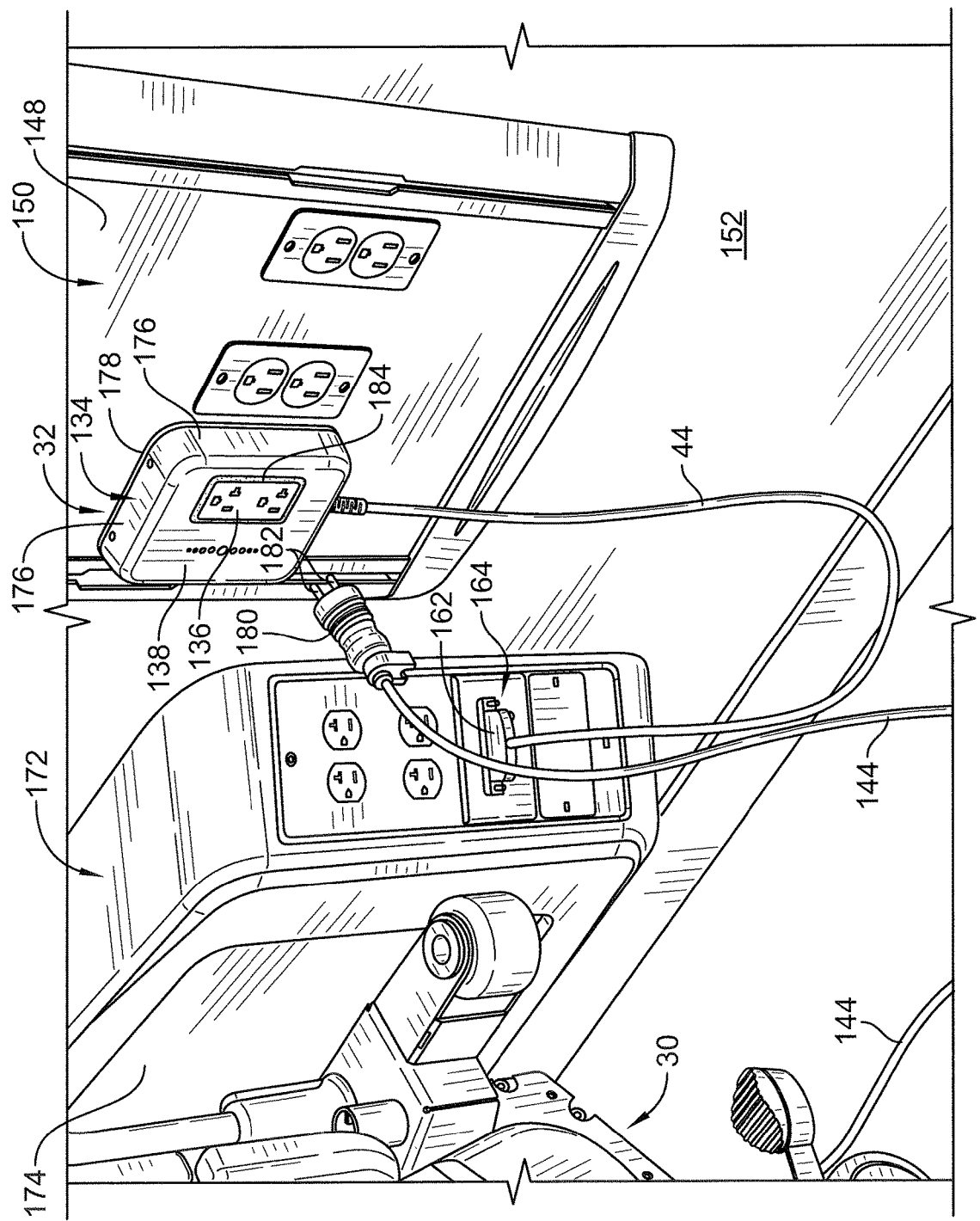

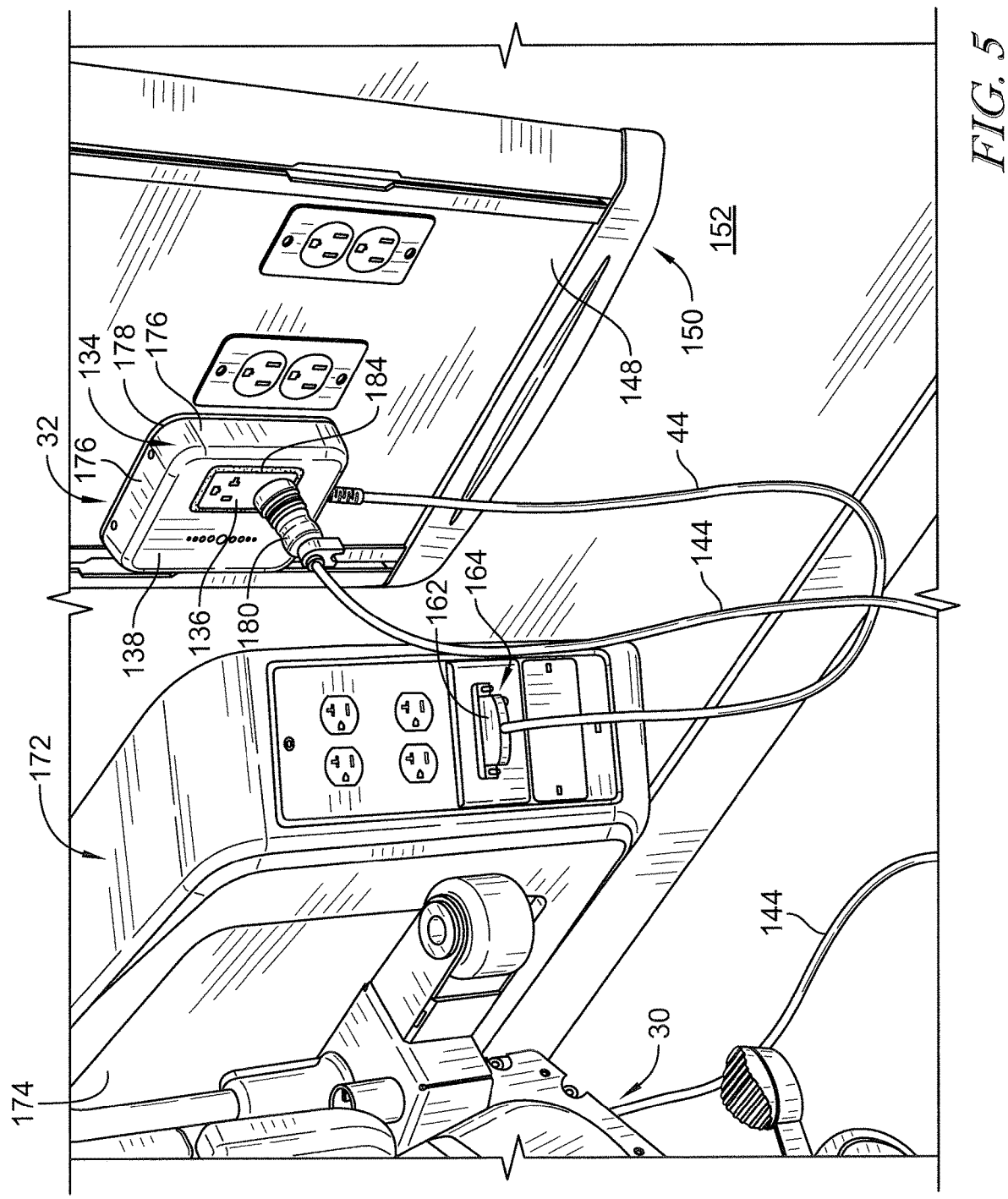

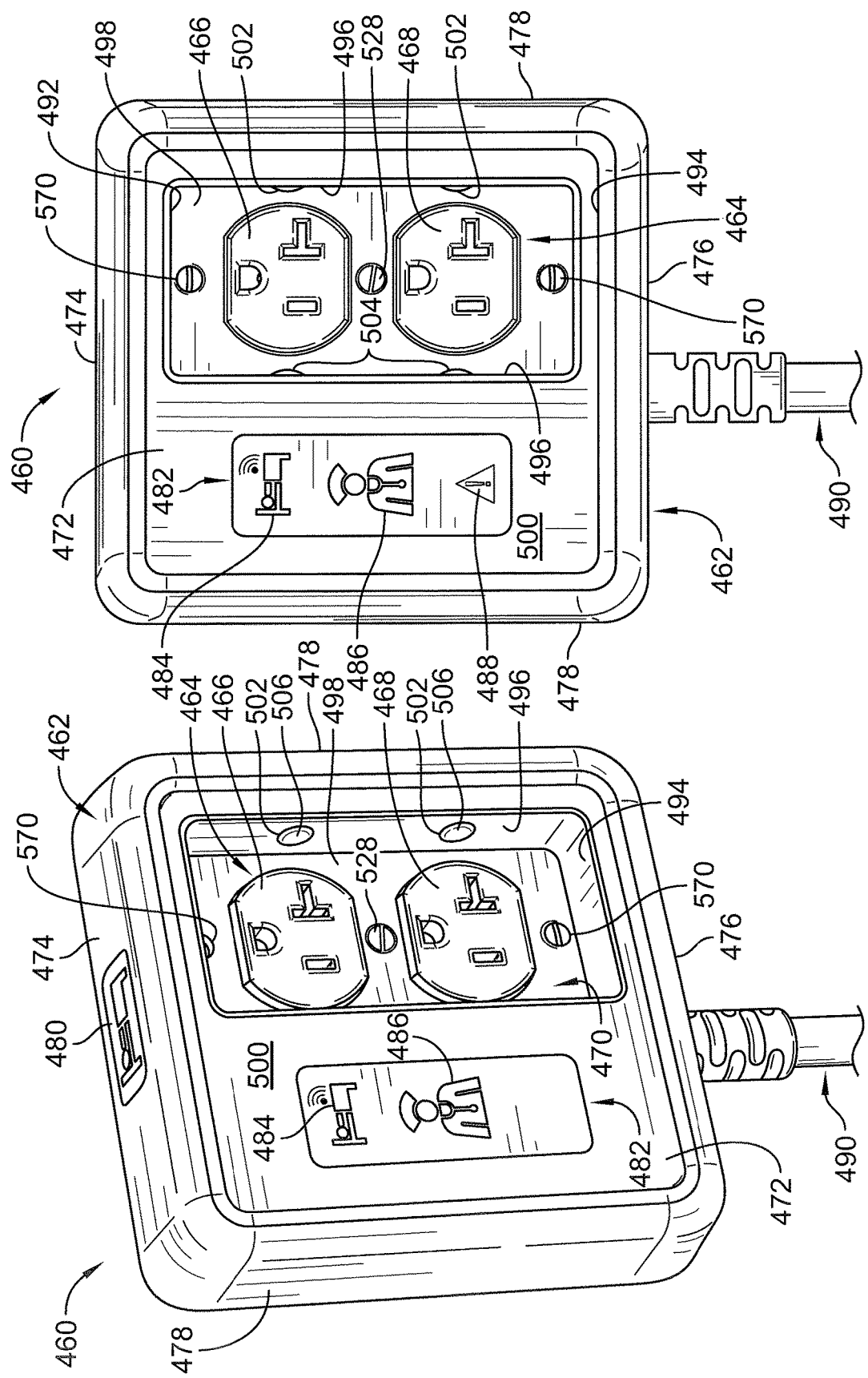

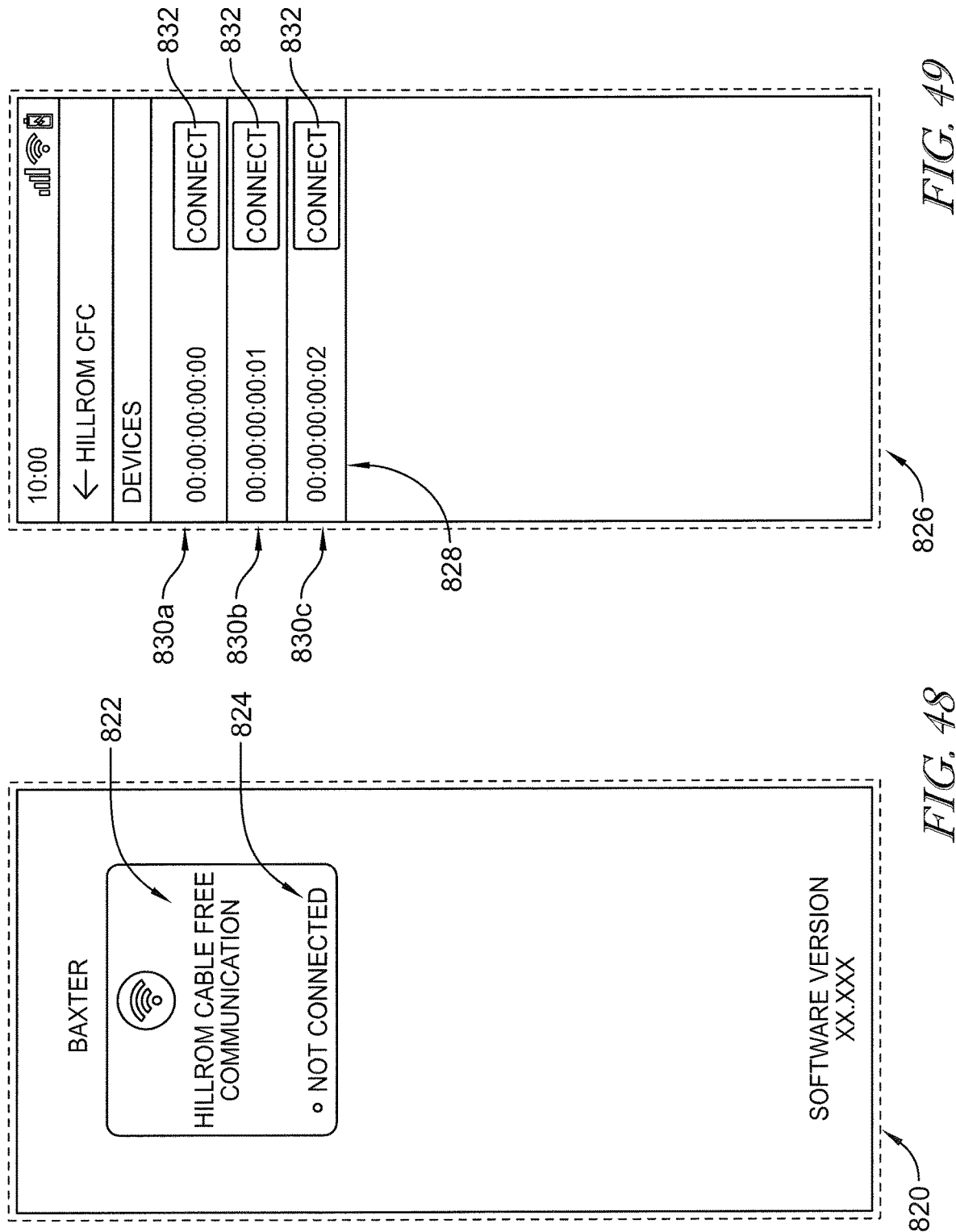

WIRELESS CONFIGURATION AND AUTHORIZATION OF A WALL UNIT THAT PAIRS WITH A MEDICAL DEVICE

The present application claims the benefit, under 35 U.S.C. § 119(e), of U.S. Provisional Application No. 63/344, 723, filed May 23, 2022, and the present application is also a continuation-in-part of U.S. application Ser. No. 17/577, 496, filed Jan. 18, 2022, which claims the benefit, under 35 U.S.C. § 119(e), of U.S. Provisional Application No. 63/140, 601, filed Jan. 22, 2021; U.S. Provisional Application No. 63/168,371, filed Mar. 31, 2021; U.S. Provisional Application No. 63/193,680, filed May 27, 2021; and U.S. Provisional Application No. 63/232,737, filed Aug. 13, 2021; each of which is hereby expressly incorporated by reference herein in its entirety.

BACKGROUND

The present disclosure relates to wireless pairing of medical devices with wall units in a patient room for wireless communication of device data. More particularly, the present disclosure relates to pairing between patient beds and wall units for wireless communication of bed status data and alerts to nurse call systems and other systems of a healthcare facility.

Known patient beds are configured to couple to nurse call systems via wired connections such as nurse call cables. For example, patient beds marketed by Hill-Rom Company, Inc. oftentimes connect to wall-mounted audio station bed connectors (ASBC's) or bed interface units (BIU's) of nurse call systems, such as the NAVICARE® Nurse Call System, using a nurse call cable having 37-pin connectors at its opposite ends. If a caregiver forgets to disconnect the nurse call cable from the ASBC, BIU, or other similar type of wall module prior to attempting to move the patient bed to another location, the nurse call cable can potentially become damaged when it is abruptly ripped out of the wall module. The connector on the wall module or the wall module itself can also potentially become damaged.

In more recent times, patient beds with wireless communication capability have entered the market. However, elimination of the wired connection to a wall module introduces challenges with regard to wireless pairing of the patient bed with the proper wall module so that the proper bed location in a healthcare facility can be determined. For the prior art beds that connect to wall modules using cables, bed identification data (ID) is typically sent to the wall module which contains a location ID or some other ID (e.g., wall module ID, MAC address, or the like) that correlates to the room location. The wall module transmits the bed ID received over the nurse call cable from the bed along with the location ID stored in the wall module to a nurse call system server or some other locating server which is able to determine the bed location based on the received bed and location ID's.

When beds transmit the corresponding bed ID's wirelessly, especially when transmitting using radio frequency (RF) signals, the bed ID's are oftentimes received at multiple wall modules or other fixed receiving units such as wireless access points (WAP's), depending upon the signal strength of the RF transmissions and the wireless technology used for making the RF transmissions. In fact, the RF transmissions from the beds are able to pass through walls, ceilings, and floors in some instances and then are potentially received by multiple wall modules including those in entirely different rooms. Thus, there is a continuing need for improvements in wireless pairing of medical devices, such as patient beds, with wall modules in patient rooms.

SUMMARY

An apparatus, system, or method may comprise one or more of the features recited in the appended claims and/or the following features which, alone or in any combination, may comprise patentable subject matter:

According to a first aspect of the present disclosure, a system for use in a healthcare facility that may comprise a network and a nurse call system is provided. The system may include a medical device that may have a first wireless transceiver, a first timer, and a power cord that may terminate at a power plug. The medical device may have a first sensor to determine that the medical device may be receiving power via the power plug and power cord. The system further may have a wall unit that may be mounted at a fixed location in a patient room of the healthcare facility. The wall unit may have a second wireless transceiver and a second timer. The wall unit may be plugged into a first alternating current (AC) outlet of the healthcare facility. The wall unit may have a second AC outlet into which the power plug of the medical device may be coupleable. The wall unit may have an AC plug sensor that may sense the power plug being plugged into the second AC outlet. The first timer may be started to measure a first uptime in response to the first sensor sensing that the medical device is receiving power via the power plug and the power cord. The second timer may be started to measure a second uptime in response to the power plug being plugged into the second AC outlet of the wall unit. The medical device may be configured to transmit to the wall unit from the first wireless transceiver an advertisement including the first uptime. The wall unit may compare the first uptime with the second uptime and, if the first uptime is within a predetermined tolerance range of the second uptime, the wall unit may send a pairing message to the medical device which results in the wall unit and medical device becoming automatically paired for subsequent wireless communications.

In some embodiments of the first aspect, the system further may include a nurse call cord extending from the wall unit. The nurse call cord may terminate at a first nurse call connector that may be configured for connection to a nurse call port of the nurse call system. Optionally, the nurse call cord may include an auxiliary cord branch that may terminate at a second nurse call connector. In such embodiments, the second nurse call connector may be coupleable to a third nurse call connector that may be at an end of a device nurse call cord that may extend from the medical device. Further optionally, the first nurse call connector may be provided in a connector body of the nurse call cord. In such embodiments, the connector body may have a second nurse call connector that may be configured to couple to a third nurse call connector that may be at an end of a device nurse call cord that may extend from the medical device. Still further optionally, the wall unit may include a first nurse call connector that may be configured to couple to a second nurse call connector that may be at an end of a device nurse call cord that may extend from the medical device.

It is contemplated by the present disclosure that the medical device of the first aspect may further may include a first wireless fidelity (WiFi) transceiver that may be configured to send WiFi messages to, and receive WiFi messages from, at least one wireless access point of the network. If desired, the first wireless transceiver may include a first Bluetooth transceiver that may be mounted to a first circuit board of the medical device and the first WiFi transceiver may be mounted to a second circuit board of the medical device. Optionally, the wall unit may include a second WiFi transceiver that may be configured to send WiFi messages to, and receive WiFi messages from, the at least one wireless access point of the network.

In some embodiments of the first aspect, the second wireless transceiver may include a second Bluetooth transceiver and the system further may include a first set of switches on the first circuit board to provide first contact closures that may be indicative of a plurality of states of the medical device and a second set of switches in the wall unit. The second set of switches may have second contact closures that may be controlled by a controller of the wall unit to match the plurality of states of the first contact closures based on data that may be contained in Bluetooth messages received by the second Bluetooth transceiver from the first Bluetooth transceiver.

Optionally, at least one of the second contact closures may be closed to control a television in the patient room. Alternatively or additionally, at least one of the second contact closures may be closed to turn on a light in the patient room. Further alternatively or additionally, the medical device may include a patient bed and at least one of the second contact closures may be closed to indicate an alarm state of a bed exit system of the patient bed. Still further alternatively or additionally, the medical device may include a patient bed and at least one of the second contact closures may be closed to indicate that a siderail of the patient bed may have been moved to a lowered position. Yet further alternatively or additionally, the medical device may include a patient bed and at least one of the second contact closures may be closed to indicate that brakes of casters of the patient bed may be in a released condition. Alternatively or additionally, the medical device may include a patient bed and at least one of the second contact closures may be closed to indicate that an upper frame of the patient bed may have been raised out of its lowest position. Further alternatively or additionally, the medical device may include a patient bed and at least one of the second contact closures may be closed to indicate that a nurse call button of the patient bed has been pressed.

Optionally, the medical device of the first aspect may include a speaker and a microphone and the first and second wireless transceivers may be configured for transmission and receipt of audio messages after the medical device and the wall unit are paired. Further optionally, the wall unit may include a light that may be illuminated to indicate a pairing state between the medical device and the wall unit. For example, the light may surround a perimeter of the second AC outlet.

In some embodiments of the first aspect, the wall unit may determine whether to initiate unpairing from the medical device based on device data that may be received by the second wireless transceiver from the first wireless transceiver of the medical device. For example, the medical device may include a frame and casters that may be coupled to the frame and the wall unit may initiate unpairing based on the device data indicating that brakes of the casters may be released. Alternatively or additionally, the wall unit may initiate unpairing based on the device data indicating that the power plug of the medical device may have been unplugged. Further alternatively or additionally, the wall unit may determine whether to initiate unpairing from the medical device in response to the AC plug sensor sensing that the power plug may have been unplugged from the second AC outlet.

If desired, the AC plug sensor of the wall unit may include a photo emitter and a photo detector that may cooperate to detect presence of at least one prong of the power plug of the medical device being inserted into the second AC outlet of the wall unit. For example, the photo emitter may emit infrared (IR) light in a generally horizontal direction for detection by the photo detector and the at least one prong may block the IR light from reaching the photo detector after the power plug is plugged into the second AC outlet. Alternatively, the photo emitter may emit infrared (IR) light in a generally vertical direction for detection by the photo detector and the at least one prong may block the IR light from reaching the photo detector after the power plug is plugged into the second AC outlet.

In some embodiments of the first aspect, the AC plug sensor may include a mechanical switch that may move from a first state to a second state in response to the power plug of the medical device being plugged into the second AC outlet of the wall unit. For example, the mechanical switch may include a plunger switch that may have a plunger that may be pressed inwardly by a plug body of the power plug when the power plug is plugged into the second AC outlet. Alternatively or additionally, the AC plug sensor may include a current sensor to sense current flowing to at least one prong of the power plug after the power plug is plugged into the second AC outlet of the wall unit.

The present disclosure further contemplates that the AC plug sensor of the wall unit may include a reader that may detect a tag that may be coupled to the power plug. If desired, the tag may carry a transponder that may be read by the reader. For example, the transponder may include a near field communication (NFC) transponder. If desired, the NFC transponder may be included in an NFC integrated circuit chip. Optionally, the reader may emit energy to power the transponder to enable the transponder to send a signal back to the reader.

In some embodiments of the first aspect, the medical device may be configured to transmit a device identification (ID) to the wall unit and the wall unit may be configured to transmit the device ID and a location ID to at least one server of the network of the healthcare facility. The location ID may be correlatable to a location at which the medical device may be located in the healthcare facility. If desired, the medical device may include a graphical display screen and the wall unit may be configured to transmit from the second wireless transceiver to the first wireless transceiver of the medical device a smart text string that may be displayed on the graphical display screen. The smart text string may include a name of the location at which the medical device is located and may be different than the location ID. In such embodiments, the medical device may not receive the location ID from the wall unit and may not retransmit the smart text string.

According to a second aspect of the present disclosure, a wall unit may be configured for wireless communication with a medical device. The wall unit may include a housing that may be configured to be mounted at a fixed location in a patient room of the healthcare facility. A wireless transceiver and a timer may be carried by the housing. The wall unit may be configured to plug into a first alternating current (AC) outlet of the healthcare facility. A second AC outlet may be carried by the housing and into which a power plug of the medical device is coupleable. An AC plug sensor may be carried by the housing and may be configured to sense a power plug of the medical device being plugged into the second AC outlet. The timer may be started to measure a first uptime in response to the power plug being plugged into the second AC outlet of the wall unit. The wireless transceiver of the wall unit may be configured to receive at least one transmission from the medical device that may include a second uptime. The wall unit may compare the first uptime with the second uptime and, if the first uptime is within a predetermined tolerance range of the second uptime, the wall unit may send a pairing message to the medical device which results in the wall unit and medical device becoming automatically paired for subsequent wireless communications.

In some embodiments of the second aspect, the wall unit further may include a nurse call cord that may extend from the housing. The nurse call cord may terminate at a first nurse call connector that may be configured for connection to a nurse call port of a nurse call system of the healthcare facility. Optionally, the nurse call cord may include an auxiliary cord branch that may terminate at a second nurse call connector. In such embodiments, the second nurse call connector may be coupleable to a third nurse call connector that may be at an end of a device nurse call cord that may extend from the medical device. Further optionally, the first nurse call connector may be provided in a connector body of the nurse call cord. In such embodiments, the connector body may have a second nurse call connector that may be configured to couple to a third nurse call connector that may be at an end of a device nurse call cord that may extend from the medical device. Still further optionally, the housing of the wall unit may carry a first nurse call connector that may be configured to couple to a second nurse call connector that may be at an end of a device nurse call cord that may extend from the medical device.

It is contemplated by the present disclosure that the housing of the wall unit of the second aspect may carry a first wireless fidelity (WiFi) transceiver that may be configured to send WiFi messages to, and receive WiFi messages from, at least one wireless access point of a network of the healthcare facility. If desired, the wireless transceiver carried by the housing of the wall unit may include a Bluetooth transceiver.

In some embodiments of the second aspect, the wall unit further may include a controller and a set of switches that may be carried by the housing. The set of switches may be configured to provide contact closures that may be indicative of a plurality of states of the medical device based on data contained in Bluetooth messages received by the Bluetooth transceiver from the medical device.

Optionally, at least one of the contact closures may be closed to control a television in the patient room. Alternatively or additionally, at least one of the contact closures may be closed to turn on a light in the patient room. Further alternatively or additionally, the medical device may include a patient bed and at least one of the contact closures may be closed to indicate an alarm state of a bed exit system of the patient bed. Still further alternatively or additionally, the medical device may include a patient bed and at least one of the contract closures may be closed to indicate that a siderail of the patient bed may have been moved to a lowered position. Yet further alternatively or additionally, the medical device may include a patient bed and at least one of the contact closures may be closed to indicate that brakes of casters of the patient bed may be in a released condition. Alternatively or additionally, the medical device may include a patient bed and at least one of the contact closures may be closed to indicate that an upper frame of the patient bed may have been raised out of its lowest position. Further alternatively or additionally, the medical device may include a patient bed and at least one of the second contact closures may be closed to indicate that a nurse call button of the patient bed has been pressed.

Optionally, the medical device of the second aspect may include a speaker and a microphone and the wireless transceiver may be configured for transmission and receipt of audio messages after the medical device and the wall unit are paired. Further optionally, the housing of the wall unit may carry a light that may be illuminated to indicate a pairing state between the medical device and the wall unit. For example, the light may surround a perimeter of the second AC outlet.

In some embodiments of the second aspect, the wall unit may include a controller that may be configured to determine whether to initiate unpairing from the medical device based on device data that may be received by the wireless transceiver from the medical device. For example, the medical device may include a frame and casters that may be coupled to the frame and wherein the controller may initiate unpairing based on the device data indicating that brakes of the casters may be released. Alternatively or additionally, the controller may initiate unpairing based on the device data indicating that the power plug of the medical device may have been unplugged. Further alternatively or additionally, the controller may determine whether to initiate unpairing from the medical device in response to the AC plug sensor sensing that the power plug may have been unplugged from the second AC outlet.

If desired, the AC plug sensor may include a photo emitter and a photo detector that may cooperate to detect presence of at least one prong of the power plug of the medical device being inserted into the second AC outlet. For example, the photo emitter may emit infrared (IR) light in a generally horizontal direction for detection by the photo detector and the at least one prong may block the IR light from reaching the photo detector after the power plug is plugged into the second AC outlet. Alternatively, the photo emitter may emit infrared (IR) light in a generally vertical direction for detection by the photo detector and the at least one prong may block the IR light from reaching the photo detector after the power plug is plugged into the second AC outlet.

In some embodiments of the second aspect, the AC plug sensor may include a mechanical switch that may move from a first state to a second state in response to the power plug of the medical device being plugged into the second AC outlet. For example, the mechanical switch may include a plunger switch that may have a plunger that may be pressed inwardly by a plug body of the power plug when the power plug is plugged into the second AC outlet. Alternatively or additionally, the AC plug sensor may include a current sensor to sense current flowing to at least one prong of the power plug after the power plug is plugged into the second AC outlet.

The present disclosure further contemplates that the AC plug sensor may include a reader that may detect a tag that may be coupled to the power plug. If desired, the reader may be configured to detect the tag by reading a transponder that may be carried by the tag. For example, the reader may be configured to detect the tag by reading a near field communication (NFC) transponder that may be carried by the tag. Optionally, the reader may emit energy to power the NFC transponder to enable the NFC transponder to send a signal back to the reader.

According to a third aspect of the present disclosure, a system for use in a healthcare facility having a network may include a medical device that may have a first wireless transceiver, a first timer, and a first sensor. The system may further include a communication unit. The first sensor may be operable to determine that the medical device may be hardwire connected to the communication unit via a cord. The communication unit may have a second wireless transceiver and a second timer. The communication unit may have a port with which the cord from the medical device may be coupleable. The communication unit may have a cord sensor to sense that the communication unit may be hardwire connected to the medical device via the port. The first timer may be started to measure a first hardwire connection time in response to the first sensor sensing that the medical device may be hardwire connected to the communication unit via the cord. The second timer may be started to measure a second hardwire connection time in response to the cord being plugged into the port. The medical device may be configured to transmit to the communication unit from the first wireless transceiver an advertisement that may include the first hardwire connection time. The communication unit may compare the first hardwire connection time with the second hardwire connection time and, if the first hardwire connection time is within a predetermined tolerance range of the second hardwire connection time, the communication unit may send a pairing message to the medical device which may result in the communication unit and the medical device becoming automatically paired for subsequent wireless communications.

In some embodiments of the third aspect, the medical device may include a speaker and a microphone and the first and second wireless transceivers may be configured for transmission and reception of audio messages after the medical device and the communication unit are paired. Optionally, the communication unit may include a light that may be illuminated to indicate a pairing state between the medical device and the communication unit.

If desired, the communication unit may determine whether to initiate unpairing from the medical device based on device data received by the second wireless transceiver from the first wireless transceiver of the medical device. For example, the medical device may include a frame and casters that may be coupled to the frame and at least one of the communication unit and medical device may initiate unpairing based on the device data indicating that brakes of the casters may be released. Alternatively or additionally, at least one of the communication unit and medical device may initiate unpairing based on the device data indicating that the cord of the medical device may have been disconnected.

In some embodiments of the third aspect, the cord sensor of the communication unit may include a photo emitter and a photo detector that may cooperate to detect presence of the cord. Alternatively, the cord sensor may include a mechanical switch that may move from a first state to a second state in response to the cord being plugged in. Further alternatively, the cord sensor may include a current sensor to sense current flowing in the cord. Still further alternatively, the cord sensor of the communication unit may include a reader that may detect a tag that may be coupled to the cord.

According to a fourth aspect of the present disclosure, a system for use in a healthcare facility having a network and a nurse call system may include a medical device that may have a first wireless transceiver, a first timer, and a power cord that may terminate at a power plug. The medical device may have a first sensor to determine that the medical device may be receiving power via the power plug and power cord. The system may further have a wall unit that may be mounted at a fixed location in a patient room of the healthcare facility. The wall unit may have a second wireless transceiver and a second timer. The wall unit may receive AC power from the healthcare facility. The wall unit may carry an AC outlet into which the power plug of the medical device may be coupleable. The wall unit may have an AC plug sensor that senses the power plug being plugged into the AC outlet. The first timer may be started to measure a first uptime in response to the first sensor sensing that the medical device may be receiving power via the power plug and the power cord. The second timer may be started to measure a second uptime in response to the power plug being sensed by the AC plug sensor of the wall unit. The wall unit may be configured to transmit to the medical device from the second wireless transceiver an advertisement that may include the second uptime. The medical device may compare the second uptime with the first uptime and, if the second uptime is within a predetermined tolerance range of the first uptime, the medical device may send a pairing message to the wall unit which may result in the wall unit and medical device becoming automatically paired for subsequent wireless communications.

In some embodiments of the fourth aspect, the system further may include a nurse call cord extending from the wall unit. The nurse call cord may terminate at a first nurse call connector that may be configured for connection to a nurse call port of the nurse call system. Optionally, the nurse call cord may include an auxiliary cord branch that may terminate at a second nurse call connector. In such embodiments, the second nurse call connector may be coupleable to a third nurse call connector that may be at an end of a device nurse call cord that may extend from the medical device. Further optionally, the first nurse call connector may be provided in a connector body of the nurse call cord. In such embodiments, the connector body may have a second nurse call connector that may be configured to couple to a third nurse call connector that may be at an end of a device nurse call cord that may extend from the medical device. Still further optionally, the wall unit may include a first nurse call connector that may be configured to couple to a second nurse call connector that may be at an end of a device nurse call cord that may extend from the medical device.

It is contemplated by the present disclosure that the medical device of the first aspect may further may include a first wireless fidelity (WiFi) transceiver that may be configured to send WiFi messages to, and receive WiFi messages from, at least one wireless access point of the network. If desired, the first wireless transceiver may include a first Bluetooth transceiver that may be mounted to a first circuit board of the medical device and the first WiFi transceiver may be mounted to a second circuit board of the medical device. Optionally, the wall unit may include a second WiFi transceiver that may be configured to send WiFi messages to, and receive WiFi messages from, the at least one wireless access point of the network.

In some embodiments of the fourth aspect, the second wireless transceiver may include a second Bluetooth transceiver and the system further may include a first set of switches on the first circuit board to provide first contact closures that may be indicative of a plurality of states of the medical device and a second set of switches in the wall unit. The second set of switches may have second contact closures that may be controlled by a controller of the wall unit to match the plurality of states of the first contact closures based on data that may be contained in Bluetooth messages received by the second Bluetooth transceiver from the first Bluetooth transceiver.

Optionally, at least one of the second contact closures may be closed to control a television in the patient room. Alternatively or additionally, at least one of the second contact closures may be closed to turn on a light in the patient room. Further alternatively or additionally, the medical device may include a patient bed and at least one of the second contact closures may be closed to indicate an alarm state of a bed exit system of the patient bed. Still further alternatively or additionally, the medical device may include a patient bed and at least one of the second contact closures may be closed to indicate that a siderail of the patient bed may have been moved to a lowered position. Yet further alternatively or additionally, the medical device may include a patient bed and at least one of the second contact closures may be closed to indicate that brakes of casters of the patient bed may be in a released condition. Alternatively or additionally, the medical device may include a patient bed and at least one of the second contact closures may be closed to indicate that an upper frame of the patient bed may have been raised out of its lowest position. Further alternatively or additionally, the medical device may include a patient bed and at least one of the second contact closures may be closed to indicate that a nurse call button of the patient bed has been pressed.

Optionally, the medical device of the fourth aspect may include a speaker and a microphone and the first and second wireless transceivers may be configured for transmission and receipt of audio messages after the medical device and the wall unit are paired. Further optionally, the wall unit may include a light that may be illuminated to indicate a pairing state between the medical device and the wall unit. For example, the light may surround a perimeter of the AC outlet.

In some embodiments of the fourth aspect, the wall unit may determine whether to initiate unpairing from the medical device based on device data that may be received by the second wireless transceiver from the first wireless transceiver of the medical device. For example, the medical device may include a frame and casters that may be coupled to the frame and the wall unit may initiate unpairing based on the device data indicating that brakes of the casters may be released. Alternatively or additionally, the wall unit may initiate unpairing based on the device data indicating that the power plug of the medical device may have been unplugged. Further alternatively or additionally, the wall unit may determine whether to initiate unpairing from the medical device in response to the AC plug sensor sensing that the power plug may have been unplugged from the AC outlet.

If desired, the AC plug sensor of the wall unit may include a photo emitter and a photo detector that may cooperate to detect presence of a plug body of the power cord or presence of at least one prong of the power plug of the medical device being inserted into the AC outlet of the wall unit. For example, the photo emitter may emit infrared (IR) light in a generally horizontal direction for detection by the photo detector and the plug body or the at least one prong may block the IR light from reaching the photo detector after the power plug is plugged into the AC outlet. Alternatively, the photo emitter may emit infrared (IR) light in a generally vertical direction for detection by the photo detector and the plug body or the at least one prong may block the IR light from reaching the photo detector after the power plug is plugged into the AC outlet.

In some embodiments of the fourth aspect, the AC plug sensor may include a mechanical switch that may move from a first state to a second state in response to the power plug of the medical device being plugged into the AC outlet of the wall unit. For example, the mechanical switch may include a plunger switch that may have a plunger that may be pressed inwardly by a plug body of the power plug when the power plug is plugged into the AC outlet. Alternatively or additionally, the AC plug sensor may include a current sensor to sense current flowing to at least one prong of the power plug after the power plug is plugged into the AC outlet of the wall unit.

The present disclosure further contemplates that the AC plug sensor of the wall unit may include a reader that may detect a tag that may be coupled to the power plug. If desired, the tag may carry a transponder that may be read by the reader. For example, the transponder may include a near field communication (NFC) transponder. If desired, the NFC transponder may be included in an NFC integrated circuit chip. Optionally, the reader may emit energy to power the transponder to enable the transponder to send a signal back to the reader.

In some embodiments of the fourth aspect, the medical device may be configured to transmit a device identification (ID) to the wall unit and the wall unit may be configured to transmit the device ID and a location ID to at least one server of the network of the healthcare facility. The location ID may be correlatable to a location at which the medical device may be located in the healthcare facility. If desired, the medical device may include a graphical display screen and the wall unit may be configured to transmit from the second wireless transceiver to the first wireless transceiver of the medical device a smart text string that may be displayed on the graphical display screen. The smart text string may include a name of the location at which the medical device is located and may be different than the location ID. In such embodiments, the medical device may not receive the location ID from the wall unit and may not retransmit the smart text string.

According to a fifth aspect of the present disclosure, a medical device may be configured for wireless communication with a wall unit in a healthcare facility and may include a frame that may be configured for transport within the healthcare facility, control circuitry that may be carried by the frame, and a wireless transceiver and a timer that may be carried by the frame and that may be coupled to the control circuitry. The medical device may have a power cord that may include a power plug that may be configured to plug into an AC outlet that may be carried by the wall unit. The medical also may have an AC plug sensor that may be carried by the frame and that may be configured to sense that the power plug of the medical device may be plugged into the AC outlet. The timer may be started to measure a first uptime in response to the power plug being plugged into the AC outlet of the wall unit. The wireless transceiver may be configured to receive at least one transmission from the wall unit that may include a second uptime. The control circuitry of the medical device may be configured to compare the first uptime with the second uptime and, if the first uptime is within a predetermined tolerance range of the second uptime, the control circuitry may command the wireless transceiver to send a pairing message to the wall unit which may result in the wall unit and medical device becoming automatically paired for subsequent wireless communications.

In some embodiments of the fifth aspect, the wireless transceiver may include a Bluetooth transceiver. If desired, the medical device further may include a set of switches that may be carried by the frame and that may be coupled to the control circuitry. The set of switches may be configured to provide contact closures that may be indicative of a plurality of states of the medical device. The control circuitry may be configured to command the Bluetooth transceiver to transmit Bluetooth messages that may include data pertaining to positions of the contact closures of the set of switches.

Optionally, at least one of the contact closures may be closed to control a television in a patient room. Alternatively or additionally, at least one of the contact closures may be closed to turn on a light in a patient room. Further alternatively or additionally, the medical device may include a patient bed and at least one of the contact closures may be closed to indicate an alarm state of a bed exit system of the patient bed. Still further alternatively or additionally, the medical device may include a patient bed and at least one of the contract closures may be closed to indicate that a siderail of the patient bed may have been moved to a lowered position. Yet further alternatively or additionally, the medical device may include a patient bed and at least one of the contact closures may be closed to indicate that brakes of casters of the patient bed may be in a released condition. Yet still further alternatively or additionally, the medical device may include a patient bed, the frame may include an upper frame, and at least one of the contact closures may be closed to indicate that the upper frame of the patient bed has been raised out of its lowest position. Alternatively or additionally, the medical device may include a patient bed and at least one of the contract closures may be closed to indicate that a nurse call button of the patient bed may have been pressed.

In some embodiments of the fifth aspect, the medical device may include a speaker and a microphone and the wireless transceiver may be configured for transmission and receipt of audio messages after the medical device and the wall unit are paired. The medical device of the fifth aspect further may include a graphical user interface (GUI) that may be carried by the frame and that may be coupled to the control circuitry. In such embodiments, the control circuitry may be configured to command the GUI to display information indicating a pairing state between the medical device and the wall unit.

Optionally, the medical device of the fifth aspect unpairs from the wall unit in response to an unpairing message received from the wall unit. For example, the unpairing message may be generated by the wall unit based on device data that may be included in a wireless communication from the medical device to the wall unit. In some embodiments of the fifth aspect, the medical device further may include casters that may be coupled to the frame and the wall unit may initiate unpairing based on the device data indicating that brakes of the casters may be released. Alternatively, the wall unit may initiate unpairing based on the device data indicating that the power plug of the medical device may have been unplugged. For example, the AC plug sensor of the medical device may sense that the power plug may have been unplugged from the AC outlet of the wall unit.

According to a sixth aspect of the present disclosure, a system for use in a healthcare facility having a network may include a medical device that may have a first wireless transceiver, a first timer, and a first sensor. The system also may have a communication unit. The first sensor may be operable to determine that the medical device may be hardwire connected to the communication unit via a cord. The communication unit may have a second wireless transceiver and a second timer. The communication unit may have a port with which the cord from the medical device may be coupleable. The communication unit may have a cord sensor to sense that the communication unit may be hardwire connected to the medical device via the port. The first timer may be started to measure a first hardwire connection time in response to the first sensor sensing that the medical device may be hardwire connected to the communication unit via the cord. The second timer may be started to measure a second hardwire connection time in response to the cord being plugged into the port. The medical device may be configured to transmit to the communication unit from the first wireless transceiver an advertisement that may include the first hardwire connection time. The communication unit may compare the first hardwire connection time with the second hardwire connection time and, if the first hardwire connection time is within a predetermined tolerance range of the second hardwire connection time, the communication unit may send a pairing message to the medical device which may result in the communication unit and the medical device becoming automatically paired for subsequent wireless communications.

In some embodiments of the sixth aspect, the medical device may include a speaker and a microphone and the first and second wireless transceivers may be configured for transmission and reception of audio messages after the medical device and the communication unit are paired. Optionally, the communication unit may include a light that may be illuminated to indicate a pairing state between the medical device and the communication unit.

If desired, the communication unit may determine whether to initiate unpairing from the medical device based on device data received by the second wireless transceiver from the first wireless transceiver of the medical device. For example, the medical device may include a frame and casters that may be coupled to the frame and at least one of the communication unit and medical device may initiate unpairing based on the device data indicating that brakes of the casters may be released. Alternatively or additionally, at least one of the communication unit and medical device may initiate unpairing based on the device data indicating that the cord of the medical device may have been disconnected.

In some embodiments of the sixth aspect, the cord sensor of the communication unit may include a photo emitter and a photo detector that may cooperate to detect presence of the cord. Alternatively, the cord sensor may include a mechanical switch that may move from a first state to a second state in response to the cord being plugged in. Further alternatively, the cord sensor may include a current sensor to sense current flowing in the cord. Still further alternatively, the cord sensor of the communication unit may include a reader that may detect a tag that may be coupled to the cord.

According to a seventh aspect of the present disclosure, a system for use in a healthcare facility having a network may include a medical device that may have a first wireless transceiver, a first timer, and a first sensor. The system also may include a communication unit. The first sensor may be operable to determine that the medical device may be hardwire connected to the communication unit via a cord. The communication unit may have a second wireless transceiver and a second timer. The communication unit may have a port with which the cord from the medical device may be coupleable. The communication unit may have a cord sensor to sense that the communication unit may be hardwire connected to the medical device via the port. The first timer may be started to measure a first hardwire connection time in response to the first sensor sensing that the medical device may be hardwire connected to the communication unit via the cord. The second timer may be started to measure a second hardwire connection time in response to the cord being plugged into the port. The communication unit may be configured to transmit to the medical device from the second wireless transceiver an advertisement that may include the second hardwire connection time. The medical device may compare the second hardwire connection time with the first hardwire connection time and, if the second hardwire connection time is within a predetermined tolerance range of the first hardwire connection time, the medical device may send a pairing message to the communication unit which may result in the communication unit and the medical device becoming automatically paired for subsequent wireless communications.

In some embodiments of the seventh aspect, the medical device may include a speaker and a microphone and the first and second wireless transceivers may be configured for transmission and reception of audio messages after the medical device and the communication unit are paired. Optionally, the communication unit may include a light that may be illuminated to indicate a pairing state between the medical device and the communication unit.

If desired, the communication unit may determine whether to initiate unpairing from the medical device based on device data received by the second wireless transceiver from the first wireless transceiver of the medical device. For example, the medical device may include a frame and casters that may be coupled to the frame and at least one of the communication unit and medical device may initiate unpairing based on the device data indicating that brakes of the casters may be released. Alternatively or additionally, at least one of the communication unit and medical device may initiate unpairing based on the device data indicating that the cord of the medical device may have been disconnected.

In some embodiments of the seventh aspect, the cord sensor of the communication unit may include a photo emitter and a photo detector that may cooperate to detect presence of the cord. Alternatively, the cord sensor may include a mechanical switch that may move from a first state to a second state in response to the cord being plugged in. Further alternatively, the cord sensor may include a current sensor to sense current flowing in the cord. Still further alternatively, the cord sensor of the communication unit may include a reader that may detect a tag that may be coupled to the cord.

According to an eighth aspect of the present disclosure, a system may include a first device that may have a first wireless transceiver and a first sensor. The system also may have a second device. The first sensor may be operable to determine that the first device may be hardwire connected to the second device via a hardwire connection. The second device may have a second wireless transceiver. In response to the hardwire connection being made between the first and second devices, the first and second devices may implement a dual-mode Bluetooth pairing operation in which wireless pairing may be accomplished by use of Bluetooth Low Energy (BLE) communications during a first mode of wireless pairing and by use of Basic Rate/Enhanced Data Rate (BR/EDR) communications during a second mode of wireless pairing.

In some embodiments of the eighth aspect, during the first mode of wireless pairing, at least one BLE advertisement may be transmitted from the first device to the second device. The at least one BLE advertisement may include manufacturer data that may identify a manufacturer of the first device. Optionally, the BLE advertisement further may include a first uptime that may indicate a first amount of time that may have elapsed subsequent to the hardwire connection being sensed by the first device. Further optionally, the second device may be configured to determine a second uptime that may indicate a second amount of time that may have elapsed subsequent to the hardwire connection being sensed by the second device.

If desired, the second device of the eighth aspect may be configured to compare the first uptime to the second uptime and to wirelessly pair the first and second devices based on a set of conditions including: (i) the first uptime is within a threshold amount of time of the second uptime; and (ii) the manufacturer data matches authorized device data stored in memory of the second device. The at least one BLE advertisement may include a media access control (MAC) address of the first device and, if the set of conditions (i) and (ii) are met, the second device may store the MAC address of the first device in memory, the second device may be configured to send a BR/EDR pairing message to the first device in the second mode of wireless pairing, and the BR/EDR pairing message may include the MAC address of the first device.

In some embodiments of the eighth aspect, the second device may be configured to wirelessly pair the first and second devices if the manufacturer data matches authorized device data stored in memory of the second device. Optionally, the at least one BLE advertisement may include a media access control (MAC) address of the first device and, if the manufacturer data matches the authorized device data, the second device may store the MAC address of the first device in memory, the second device may be configured to send a BR/EDR pairing message to the first device in the second mode of wireless pairing, and the BR/EDR pairing message may include the MAC address of the first device.

The present disclosure contemplates that the first device may include a patient bed and the second device may include a wall unit that may be mounted at a fixed location in a healthcare facility. In such embodiments of the eighth aspect, the hardwire connection may include a power cord of the patient bed that may be configured to plug into an AC outlet that may be carried by the wall unit. The system of the eighth aspect further may include a nurse call cord extending from the wall unit. The nurse call cord may terminate at a first nurse call connector that may be configured for connection to a nurse call port of a nurse call system.

Further according to the eighth aspect, the first device may include a wall unit that may be mounted at a fixed location in a healthcare facility and the second device may include a patient bed. In such embodiments, the hardwire connection may include a power cord of the patient bed that may be configured to plug into an AC outlet that may be carried by the wall unit. Furthermore, a nurse call cord may extend from the wall unit and the nurse call cord may terminate at a first nurse call connector that may be configured for connection to a nurse call port of a nurse call system.

According to a ninth aspect of the present disclosure, a system may include a first device that may have a first wireless transceiver and a first sensor. The system also may have a second device that may have a second wireless transceiver and a second sensor. The first sensor may be operable to sense that the first device may be hardwire connected to the second device via a hardwire connection. The second sensor may be operable to sense that the second device may be hardwire connected to the first device via the hardwire connection. In response to the hardwire connection being made between the first and second devices, the first and second devices may implement a time-based Bluetooth pairing operation in which a first uptime that may be calculated by the first device may be compared to a second uptime that may be calculated by the second device. The first uptime may be a first amount of time that may have elapsed since the first sensor sensed the hardwire connection to the second device. The second uptime may be a second amount of time that may have elapsed since the second sensor sensed the hardwire connection to the first device.

In some embodiments of the ninth aspect, the first device may include a patient bed and the second device may include a medical monitor. Optionally, the hardwire connection may include a Universal Serial Bus (USB) cord. Further optionally, the Bluetooth pairing operation may include the patient bed sending Bluetooth advertisements including the first uptime to the medical monitor and the medical monitor scanning for the Bluetooth advertisements.

If desired, the medical monitor of the ninth aspect may be configured to compare the first and second uptimes by subtracting the first and second uptimes to determine an uptime difference and comparing the uptime difference to a threshold. The medical monitor may send a pairing message to the patient bed to wirelessly pair the medical monitor and the patient bed if the uptime difference is less than the threshold. After the patient bed and medical monitor are paired, the medical monitor may send monitor data to the patient bed for display on a graphical user interface (GUI) of the patient bed.

In some embodiments of the ninth aspect, the Bluetooth pairing operation may include the medical monitor sending Bluetooth advertisements that may include the second uptime to the patient bed and the patient bed may scan for the Bluetooth advertisements. If desired, the patient bed may be configured to compare the first and second uptimes by subtracting the first and second uptimes to determine an uptime difference and comparing the uptime difference to a threshold. The patient bed may send a pairing message to the medical monitor to wirelessly pair the medical monitor and the patient bed if the uptime difference is less than the threshold. After the patient bed and medical monitor are paired, the medical monitor may send monitor data to the patient bed for display on a graphical user interface (GUI) of the patient bed.

The present disclosure further contemplates that the first device may include a mobile phone and the second device may include a speaker unit. Optionally, the hardwire connection may include a cord that may have a first connector at one end and a second connector at an opposite end. The first connector may be of a different type than the second connector. The Bluetooth pairing operation may include the mobile phone sending Bluetooth advertisements that may include the first uptime to the speaker unit and the speaker unit may scan for the Bluetooth advertisements. If desired, the speaker unit may be configured to compare the first and second uptimes by subtracting the first and second uptimes to determine an uptime difference and comparing the uptime difference to a threshold. The speaker unit may send a pairing message to the mobile phone to wirelessly pair the speaker unit and the mobile phone if the uptime difference is less than the threshold.

Alternatively or additionally, the Bluetooth pairing operation may include the speaker unit sending Bluetooth advertisements that may include the second uptime to the mobile phone and the mobile phone may scan for the Bluetooth advertisements. Optionally, the mobile phone may be configured to compare the first and second uptimes by subtracting the first and second uptimes to determine an uptime difference and comparing the uptime difference to a threshold. The mobile phone may send a pairing message to the speaker unit to wirelessly pair the speaker unit and the mobile phone if the uptime difference is less than the threshold.

In some embodiments of the ninth aspect, the Bluetooth pairing operation comprises the first device sending Bluetooth advertisements that may include the first uptime to the second device and the second device may scan for the Bluetooth advertisements. If desired, the second device may be configured to compare the first and second uptimes by subtracting the first and second uptimes to determine an uptime difference and comparing the uptime difference to a threshold. The second device sends a pairing message to the first device to wirelessly pair the first device and the second device if the uptime difference is less than the threshold.

According to a tenth aspect of the present disclosure, a system may include a first device that may have a first wireless transceiver, a first sensor, and a first hardwire port. The system also may include a second device that may have a second wireless transceiver, a second sensor, and a second hardwire port. The first sensor may be operable to sense that the first device may have a hardwire connected to the first hardwire port. The second sensor may be operable to sense that the second device may have the hardwire connected to the second hardwire port. In response to the hardwire connected to the first and second hardwire ports, respectively, the first and second devices may implement a time-based Bluetooth pairing operation in which a first connection time determined by the first device may be compared to a second connection time determined by the second device.

In some embodiments of the tenth aspect, the first connection time may be a first amount of time that has elapsed since the first sensor sensed the hardwire connection to the first port, and the second connection time may be a second amount of time that has elapsed since the second sensor sensed the hardwire connection to the second port. If desired, the Bluetooth pairing operation may include the first device sending Bluetooth advertisements that may include the first connection time to the second device and the second device may scan for the Bluetooth advertisements. Optionally, the second device may be configured to compare the first and second connection times by subtracting the first and second connection times to determine a connection time difference and comparing the connection time difference to a threshold. The second device may send a pairing message to the first device to wirelessly pair the first device and the second device if the connection time difference is less than the threshold.

It is contemplated by the present disclosure that the first device of the tenth aspect may include a patient bed and the second device of the tenth aspect may include a medical monitor. Optionally, the Bluetooth pairing operation may include the patient bed sending Bluetooth advertisements that may include the first connection time to the medical monitor and the medical monitor may scan for the Bluetooth advertisements. Alternatively or additionally, the medical monitor may be configured to compare the first and second connection times by subtracting the first and second connection times to determine a connection time difference and comparing the connection time difference to a threshold. The medical monitor may send a pairing message to the patient bed to wirelessly pair the medical monitor and the patient bed if the connection time difference is less than the threshold. If desired, after the patient bed and medical monitor are paired, the medical monitor may send monitor data to the patient bed for display on a graphical user interface (GUI) of the patient bed.

Optionally, the Bluetooth pairing operation may include the medical monitor sending Bluetooth advertisements that may include the second connection time to the patient bed and the patient bed may scan for the Bluetooth advertisements. Alternatively or additionally, the patient bed may be configured to compare the first and second connection times by subtracting the first and second connection times to determine a time difference and comparing the time difference to a threshold. The patient bed may send a pairing message to the medical monitor to wirelessly pair the medical monitor and the patient bed if the time difference is less than the threshold. If desired, after the patient bed and medical monitor are paired, the medical monitor may send monitor data to the patient bed for display on a graphical user interface (GUI) of the patient bed.

With regard to the tenth aspect, the first and second hardwire ports may include Universal Serial Bus (USB) ports. Alternatively or additionally, the hardwire may include a cord that may have a first connector at one end and a second connector at an opposite end. The first connector may be of a different type than the second connector.

It is further contemplated by the present disclosure that the first device of the tenth aspect may include a mobile phone and the second device may include a speaker unit. Optionally, the Bluetooth pairing operation may include the mobile phone sending Bluetooth advertisements that may include the first connection time to the speaker unit and the speaker unit may scan for the Bluetooth advertisements. Alternatively or additionally, the speaker unit may be configured to compare the first and second connection times by subtracting the first and second connection times to determine a connection time difference and comparing the connection time difference to a threshold. The speaker unit may send a pairing message to the mobile phone to wirelessly pair the speaker unit and the mobile phone if the connection time difference is less than the threshold.

If desired, the Bluetooth pairing operation may include the speaker unit sending Bluetooth advertisements that may include the second connection time to the mobile phone and the mobile phone may scan for the Bluetooth advertisements. Alternatively or additionally, the mobile phone may be configured to compare the first and second connection times by subtracting the first and second connection times to determine a connection time difference and comparing the connection time difference to a threshold. The mobile phone may send a pairing message to the speaker unit to wirelessly pair the speaker unit and the mobile phone if the connection time difference is less than the threshold.

According to an eleventh aspect of the present disclosure, a wall module may be configured for wireless communication with a medical device in a healthcare facility. The wall module may include a housing that may be configured to be mounted at a fixed location in a patient room of the healthcare facility. The housing may have a front wall shell that may be formed to include a first recess and a rear wall shell that may be formed to include a second recess that may be in alignment with the first recess of the front wall shell. The second recess may be sized to receive at least a portion of a duplex AC outlet therein. The front and rear wall shells each may include at least one opening therethrough for communication with the respective front and rear recesses so that an AC receptacle of the duplex AC outlet may be accessible through the front recess. The wall module further may include circuitry that may be situated within the housing. The circuitry may include a wireless transceiver. The wall module also may include first and second conductors that may extend from the circuitry and out of the housing for coupling to a hot bus and a neutral bus of the duplex AC outlet. The wall module still further may include an AC plug sensor that may be carried by the housing and that may be configured to sense a power plug of the medical device that may be plugged into the AC receptacle of the duplex AC outlet.

In some embodiments of the eleventh aspect, the front wall shell may include a front main wall and the rear wall shell may include a rear main wall. The first recess may be defined, in part, by a first recess wall that may be substantially parallel with the front main wall and that may be located about midway between the front main wall and the rear main wall. If desired, the second recess may be defined, in part, by a second recess wall that may be substantially parallel with the rear main surface and the second recess wall may be positioned against the first recess wall.

The present disclosure further contemplates that the front wall shell of the eleventh aspect may include a front main wall and the first recess may be defined, in part, by a first recess sidewall and a second recess sidewall that each may extend inwardly from the front main wall toward a middle region of the housing. Optionally, the AC plug sensor may include a photo emitter that may be aligned with a first aperture formed in the first recess sidewall and a photodetector that may be aligned with a second aperture formed in the second recess sidewall. In such embodiments, the photo emitter and photodetector may be positioned so that an optical beam that may be transmitted from the photo emitter to the photodetector may be broken in response to the power plug of the medical device being plugged into the AC receptacle of the duplex AC outlet.

If desired, the circuitry of the wall module of the eleventh aspect may include a timer that may be started to measure a first uptime in response to the power plug being plugged into the AC receptacle of the wall unit. The wireless transceiver of the wall module may be configured to receive at least one transmission from the medical device that may include a second uptime. The wall module of the eleventh aspect may compare the first uptime with the second uptime and, if the first uptime is within a predetermined tolerance range of the second uptime, the wall module may send a pairing message to the medical device which results in the wall module and the medical device becoming automatically paired for subsequent wireless communications.

In some embodiments of the eleventh aspect, the circuitry of the wall module may include a circuit board that may include a circuit board opening through which the first and second recess sidewalls may extend. In such embodiments, the photo emitter may be supported on a first portion of the circuit board adjacent the first recess sidewall and the photodetector may be supported on a second portion of the circuit board adjacent the second recess sidewall.

The present disclosure further contemplates that the wall module of the eleventh aspect further may include a nurse call cord that may extend from the circuitry and out of the housing. The nurse call cord may terminate at a first nurse call connector that may be configured for connection to a nurse call port of a nurse call system of the healthcare facility, for example. Optionally, the nurse call cord of the eleventh aspect may include an auxiliary cord branch that may terminate at a second nurse call connector. The second nurse call connector may be coupleable to a third nurse call connector that may be at an end of a device nurse call cord that may extend from the medical device. Alternatively or additionally, the first nurse call connector may be provided in a connector body of the nurse call cord. The connector body of the eleventh aspect may have a second nurse call connector that may be configured to couple to a third nurse call connector that may be at an end of a device nurse call cord extending from the medical device.

If desired, the housing of the wall module of the eleventh aspect may carry a first wireless fidelity (WiFi) transceiver that may be configured to send WiFi messages to, and receive WiFi messages from, at least one wireless access point of a network of the healthcare facility. Optionally, the wireless transceiver of the wall module may include a Bluetooth transceiver. Further optionally, the circuitry further may include a controller and a set of switches. The set of switches may be configured to provide contact closures that may be indicative of a plurality of states of the medical device based on data that may be contained in Bluetooth messages that may be received by the Bluetooth transceiver from the medical device.

In the embodiments of the wall module of the eleventh aspect that may have the set of switches providing contact closures, at least one of the contact closures may change states to control a television in the patient room. Alternatively or additionally, at least one of the contact closures may change states to turn on a light in the patient room. Further alternatively or additionally, the medical device may include a patient bed and at least one of the contact closures may change states to indicate an alarm state of a bed exit system of the patient bed. Still further alternatively or additionally, the medical device may include a patient bed and at least one of the contract closures may change states to indicate that a siderail of the patient bed has been moved to a lowered position.

With regard to the embodiments of the wall module of the eleventh aspect that may have the set of switches providing contact closures, the present disclosure further contemplates that the medical device may include a patient bed and at least one of the contact closures may change states to indicate that brakes of casters of the patient bed are in a released condition. Alternatively or additionally, the medical device may include a patient bed and at least one of the contact closures may change states to indicate that an upper frame of the patient bed has been raised out of its lowest position. Further alternatively or additionally, the medical device may include a patient bed and at least one of the second contact closures may change states to indicate that a nurse call button of the patient bed has been pressed.

In some embodiments of the eleventh aspect, the medical device may include a speaker and a microphone and the circuitry of the wall module may be configured for transmission and receipt of audio messages via the wireless transceiver after the medical device and the wall unit are paired. Optionally, the housing of the eleventh aspect may carry a light that may be illuminated to indicate a pairing state between the medical device and the wall module. For example, the light may illuminate an icon that may be located on the front wall shell next to the first recess.

The present disclosure also contemplates that the circuitry of the wall module of the eleventh aspect may be configured to participate in a time-based wireless pairing operation with the medical device. The time-based wireless pairing operation may occur in response to the AC plug sensor sensing the power plug of the medical device being plugged into the AC receptacle of the duplex AC outlet. Optionally, the circuitry of the wall module of the eleventh aspect may include a controller that may be configured to determine whether to initiate an unpairing from the medical device based on device data that may be received by the wireless transceiver from the medical device. For example, the medical device may include a frame and casters coupled to the frame and the controller may initiate the unpairing based on the device data indicating that brakes of the casters may be released. Alternatively or additionally, the controller may initiate the unpairing based on the device data indicating that the power plug of the medical device may have been unplugged. Alternatively or additionally, the wall unit may determine whether to initiate the unpairing from the medical device in response to the AC plug sensor of the wall module sensing that the power plug may have been unplugged from the AC receptacle.

According to a twelfth aspect of the present disclosure, a method of installing a wall module for wireless communication with a medical device in a healthcare facility may be provided. The method may include detaching an AC outlet of the healthcare facility from a gang box of the healthcare facility, attaching electrical conductors that may extend from a housing of the wall module to a hot bus and a neutral bus of the AC outlet, inserting the AC outlet into an outlet receiving recess that may be formed in a back of the wall module, and attaching the AC outlet to the wall module with at least one first fastener.

In some embodiments, the method of the twelfth aspect further may include attaching the wall module to the gang box with at least one second fastener. For example, attaching the wall module to the gang box may include inserting the at least one second fastener through an aperture that may be formed in a ground frame of the AC outlet. Optionally, the method of the twelfth aspect further may include placing at least one spacer in the outlet receiving recess adjacent to the ground frame of the AC outlet and inserting the at least one second fastener through a passage that may be formed in the at least one spacer. Further optionally, the at least one first fastener may include a first screw and the at least one second fastener may include a second screw that may be longer than the first screw.

If desired, the method of the twelfth aspect further may include attaching the wall module to the gang box with a pair of second fasteners. For example, attaching the wall module to the gang box may include inserting the pair of second fasteners through respective apertures that may be formed in a ground frame of the AC outlet. Optionally, the method of the twelfth aspect further may include placing first and second spacers in the outlet receiving recess adjacent to the ground frame of the AC outlet and inserting the pair of second fasteners through respective passages that may be formed in the first and second spacers. Further optionally, the at least one first fastener may include a first screw and the pair of second fasteners may include second screws that may be longer than the first screw. Still further optionally, the first fastener may be situated between the pair of second fasteners.

In some embodiments, the method of the twelfth aspect further may include attaching a nurse call connector that may be at an end of a nurse call cord that may extend from a housing of the wall module to a nurse call port of a nurse call system of the healthcare facility. If desired, the AC outlet of the twelfth aspect may include a duplex AC outlet that may have a first AC receptacle and a second AC receptacle. In such embodiments, after the AC outlet is attached to the wall module with the first fastener, the first fastener may be situated between the first and second AC receptacles. Alternatively or additionally, the method includes attaching the wall module of the twelfth aspect to the gang box with a pair of second fasteners such that one of the pair of second fasteners may be situated above the first AC receptacle and the other of the second fasteners may be situated below the second AC receptacle.

Optionally, attaching the wall module of the twelfth aspect to the gang box with the pair of second fasteners may include inserting the pair of second fasteners through first and second apertures, respectively, of a ground frame of the duplex AC outlet. Further optionally, attaching the electrical conductors that may extend from the housing of the wall module to the hot bus and the neutral bus of the AC outlet may include tightening screws to clamp the electrical conductors to the hot bus and the neutral bus.

According to a thirteenth aspect of the present disclosure, a system for use in a healthcare facility that may have a patient room may be provided. The system may include a patient bed that may have bed circuitry that may include a first wireless transceiver and an AC power cord. The system of the thirteenth aspect may also include a wall module that may include a housing that may be configured to be mounted at a fixed location in the patient room of the healthcare facility. The housing may carry an AC receptacle and may have a front wall that may be formed to include a first recess in which the AC receptacle may be accessible. The wall module of the thirteenth aspect further may include module circuitry that may be carried by the housing. The module circuitry may include a second wireless transceiver and an AC plug sensor that may form an optical beam in the recess in front of the AC receptacle. In response to the optical beam being interrupted by a plug of the AC power cord being plugged into the AC receptacle, the second wireless transceiver may communicate with the first wireless transceiver to implement a time-based wireless pairing operation between the wall module and the patient bed.

In some embodiments, the time-based wireless pairing operation of the thirteenth aspect may involve comparison of a first connection time that the patient bed may have received power via the AC power cord, as calculated by the bed circuitry, with a second connection time that the plug may have been plugged into the AC receptacle, as calculated by the module circuitry. Optionally, the time-based pairing operation of the thirteenth aspect may include a Bluetooth pairing operation in which the patient bed may send Bluetooth advertisements that may include the first connection time to the wall module and the wall module may scan for the Bluetooth advertisements. Further optionally, the wall module may be configured to compare the first and second connection times by subtracting the first and second connection times to determine a connection time difference and comparing the connection time difference to a threshold. Thereafter, the wall module may send a pairing message to the patient bed to wirelessly pair the wall module and the patient bed if the connection time difference is less than the threshold.

In other embodiments, the time-based pairing operation of the thirteenth aspect may include a Bluetooth pairing operation in which the wall module may send Bluetooth advertisements that may include the second connection time to the patient bed and the patient bed may scan for the Bluetooth advertisements. If desired, the patient bed may be configured to compare the first and second connection times by subtracting the first and second connection times to determine a connection time difference and comparing the connection time difference to a threshold. Thereafter, the patient bed may send a pairing message to the wall module to wirelessly pair the wall module and the patient bed if the connection time difference is less than the threshold.

The present disclosure contemplates that the first recess of the wall module of the thirteenth aspect may be defined between a first recess sidewall and a second recess sidewall. In such embodiments, the AC plug sensor may include a photo emitter that may be aligned with a first aperture that may be formed in the first recess sidewall and a photodetector that may be aligned with a second aperture that may be formed in the second recess sidewall. Optionally, the photo emitter and photodetector may be positioned so that the optical beam in front of the AC receptacle may be oriented substantially horizontally. Further optionally, the module circuitry may include a circuit board that may include a circuit board opening through which the first and second recess sidewalls may extend. The photo emitter may be supported on a first portion of the circuit board adjacent the first recess sidewall and the photodetector may be supported on a second portion of the circuit board adjacent the second recess sidewall.

In some embodiments, the system of the thirteenth aspect further may include a nurse call cord that may extend from the module circuitry and out of the housing of the wall module. The nurse call cord may terminate at a first nurse call connector that may be configured for connection to a nurse call port of a nurse call system of the healthcare facility. If desired, the nurse call cord may include an auxiliary cord branch that may terminate at a second nurse call connector. The second nurse call connector may be coupleable to a third nurse call connector that may be at an end of a bed nurse call cord that may extend from the patient bed of the thirteenth aspect. Alternatively or additionally, the first nurse call connector may be provided in a connector body of the nurse call cord. The connector body may have a second nurse call connector that may be configured to couple to a third nurse call connector at an end of a bed nurse call cord that may extending from the patient bed of the thirteenth aspect.

Optionally, the module circuitry of the wall module of the thirteenth aspect may include a first wireless fidelity (WiFi) transceiver that may be configured to send WiFi messages to, and receive WiFi messages from, at least one wireless access point of a network of the healthcare facility. Further optionally, the bed circuitry may include a second wireless fidelity (WiFi) transceiver that may be configured to send WiFi messages to, and receive WiFi messages from, the at least one wireless access point of the network of the healthcare facility. Still further optionally, the module circuitry of the thirteenth aspect further may include a controller and a set of switches. The set of switches may be configured to provide contact closures that may be indicative of a plurality of states of the patient bed based on data that may be contained in wireless messages that may be received by the second wireless transceiver from the patient bed.

In the embodiments of the system of the thirteenth aspect that may have the set of switches providing contact closures, at least one of the contact closures may change states to control a television in the patient room. Alternatively or additionally, at least one of the contact closures may change states to turn on a light in the patient room. Further alternatively or additionally, the medical device may include a patient bed and at least one of the contact closures may change states to indicate an alarm state of a bed exit system of the patient bed. Still further alternatively or additionally, the medical device may include a patient bed and at least one of the contract closures may change states to indicate that a siderail of the patient bed has been moved to a lowered position.

With regard to the embodiments of the system of the thirteenth aspect that may have the set of switches providing contact closures, the present disclosure further contemplates that at least one of the contact closures may change states to indicate that brakes of casters of the patient bed are in a released condition. Alternatively or additionally, the at least one of the contact closures may change states to indicate that an upper frame of the patient bed has been raised out of its lowest position. Further alternatively or additionally, the at least one of the contact closures may change states to indicate that a nurse call button of the patient bed has been pressed.

If desired, the patient bed of the thirteenth aspect may include a speaker and a microphone. In such embodiments, the bed circuitry and module circuitry each may be configured for transmission and receipt of audio messages via the respective first and second wireless transceivers after the patient bed and the wall module are paired. Optionally, the housing of the wall module of the thirteenth aspect may carry a light that may be illuminated to indicate a pairing state between the patient bed and the wall module. For example, the light may illuminate an icon located on the front wall of the housing next to the first recess.

In some embodiments of the thirteenth aspect, the module circuitry may include a controller that may be configured to determine whether to initiate unpairing from the patient bed based on device data that may be received by the second wireless transceiver from the first wireless transceiver of the patient bed. For example, the patient bed may include a frame and casters coupled to the frame and the controller of the module circuitry may initiate unpairing based on the device data indicating that brakes of the casters may be released. Alternatively or additionally, the controller of the module circuitry may initiate unpairing based on the device data indicating that the power plug of the patient bed may have been unplugged. Alternatively or additionally, the controller of the module circuitry initiates the unpairing from the patient bed in response to the AC plug sensor of the wall module sensing that the power plug may have been unplugged from the AC receptacle.

With regard to the system of the first and fourth aspects, the medical device may include an ambient light sensor, the wall unit may include at least one illuminable indicator, and a brightness of the at least one illuminable indicator of the wall unit may be controlled based on information that may be transmitted wirelessly from the medical device to the wall unit and that may pertain to ambient light that may be detected by the ambient light sensor. In embodiments of the first and fourth aspects in which the wall unit includes a light as the illuminable indicator, the medical device may include an ambient light sensor and a brightness of the light of the wall unit may be controlled based on information that may be transmitted wirelessly from the medical device to the wall unit and that may pertain to ambient light that may be detected by the ambient light sensor.

With regard to the second aspect, the wall unit further may include at least one illuminable indicator and a brightness of the at least one illuminable indicator may be controlled based on information that may be received wirelessly by the wireless transceiver from the medical device and that may pertain to ambient light that may be detected by an ambient light sensor of the medical device. In embodiments of the second aspect in which the wall unit includes a light as the illuminable indicator, a brightness of the light of the wall unit may be controlled based on information that may be received wirelessly by the wireless transceiver from the medical device and that may pertain to ambient light that may be detected by an ambient light sensor of the medical device.

With regard to the system of the third and sixth aspects, the medical device may include an ambient light sensor, the communication unit may include at least one illuminable indicator, and a brightness of the at least one illuminable indicator of the communication unit may be controlled based on information that may be transmitted wirelessly from the medical device to the communication unit and that may pertain to ambient light that may be detected by the ambient light sensor. In embodiments of the third and sixth aspects, as well as embodiments of the seventh aspect, in which the communication unit includes a light as the illuminable indicator, the medical device may include an ambient light sensor and a brightness of the light of the communication unit may be controlled based on information that may be transmitted wirelessly from the medical device to the communication unit and that may pertain to ambient light that may be detected by the ambient light sensor.

With regard to the sixth aspect, the medical device further may include an ambient light sensor that may be carried by the frame and that may be coupled to the control circuitry. The control circuitry may be configured to command the wireless transceiver to send information to the wall unit to control a brightness of an illuminable indicator of the wall unit.

With regard to the system of the eighth, ninth, and tenth aspects, the first device may include an ambient light sensor, the second device may include at least one illuminable indicator, and a brightness of the at least one illuminable indicator of the second device may be controlled based on information that may be transmitted wirelessly from the first device to the second device and that may pertain to ambient light that may be detected by the ambient light sensor.

With regard to the eleventh aspect, the wall module further may include at least one illuminable indicator and a brightness of the at least one illuminable indicator may be controlled based on information that may be received wirelessly by the wireless transceiver from the medical device and that may pertain to ambient light that may be detected by an ambient light sensor of the medical device. In embodiments of the eleventh aspect in which the wall module includes a light as the illuminable indicator, a brightness of the light of the wall module may be controlled based on information that may be received wirelessly by the wireless transceiver from the medical device and that may pertain to ambient light that may be detected by an ambient light sensor of the medical device.

With regard to the system of the thirteenth aspect, the patient bed may include an ambient light sensor, the wall module may include at least one illuminable indicator, and a brightness of the at least one illuminable indicator of the wall module may be controlled based on information that may be transmitted wirelessly from the patient bed to the wall module and that may pertain to ambient light that may be detected by the ambient light sensor. In embodiments of the thirteenth aspect in which the wall module includes a light as the illuminable indicator, the patient bed may include an ambient light sensor and a brightness of the light of the wall module may be controlled based on information that may be transmitted wirelessly from the patient bed to the wall module and that may pertain to ambient light that may be detected by the ambient light sensor.

According to a fourteenth aspect of the present disclosure, a system may include a patient bed that may have circuitry that may include at least one first controller, a first wireless transceiver that may be coupled to the at least one first controller, and an ambient light sensor that may be coupled to the at least one first controller. A wall unit of the system may be spaced from the patient bed and may include at least one second controller, a second wireless transceiver that may be coupled to the at least one second controller, and an illuminable indicator that may be coupled to the at least one second controller. The at least one first controller may be configured to transmit information via the first wireless transceiver to the second wireless transceiver. The information may pertain to an amount of ambient light that may be detected by the ambient light sensor. The at least one second controller may control a brightness of the illuminable indicator based on the information.

In some embodiments of the fourteenth aspect, the at least one second controller may be configured to operate the illuminable indicator to illuminate at a first brightness if the information indicates that the amount of light detected by the ambient light sensor may be below a threshold amount. The at least one second controller may be configured to operate the illuminable indicator to illuminate at a second brightness if the information indicates that the amount of light detected by the ambient light sensor may be above the threshold amount. The second brightness may be brighter than the first brightness. If desired, the illuminable indicator may include a light emitting diode (LED).

Optionally, the at least one second controller of the fourteenth aspect may output a first pulse width modulated (PWM) signal of a first duty cycle to the illuminable indicator to operate the illuminable indicator at the first brightness and the at least one second controller may output a second PWM signal of a second duty cycle to the illuminable indicator to operate the illuminable indicator at the second brightness.

In some embodiments of the fourteenth aspect, the patient bed may include a frame and a siderail that may be coupled to the frame. In such embodiments, the ambient light sensor may be coupled to the siderail. In other embodiments of the fourteenth aspect, the patient bed may include a frame, a first siderail that may be coupled to the frame, and a second siderail that may be coupled to the frame. In such other embodiments, the ambient light sensor may include a first ambient light sensor that may be coupled to the first siderail and a second ambient light sensor that may be coupled to the second siderail.

Optionally, the patient bed of the fourteenth aspect further may include at least one light and a brightness of the at least one light may controlled by the at least one first controller based on the amount of ambient light that may be detected by the ambient light sensor. Further optionally, the at least one light may be operated to illuminate at a first brightness if the amount of light detected by the ambient light sensor may be below a threshold amount and the at least one light may be operated to illuminate at a second brightness if the amount of light detected by the ambient light sensor may be above the threshold amount. The second brightness may be brighter than the first brightness, for example.

In some embodiments of the fourteenth aspect, the at least one first controller may output a first pulse width modulated (PWM) signal of a first duty cycle to the at least one light to operate the at least one light at the first brightness and the at least one first controller may output a second PWM signal of a second duty cycle to the at least one light to operate the at least one light at the second brightness.

If desired, the at least one light of the fourteenth aspect may include at least one light emitting diode (LED). Alternatively, the at least one light may include a plurality of lights and each light of the plurality of lights may include at least one light emitting diode (LED). Optionally, the patient bed further may include a graphical user interface (GUI) and a brightness of the GUI may be controlled by the at least one first controller based on the amount of ambient light that may be detected by the ambient light sensor. For example, the GUI may be operated to illuminate at a first brightness if the amount of light detected by the ambient light sensor is below a threshold amount and the GUI may be operated to illuminate at a second brightness if the amount of light detected by the ambient light sensor is above the threshold amount. If desired, the second brightness may be brighter than the first brightness.

In some embodiments of the fourteenth aspect, the patient bed may include an AC power cord, the wall unit may include a housing that may carry an AC receptacle and that may have a front wall that may be formed to include a first recess in which the AC receptacle is accessible. The wall unit further may include an AC plug sensor that may form an optical beam in the recess in front of the AC receptacle. In response to the optical beam being interrupted by a plug of the AC power cord being plugged into the AC receptacle, the second wireless transceiver may communicate with the first wireless transceiver to implement a time-based wireless pairing operation between the wall unit and the patient bed.

Optionally, the time-based wireless pairing operation of the fourteenth aspect may involve a comparison of a first connection time that the patient bed may have received power via the AC power cord, as calculated by the at least one first controller of the patient bed, with a second connection time that the plug may have been plugged into the AC receptacle, as calculated by the at least one second controller. Further optionally, the time-based pairing operation may include a Bluetooth pairing operation in which the patient bed may send Bluetooth advertisements that may include the first connection time to the wall unit and the wall unit may scan for the Bluetooth advertisements. Alternatively, the time-based pairing operation may include a Bluetooth pairing operation in which the wall unit may send Bluetooth advertisements that may include the second connection time to the patient bed and the patient bed may scan for the Bluetooth advertisements.

In some embodiments of the fourteenth aspect, the first recess may be defined between a first recess sidewall and a second recess sidewall and the AC plug sensor may include a photo emitter that may be aligned with a first aperture formed in the first recess sidewall and a photodetector that may be aligned with a second aperture formed in the second recess sidewall. If desired, the photo emitter and photodetector of the fourteenth aspect may be positioned so that the optical beam in front of the AC receptacle may be oriented substantially horizontally.

It is contemplated by the present disclosure that the system of the fourteenth aspect further may include a nurse call system and the wall unit further may include a nurse call cord communicatively coupled to the at least one second controller and extending out of the housing of the wall unit. The nurse call cord may terminate at a first nurse call connector that may be configured for connection to a nurse call port of the nurse call system.

Optionally, the nurse call cord of the fourteenth aspect may include an auxiliary cord branch that may terminate at a second nurse call connector. The second nurse call connector may be coupleable to a third nurse call connector that may be at an end of a bed nurse call cord that may extend from the patient bed. Further optionally, the first nurse call connector may be provided in a connector body of the nurse call cord. The connector body may have a second nurse call connector that may be configured to couple to a third nurse call connector that may be at an end of a bed nurse call cord that may extend from the patient bed.

In some embodiments of the fourteenth aspect, the at least one second controller may be configured to initiate an unpairing from the patient bed based on device data that may be received by the second wireless transceiver from the first wireless transceiver of the patient bed. For example, the patient bed of the fourteenth aspect may include a frame and casters coupled to the frame. The at least one second controller may initiate the unpairing based on the device data indicating that brakes of the casters may be released. Alternatively or additionally, the at least one second controller of the fourteenth aspect may be configured to initiate the unpairing based on the device data indicating that the power plug of the patient bed may have been unplugged or the at least one second controller may be configured to initiate the unpairing in response to the AC plug sensor of the wall unit sensing that the power plug may have been unplugged from the AC receptacle.

If desired, the wall unit may include a first wireless fidelity (WiFi) transceiver that may be configured to send WiFi messages to, and receive WiFi messages from, at least one wireless access point of a network of a healthcare facility. Further optionally, the patient bed of the fourteenth embodiment may include a second wireless fidelity (WiFi) transceiver that may be configured to send WiFi messages to, and receive WiFi messages from, the at least one wireless access point of the network of the healthcare facility.

In some embodiments, the system of the fourteenth aspect further may include a nurse call system and the wall unit further may include a set of switches. The set of switches may be configured to provide contact closures that indicate to the nurse call system a plurality of states of the patient bed based on data that may be contained in wireless messages that may be received by the second wireless transceiver from the patient bed. For example, at least one of the contact closures may change states to control a television in the patient room or to control a room light. By way of additional examples, at least one of the contact closures may change states to indicate one or more of the following: an alarm condition of a bed exit system of the patient bed, that a siderail of the patient bed may have been moved to a lowered position, that brakes of casters of the patient bed may be in a released condition, that an upper frame of the patient bed may have been raised out of its lowest position, or that a nurse call button of the patient bed may have been pressed.

The patient bed of the fourteenth aspect may include a speaker and a microphone. In such embodiments, the patient bed and the wall unit each may be configured for transmission and reception of audio messages via the respective first and second wireless transceivers.

According to a fifteenth aspect of the present disclosure, a system may include a wall module that may have a first controller, an analog audio input, an analog audio output, a first wireless transceiver that may be coupled to the controller and that may be configured to wirelessly transmit and wirelessly receive data, and a second wireless transceiver that may be coupled to the analog audio input and analog audio output. The second wireless transceiver may be configured to wirelessly transmit first audio signals that are received at the analog audio input and to wirelessly receive second audio signals that may be, in turn, communicated to the analog audio output. The system of the fifteenth aspect may also include a patient bed that may have a second controller, a microphone, a speaker, a third wireless transceiver that may be coupled to the controller and that may be configured to wirelessly receive data transmitted by the first transceiver and to wirelessly transmit data for receipt by the first transceiver, and a fourth wireless transceiver that may be configured to wirelessly receive the first audio signals that may be transmitted by the third wireless transceiver for playing through the speaker and to wirelessly transmit to the second wireless transceiver the second audio signals that may be received from the microphone. A first communication latency between the first and third wireless transceivers may be greater than 50 milliseconds and a second communication latency between the second and fourth wireless transceivers may be less than 50 milliseconds.

In some embodiments of the fifteenth aspect, the first and third wireless transceivers may communicate according to the Bluetooth protocol. Alternatively or additionally, the second and fourth wireless transceivers may communicate via frequency modulation (FM). That is, the second and fourth wireless transceivers may communicate via FM regardless of the type of wireless communication that takes place between the first and third wireless transceivers.

Optionally, the wall module of the fifteenth aspect may use the second wireless transceiver to scan FM spectrum channels to determine which FM channels may be currently in use by other devices and the wall module may select an available FM transmission channel and an available FM reception channel that may not be currently in use by the other devices. For example, the second wireless transceiver may scan the FM spectrum channels by scanning at even frequencies in 200 kilohertz (kHz) steps from a minimum frequency of 76.0 megahertz (MHz) to a maximum frequency of 108.0 MHz so as to avoid commercial FM radio frequencies that broadcast at odd frequencies in 200 kHz steps from a minimum commercial radio frequency of 76.1 MHz to a maximum commercial radio frequency 108.1 MHz.

In some embodiments of the fifteenth aspect, the wall module may transmit the available FM transmission channel and the available FM reception channel to the third transceiver of the patient bed using the first wireless transceiver. Optionally, the wall module may transmits the available FM transmission channel and the available FM reception channel to the third transceiver of the patient bed using the first wireless transceiver only after the wall module and patient bed may become paired via communications between the first and third wireless transceivers. Further optionally, the wall module and the patient bed may become paired via communications between the first and third wireless transceivers by implementing a time-based pairing operation.

The present disclosure contemplates that pairing between the wall module and the patient bed may include an exchange of unique identifiers between the first wireless transceiver of the wall module and the third wireless transceiver of the patient bed. If desired, the patient bed and the wall module of the fifteenth aspect may communicate using a side channel to verify that the respective unique identifier from the other of the patient bed and the wall module may be present to confirm the audio transmission received by the corresponding second wireless transceiver or fourth wireless transceiver originates from an expected source. Optionally, the patient bed may be configured to tune transmitter and receiver frequencies of the fourth wireless transceiver to match the available FM transmission channel and the available FM reception channel that may be received by the third wireless transceiver of the patient bed from the first wireless transceiver of the wall module.

The present disclosure contemplates that the wall module of the fifteenth aspect may comprise a first wall module and the system of the fifteenth aspect may further include at least one additional wall module that may be within reception range of the first wall module and the patient bed. In such embodiments, the at least one additional wall module may receive a transmission indicating the available FM transmission channel and the available FM reception channel and may save them in memory of the at least one additional wall module as FM channels that may be currently in use by other devices.

Optionally, the system of the fifteenth aspect further may include a cable that may be configured to form a wired connection between the wall module and the patient bed for communication of the first and second audio signals between the wall module and the patient bed, respectively. In such embodiments, the wall module may continue to use the second wireless transceiver to scan FM spectrum channels to determine which FM channels may be currently in use by other devices and the wall module may continue to select an available FM transmission channel and an available FM reception channel that are not currently in use by the other devices even when the wired connection may be formed between the wall module and the patient bed.

In some embodiments of the fifteenth aspect, the second communication latency may include a time it takes between receipt of the first audio signals at the analog audio input of the wall module and playing of the first audio signals by the speaker of the patient bed. Alternatively or additionally, the second communication latency may include a time it takes between receipt of the second audio signals at the microphone of the patient bed and outputting of the second audio signals at the analog audio output of the wall module.

If desired, the system of the fifteenth aspect further may include an audio station bed connector (ASBC) that may be coupled by a hardwire connection to the analog audio input of the wall module. The system of the fifteenth aspect also may include an audio source that may be in communication with the ASBC. Audio from the audio source may comprise the first audio signals that may be played by the speaker of the patient bed after being transmitted wirelessly from the second wireless transceiver of the wall module to the fourth wireless transceiver of the patient bed.

Optionally, the audio source of the fifteenth aspect may include a television. Alternatively or additionally, the audio source may include one or more of the following: a microphone of a master nurse station computer that may be located at a master nurse station or a microphone of an audio station that may be located in a patient room or a microphone of a staff station that may be located outside of the patient room. Further alternatively or additionally, the audio source may include a microphone of a mobile wireless device carried by a caregiver.

In some embodiments, the system of the fifteenth embodiment further may include a pillow speaker unit that may be coupled to the ASBC by a pillow speaker cable. The pillow speaker unit may have a pillow speaker that may play audio from the audio source substantially synchronously (e.g., within 50 milliseconds) with the first audio signals being played by the speaker of the patient bed.

According to a sixteenth aspect of the present disclosure, a system may include a wall module that may have a first controller, a first audio input that may provide a first audio signal to the first controller, and a first wireless transceiver that may be coupled to the controller and that may be configured to wirelessly transmit data and wirelessly receive data. The wirelessly received data may include audio packets that may be provided to the first controller as a second audio signal such that the first wireless transceiver may serve as a second audio input to the controller. The system of the sixteenth aspect further may include a first audio source that may be coupled to the first audio input of the wall module and that may provide the first audio signal to the first audio input. The system of the sixteenth aspect also may include a patient bed that may have a second controller, a microphone, a speaker, and a second wireless transceiver that may be coupled to the controller and that may be configured to wirelessly receive data transmitted by the first wireless transceiver and to wirelessly transmit data for receipt by the first wireless transceiver. The data transmitted by the second wireless transceiver may include audio packets that may correspond to audio detected by the microphone of the patient bed and transmitted to the first wireless transceiver to form the second audio signal. The wall module of the sixteenth aspect further may include a correlator to compare the first and second audio signals to determine a correlation parameter. If the correlation parameter has a value that violates a threshold condition, then the wall module may operate to mute the speaker of the bed.

In some embodiments of the sixteenth aspect, the correlator may be a software correlator that may be executed by the first controller. Alternatively or additionally, the correlator may operates to determine a correlation coefficient having an absolute value between 0 and 1. If desired, the system of the sixteenth aspect further may include a pillow speaker unit that may be coupled to the wall module via a hardwire connection. The pillow speaker unit may include a pillow speaker that may play sound originating from the first audio source. Prior to the speaker of the bed being muted, the speaker of the bed also may play sound originating from the first audio source and transmitted as wireless audio data from the first wireless transceiver to the second wireless transceiver such that communication latency between the first wireless transceiver and the second wireless transceiver may cause a delay between the first and second audio signals.

Optionally, the audio source of the sixteenth aspect may include a television. Alternatively or additionally, the audio source of the sixteenth aspect may include one or more of the following: a microphone of a master nurse station computer that may be located at a master nurse station or a microphone of an audio station that may be located in a patient room or a microphone of a staff station that may be located outside of the patient room. Further alternatively or additionally, the audio source of the sixteenth aspect may include a microphone of a mobile wireless device carried by a caregiver.

In some embodiments of the sixteenth aspect, the wall module may operate to mute the speaker of the bed by disabling transmissions of any audio packets from the first wireless transceiver to the second wireless transceiver. In other embodiments, the wall module of the sixteenth aspect may operate to mute the speaker of the bed by wirelessly transmitting a mute command signal from the first wireless transceiver to the second wireless transceiver such that the second controller may mute the speaker of the bed in response to the mute command signal.

Optionally, after the bed speaker is muted, the second wireless transceiver may continue to transmit to the first wireless transceiver audio packets corresponding to audio detected by the microphone of the patient bed such that the first wireless transceiver may continue to receive the second audio signal. In such embodiments, the wall module may operate to unmute the speaker of the bed if the correlation parameter is determined to no longer be violating the threshold condition. For example, the wall module may operate to unmute the speaker of the bed by re-enabling transmissions of audio packets from the first wireless transceiver to the second wireless transceiver. Alternatively, the wall module may operate to unmute the speaker of the bed by wirelessly transmitting an unmute command signal from the first wireless transceiver to the second wireless transceiver such that the second controller unmutes the speaker of the bed in response to the unmute command signal.

In some embodiments of the sixteenth aspect, the second wireless transceiver may transmit to the first wireless transceiver audio packets corresponding to audio detected by the microphone of the patient bed only after the wall module and patient bed may have become paired via communications between the first and second wireless transceivers. Optionally, the wall module and patient bed may become paired via communications between the first and second wireless transceivers by implementing a time-based pairing operation. Further optionally, pairing between the wall module and the patient bed may include an exchange of unique identifiers between the first wireless transceiver of the wall module and the second wireless transceiver of the patient bed.

In some embodiments of the system of the first and fourth aspects, the wall unit may include a first frequency modulation (FM) transceiver, the medical device may include a second FM transceiver, and audio signals may be communicated between the wall unit and the medical device using the first and second FM transceivers. Optionally, the first and second FM transceivers may be included in embodiments of the system of the first and fourth aspects in combination with the features mentioned above in paragraph 102.

In some embodiments of the wall unit of the second aspect, the wall unit further may include a frequency modulation (FM) transceiver to send audio signals to, and receive audio signals from, the medical device. Optionally, the FM transceiver may be included in embodiments of the wall unit in combination with the features mentioned above in paragraph 103.

In some embodiments of the system of the third, sixth, and seventh aspects, the communication unit may include a first frequency modulation (FM) transceiver, the medical device may include a second FM transceiver, and audio signals may be communicated between the communication unit and the medical device using the first and second FM transceivers. Optionally, the first and second FM transceivers may be included in embodiments of the system of the third, sixth, and seventh aspects in combination with the features mentioned above in paragraphs 104 and 105.

In some embodiments of the fifth aspect, the medical device further may include a frequency modulation (FM) transceiver to send audio signals to, and receive audio signals from, the wall unit. Optionally, the FM transceiver may be included in embodiments of the medical device having an ambient light sensor that generates a signal which is used to control brightness of a light on the wall unit.

In some embodiments of the system of any of the eighth, ninth, and aspects, the first device may include a first frequency modulation (FM) transceiver, the second device may include a second FM transceiver, and audio signals may be communicated between the first device and the second device using the first and second FM transceivers. Optionally, the first and second FM transceivers may be included in embodiments of the system of the eighth, ninth, and tenth aspects in combination with the features mentioned above in paragraph 106.

In some embodiments of the eleventh aspect, the wall module further may include a frequency modulation (FM) transceiver to send audio signals to, and receive audio signals from, the medical device. Optionally, the FM transceiver may be included in embodiments of the wall module in combination with the features mentioned above in paragraph 107.

In some embodiments of the system of the thirteenth aspect, the wall module may include a first frequency modulation (FM) transceiver, the patient bed may include a second FM transceiver, and audio signals may be communicated between the wall module and the patient bed using the first and second FM transceivers. Optionally, the first and second FM transceivers may be included in embodiments of the system of the thirteenth aspect in combination with the features mentioned above in paragraph 108.

In some embodiments of the system of the first and fourth aspects, the wall unit may include a correlator to compare a first audio signal received via a wired connection and a second audio signal received wirelessly to determine a correlation parameter. If the correlation parameter has a value that violates a threshold condition, then the wall unit may operate to mute a speaker of the medical device. Optionally, the correlator may be included in embodiments of the first and fourth aspects in combination with the features mentioned above in paragraph 102.

In some embodiments of the wall unit of the second aspect, the wall unit further may include a correlator to compare a first audio signal received via a wired connection and a second audio signal received wirelessly to determine a correlation parameter. If the correlation parameter has a value that violates a threshold condition, then the wall unit of the second aspect may operate to mute a speaker of the medical device. Optionally, the correlator may be included in embodiments of the second aspect in combination with the features mentioned above in paragraph 103.

In some embodiments of the system of the third, sixth, and seventh aspects, the communication unit may include a correlator to compare a first audio signal received via a wired connection and a second audio signal received wirelessly to determine a correlation parameter. If the correlation parameter has a value that violates a threshold condition, then the communication unit of the third, sixth, and seventh aspects, may operate to mute a speaker of the medical device. Optionally, the correlator may be included in embodiments of the first and fourth aspects in combination with the features mentioned above in paragraphs 104 and 105.

In some embodiments of the medical device of the fifth aspect, a speaker of the medical device may be muted if a correlation parameter that is calculated by a correlator of the wall unit by comparing a first audio signal received via a wired connection and a second audio signal received wirelessly has a value that violates a threshold condition. Optionally, the correlator may be included in embodiments of the medical device having an ambient light sensor that generates a signal which is used to control brightness of a light on the wall unit.

In some embodiments of the system of the eighth, ninth, and tenth aspects, the second device may include a correlator to compare a first audio signal received via a wired connection and a second audio signal received wirelessly to determine a correlation parameter. If the correlation parameter has a value that violates a threshold condition, then the second device of the eighth, ninth, and tenth aspects may operate to mute a speaker of the first device. Optionally, the correlator may be included in embodiments of the eighth, ninth, and tenth aspects in combination with the features mentioned above in paragraph 106.

In some embodiments of the eleventh aspect, the wall module further may include a correlator to compare a first audio signal received via a wired connection and a second audio signal received wirelessly to determine a correlation parameter. If the correlation parameter has a value that violates a threshold condition, then the wall module of the eleventh aspect may operate to mute a speaker of the medical device. Optionally, the correlator may be included in embodiments of the wall module of the eleventh aspect in combination with the features mentioned above in paragraph 107.

In some embodiments of the system of the thirteenth aspect, the wall module may include a correlator to compare a first audio signal received via a wired connection and a second audio signal received wirelessly to determine a correlation parameter. If the correlation parameter has a value that violates a threshold condition, then the wall module of the thirteenth aspect may operate to mute a speaker of the patient bed. Optionally, the correlator may be included in embodiments of the thirteenth aspect in combination with the features mentioned above in paragraph 108.

According to a seventeenth aspect of the present disclosure, a system may include a wall module that may have a first wireless transceiver and first circuitry that may be configured to receive an audio feed and a data feed. The system may include a patient bed that may have a second wireless transceiver, a speaker, and second circuitry that may be coupled to the speaker and the second wireless transceiver. The second wireless transceiver may be configurable for wireless communication with the first wireless transceiver. The system of the seventeenth aspect may further include a mobile device that may be configured to link temporarily with the first wireless transceiver for wireless communication for configuration of the circuitry of the wall module. The mobile device may be configured to receive a first user input to command the circuitry of the wall module to mute the speaker of the patient bed. In response to receipt of the first user input to mute the speaker of the patient bed, the circuitry of the wall module may communicate with the second wireless transceiver via the first wireless transceiver in a first manner that may prevent the audio feed from being audibly played through the speaker of the patient bed.

In some embodiments of the seventeenth aspect, in response to receipt of the first user input to mute the speaker of the patient bed, the first circuitry may command the first wireless transceiver to transmit audio packets that may correspond to silence. For example, the audio packets that correspond to silence may comprise all zeroes. Optionally, the mobile device may be configured to receive a second user input to unmute the speaker of the patient bed. In response to receipt of the second user input to unmute the speaker of the patient bed, the first circuitry of the wall module may communicate with the second wireless transceiver via the first wireless transceiver in a second manner that may allow the audio feed to be audibly played through the speaker of the patient bed.

Optionally, the mobile device may be configured to display a mute/unmute slider. Thus, the first user input may correspond to the mute/unmute slider being in a first position and the second user input may correspond to the mute/unmute slider being in a second position. If desired, the mobile device may be configured to receive a firmware installation input from a user to upload firmware to the circuitry of the wall module via the first transceiver.

The patient bed of the seventeenth aspect may include a graphical user interface (GUI) that may be configured to receive inputs from a user to control functions of the patient bed. The GUI may be configured to receive a third user input which may result in a mute command being transmitted from the second wireless transceiver of the patient bed to the first wireless transceiver of the wall module to command the circuitry of the wall module to operate in the first manner to mute the speaker of the patient bed. The GUI may be configured to receive a fourth user input which may result in an unmute command being transmitted from the second wireless transceiver of the patient bed to the first wireless transceiver of the wall module to command the circuitry of the wall module to operate in a second manner that allows the audio feed to be audibly played through the speaker of the patient bed.

Further according to the seventeenth aspect, the first circuitry of the wall module and the second circuitry of the patient bed may implement a time-based pairing operation to pair the patient bed with the wall module. If desired, the time-based pairing operation may be initiated by plugging a power plug of the patient bed in to a power receptacle of the wall module.

In some embodiments of the seventeenth aspect, plugging in the power cord to the power receptacle may result in a first timer of the patient bed being started to measure a first uptime. Additionally, plugging in the power cord to the power receptacle may result in a second timer of the wall module being started to measure a second uptime. The wall module may be configured to transmit to the patient bed from the first wireless transceiver an advertisement that may include the second uptime. The patient bed may compare the second uptime with the first uptime and, if the second uptime is within a predetermined tolerance range of the first uptime, the patient bed may send a pairing message to the wall module which may result in the wall module and the patient bed becoming automatically paired for subsequent wireless communications.

In other embodiments of the seventeenth aspect, plugging in the power cord to the power receptacle may result in a first timer of the patient bed being started to measure a first uptime. Additionally, plugging in the power cord to the power receptacle may result in a second timer of the wall module being started to measure a second uptime. The patient bed may be configured to transmit to the wall module from the second wireless transceiver a message that may include the first uptime. The wall module may compare the first uptime with the second uptime and, if the first uptime is within a predetermined tolerance range of the second uptime, the wall module may send a pairing message to the patient bed which may result in the wall module and the patient bed becoming automatically paired for subsequent wireless communications.

Optionally, a nurse call cord may extend from the wall module and the nurse call cord may terminate at a first nurse call connector that may be configured for connection to a nurse call port of a nurse call system. If desired, the nurse call cord may include an auxiliary cord branch that may terminate at a second nurse call connector. The second nurse call connector may be coupleable to a third nurse call connector that may be at an end of a bed nurse call cord that may extend from the patient bed. Optionally, the patient bed may include a first WiFi transceiver and the wall module may include a second WiFi transceiver. The first and second WiFi transceivers each may be configured to send WiFi messages to, and receive WiFi messages from, at least one wireless access point of a network.

According to an eighteenth aspect of the present disclosure, a system may include a wall module that may have a first wireless transceiver and first circuitry that may be configured to receive an audio feed and a data feed. The system of the eighteenth aspect may also include a patient bed that may have a second wireless transceiver, a speaker, and second circuitry that may be coupled to the speaker and the second wireless transceiver. The second wireless transceiver may be configurable for wireless communication with the first wireless transceiver. The patient bed may include a graphical user interface (GUI) that may be configured to receive inputs from a user to control functions of the patient bed. The GUI may be configured to receive a first user input which may result in a mute command being transmitted from the second wireless transceiver of the patient bed to the first wireless transceiver of the wall module to command the first circuitry of the wall module to mute the speaker of the patient bed. In response to receipt of the mute command to mute the speaker of the patient bed, the first circuitry of the wall module may communicate with the second wireless transceiver via the first wireless transceiver in a first manner that may prevent the audio feed from being audibly played through the speaker of the patient bed.

In some embodiments of the eighteenth aspect, in response to receipt of the mute command to mute the speaker of the patient bed, the first circuitry may command the first wireless transceiver to transmit audio packets that may correspond to silence. For example, the audio packets that correspond to silence may comprise all zeroes. Optionally, the GUI may be configured to receive a second user input to unmute the speaker of the patient bed. Receipt of the second user input may result in an unmute command being transmitted from the second wireless transceiver of the patient bed to the first wireless transceiver of the wall module to command the first circuitry of the wall module to communicate with the second wireless transceiver via the first wireless transceiver in a second manner that may allow the audio feed to be audibly played through the speaker of the patient bed.

Optionally, the GUI of the eighteenth aspect may be configured to display an On button and an Off button. The On button may be selectable to cause the wall module to unmute the speaker of the patient bed and the Off button may be selectable to cause the wall module to mute the speaker of the patient bed. If desired, the system of the eighteenth aspect further may include a mobile device that may be configured to link temporarily with the first wireless transceiver for wireless communication for configuration of the circuitry of the wall module. The mobile device may be configured to receive a third user input to command the first circuitry of the wall module to mute the speaker of the patient bed. Optionally, the mobile device may be configured to receive a firmware installation input from a user to upload firmware to the first circuitry of the wall module via the first transceiver. Further optionally, the first circuitry of the wall module and the second circuitry of the patient bed may implement a time-based pairing operation to pair the patient bed with the wall module. The time-based pairing operation may be initiated by plugging a power plug of the patient bed in to a power receptacle of the wall module.

In some embodiments of the eighteenth aspect, plugging in the power cord to the power receptacle may result in a first timer of the patient bed being started to measure a first uptime. Additionally, plugging in the power cord to the power receptacle may result in a second timer of the wall module being started to measure a second uptime. The wall module may be configured to transmit to the patient bed from the first wireless transceiver an advertisement that may include the second uptime. The patient bed may compare the second uptime with the first uptime and, if the second uptime is within a predetermined tolerance range of the first uptime, the patient bed may send a pairing message to the wall module which may result in the wall module and the patient bed becoming automatically paired for subsequent wireless communications.

In other embodiments of the eighteenth aspect, plugging in the power cord to the power receptacle may result in a first timer of the patient bed being started to measure a first uptime. Additionally, plugging in the power cord to the power receptacle may result in a second timer of the wall module being started to measure a second uptime. The patient bed may be configured to transmit to the wall module from the second wireless transceiver a message that may include the first uptime. The wall module may compare the first uptime with the second uptime and, if the first uptime is within a predetermined tolerance range of the second uptime, the wall module may send a pairing message to the patient bed which may result in the wall module and the patient bed becoming automatically paired for subsequent wireless communications.

Optionally, a nurse call cord may extend from the wall module. The nurse call cord may terminate at a first nurse call connector that may be configured for connection to a nurse call port of a nurse call system. If desired, the nurse call cord may include an auxiliary cord branch that may terminate at a second nurse call connector. The second nurse call connector may be coupleable to a third nurse call connector at an end of a bed nurse call cord that may extending from the patient bed. Optionally, the patient bed may include a first WiFi transceiver and the wall module may include a second WiFi transceiver. The first and second WiFi transceivers each may be configured to send WiFi messages to, and receive WiFi messages from, at least one wireless access point of a network.

According to a nineteenth aspect of the present disclosure, a system for wireless pairing may include a connecting device that may have first device circuitry that may include a first wireless transceiver. The system may also include an advertising device that may have second device circuitry that may include a second wireless transceiver. The second device circuitry may be configured to broadcast advertisements via the second wireless circuitry to initiate a pairing operation with other devices. The connecting device may be configured to receive at least one of the advertisements via the first wireless transceiver. The first device circuitry may be configured to transmit via the first wireless transceiver a connect message in response to receipt of the at least one of the advertisements. In response to receipt of the connect message by the advertising device, the advertising device may transmit an authorization challenge. The connecting device may be configured to receive and process the authorization challenge and may transmit an authorization response message to the advertising device. The advertising device may pair with the connecting device automatically for subsequent wireless communications if the authorization response message indicates that the connecting device is an authorized device.

In some embodiments of the nineteenth aspect, the authorization challenge transmitted by the advertising device may include randomized salt. Optionally, the connecting device may perform a hashing operation on the randomized salt to create the authorization response message. Further optionally, the advertising device also may perform the hashing operation on the randomized salt to generate a hashed randomized salt. Accordingly, the advertising device may determine that the connecting device is the authorized device by comparing the authorization response message with the hashed randomized salt to determine if there is a match. The present disclosure further contemplates that the connecting device and the advertising device also may implement a time-based pairing operation to determine whether to pair. For example, the time-based pairing operation may be initiated by plugging a power plug of the connecting device in to a power receptacle of the advertising device.

In some embodiments of the nineteenth aspect, plugging in the power cord to the power receptacle may result in a first timer of the connecting device being started to measure a first uptime. Additionally, plugging in the power cord to the power receptacle may result in a second timer of the advertising device being started to measure a second uptime. The advertisements transmitted by the advertising device may include the second uptime. The connecting device may compare the second uptime with the first uptime and, if the second uptime is within a predetermined tolerance range of the first uptime, the connecting device may send a pairing message to the advertising device which may result in the advertising device and the connecting device becoming automatically paired for subsequent wireless communications on the condition that the authorization response message also indicates that the connecting device is the authorized device.

In other embodiments of the nineteenth aspect, plugging in the power cord to the power receptacle may result in a first timer of the connecting device being started to measure a first uptime. Additionally, plugging in the power cord to the power receptacle may result in a second timer of the advertising device being started to measure a second uptime. The connecting device may be configured to transmit to the advertising device a message including the first uptime. The advertising device may compare the first uptime with the second uptime and, if the first uptime is within a predetermined tolerance range of the second uptime, the advertising device may send a pairing message to the connecting device which may result in the advertising device and the connecting device becoming automatically paired for subsequent wireless communications on the condition that the authorization response message also indicates that the connecting device is the authorized device. Regardless of the time-based pairing operation used, the advertising device may ignore transmissions from any of the other device that do not successfully respond to the authorization challenge.

Optionally, the connecting device of the nineteenth aspect may include a patient bed and the advertising device may include a wall module that may be mounted at a fixed location in a patient room. Further optionally, the wall module may be connected to at least one nurse call computer and may be configured to transmit messages received from the patient bed wirelessly to the nurse call computer.

According to a twentieth aspect of the present disclosure, a wireless adapter is provided for use with a patient bed that may have a power port and a nurse call connector port, and for use with a wall module that may have wireless communication capability. The wireless adapter may include a housing that may be configured for mounting to the patient bed, circuitry that may be configured for wireless communication with the wall module, a first power cord that may extend from the housing and that may be configured to couple to the power port of the patient bed, a nurse call cable that may extend from the housing and that may be configured to couple to the nurse call connector port of the patient bed, and a second power cord that may extend from the housing and that may be configured to couple to an alternating current (AC) receptacle that may be carried by the wall module. Power may be provided to the patient bed from the AC receptacle via the first and second power cords.

In some embodiments of the twentieth aspect, the circuitry may be configured to implement a time-based pairing operation with the wall module to pair for subsequent wireless communications. For example, the time-based pairing operation may be initiated in response to plugging a power plug of the second power cord in to the AC receptacle. Optionally, the circuitry of the wireless adapter includes a current sensor that may sense whether the second power cord may be receiving AC power.

In some embodiments of the twentieth aspect, plugging in the second power cord to the AC receptacle may result in a first timer of the circuitry of the wireless adapter being started to measure a first uptime. Additionally, plugging in the second power cord to the AC receptacle may result in a second timer of the wall module being started to measure a second uptime. The wall module may be configured to transmit to the wireless adapter an advertisement that may include the second uptime. The wireless adapter may compare the second uptime with the first uptime and, if the second uptime is within a predetermined tolerance range of the first uptime, the wireless adapter may send a pairing message to the wall module which may result in the wall module and the wireless adapter becoming automatically paired for subsequent wireless communications.

In other embodiments of the twentieth aspect, plugging in the power cord to the AC receptacle may result in a first timer of the circuitry of the wireless adapter being started to measure a first uptime. Additionally, plugging in the power cord to the AC receptacle may result in a second timer of the wall module being started to measure a second uptime. The wireless adapter may be configured to transmit to the wall module a message that may include the first uptime. The wall module may compare the first uptime with the second uptime and, if the first uptime is within a predetermined tolerance range of the second uptime, the wall module may send a pairing message to the wireless adapter which may result in the wall module and the patient bed becoming automatically paired for subsequent wireless communications.

Optionally, the circuitry of the wireless adapter comprises a controller and an AC/DC converter that may be coupled to the second power cord and that may be coupled to the controller. The AC/DC converter may be configured to convert AC power into DC power which may be used to power the controller. Further optionally, the circuitry may include a wall module AC connector that may be accessible on an exterior of the housing and that may be configured to couple to a power connector that may be at an end of the second power cord. If desired, AC power received by the wall module AC connector from the second power cord may be fed to the first power cord.

In some embodiments of the twentieth aspect, the circuitry of the wireless adapter may include a controller and at least one shift register or relay may be coupled to the controller. The nurse call cord may include one or more conductors that may couple to the at least one shift register or relay. Alternatively or additionally, the circuitry of the wireless adapter may include a controller and at least one audio coder/decoder (codec) that may be coupled to the controller. The nurse call cord may include one or more conductors that may couple to the audio codec. Further alternatively or additionally, the circuitry of the wireless adapter may include a controller and the nurse call cord may include at least one serial peripheral interface (SPI) conductor that may couples to the controller to communicate bed data that may be received via the nurse call cord to the controller for wireless transmission to the wall module.

According to a twenty-first aspect of the present disclosure, a system may include a patient bed that may have a power port and a nurse call connector port, a wall module that may have wireless communication capability and having an alternating current (AC) receptacle, and a wireless adapter that may be configured to provide wireless communication capability to the patient bed. The wireless adapter may include a housing that may be configured for mounting to the patient bed, circuitry that may be situated in the housing and that may be configured for wireless communication with the wall module, a first power cord that may extend from the housing and that may be configured to couple to the power port of the patient bed, a nurse call cable that may extend from the housing and that may be configured to couple to the nurse call connector port of the patient bed, and a second power cord that may extend from the housing and that may be configured to couple to the AC receptacle of the wall module. Power may be provided to the patient bed from the AC receptacle via the first and second power cords.

In some embodiments of the twenty-first aspect, the circuitry may be configured to implement a time-based pairing operation with the wall module to pair for subsequent wireless communications. For example, the time-based pairing operation may be initiated in response to plugging a power plug of the second power cord in to the AC receptacle. If desired, the circuitry of the wireless adapter may include a current sensor that senses whether the second power cord is receiving AC power.

In some embodiments of the twenty-first aspect, plugging in the second power cord to the AC receptacle may result in a first timer of the circuitry of the wireless adapter being started to measure a first uptime. Additionally, plugging in the second power cord to the AC receptacle may result in a second timer of the wall module being started to measure a second uptime. The wall module may be configured to transmit to the wireless adapter an advertisement that may include the second uptime. The wireless adapter may compare the second uptime with the first uptime and, if the second uptime is within a predetermined tolerance range of the first uptime, the wireless adapter may send a pairing message to the wall module which may result in the wall module and the wireless adapter becoming automatically paired for subsequent wireless communications.

In other embodiments of the twenty-first aspect, plugging in the power cord to the AC receptacle may result in a first timer of the circuitry of the wireless adapter being started to measure a first uptime. Additionally, plugging in the power cord to the AC receptacle may result in a second timer of the wall module being started to measure a second uptime. The wireless adapter may be configured to transmit to the wall module a message that may include the first uptime. The wall module may compare the first uptime with the second uptime and, if the first uptime is within a predetermined tolerance range of the second uptime, the wall module may send a pairing message to the wireless adapter which may result in the wall module and the patient bed becoming automatically paired for subsequent wireless communications.

Optionally, the circuitry of the wireless adapter of the twenty-first aspect may include a controller and an AC/DC converter that may be coupled to the second power cord and that may be coupled to the controller. The AC/DC converter may be configured to convert AC power into DC power which may be used to power the controller. Alternatively or additionally, the circuitry of the wireless adapter may include a wall module AC connector that may be accessible on an exterior of the housing and that may be configured to couple to a power connector that may be at an end of the second power cord. If desired, AC power received by the wall module AC connector from the second power cord may be fed to the first power cord.

The present disclosure further contemplates that the circuitry of the wireless adapter of the twenty-first aspect may include a controller and at least one shift register or relay that may be coupled to the controller. The nurse call cord may include one or more conductors that may couple to the at least one shift register or relay. Alternatively or additionally, the circuitry may include a controller and at least one audio coder/decoder (codec) that may be coupled to the controller. The nurse call cord may include one or more conductors that may couple to the audio codec. Further alternatively or additionally, the circuitry may include a controller and the nurse call cord may include at least one serial peripheral interface (SPI) conductor that may couple to the controller to communicate bed data received via the nurse call cord to the controller for wireless transmission to the wall module.

According to a twenty-second aspect of the present disclosure, a method of adding wireless communication capability to a patient bed that lacks wireless communication capability is provided. The method may include attaching a housing of a wireless adapter to the patient bed, plugging in a first power cord that may extend from the housing in to a power port of the patient bed, plugging in a nurse call cable that may extend from the housing in to a nurse call connector port of the patient bed, and plugging in a second power cord that may extend from the housing in to an alternating current (AC) receptacle that may be carried by a wall module so that power may be provided to the patient bed from the AC receptacle via the first and second power cords.

In some embodiments, the method further may include implementing with circuitry of the wireless adapter a time-based pairing operation with the wall module to pair for subsequent wireless communications. For example, the time-based pairing operation may be initiated in response to plugging a power plug of the second power cord in to the AC receptacle. If desired, the circuitry of the wireless adapter may include a current sensor that may sense whether the second power cord may be receiving AC power.

In some embodiments, the method of the twenty-second aspect further may include starting a first timer of the circuitry of the wireless adapter to measure a first uptime in response to plugging in the second power cord to the AC receptacle, starting a second timer of the wall module to measure a second uptime in response to plugging in the second power cord to the AC receptacle, transmitting from the wall module to the wireless adapter an advertisement that may include the second uptime, comparing with the circuitry of the wireless adapter the second uptime with the first uptime and, if the second uptime is within a predetermined tolerance range of the first uptime, sending from the wireless adapter a pairing message to the wall module which may result in the wall module and the wireless adapter becoming automatically paired for subsequent wireless communications.

In other embodiments, the method of the twenty-second aspect further may include starting a first timer of the circuitry of the wireless adapter to measure a first uptime in response to plugging in the second power cord to the AC receptacle, starting a second timer of the wall module to measure a second uptime in response to plugging in the second power cord to the AC receptacle, transmitting from the wireless adapter to the wall module a message that may include the first uptime, comparing with the wall module the first uptime with the second uptime and, if the first uptime is within a predetermined tolerance range of the second uptime, sending a pairing message from the wall module to the wireless adapter which may result in the wall module and the wireless adapter becoming automatically paired for subsequent wireless communications.

Optionally, the circuitry of the wireless adapter of the twenty-second aspect may include a controller and an AC/DC converter that may be coupled to the second power cord and that may be coupled to the controller. In such embodiments, the method further may include converting with the AC/DC converter AC power into DC power which is used to power the controller. Alternatively or additionally, the method further may include plugging in a power connector at an end of the second power cord to a wall module AC connector that is accessible on an exterior of the housing. Further alternatively or additionally, the method further may include feeding AC power received by the wall module AC connector from the second power cord to the first power cord.

The present disclosure further contemplates that the circuitry of the wireless adapter further includes a controller and at least one shift register or relay that may be coupled to the controller. In such embodiments, the method further may include coupling signals received on one or more conductors of the nurse call cord to the at least one shift register or relay. Alternatively, the circuitry of the wireless adapter may include a controller and at least one audio coder/decoder (codec) that may be coupled to the controller. In such embodiments, the method further may include coupling signals received on one or more conductors of the nurse call cord to the audio codec. Further alternatively or additionally, the circuitry of the wireless adapter may include a controller and the nurse call cord may include at least one serial peripheral interface (SPI) conductor. In such embodiments, the method further may include communicating bed data via the at least one SPI conductor to the controller and transmitting the bed data wirelessly to the wall module.

According to a twenty-third aspect of the present disclosure, a system may include a first medical device that may have a first wireless transceiver, a first sensor, and an alternating current (AC) receptacle. The system of the twenty-third aspect also may include a second device that may have a second wireless transceiver, a second sensor, and a power cord that may terminate at a power plug. The first and second sensors each may be operable to sense that the power plug of the power cord of the second medical device may be plugged into the AC receptacle of the first medical device. In response to the power plug of the second medical device being plugged into the AC receptacle of the first medical device, the first and second medical devices may implement a time-based wireless pairing operation in which a first uptime that may be calculated by the first medical device may be compared to a second uptime that may be calculated by the second medical device. The first uptime may be a first amount of time that may have elapsed since the first sensor may have sensed the power plug being plugged into the AC receptacle. The second uptime may be a second amount of time that may have elapsed since the second sensor may have sensed the power plug being plugged into the AC receptacle.

In some embodiments of the twenty-third aspect, the first device may include a patient bed and the second device may include a medical monitor. In such embodiments, the patient bed may include a frame and the AC receptacle may be mounted to the frame. Optionally, the wireless pairing operation may include the patient bed sending advertisements that may include the first uptime to the medical monitor and the medical monitor may scan for the advertisements. If desired, the medical monitor may be configured to compare the first and second uptimes by subtracting the first and second uptimes to determine an uptime difference and the medical monitor may compare the uptime difference to a threshold. The medical monitor may send a pairing message to the patient bed to wirelessly pair the medical monitor and the patient bed if the uptime difference is less than the threshold. Further optionally, after the patient bed and medical monitor are paired in this manner, the medical monitor may send monitor data to the patient bed for display on a graphical user interface (GUI) of the patient bed.

The present disclosure further contemplates that the wireless pairing operation may include the medical monitor sending advertisements that may include the second uptime to the patient bed and the patient bed may scan for the advertisements. If desired, the patient bed may be configured to compare the first and second uptimes by subtracting the first and second uptimes to determine an uptime difference and the patient bed may compare the uptime difference to a threshold. The patient bed may send a pairing message to the medical monitor to wirelessly pair the medical monitor and the patient bed if the uptime difference is less than the threshold. Further optionally, after the patient bed and medical monitor are paired in this alternative manner, the medical monitor may send monitor data to the patient bed for display on a graphical user interface (GUI) of the patient bed.

In general, the wireless pairing operation of the twenty-third aspect may include the first medical device sending advertisements that may include the first uptime to the second medical device and the second medical device may scan for the advertisements. If desired, the second medical device may be configured to compare the first and second uptimes by subtracting the first and second uptimes to determine an uptime difference and the second medical device may compare the uptime difference to a threshold. In such embodiments, the second medical device may send a pairing message to the first medical device to wirelessly pair the first medical device and the second medical device if the uptime difference is less than the threshold.

Alternatively, the wireless pairing operation of the twenty-third aspect may include the second medical device sending advertisements that may include the first uptime to the first medical device and the first medical device may scan for the advertisements. If desired, the first medical device may be configured to compare the first and second uptimes by subtracting the first and second uptimes to determine an uptime difference and the first medical device may compare the uptime difference to a threshold. In such embodiments, the first medical device may send a pairing message to the second medical device to wirelessly pair the first medical device and the second medical device if the uptime difference is less than the threshold.

Optionally, the first medical device may include an ambient light sensor, the second medical device may include at least one illuminable indicator, and a brightness of the at least one illuminable indicator of the second medical device may be controlled based on information that may be transmitted wirelessly from the first medical device to the second medical device and that may pertain to ambient light detected by the ambient light sensor. If desired, after the first and second medical devices are paired, the second medical device may send data to the first medical device for display on a graphical user interface (GUI) of the first medical device.

In some embodiments of the twenty-third aspect, after the first and second medical devices are paired, the second medical device may send data to the first medical device wirelessly for subsequent transmission by the first medical device to a remote computer. For example, the remote computer may include one of a nurse call server, a nurse call master station computer, an electronic medical records server, or a healthcare information system server.

If desired, the first medical device may be coupled via a data cable to a data port that may be located in a patient room with the first and second medical devices. In such embodiments, the data that may be received wirelessly by the first medical device from the second medical device may be transmitted to the remote computer via the data cable and data port. Alternatively or additionally, the first medical device may be configured to communicate wirelessly with a wall unit that may be located in a patient room with the first and second medical devices. In such embodiments, the data received wirelessly by the first medical device from the second medical device may be transmitted wirelessly to the wall unit which forwards the data to the remote computer.

In some embodiments of the twenty-third aspect, the first medical device further may include a second power cord that may terminate at a second power plug and the wall unit may include a second AC receptacle. In response to the second power plug of the first medical device being plugged into the second AC receptacle of the wall unit, the first medical device and the wall unit may implement a second time-based wireless pairing operation in which a third uptime calculated by the first medical device may be compared to a fourth uptime calculated by the wall unit.

According to a twenty-fourth aspect of the present disclosure, a system may include a wall module that may have a first wireless transceiver and first circuitry that may be configured to send an audio feed. The system of the twenty-fourth aspect may also have a patient bed that may include a second wireless transceiver, a speaker, and second circuitry that may be coupled to the speaker and the second wireless transceiver. The second wireless transceiver may be configurable for wireless communication with the first wireless transceiver. The first circuitry of the wall module may be configured to detect the presence of a pillow speaker unit, and in response to the detection of the pillow speaker unit by the circuitry of the wall module, the wall module may be configured to communicate with the second wireless transceiver via the first wireless transceiver in a first manner that may prevent the audio feed from being audibly played through the speaker of the patient bed.

In some embodiments of the system of the twenty-fourth aspect, in response to detection of the presence of the pillow speaker unit, the first circuitry may command the first wireless transceiver to transmit audio packets that may correspond to silence. For example, the audio packets that correspond to silence may comprise all zeroes. Optionally, the first circuitry of the wall module further may be configured to detect absence of the pillow speaker unit and, in response to detection of the absence of the pillow speaker unit by the first circuitry, the wall module may be configured to communicate with the second wireless transceiver via the first wireless transceiver in a second manner that may allow the audio feed to be audibly played through the speaker of the patient bed.

If desired, the system of the twenty-fourth aspect further may include a mobile device that may be configured to communicate wirelessly with the wall module and that may be configured to display a user input that may be usable to command the wall module whether to operate in the first manner or the second manner. Optionally, the mobile device further may be configured to receive a firmware installation input from a user to upload firmware to the first circuitry of the wall module via the first transceiver.

In some embodiments of the system of the twenty-fourth aspect, the patient bed may include a graphical user interface (GUI) that may be configured to receive inputs from a user to control functions of the patient bed. In such embodiments, the GUI may be configured to receive a first user input which may result in a mute command being transmitted from the second wireless transceiver of the patient bed to the first wireless transceiver of the wall module to command the first circuitry of the wall module to operate in the first manner to mute the speaker of the patient bed. If desired, the GUI of the twenty-fourth aspect may be configured to receive a second user input which may result in an unmute command being transmitted from the second wireless transceiver of the patient bed to the first wireless transceiver of the wall module to command the first circuitry of the wall module to operate in a second manner that may allow the audio feed to be audibly played through the speaker of the patient bed.

Optionally, with regard to the system of the twenty-fourth aspect, the first circuitry of the wall module and the second circuitry of the patient bed may implement a time-based pairing operation to pair the patient bed with the wall module. For example, the time-based pairing operation may be initiated by plugging a power plug of the patient bed in to a power receptacle of the wall module.

In some embodiments of the twenty-fourth aspect, plugging in the power cord to the power receptacle may result in a first timer of the patient bed being started to measure a first uptime and may result in a second timer of the wall module being started to measure a second uptime. The wall module of the twenty-fourth aspect may be configured to transmit to the patient bed from the first wireless transceiver an advertisement that may include the second uptime and the patient bed may be configured to compare the second uptime with the first uptime. If the second uptime is within a predetermined tolerance range of the first uptime, the patient bed of the twenty-fourth aspect may be configured to send a pairing message to the wall module which may result in the wall module and the patient bed becoming automatically paired for subsequent wireless communications. Alternatively, the patient bed of the twenty-fourth aspect may be configured to transmit to the wall module from the second wireless transceiver a message that may include the first uptime and the wall module may be configured to compare the first uptime with the second uptime and, if the first uptime is within a predetermined tolerance range of the second uptime, the wall module may be configured to send a pairing message to the patient bed which may result in the wall module and the patient bed becoming automatically paired for subsequent wireless communications.

Optionally, the system of the twenty-fourth aspect further may include a nurse call cord that may extend from the wall module and that may terminate at a first nurse call connector that may be configured for connection to a nurse call port of a nurse call system. Further optionally, the nurse call cord may include an auxiliary cord branch that may terminate at a second nurse call connector and the second nurse call connector may be coupleable to a third nurse call connector that may be at an end of a bed nurse call cord that may extend from the patient bed.

If desired, the patient bed of the twenty-fourth aspect may include a first WiFi transceiver and the wall module may include a second WiFi transceiver. The first and second WiFi transceivers each may be configured to send WiFi messages to, and receive WiFi messages from, at least one wireless access point of a network.

In some embodiments, the first circuitry of the wall module of the twenty-fourth aspect may be configured to detect the presence of the pillow speaker unit by determining the presence of an echo due to the pillow speaker unit and the speaker of the patient bed playing the same or similar audio. Alternatively or additionally, the first circuitry of the wall module of the twenty-fourth aspect may be configured to detect the presence of the pillow speaker unit by receiving a signal from a nurse call system that a pillow speaker unit may be connected to the nurse call system.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 4 is a perspective view, similar to FIG. 3, showing the wall module coupled to the AC duplex outlet, the nurse call connector coupled to the nurse call port, and a power plug of a power cable extending from the patient bed arranged for coupling to an AC outlet of the wall module;

FIG. 5 is a perspective view, similar to FIG. 5, showing the power plug of the power cable of the patient bed plugged into the wall module which commences a time-based wireless pairing operation between the patient bed and the wall module;

FIG. 24 is a perspective view of an alternative embodiment wall module showing a healthcare facility AC duplex outlet accessible within a recess formed in a front wall of a housing of the alternative embodiment wall module, showing an illuminateable wireless bed communication icon on the front wall of the housing to the left of the recess, and showing a bed icon label on a top wall of the housing to indicate that a power cord from a bed should be plugged into one of the AC outlets of the duplex outlet;

FIG. 25 is a front elevation view of the wall module of FIG. 24 showing a caution icon illuminated beneath the nurse call icon;

FIG. 48 is a screen shot of an example of a landing page that appears on a service technician's mobile device during initial configuration of the wall module in response to the service technician launching a configuration application;

FIG. 49 is a screen shot an example of a devices page that appears on the service technician's mobile device in response to a cable free communication icon or button being selected on the landing page of FIG. 48, the devices page listing wall module ID's of the wall modules that are within Bluetooth communication range of the service technician's mobile device;

DETAILED DESCRIPTION

Figure 1:
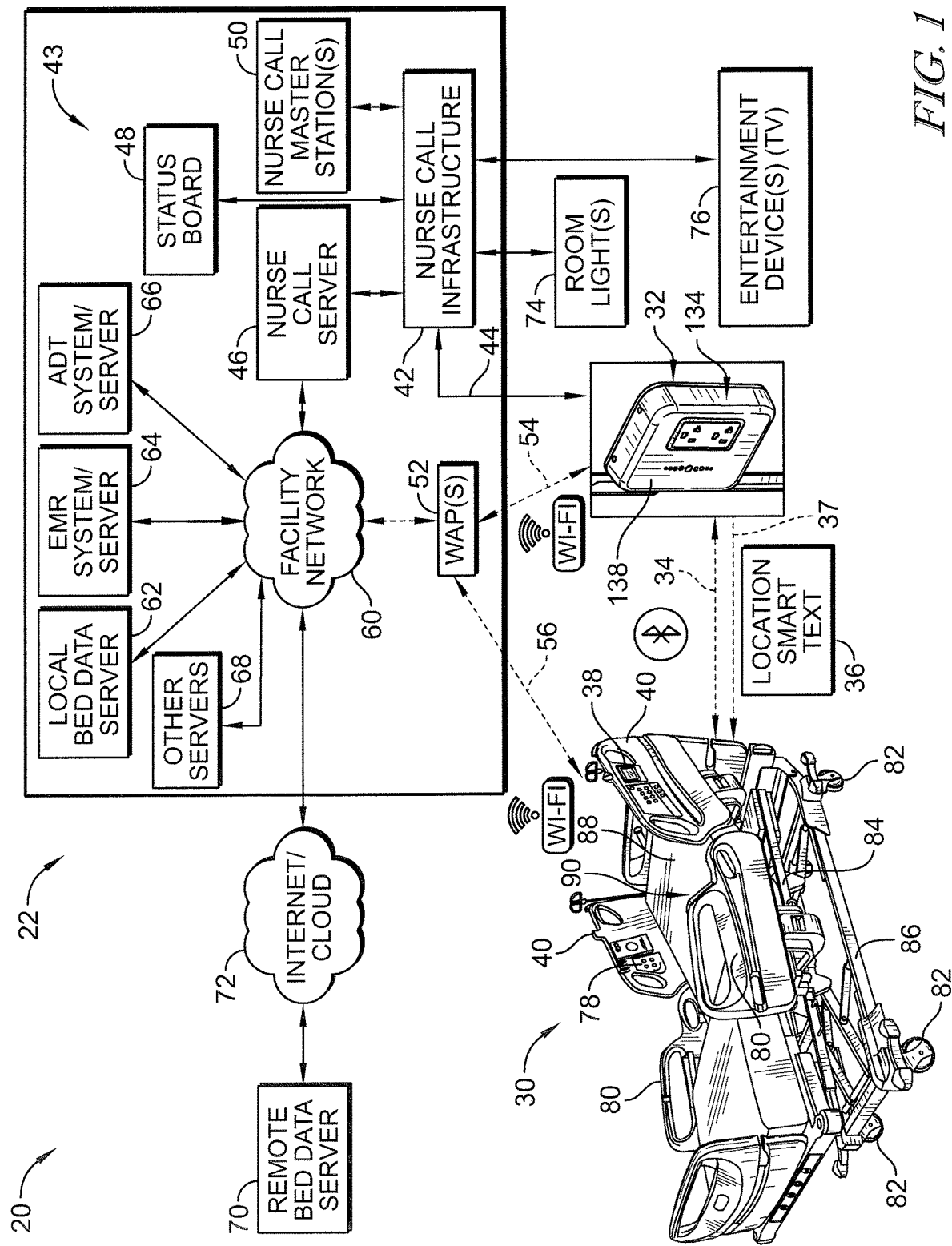
FIG. 1 is a partly perspective, partly diagrammatic view of a network of a healthcare facility in which a patient bed pairs and communicates wirelessly with a wall module which, in turn, communicates via a wired connection with a nurse call system and which is also able to communicate wirelessly with one or more wireless access points (WAP's), the bed also being able to communicate wirelessly with the one or more WAP's.

A system 20 for use in a healthcare facility 22 includes a medical device 30 and a wall module or wall unit 32 that communicates wirelessly with medical device 30 according to a first wireless communication technology as shown in FIG. 1. The terms "wall module" and "wall unit" are used interchangeably herein. Wall unit 32 is one example of a communication unit according to the present disclosure. Illustrative medical device 30 comprises a patient bed 30 but the principles of the present disclosure are applicable to other types of medical devices as well. Such other types of medical devices may include but are not limited to, for example, physiological monitors such as electrocardiographs (EKG's), electroencephalographs (EEG's), pulse oximeters, blood pressure monitors, heart rate monitors, respiration rate monitors, and temperature monitors; other patient care equipment including intravenous (IV) pumps, drug infusion pumps, respiratory therapy devices, ventilators, sequential compression devices (SCD's) for preventing deep vein thrombosis (DVT), hemodialysis equipment, renal therapy equipment, and passive motion machines; as well as other types of patient support apparatuses such as stretchers, chairs, wheelchairs, surgical tables, patient lifts, and examination tables; just to name a few.

Bed 30 and wall module 32 communicate via a wireless, bidirectional communication link 34 as shown diagrammatically in FIG. 1. In the illustrative example, the wireless communication between bed 30 and wall unit 30 is according to the Bluetooth communication protocol and so communication link 34 comprises a Bluetooth communication link 34. The communication range of Bluetooth (BT) technology is generally dependent upon the power of the BT transmitter but BT devices include class 1 devices which are the most powerful and can operate up to about 100 meters (m) (about 330 feet), class 2 devices which are the most common type of BT devices and which can operate up to about 10 m (about 33 feet), and class 3 devices which don't typically operate beyond about 1 m (3.3 feet). For BT communications between beds 30 and wall modules 32 as contemplated herein, the use of class 2 or class 3 BT devices suffice, but this is not to rule out the possibility of using class 1 BT devices in beds 30 and wall modules 32. In the illustrative embodiment, Bluetooth Low Energy (BLE) is used as the communication technology between beds 30 and wall modules 30.

The wireless communications over link 34 from bed 30 to wall unit 32 includes wireless bed data, including a bed identification (ID), and in appropriate circumstances, wireless audio data. The wireless communications over link 34 from bed 30 to wall unit 32 also include nurse calls, bed alerts, and room equipment control signals under appropriate circumstances. The wireless communications over link 34 from wall unit 32 to bed 30 includes wireless command messages to control various features and functions of bed 30 and, in appropriate circumstances, wireless audio data. Bed 30 and wall unit 32 also exchange wireless pairing messages so that the bed 30 and wall unit 32 become "paired" as will be described in further detail below, particularly in connection with FIGS. 6A and 6B. In the illustrative embodiment, Bluetooth technology is the only wireless communication technology that is used for wireless communications between bed 30 and wall unit 32.

After pairing, wall unit 32 sends a location smart text string 36 as a unidirectional message 37 as shown diagrammatically in FIG. 1. The smart text string 36 matches the name of the room location at which wall module 32, and therefore bed 30, is located. Smart text string 36 may have a format such as "Room 308-A," just to give one example. The smart text string 36 is displayed by bed 30 on a graphical user interface (GUI) 38 in some embodiments. In the illustrative example, bed 30 is a CENTRELLA® bed available from Hill-Rom Company, Inc. of Batesville, Indiana and has GUI 38 on one or both of head end siderails 40. Additional details of bed 30 can be found, for example, in U.S. Pat. No. 10,517,784 which is hereby incorporated by reference herein in its entirety for all that it teaches to the extent not inconsistent with the present disclosure which shall control as to any inconsistencies.

Still referring to FIG. 1, wall module 32 connects to nurse call infrastructure 42 via a wired data link 44. Nurse call infrastructure 42 includes nurse call components such as graphical room stations (GRS's), graphical audio stations (GAS's), standard room stations (SRS's), staff audio stations (SAS's), indicator lights (aka dome lights) provided in hallways of healthcare facilities adjacent to doorways of patient rooms, input/output (I/O) boards, routers, gateways, and other equipment that provides overall system 20 with a nurse call system portion 43, sometimes referred to herein as simply nurse call system 43. As shown in FIG. 1, nurse call system 43 also includes a nurse call server 46, one or more status boards 48, and one or more nurse call master stations 50 coupled to nurse call infrastructure 42 such as via suitable cabling and the like.

In some embodiments, nurse call system 43 is the NAVICARE® nurse call system available from Hill-Rom Company, Inc. of Batesville, Indiana. Additional details of suitable nurse call systems 43 contemplated by the present disclosure are shown and described in U.S. Pat. Nos. 8,598,995; 8,384,526; 8,169,304; 8,046,625; 7,746,218; 7,538,659; 7,319,386; 7,242,308; 6,897,780; 6,362,725; 6,147,592; 5,838,223; 5,699,038 and 5,561,412, each of which is hereby incorporated by reference herein in its entirety to the extent not inconsistent with the present disclosure which shall control as to any inconsistencies. Additional details of status board 48 and the types of information displayed thereon can be found in U.S. Pat. No. 8,779,924 which is hereby incorporated by reference herein in its entirety to the extent not inconsistent with the present disclosure which shall control as to any inconsistencies.

As shown in FIG. 1, wall module 32 is further configured to communicate with one or more wireless access points (WAP's) 52 of healthcare facility 22 via a wireless communications link 54. Bed 30, in some embodiments, is also configured to communicate with one or more of WAP's 52 via a wireless communications link 56. Wireless communication over links 54, 56 is according to one or more of the IEEE 802.11 WiFi communications protocols, for example. Links 54, 56 are each bidirectional communication links such that wireless data and/or messages can be transmitted from wall module 32 and bed 30 over respective links 54, 56 and such that wireless data and/or messages can be received by wall module 32 and bed 30 over respective links 54, 56. It should be appreciated that bed 30 and wall module 32 may or may not be in communication with the same one or more WAP's 52 via links 54, 56.

WAP's 52 are coupled to facility network 60 via suitable cabling or the like for bidirectional communications as indicated diagrammatically in FIG. 1. Facility network 60 is coupled to, or includes, one or more servers such as a local bed data server 62, an electronic medical records (EMR) server 64, an admission/discharge/transfer (ADT) server 66, and one or more other servers 68 of system 20. In some embodiments, various ones of servers 46, 62, 64, 66, 68 are combined together in a single sever. For example, in some embodiments of system 20, the software that implements functions of the local bed data server 62 is SMARTSYNC™ software available from Hill-Rom Company, Inc. and the software that implements functions of nurse call server 46 is NAVICARE® nurse call software, also available from Hill-Rom Company, Inc., each of which is stored and run by the same server. In other words, local bed data server 62 and nurse call server 46 are combined as one server in some embodiments.

In the illustrative example, facility network 60 is also communicatively coupled to a remote bed data server 70 via the cloud or Internet 72. Thus, whereas local bed data server 62 is located at healthcare facility 22, remote bed data server 70 is located geographically distant from the healthcare facility 22. For example, remote bed data server 70 may be located at a facility of a manufacturer of bed 30. Also in the illustrative example, system 20 includes one or more room lights 74 and one or more entertainment devices 76, such as one or more televisions (TV's) 76, that are coupled to nurse call infrastructure 42 via suitable cabling or conductors. Bed 30 includes a patient control panel 78 having inputs that are pressed to control room lights 74 and entertainment devices 76. For example, a patient supported on bed 30 is able to turn room lights 74 on and off, is able to turn the TV on and off, is able to change TV channels, and is able to turn the TV volume up and down using inputs on control panel 78. Such commands for control of lights 74 and TV 76 are transmitted by bed 30 via wireless link 34 to wall module 32, then to nurse call infrastructure 42 via wired link 44, then to the light(s) 74 or TV 76, as the case may be.

Control panel 78 of bed 30 also includes a nurse call input, typically a button that is used by the patient to place a nurse call. When a nurse call is placed, a nurse call signal is sent from bed 30 via wireless link 34 to wall module 32, then to nurse call infrastructure 42 via wired link 44, and then to one or more of nurse call master station 50, status board 48, and nurse call server 46. A caregiver at the master station 50 is then able to open up an audio communication channel from station 50 to bed 30, including via the wireless link 34 between wall module 32 and bed 30, to speak with the patient placing the nurse call. Thus, bidirectional audio communications between the patient and the caregiver at the master nurse station 50 takes place over wireless communications link 34 between bed 30 and wall unit 32.

Various bed alerts generated by bed 30 are also communicated from bed 30 to one or more of nurse call server 46, status board 48, and master station 50 via the same communication path that includes wireless link 34, wall module 32, wired link 44, and nurse call infrastructure 42. Such bed alerts include, for example, bed exit alerts generated by a bed exit system of bed 30 indicating that a patient has exited the bed 30 or has moved by a threshold amount toward exiting the bed 30, siderail down alerts indicating that one of the head end siderails 40 or foot end siderails 80 of bed 30 has been moved from a raised position shown in FIG. 1 to a lowered position (not shown, but well known in the art), caster brake alerts if one or more of casters 82 of bed 30 becomes unbraked (aka released), bed not low alerts if an upper frame 84 of bed 30 is raised out of its lowest position relative to a base frame 86 of bed 30, and a head-of-bed (HOB) angle alert if a head section of bed 30 that supports an upper body support region 88 of a mattress 90 is lowered below a threshold angle (e.g., 30 degrees) relative to horizontal or relative to upper frame 84.

It should be appreciated that the foregoing bed alerts are communicated from bed 30 only when the circuitry of bed 30 has been enabled (e.g., turned on) to monitor the particular feature corresponding to the alert. Thus, when monitoring of the particular feature is disabled (e.g., turned off), the corresponding alert is not sent from bed 30 via wireless link 34. Other types of bed alerts, such as alerts pertaining to mattress bladder inflation (e.g., inability of a pneumatic system of bed 30 to inflate one or more bladders to a target pressure) and motor over temperature alerts (e.g., a motor of bed 30 gets too hot), just to name a couple, are also transmitted from bed 30 via wireless link 34 in some embodiments.

In some embodiments, nurse calls initiated by a patient and bed alerts generated by bed 30 are also sent to wireless communication devices carried by caregivers. Such wireless communication devices may include, for example, tablet computers or portable phones such as smart phones or wireless phone handsets. In this regard, see, for example, U.S. Pat. No. 7,319,386 and U.S. Patent Application Publication Nos. 2020/0411179 and 2020/0066415, each of which is hereby incorporated by reference herein in its entirety to the extent not inconsistent with the present disclosure which shall control as to any inconsistencies. Thus, other servers 68 of system 20 may include a communication server such as a voice over Internet protocol (VoIP) in some embodiments. The communication of such alerts to the wireless communication devices of caregivers is initiated by nurse call server 46, for example.

According to the present disclosure, bed 30 also detects and transmits a whole host of bed data unrelated to nurse calls and bed alerts for storage in one or more of nurse call server 46, local bed data server 62, and remote bed data server 70. In this regard, see U.S. Patent Application Publication No. 2012/0316892 which is hereby incorporated by reference herein in its entirety to the extent not inconsistent with the present disclosure which shall control as to any inconsistencies and which includes a Table 1 that lists a wide variety of bed data. In some embodiments, all of the available bed data is transmitted to both server 62 and server 70. In other embodiments, different subsets of bed data are transmitted to different ones of servers 46, 62, 70 at the discretion of the system designer or system administrator.

Some bed data may be transmitted from bed 30 only via wireless communications link 56 and some bed data may be transmitted from bed 30 only via wireless communications link 34. The bed data received by wall module 32 may, in turn, be transmitted via either or both of communications links 44, 54. The wall module 32, in some embodiments, transmits some of the received bed data over wired communications link 44 and transmits some of the received bed data over wireless communications link 54. Again, the types of bed data transmitted by bed 30 and wall module 32 over the various communications links 34, 44, 54, 56 is at the discretion of the system designer or system administrator. The transmitted messages from bed 30 and wall module 32 containing the bed data include a destination address (e.g., IP address or media access control (MAC) address) of the device (e.g., wall module 32 or server 46, 62, 70) that is to receive the message containing the bed data.

Figure 2:
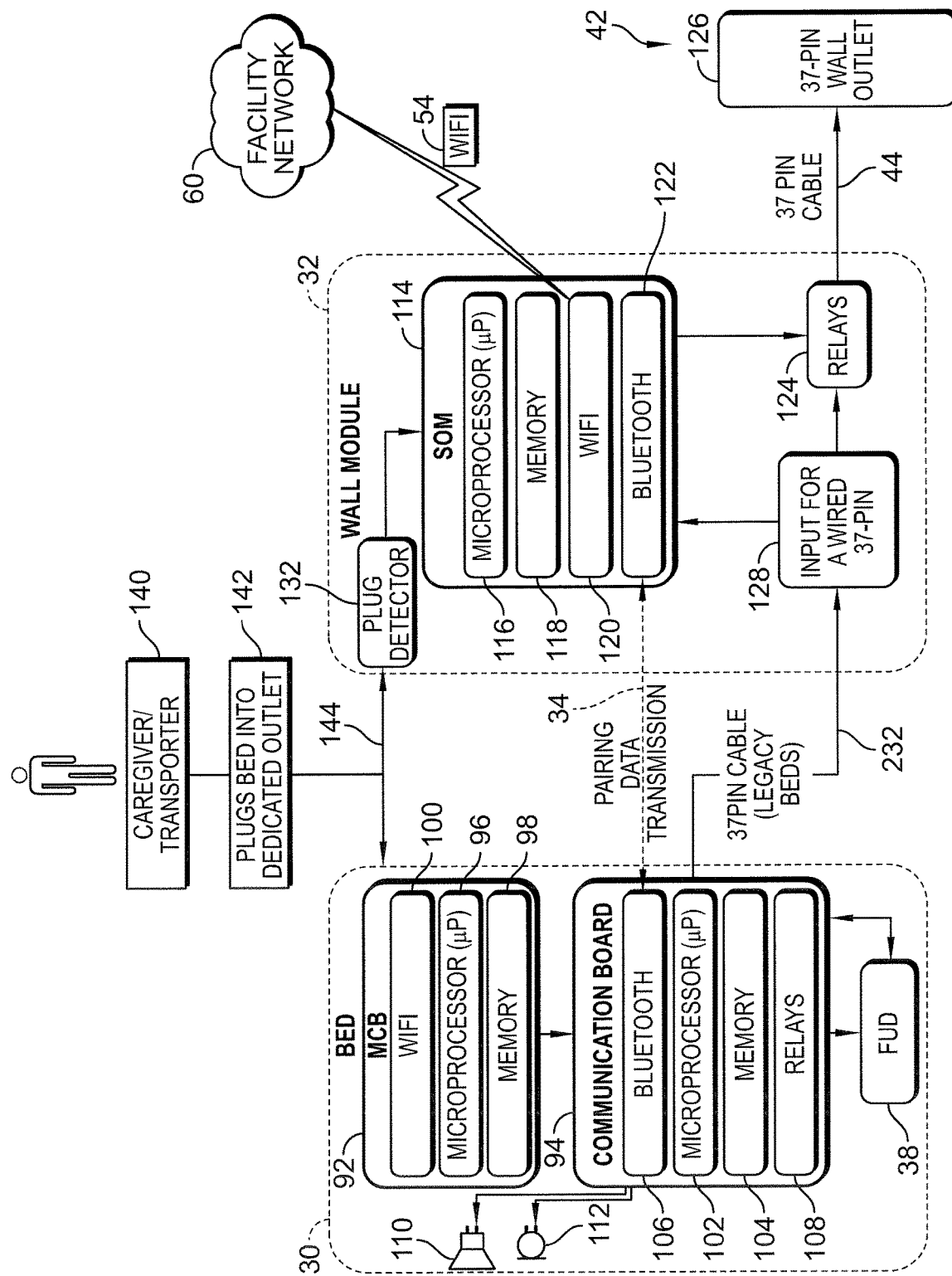
FIG. 2 is a diagrammatic view showing electrical componentry of the bed and the wall module.

Referring now to FIG. 2, bed 30 includes a main control board (MCB) 92 and a separate communication board 94. MCB 92 includes a microprocessor 96 and a memory 98 that stores bed operating software which is executed by microprocessor 96 to carry out the various bed functions of MCB 92. In some embodiments, microprocessor 96 and memory 98 are included in a microcontroller. MCB 92 also includes a WiFi module or transceiver 100 such as a WiFi radio that provides bed 30 with the capability of communicating bidirectionally with WAP's 52 via the wireless communications link 56. In some embodiments, some or all of microprocessor 96, memory 98, and WiFi transceiver 100 are included in a System on Chip (SoC), a Programmable System on Chip (PSoC), a Computer on Module (CoM), or a System on Module (SoM). In some embodiments, a model no. VAR-SOM-MX6 System on Module (SoM) available from Variscite Ltd. of Lod, Israel serves as or is provided on MCB 92 of bed 30.

Communication board 94 includes a microprocessor 102 and a memory 104 that stores operating software which is executed by microprocessor 102 to carry out the various functions of communication board 94. In some embodiments, microprocessor 102 and memory 104 are included in a microcontroller.

Communication board 94 also includes a Bluetooth module 106 such as a Bluetooth radio or transceiver that provides bed 30 with the capability of communicating bidirectionally with wall module 32 via the wireless communications link 34. Furthermore, communication board 94 includes a set of relays 108 or similar elements (e.g., microswitches or the like) that have open and closed states based on user inputs and bed alerts. For example, one of relays 108 closes when a patient places a nurse call, another of relays 108 closes in response to a bed exit alert occurring, yet another of relays 108 closes in response to a room light being turned on, and so forth.

Bed 30 further includes a speaker 110 and a microphone 112 to provide bed 30 with audio communications capability. In some embodiments, speaker 110 also serves as a microphone and the separate microphone 112 is omitted. In FIG. 2, GUI 38 of bed 30 is designated by the acronym "FUD" which is short for "flip-up display." The acronym FUD is used because, in the illustrative example, GUI 38 is pivotable upwardly from a recess in siderail 40 for more ergonomic viewing by a caregiver standing next to bed 30. In any event, GUI 38 and FUD 38 are used interchangeable herein. In the illustrative example, FUD 38 is electrically coupled to communication board 94. In other embodiments, FUD 38 is electrically coupled to MCB 92.

Still referring to FIG. 2, wall module 32 includes a System on Module (SoM) 114 that includes a microprocessor 116 and a memory 118 that stores wall module operating software which is executed by microprocessor 116 to carry out the various functions of SOM 114. SOM 114 also includes a WiFi module 120 such as a WiFi radio or transceiver and a Bluetooth module 122 such as a Bluetooth radio or transceiver. WiFi transceiver 120 provides wall module 32 with the capability of communicating bidirectionally with WAP's 52 via the wireless communications link 54. Bluetooth transceiver 122 provides wall module 32 with the capability of communicating bidirectionally with bed 30 via the wireless communications link 54. In some embodiments, SOM 114 is a model no. DART 6UL available from Variscite Ltd. of Lod, Israel.

Wall module 32 also includes a set of relays 124 as shown diagrammatically in FIG. 2. Relays 124 of wall module 32 are basically the same as relays 108 of communication board 94 of MCB 92 of bed 30. Based on bed data received from bed 30 by Bluetooth radio 122 of SOM 114 of wall module 32 via wireless communications link 34, SOM 114 sends signals to relays 124 so that the open and closed states of the various relays 124 match those occurring in relays 108 of bed 30. Wall module 32 also includes a nurse call cable, illustratively a 37-pin cable, that forms the wired communication link 44 from wall module 32 to the nurse call infrastructure. In FIG. 2, 37-pin nurse call cable 44 connects to a nurse call wall outlet, illustratively a 37-pin wall outlet or port 126, which is included as one of the components of the nurse call infrastructure 42. The 37-pin cable 44 includes one or more conductors that are data conductors on which serial data, such as data according to a Serial Peripheral Interface (SPI) protocol, is transmitted to the nurse call system 43. These data conductors do not have any relay 124 associated with them but instead are simply conductors that are routed from SOM 114 to 37-pin cable 44. This will become more apparent in connection with the discussion below of FIG. 9.

Optionally, wall module 32 includes a port or input 128 for a wired 37-pin connection to a 37-pin cable 232 that extends between bed 30 and wall module 32. Cable 232 is, for example, a standard nurse call cable of the type that is in use today to connect bed 30 with wall outlet 126 of nurse call system 43 without the use of wall module 32. In addition to the FIG. 2 illustration, an embodiment of wall module 32 that includes 37-pin port 128 is shown and described below in connection with FIGS. 12 and 13. Port 128 is electrically coupled to relays 124 which are, in turn, coupled to wall outlet 126 of nurse call system 43 by cable 44. Thus, port 128 allows for pass-through of wired communications between bed 30 and nurse call system 43 via wall module 32. In some embodiments, when cable 232 is coupled to port 128, Bluetooth communications between wall module 32 and bed 30 are not established or, if already established, are suspended. Thus, wired communications over cable 232 between bed 30 and wall module 32 takes precedence over the wireless communications between bed 30 and wall module 32 over wireless communications link 34.

In the illustrative FIG. 2 example, port 128 is electrically coupled to SOM 114. Thus, in embodiments of wall module 32 having port 128, some or all of the data and signals received at port 128 from bed 30 via cable 232 are also communicated to SOM 114 in addition to being passed through to cable 44 and wall outlet 126 such as via relays 124. This permits some or all of the data and signals received at port 128 from bed 30 via cable to be transmitted by WiFi radio 120 to network 60 over the wireless communication link 54 via WAP's 52.

As also shown in FIG. 2, wall module 32 includes a plug detector 132 that is electrically coupled to SOM 114. As shown in FIGS. 1 and 3-5, wall module 32 includes a box-shaped housing 134 having a duplex AC receptacle 136 accessible at a front wall 138 of the housing 134. In some embodiments, housing 134 has a width on the order of about 4.5 inches to about 5 inches, a height of about 5.5 inches, and a depth of about 1.25 inches to about 2.25 inches. SOM 114, relays 124, and plug detector 132 are located within an interior region of housing 134 of wall module 32. As indicated diagrammatically in FIG. 2 by blocks 140, 142, a caregiver or other staff member such as a transporter that moves bed 30 to a patient room and then plugs a power cord 144 of bed 30 into one of the receptacles of duplex receptacle 136 of wall module 32. In response to power cord 144 being plugged into wall module 32, plug detector 132 sends a signal to SOM 114 that begins the wireless pairing process between wall module 32 and bed 30 as will be described in further detail below in connection with FIGS. 6A and 6B. Various embodiments of plug detector 132 are discussed below in connection with FIGS. 14-17.

In connection with the transmission of bed alerts, nurse calls, and bed data from wall unit 32 via wired communications link 44 or wireless communications link 54, the messages containing the data corresponding to the bed alerts, nurse calls, and bed data include a location ID that is appended to the messages by SOM 114 of wall unit 32. Thus, memory 118 stores a location ID therein. The location ID is different than the location smart text 36 in some embodiments. The location ID is assigned to wall unit 32 at the time of manufacture in some embodiments and is assigned at the time of installation in other embodiments. If assigned at the time of manufacture, the location ID is simply a unique ID stored in the memory of wall unit 32. Once the wall module 32 is installed in a healthcare facility, the unique ID is correlated to the actual room location at a remote computer such as a computer coupled to nurse call server 46 (e.g., master station 50), a computer coupled to local bed data server 62, or a computer coupled to a real time locating system (RTLS) server which is among the other servers 68 in some embodiments.

If the location ID is assigned to wall module 32 at the time of installation, a message containing the assigned location ID is transmitted to wall module 32 via one of communications links 44, 54 for storage in memory 118 of SOM 114. Again, the assigned location ID is different than the location smart text 36 in some embodiments. The transmission of the location ID to the installed wall unit 32 is initiated by a remote computer, under the control of a system administrator or other user of the remote computer. The remote computer used to send the location ID to the wall module 32 may include, for example, a computer coupled to nurse call server 46 (e.g., master station 50), a computer coupled to local bed data server 62, or a computer coupled to a real time locating system (RTLS) server which is among the other servers 68 in some embodiments as noted above. Alternatively, in order to provide wall module 32 with the location ID, a technician installing wall module 32 may link a tablet computer or other hand held device to wall module 32 via a wired connection to a Universal Serial Bus (USB) port or other type of port such as a Joint Test Action Group (JTAG) port provided on housing 32 or inside of housing 134. Thus, to gain access to the port for programming the location ID into SOM 114, a portion of housing 134 is disassembled in some embodiments.

Figure 3:
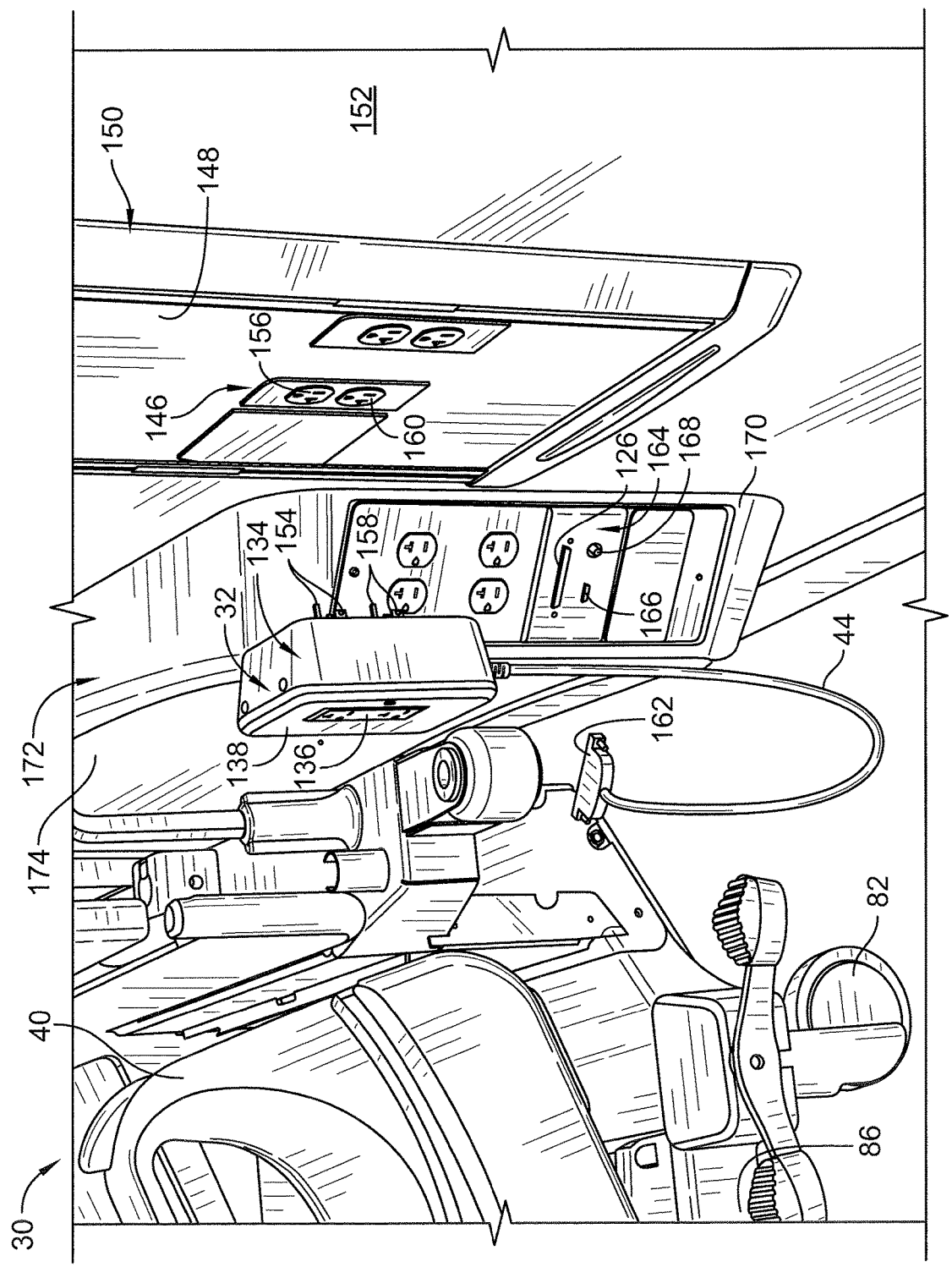
FIG. 3 is a perspective view showing the wall module arranged for coupling to an alternating current (AC) duplex outlet mounted to a panel attached to a wall of a patient room in the vicinity of a head end of the patient bed and showing a nurse call cable extending from a bottom of the wall module and terminating at a nurse call connector arranged for coupling to a nurse call port of an audio station bed connector (ASBC) mounted to a bed locator unit that is mounted to the wall of the patient room.

Referring now to FIG. 3, wall module 32 is shown arranged for coupling to an alternating current (AC) duplex outlet 146 mounted to a panel 148 of a service chase 150 that is attached to a wall 152 of the patient room. Wall module 32 has a first set of prongs 154 that are configured for insertion into complementary openings of a first receptacle 156 of outlet 146 and a second set of prongs 158 that are configured for insertion into complementary openings of a second receptacle 160 of outlet 146. After wall module 32 is plugged into outlet 146, power received by prongs 154 from receptacle 156 of outlet 146 is passed through wall module 32 to an upper receptacle of duplex receptacle 136 and power received by prongs 158 from receptacle 160 of outlet 146 is passed through wall module to a lower receptacle of the duplex receptacle 136.

As also shown in FIG. 3, cable 44 extends downwardly from a bottom wall of wall unit 32 and terminates at a nurse call connector 162, illustratively a 37-pin nurse call connector, that is configured for coupling to wall outlet 126. In the illustrative example, wall outlet 126 is included in an audio station bed connector (ASBC) unit 164 of the type available from Hill-Rom Company, Inc. of Batesville, Indiana. As noted above, ASBC's are among the types of components included in nurse call infrastructure 42 of nurse call system 43.

ASBC unit 164, sometimes referred to herein as just ASBC 164, includes a pillow speaker port 166 for connection with a pillow speaker connector at the end of a cord of a pillow speaker (not shown) as is known in the art. ASBC 164 further includes a ¼ inch jack receptacle 168 for receipt of a ¼ jack provided at the end of a cable extending from a piece of patient care equipment. A generic alarm signal is provided to jack receptacle 168 of ASBC 164 by the piece of patient care equipment. Thus, the jack receptacle 168 receives a simple on or off signal to indicate presence or absence, respectively, of an alarm state of the piece of patient care equipment. The generic alarm signal is correlated with a specific type of patient care equipment in some embodiments. In this regard, see U.S. Pat. No. 9,411,934 which is hereby incorporated by reference herein to the extent not inconsistent with the present disclosure which shall control as to any inconsistencies.

In the illustrative FIG. 3 example, ASBC 164 is mounted to a sidewall 170 of a bed locator unit 172 that is mounted to the wall 152 of the patient room. Bed locator unit 172 is sometimes referred to herein as just bed locator 172. In the context of the present disclosure, bed locator 172 is an architectural product that indicates where the head end of patient bed 30 should be located in the patient room. Thus, bed 30 is generally centered relative to bed locator 172 so that its head end faces a front wall 174 of the bed locator 172 in close proximity (e.g., within a foot or less). Service chase 150 is mounted to room wall 152 so as to be offset to the side from the bed locator 172 but still in close proximity (e.g., within two feet or less) of the bed locator 172. Cable 44 has sufficient length to enable nurse call connector 162 to reach outlet 126 of ASBC 164 when wall module 32 is plugged into outlet 146. Thus, a length of cable 44 is on the order of about 3 feet or 36 inches in some embodiments. Embodiments of wall module 32 having cable 44 shorter or longer than 36 inches are within the scope of the disclosure, however.

Referring now to FIG. 4, wall module 32 is plugged into outlet 146 thereby obscuring outlet 146 from view, and nurse call connector 162 is coupled to port 126 of ASBC 164 thereby obscuring port 126 from view. In some embodiments, one or more screws (not shown) that are used to mount a cover plate of outlet 146 in place are removed prior to plugging wall module 32 into outlet 146 and then one or more longer screws are used to securely mount wall module 32 to outlet 146. In this regard, a front cover portion of housing 134 that includes front wall 138 and peripheral walls 176 (e.g., top wall, bottom wall, and sidewalls) which are molded integrally with front wall 138, are removed from a back wall 178 of wall module 32. Back wall 178 has one or more openings that are aligned with the one or more threaded openings that previously received the one or more cover plate screws. The one or more longer screws are then inserted through the one or more openings in back wall 178 and threaded into the respective threaded openings that previously received the one or more cover plate screws. After the one or more longer screws are tightened, the cover portion comprising walls 138, 176 is reattached to back wall 178. When installed in this manner, therefore, wall module 32 is fixed in place within the patient room relative to wall 152 and cannot be easily removed without disassembly and removal of the one or more longer screws.

Still referring to FIG. 4, a power plug 180 at an end of power cord 144 of bed 30 is arranged so that prongs 182 of the plug 180 are oriented for insertion into one of the pair of receptacles of the duplex receptacle 136 of wall unit 32 (only two of the three prongs 182 can be seen in FIG. 4). It should be noted that plug 180 can be plugged into either receptacle of the duplex receptacle 136 and wall module 32 will begin the Bluetooth pairing process with bed 30 regardless. Wall module 32 includes a light 184 that is illuminated to indicate a pairing state between bed 30 and wall unit 32. In the illustrative example, light 184 is generally rectangular and surrounds a perimeter of the duplex AC receptacle 136. Light 184 comprises a light pipe, such as a light pipe made of acrylic material, in some embodiments. As such, a single multi-color light emitting diode (LED) is able to emit light into the light pipe at a discrete location resulting in the entirety of the light pipe being illuminated. Alternatively, two single-color LED's are used to illuminate the light pipe of light 184. In some embodiments, light 184 is illuminated blue when wall module 32 is not wirelessly paired with any medical device, such as bed 30, and light 30 is illuminated green when wall module 32 is wirelessly paired with a medical device, such as bed 30. In other embodiments, light 184 is illumined in some other color such as amber or red to indicate a wireless pairing state.

Referring now to FIG. 5, power plug 180 is plugged into the bottom receptacle of the duplex receptacle 136. Plug detector 132 detects the connection of plug 180 to receptacle 136 and signals SOM 114 of the connection. In response, SOM 114 commences a time-based wireless pairing operation between wall module 32 and bed 30. During the time-based pairing operation, which may take up to 45 seconds to complete in some instances, light 184 continues to be illuminated blue and may blink or flash in some embodiments. After the time-based pairing operation is completed successfully, light 184 is illuminated green to provide visual feedback to caregivers that bed 30 and wall module 32 are successfully paired.

Figure 6A:
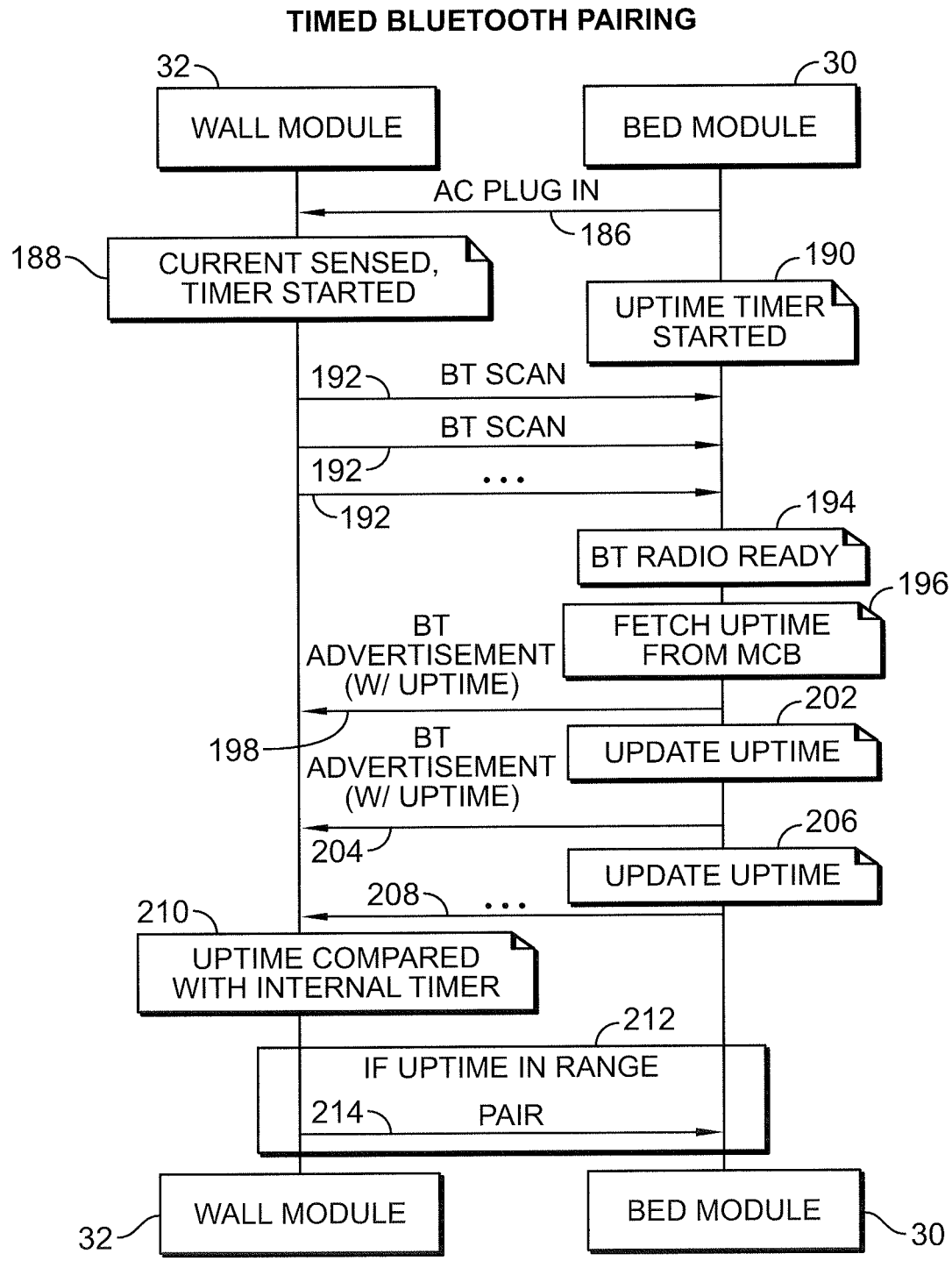
FIG. 6A is a swim lane diagram showing steps of the time-based wireless pairing operation in which the wall module starts a first timer in response to the power plug of the bed being plugged into the outlet of the wall module and in which the bed starts a second timer in response to AC power being received from the wall module, the wall module makes a series of Bluetooth (BT) scans listening for the bed, the bed transmitting one or more BT advertisements including a bed uptime as measured by the second timer, and the wall module initiating wireless pairing with the patient bed in response to the bed uptime from the patient bed being within a tolerance range of a module uptime as measured by the first timer.

Referring now to FIG. 6A, a swim lane diagram of a time-based wireless pairing operation 200 between wall module 32 and bed 30 (labeled as "bed module" in FIG. 6A) is shown. Operation 200 begins with power plug 180 of bed 30 being plugged into receptacle 136 of wall module 32 as indicated by an AC PLUG IN arrow 186. In the FIG. 6A example, plug detector 132 of wall module 32 includes circuitry that detects current flowing to power cord 144 of bed via power plug 180 and begins a wall module timer as indicated at a block 188 labeled CURRENT SENSED, TIMER STARTED. The current sense circuitry is discussed below in connection with FIG. 17. Other types of plug detectors 132 are discussed below in connection with FIGS. 14-16 and are used in wall module 32 in alternative embodiments. In alternative embodiments, the timer of wall module 32 associated with block 188 of FIG. 6A is started in response to detection of an RFID tag or near field communication (NFC) tag attached to plug 180.

Bed 30 also includes circuitry, such as current sense circuitry, that detects current flowing in power cord 144 due to plug 180 being connected to a power receptacle. In response to bed 30 detecting that power is received via power cord 144, bed 30 starts a bed timer as indicated by an UPTIME TIMER STARTED block 190. According to this disclosure, the timers of wall module 32 and bed 30 are software timers that are implemented in software. That is, a time at which plug 180 is initially detected by wall module 32 (e.g., an initial time) is stored in memory 118 and then subsequent times at discrete intervals or at the occurrences of particular events are subtracted from the initial time to arrive at an amount of time that has elapsed since plug 180 was initially detected by plug detector 132 of wall module 32.

Similarly, a time at which bed 30 initially detects power being received via power cord 144 (e.g., current flowing in power cord 144 is sensed) is stored in memory 98 of MCB 92 and then subsequent times at discrete intervals or at the occurrences of particular events are subtracted from the initial time to arrive at an amount of time that has elapsed since current flowing in power cord 144 was initially detected by bed 30. The time calculated by microprocessor 96 of MCB 92 of bed 30 is referred to in FIG. 6A as an "uptime." The elapsed time calculated by microprocessor 116 of SOM 114 of wall module 32 is also sometimes referred herein as an "uptime" as shown, for example, in FIG. 6B. In alternative embodiments, hardware timers such as clock circuits or clock chips are used to implement the timers for calculating uptimes by bed 30 and wall module 32.

After wall module 32 senses AC PLUG IN 186 at block 188, a series of Bluetooth (BT) scans 192 are transmitted from BT transceiver 122 of wall module 32 to BT transceiver 106 of bed 30. In particular, BT scans 192 include query messages to precipitate response messages from any devices in the reception range of BT transceiver 122 of wall module 32. Of course, because bed 30 is plugged into wall module 32, it will be assured to be one of the devices within the reception range of BT transceiver 122 of wall module 32. In addition to the query messages, the BT scans 192 include a media access control (MAC) address of the BT transceiver 122 of wall module 32. In the illustrative example, three BT scans 192 are shown but it is within the scope of this disclosure for more or less than three BT scans 192 to occur during the time-based wireless pairing process 200.

In response to receiving one or more BT scans 192, the BT transceiver 106 is readied for BT communications as indicated by a BT RADIO READY block 194 in FIG. 6A. Prior to sending any BT communications, microprocessor 102 of communication board 94 sends an uptime query message to microprocessor 96 of MCB 92 to obtain the current uptime value of bed 30 as indicated by a FETCH UPTIME FROM MCB block 196. The microprocessor 96 of MCB 92 calculates or otherwise obtains the current uptime in response to receiving the uptime query message from microprocessor 102 and replies with the calculated or obtained current uptime. After microprocessor 102 of communication board 94 receives the current uptime, BT radio 106 transmits a first BT ADVERTISEMENT (W/UPTIME) message as indicated by arrow 198 in FIG. 6A. In addition to the uptime, message 198 also includes a manufacturer ID of bed 30, a product ID of bed 30, and a MAC address and/or a Bluetooth ID address of the BT transceiver 106.

After message 198 is sent by BT transceiver 106 of bed 30 to BT transceiver 122 of wall module 32, microprocessor 102 of communication board 94 sends another uptime query message to microprocessor 96 of MCB 92 to obtain an updated uptime as indicated at an UPTIME BLOCK 202. After microprocessor 102 of communication board 94 receives the updated uptime, BT radio 106 transmits a second BT ADVERTISEMENT (W/UPTIME) message as indicated by arrow 204 in FIG. 3. Similar to message 198, message 204 also includes the manufacturer ID of bed 30, the product ID of bed 30, and the MAC address and/or Bluetooth ID address of the BT transceiver 106. This cycle of updating the uptime and sending another BT ADVERTISEMENT (W/UPTIME) message repeats periodically one or more additional times as indicated by another UPDATE UPTIME block 206 and another arrow 208.

When ready, the microprocessor 116 of SOM 114 of wall module 32 compares the uptime received in one or more of BT advertisement messages 198, 204, 208 from bed 30 with the elapsed time of the internal timer of the wall module 32 as indicated at an UPTIME COMPARED WITH INTERNAL TIMER block 210 of FIG. 6A. If the uptime received from bed 30 in one or more of messages 198, 204, 208 matches the elapsed uptime of the wall module timer or, in some embodiments, is within a tolerance range of the elapsed uptime of the wall module timer as indicated by an IF UPTIME IN RANGE block 212, then Bluetooth transceiver 122 of wall module 32 sends a pairing message as indicated by a PAIR arrow 214 which results in the wall module 32 and bed 30 becoming paired for subsequent communications of wireless data and messages over wireless communications link 34.

A tolerance range for comparing the uptime of bed 30 with the uptime of wall module 32 is used to account for processing time delays in the circuitry of these two devices. For example, some processing time (e.g., milliseconds or microseconds) is needed for microprocessor 102 of communication board 94 to query for and obtain the uptime from microprocessor 96 of MCB 92 which, itself, requires some processing time to calculate the uptime when requested. At wall module 32, some processing time is needed by microprocessor 116 to determine that Bluetooth transceiver 122 has received a BT advertisement message 198, 204, 208 containing the uptime and to calculate the elapsed uptime since the wall module timer was started at block 188. Thus, depending upon the number of significant figures used, which is at the discretion of the system designer or programmer, the uptime and elapsed time are unlikely to be an exact match. On the other hand, if these times are rounded to say, the nearest second or nearest 5 seconds, then the rounded uptimes are more likely to be an exact match.

In some embodiments, the comparison of the uptime from bed 30 with the elapsed uptime of the internal timer of the wall module 32 at block 210 may be required to yield a positive match for more than one of BT advertisement messages 198, 204, 208 before the pairing message 214 is transmitted from wall module 32 to bed 30 to establish the wireless pairing between these devices. For example, three positive comparisons may be required before the wireless pairing message 214 is sent, just to give one arbitrary example. More or less than three positive comparisons are within the scope of the present disclosure, however. Furthermore, in alternative embodiments, the roles of bed 30 and wall module 32 in the time-based pairing operation 200 are reversed. In such embodiments, blocks 188, 210 correspond to functions performed by bed 30; blocks 190, 194, 196, 202, 206 correspond to functions performed by wall module 32; and the directions of arrows 192, 198, 204, 208, 214 are reversed. The direction of arrow 186 remains the same, however, for this alternative embodiment because power plug 180 of power cord 144 of bed 30 is still plugged into receptacle 136 of wall module 32.

After bed 30 and wireless module 32 are successfully wirelessly paired, each message from bed 30 to wall module 32 includes the MAC address and/or Bluetooth ID address of Bluetooth transceiver 106 and/or a sequence ID and/or other protocol message header. If SOM 114 of wall module 32 determines that the MAC address and/or Bluetooth ID address and/or the sequence ID and/or the other protocol message header, as the case may be, included in the wireless message corresponds to the bed 30 with which wall module 32 is paired, then the message is processed by SOM 114. Otherwise, it is ignored. Similarly, after bed 30 and wireless module 32 are successfully wirelessly paired, each message from wall module 32 to bed 30 includes the MAC address and/or Bluetooth ID address of Bluetooth transceiver 122 and/or sequence ID and/or other protocol message header. If communication board 94 of bed 30 determines that the MAC address and/or Bluetooth ID address and/or sequence ID and/or other protocol message header, as the case may be, included in the wireless message corresponds to the wall module 32 with which bed 30 is paired, then the message is processed by communication board 94. Otherwise, it is ignored.

In some embodiments, after power plug 180 of power cord 144 is plugged into one of the receptacles of the duplex AC receptacle 136 of wall module 32 as indicated by AC PLUG IN arrow 186 of FIG. 6A, which begins the time-based Bluetooth pairing process 200, the light 184 of wall module 32 remains colored blue but starts blinking or flashing to indicate that the pairing process 200 is taking place. Thus, in some embodiments, light 184 is operated in three states as follows: 1) illuminated in blue without blinking to indicate no Bluetooth pairing to any medical device 30 exists; 2) illuminated in blue with blinking to indicate that the Bluetooth pairing process 200 is taking place between wall module 32 and medical device 30; and 3) illuminated green without blinking to indicate that the pairing process 200 is complete and the medical device 30 and wall module 32 are successfully paired.

In some embodiments of bed 30, messages are displayed on GUI 38 during the time-based wireless pairing operation 200. For example, a "PAIRING IN PROCESS" message, or a message of similar import, is displayed on GUI 38 while BT scans 192 and BT advertisements 198, 204, 208 are being exchanged between bed 30 and wall module 32. After bed 30 receives the PAIR message 214, GUI 38 displays, for example, a "PAIRING COMPLETE" message, or a message of similar import, for a threshold period of time such as 10 seconds, 30 seconds, or one minute, just to give a few arbitrary examples.

Figure 6B:
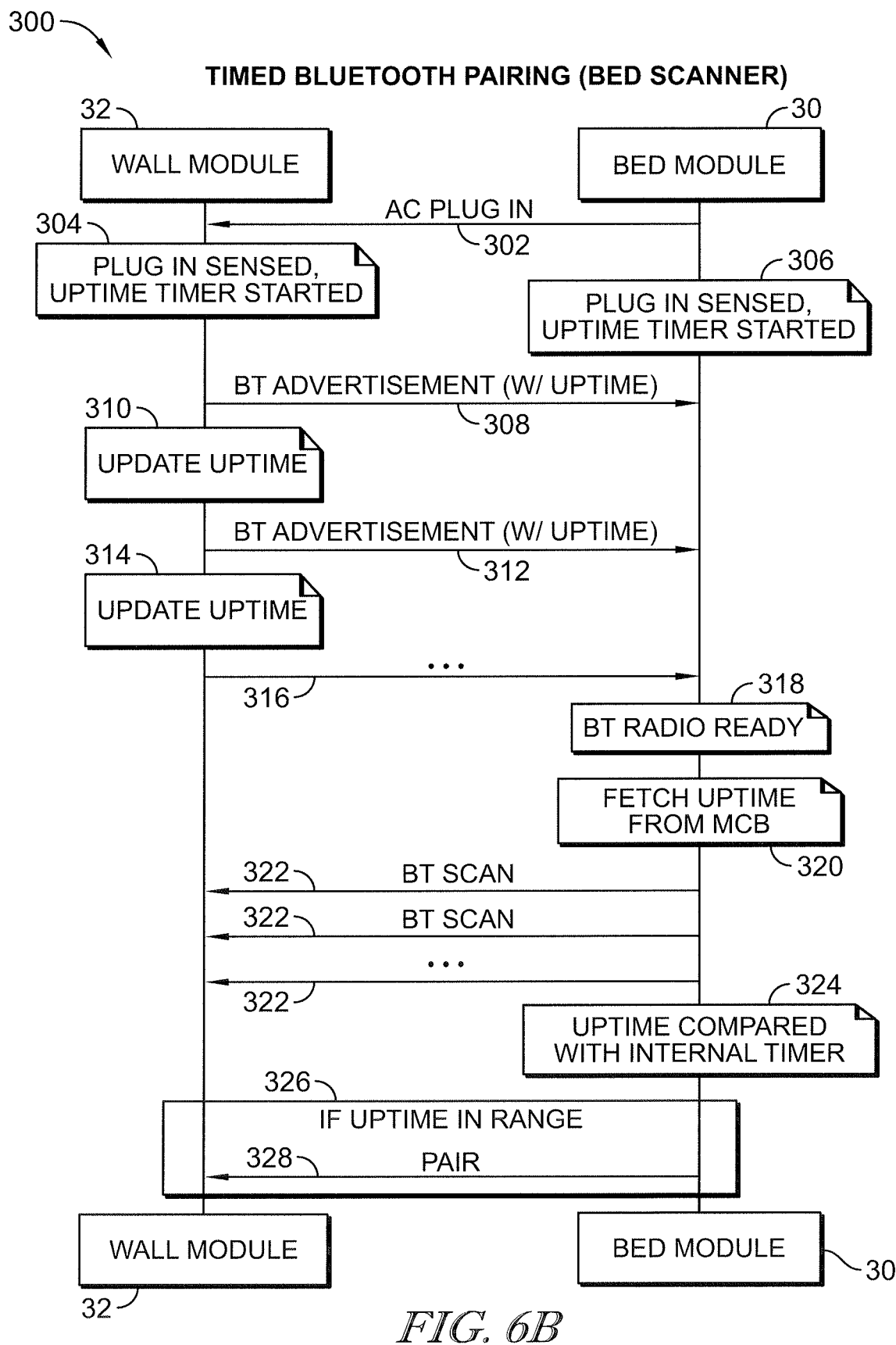
FIG. 6B is a swim lane diagram showing steps of an alternative time-based wireless pairing operation in which the wall module starts a first timer in response to the power plug of the bed being plugged into the outlet of the wall module and in which the bed starts a second timer in response to AC power being received from the wall module, the wall module transmitting to the bed a series of BT advertisements including a wall module uptime as measured by the first timer, the bed making one or more BT scans, and the bed initiating wireless pairing with the wall module in response to the wall module uptime from the wall module being within a tolerance range of a bed uptime as measured by the second timer.

Referring now to FIG. 6B, a swim lane diagram of a time-based wireless pairing operation 300 between bed 30 (labeled as "bed module" in FIG. 6B) and wall module 32 is shown. In the FIG. 6A embodiment, wall module 32 was the BT scanner but in the FIG. 6B embodiment, bed 30 is the BT scanner and so operation 300 is one version of the alternative embodiment alluded to above in which the roles of bed 30 and wall module 32 are reversed. However, like operation 200, operation 300 begins with power plug 180 of bed 30 being plugged into receptacle 136 of wall module 32 as indicated by an AC PLUG IN arrow 302. The plug detector 132 of wall module 32, as contemplated in connection with operation 300, can be any type of plug detector including any of those discussed below in connection with FIGS. 14-17. In response to wall module 32 detecting the power cord 144 of bed being plugged into receptacle 136, a wall module uptime timer is started as indicated at a block 304 labeled PLUG IN SENSED, UPTIME TIMER STARTED. In alternative embodiments, the timer of wall module 32 associated with block 304 of FIG. 6B is started in response to detection of an RFID tag or near field communication (NFC) tag attached to plug 180.

As noted above, bed 30 also includes circuitry, such as current sense circuitry, that detects current flowing in power cord 144 due to plug 180 being connected to a power receptacle. In response to bed 30 detecting that power is received via power cord 144, bed 30 starts a bed uptime timer as indicated at a block 306 labeled PLUG IN SENSED, UPTIME TIMER STARTED. One of the uptime timers of blocks 304, 306 may arbitrarily be referred to as the "first uptime timer" or "first timer" herein. The other of the uptime times of blocks 304, 306 may arbitrarily be referred to as the "second uptime timer" or "second timer" herein. In general, the adjectives "first" and "second" are simply indicating which timer is mentioned first in any given scenario or embodiment and which is mentioned second. The discussion above of operation 200 of FIG. 6A with regard to the use of software timers or hardware timers as the uptime timers of bed 30 and wall module 32 is equally applicable to operation 300 of FIG. 6B and so is not repeated.

After wall module 32 senses AC PLUG IN 302 at block 304, a first BT advertisement including the wall module uptime as measured by the timer of wall module 32 is transmitted by BT transceiver 122 of wall module 32 to BT transceiver 106 of bed 30 as indicated by a BT ADVERTISEMENT (W/UPTIME) arrow 308. Thereafter, wall module 32 updates its uptime as indicated at a first UPDATE UPTIME block 310. BT transceiver 122 of wall module 32 then transmits a second BT advertisement including the updated uptime of block 310 as indicated by a BT ADVERTISEMENT (W/UPTIME) arrow 312. This process may repeat one or more additional times as indicated by UPDATE UPTIME block 314 and arrow 316 in FIG. 6B.

In response to receiving one or more of BT advertisements 308, 312, 316 with respective uptimes of wall module 32, the BT transceiver 106 of bed 30 is readied for BT communications as indicated by a BT RADIO READY block 318 in FIG. 6B. Prior to sending any BT communications, microprocessor 102 of communication board 94 sends an uptime query message to microprocessor 96 of MCB 92 to obtain the current uptime value of bed 30 as indicated by a FETCH UPTIME FROM MCB block 320. The microprocessor 96 of MCB 92 calculates or otherwise obtains the current uptime of bed 30 in response to receiving the uptime query message from microprocessor 102 and replies with the calculated or obtained current uptime. Thereafter, BT radio 106 of bed 30 makes a series of BT scans, as indicated by BT SCAN arrows 322 in FIG. 6B, to listen for further BT advertisements from wall module 32 or to precipitate further BT advertisements from wall module 32 via query messages. Bed 30 then receipt by BT radio 122 of module 32.

When ready, the microprocessor 102 of communication board 94 of bed 30 compares the uptime received in one or more of the BT advertisement messages 308, 312, 316 from wall module 32 with the elapsed time of the internal timer of the bed 30 as indicated at an UPTIME COMPARED WITH INTERNAL TIMER block 324 of FIG. 6B. If the uptime received from wall module 32 in one or more of messages 308, 312, 316 matches the elapsed uptime of the bed timer or, in some embodiments, is within a tolerance range of the elapsed uptime of the bed timer as indicated by an IF UPTIME IN RANGE block 326, then BT transceiver 106 of bed 30 sends a pairing message to BT transceiver 122 of wall module 32 as indicated by a PAIR arrow 328 which results in the wall module 32 and bed 30 becoming paired for subsequent communications of wireless data and messages over wireless communications link 34. The discussion above in connection with operation 200 of FIG. 6A regarding the manner in which light 184 of wall module 32 and GUI 38 of bed 30 may optionally be operated during the pairing process is equally applicable to process 300 of FIG. 6B and so, is not repeated.

As to the BT advertisements 308, 312, 316, the packet sent in the advertisements includes the MAC address of the wall module 32, which is either a public or randomized address. If the bed 30, as scanner, chooses to connect or pair with the wall module, as advertiser, then the wall module 32 becomes aware of the bed 30 through a connection request packet sent by the bed 30 (aka pairing message indicated by arrow 328) which, in some embodiments, includes the MAC address of bed 30. After the MAC addresses are exchanged between the wall module 32 and bed 30 in some embodiments, they are no longer used while bed 30 and wall module 32 are paired, but instead, sequence ID's and/or other protocol message headers are used to facilitate paired communications between bed 30 and wall module 32. As noted above, other information such as manufacture ID and product ID are included in BT advertisements and active BT scans, for example.

In connection with the number of scans and advertisements depicted in FIGS. 6A and 6B, it is noteworthy that Bluetooth Low Energy (BLE) is designed for low power. Hence, in typical uses, the BT radios of devices implementing BLE communications are turned on and off in intervals to conserve power. When advertising or scanning, these intervals can be programmatically configured depending on the power needs of the application. With regard to bed 30 and wall module 32 in the depicted embodiments, there are no power limitation concerns because both devices are plugged into AC power. Thus, the advertising and scanning intervals in operations 200, 300 are fairly short and aggressive to speed up discovery and connection times. Even so, multiple advertisements and scans are usually necessary because the scanner, when operating in a passive scan mode which is typical, may not be listening on the particular channel at the moment the advertiser is advertising on that channel.

For BT pairing using BLE, the "scanning window" and the "advertising window" have to overlap on the same channel at the same time for a discovery to occur. There are three advertising channels in use for BLE. Thus, while the BT advertisements and BT scans are shown as being separated in the swim lane diagrams of FIGS. 6A and 6B, it will be appreciated that, at some point in actual practice, the BT advertisements and BT scans will overlap to achieve successful BT pairing between the two devices. Just to be clear, in FIG. 6A, bed 30 is the advertiser and wall module 32 is the scanner and in FIG. 6B, bed 30 is the scanner and wall module 32 is the advertiser.

Figure 6C:
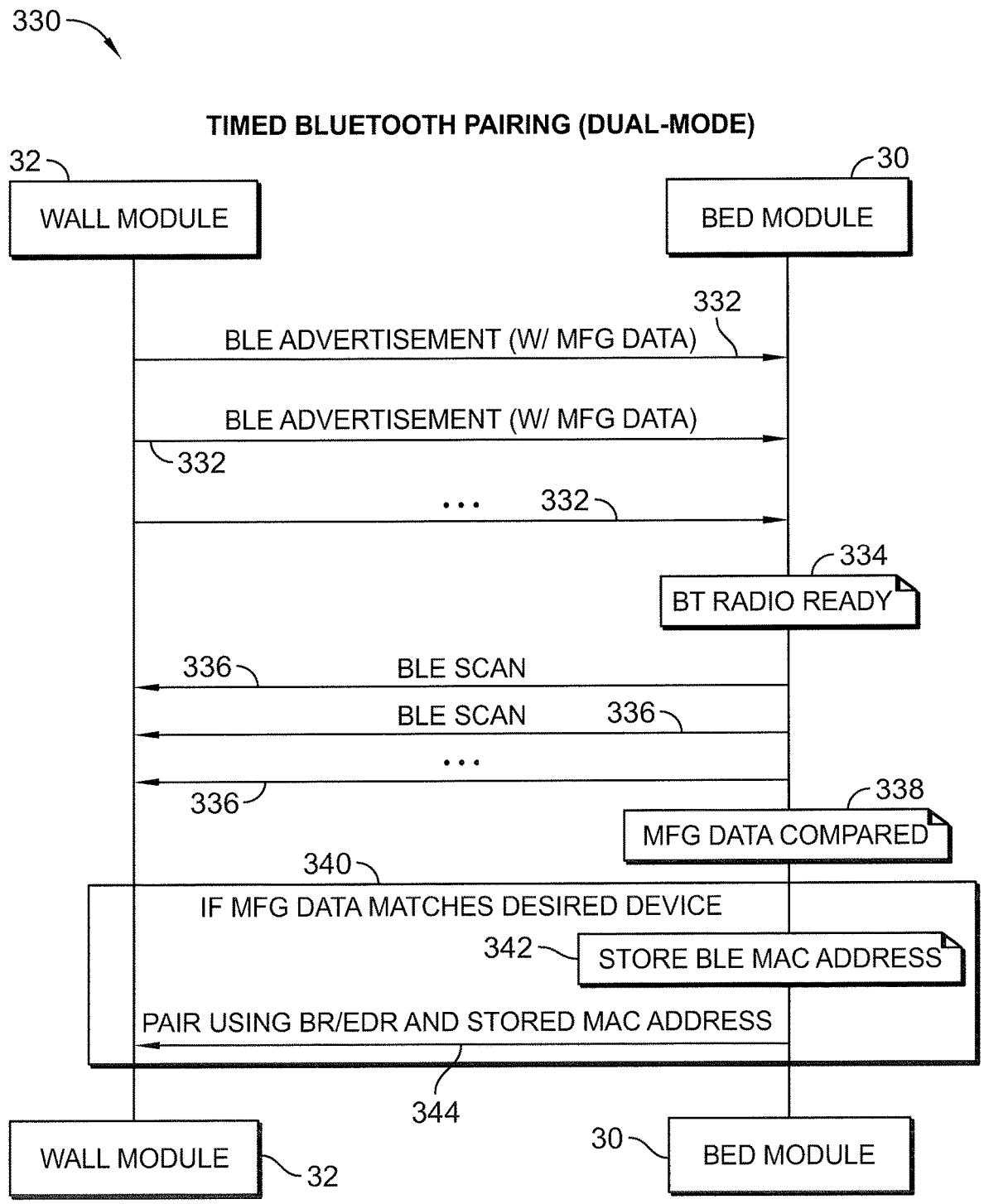
FIG. 6C is a swim lane diagram showing steps of an alternative wireless pairing operation in which the wall module transmits Bluetooth Low Energy (BLE) advertisements that include manufacturer (MFG) data, the bed makes a series of BLE scans after the bed BT radio is ready, the bed compares the received MFG data to stored MFG data and, if the MFG data matches, the bed stores a BLE media access control (MAC) address of the wall module in memory, the bed then switching from the BLE mode of communication to a BT Basic Rate/Enhanced Data Rate (BR/EDR) mode of communication in which wireless pairing occurs in response to the bed transmitting the MAC address of the wall module back to the wall module while in the BR/EDR mode of communication.

Referring now to FIG. 6C, a swim lane diagram of an alternative wireless pairing operation 330 is shown. Operation 330 is a dual-mode pairing operation in that some of the wireless communications between bed 30 and wall module 32 are Bluetooth Low Energy (BLE) communications and some are Bluetooth Basic Rate/Enhanced Data Rate (BT BR/EDR or just BR/EDR as used herein) communications. BR/EDR is sometimes referred to as Bluetooth Classic. Thus, the communications between bed 30 and wall module 32 include first and second modes, illustratively, a BLE mode and a BR/EDR mode. BLE provides advertising fields for manufacturer specific data which can be programmed at the discretion of a manufacturer. However, BLE connections are intended for short bursts of data over long intervals while BT devices are paired. Thus, BLE is not ideal for streaming audio or large amounts of data. This is by design to conserve power usage.

On the other hand, BR/EDR is designed for continuous connections including audio. However, the BR/EDR inquiry and scan procedure is not as flexible as BLE and thus, BR/EDR pairing connections need to be made based on advertised universally unique identifier (UUID) profiles instead of manufacturer provided data. To take advantage of BLE's advertising flexibility and BR/EDR's data throughput, a dual-mode approach is contemplated herein in connection with operation 330. Dual-mode Bluetooth devices are capable of communicating with both BLE and BR/EDR devices.

According to operation 330, wall module 32 transmits Bluetooth Low Energy (BLE) advertisements 332 that include manufacturer (MFG) data, such as a manufacturer ID which could be a manufacturer companies' UUID if desired, and/or a specific device type. In some embodiments, the BLE advertisements 332 are transmitted periodically by module 32 when in a discoverable mode, regardless of whether any bed 30 is present in the patient room or otherwise within communication range of wall module 32. In other embodiments, the BLE advertisements 332 begin upon detection of plug-in of bed 30 as described elsewhere herein. In some embodiments, BLE advertisements 332 also include the uptime as determined by wall module 32 in the manners described above in connection with FIGS. 6A and 6B. In BLE discoverable mode, wall module 32 is also able to connect using BR/EDR if such BR/EDR communications are received by wall module 32.

After bed 30 is plugged in to receive power, the BT radio 106 is readied for communications as indicated at BT RADIO READY block 334 and then proceeds to make a series of BLE scans 336 to listen for BLE advertisements 332. Upon detection of a BLE advertisement 332 during one of the BLE scans 336, the bed 30 compares the manufacturer data included in the detected BLE advertisement 332 with manufacturer data stored in bed 30 as indicated by a MFG DATA COMPARED block 338. For example, microprocessor 102 of communication board 94 makes the comparison and the stored manufacturer data is resident in memory 104 in some embodiments. In other embodiments, microprocessor 96 of MCB 92 makes the comparison and the stored manufacturer data is resident in memory 98. This is not to rule out the possibility that microprocessor 96 makes the comparison based on the stored manufacturer data being resident in memory 104 or the possibility that microprocessor 102 makes the comparison based on the stored manufacturer data being resident in memory 98.

Still referring to FIG. 6C, if the comparison of manufacturer data matches as indicated at block 340, the bed 30 proceeds to store a BLE media access control (MAC) address of the wall module 32 in memory (e.g., memory 98 or memory 104) as indicated at a STORE BLE MAC ADDRESS block 342. In some embodiments, bed 30 also determines an uptime in one of the same manners as described above in connection with FIGS. 6A and 6B. In such embodiments, the bed uptime is compared to the wall module uptime and if the uptimes match, within a threshold amount of time for example, then operation 330 proceeds to block 342.

After the BLE MAC address is stored at block 342, the bed 30 then switches from the BLE mode of communication to the BR/EDR mode of communication in which wireless pairing occurs in response to bed 30 transmitting a BR/EDR packet including the MAC address of wall module 32 back to wall module 32 as indicated by an arrow 344 labeled as PAIR USING BR/EDR AND STORED MAC ADDRESS. After bed 30 and wall module 32 are paired, the subsequent BT communications 34 therebetween are made according to the BR/EDR protocol, but this is not to say that BLE communications may not occur over data link 34, if desired. For example, packets of bed status data and alert/alarm data may be transmitted from bed 30 to wall module 32 according to the BLE protocol and audio communications may be transmitted between the bed 30 and wall module 32 according to the BR/EDR protocol.

According to the present disclosure, bed 30 implements a timer in some embodiments so that BLE scans 336 are made for only a threshold period of time after plug-in and/or after the BT radio 106 begins scanning, such as 5 seconds, 10 seconds, or 30 seconds, just to give a few arbitrary examples. If an advertisement 332 from wall module 32 is not detected within the threshold of period of time, then bed 30 stops scanning. In some embodiments, in which wall module 32 senses plug-in of bed 30, the BLE advertisements 332 are only transmitted during a threshold period of time, such as 5 seconds, 10 seconds, or 30 seconds, just to give a few arbitrary examples. The time threshold implemented by wall module 32 for sending advertisements 332 may or may not be the same time threshold used by bed 30. After the wall module time threshold expires, advertisements 332 are no longer sent.

Optionally, after bed 30 stops scanning due to a time out (e.g., the scanning time threshold becoming expired), a message appears on GUI 38 for a period of time, such as for 10 seconds just to give one arbitrary example, indicating that Bluetooth pairing did not occur. Furthermore, after wall module 32 and bed 30 are paired, wall module 32 stops transmitting advertisements 332 and bed 30 stops making scans 336. This prevents other beds 30 within the communication range of wall module 32 from receiving advertisements 332 and attempting to pair with wall module 32 after a pairing has already been made and not yet terminated by wall module 32 as described below. In some embodiments, after wall module 32 terminates the pairing with bed 30, as described below, wall module 32 begins transmission of advertisements 332 so as to be in discoverable mode for the next bed 30 (or the same bed 30 if it is unplugged and then plugged back in without having left the room). In other embodiments, after wall module 32 terminates pairing with bed 30, wall module 32 does not begin transmission of advertisements 332 until the next plug-in is detected by wall module 32.

Figure 6D:
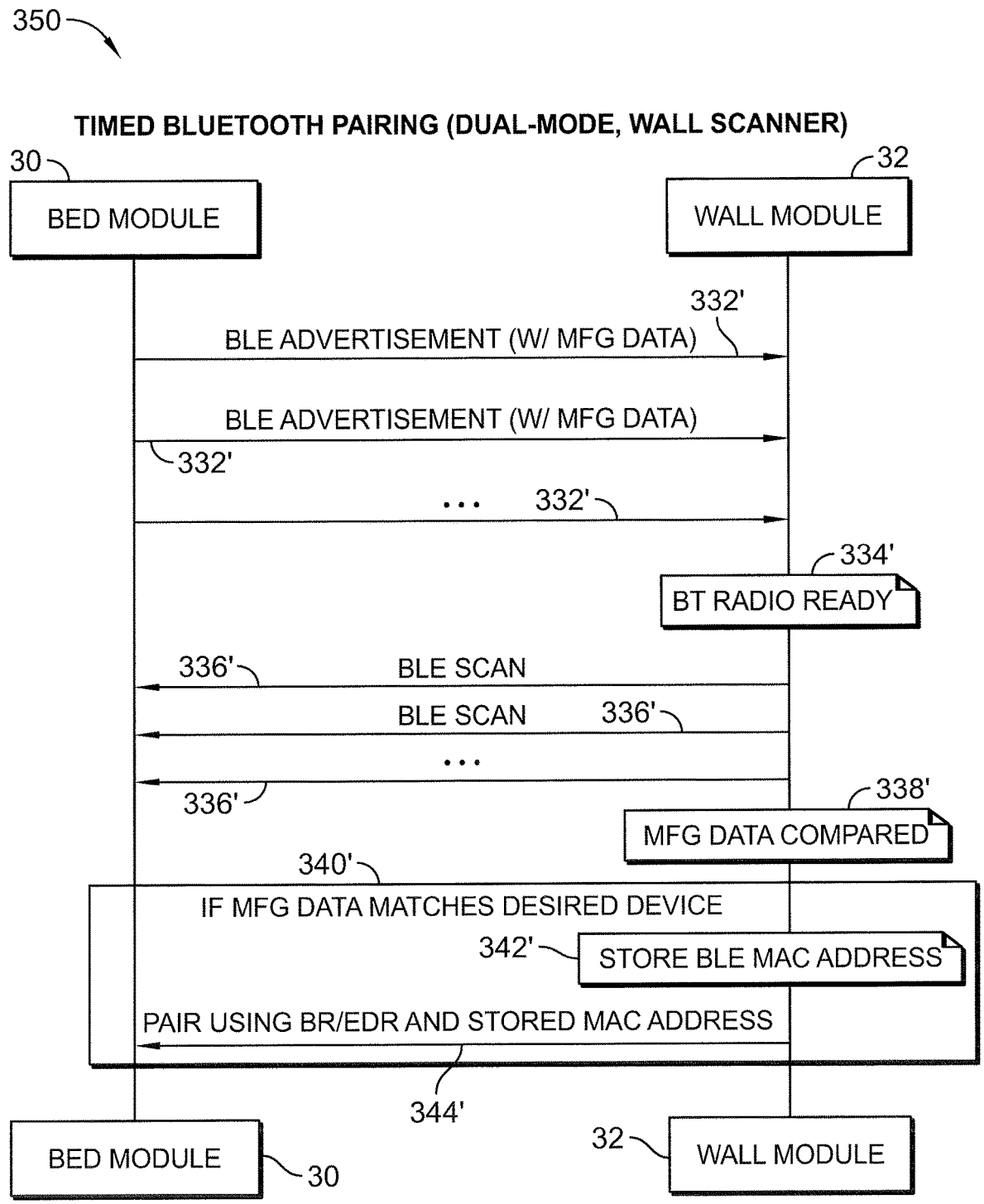
FIG. 6D is a swim lane diagram showing steps of another alternative wireless pairing operation in which the bed transmits Bluetooth Low Energy (BLE) advertisements that include manufacturer (MFG) data, the wall module makes a series of BLE scans after the wall module BT radio is ready, the wall module compares the received MFG data to stored MFG data and, if the MFG data matches, the wall module stores a BLE MAC address of the bed in memory, the wall module then switching from the BLE mode of communication to the BR/EDR mode of communication in which wireless pairing occurs in response to the wall module transmitting the MAC address of the bed back to the bed while in the BR/EDR mode of communication.

Referring now to FIG. 6D, a swim lane diagram of another alternative wireless pairing operation 350 is shown. Like operation 330, operation 350 is a dual-mode pairing operation in that some of the wireless communications between bed 30 and wall module 32 are BLE communications and some are BR/EDR communications. However, in FIG. 6D, the roles of bed 30 and wall module 32 as scanner and advertiser are reversed as compared to the operation 330 of FIG. 6C. That is, in FIG. 6C, wall module 32 is the advertiser and bed 30 is in the scanner, whereas, in FIG. 6D, bed 30 is the advertiser and wall module 32 is the scanner. Due to the similarities between FIGS. 6C and 6D, the same reference numbers are used in FIG. 6D that were using in FIG. 6C, but a prime symbol is added to the reference numbers in FIG. 6D.

In operation 350, the communications between bed 30 and wall module 32 include a BLE mode and a BR/EDR mode. As such, operation 350 also takes advantage of BLE's advertising flexibility and BR/EDR's data throughput. Much of the discussion above relating to operation 330 of FIG. 6C is equally applicable to operation 350 of FIG. 6D and is not repeated, although the discussion below of operation 350 may be somewhat redundant to the discussion of operation 330. In other words, the discussion below of operation 350 attempts to focus on the differences between operations 330, 350.

According to operation 350, bed 30 transmits BLE advertisements 332' that include manufacturer data. In some embodiments, the BLE advertisements 332' are transmitted periodically by bed 30 when in a discoverable mode which occurs after bed 30 has been plugged into AC power, regardless of whether any wall module 32 is present in the patient room. In some embodiments, BLE advertisements 332' also include the uptime as determined by bed 30 in the manners described above in connection with FIGS. 6A and 6B. In BLE discoverable mode, bed 30 is also able to connect using BR/EDR if such BR/EDR communications are received by bed 30.

After wall module detects that bed 30 has been plugged in to receive power, the BT radio 122 of wall module 32 is readied for communications as indicated at BT RADIO READY block 334' and then proceeds to make a series of BLE scans 336' to listen for BLE advertisements 332'. Thus, prior to plug-in detection by wall module 32, no BLE scans are made by wall module 32. This prevents inadvertent pairing with any beds 30 that have not been plugged in to outlets associated with module 32.

Upon detection of a BLE advertisement 332' during one of the BLE scans 336', the wall module 32 compares the manufacturer data included in the detected BLE advertisement 332' with manufacturer data stored in wall module 32 as indicated by a MFG DATA COMPARED block 338'. Thus, microprocessor 116 of SOM 114 makes the comparison and the stored manufacturer data is resident in memory 118 of wall module 32.

Still referring to FIG. 6D, if the comparison of manufacturer data matches as indicated at block 340', the wall module 32 proceeds to store a MAC address of bed 30 in memory 118 as indicated at a STORE BLE MAC ADDRESS block 342'. In some embodiments, wall module 32 also determines an uptime in one of the same manners as described above in connection with FIGS. 6A and 6B. In such embodiments, the wall module uptime is compared to the bed uptime and if the uptimes match, within a threshold amount of time for example, the operation 350 proceeds to block 342'.

After the BLE MAC address is stored at block 342', the wall module 32 then switches from the BLE mode of communication to the BR/EDR mode of communication in which wireless pairing occurs in response to wall module 32 transmitting a BR/EDR packet including the MAC address of bed 30 back to bed 30 as indicated by an arrow 344' labeled as PAIR USING BR/EDR AND STORED MAC ADDRESS. After bed 30 and wall module 32 are paired in operation 350, the subsequent BT communications 34 therebetween are made in any of the manners described above in connection with operation 330.

According to the present disclosure, wall module 32 implements a timer in some embodiments so that BLE scans 336' are made for only a threshold period of time after plug-in is detected by wall module 32 and/or after the BT radio 122 begins scanning, such as 5 seconds, 10 seconds, or 30 seconds, just to give a few arbitrary examples. If an advertisement 332' from bed 30 is not detected within the threshold of period of time, then wall module 32 stops scanning. In some embodiments, after bed 30 senses plug-in to AC power, the BLE advertisements 332' are only transmitted during a threshold period of time, such as 5 seconds, 10 seconds, or 30 seconds, just to give a few arbitrary examples. The time threshold implemented by bed 30 for sending advertisements 332' may or may not be the same time threshold used by wall module 32. After the bed time threshold expires, advertisements 332' are no longer sent.

Optionally, after wall module 32 stops scanning due to a time out (e.g., the scanning time threshold becoming expired), an indicator on wall module 32, such as light 184, is illuminated for a period of time, such as for 10 seconds just to give one arbitrary example, indicating that Bluetooth pairing did not occur. Furthermore, after wall module 32 and bed 30 are paired, bed 30 stops transmitting advertisements 332' and wall module 32 stops making scans 336'. This prevents other wall modules 32 within the communication range of bed 30 from receiving advertisements 332' and attempting to pair with bed 30 after a pairing has already been made and not yet terminated by wall module 32 as described below. After wall module 32 terminates the pairing with bed 30, as described below, wall module 32 does not begin making any scans 336' until another plug-in is detected by wall module 32.

According to the present disclosure, wall module 32 controls when the pairing between wall module 32 and medical device 30 is to be terminated. For example, if plug detector 132 of wall module 32 detects that plug 180 of power cord 144 is no longer plugged into duplex receptacle 132, a wireless pairing termination signal is sent by Bluetooth transceiver 122 of wall module 32 to Bluetooth transceiver 106 of bed 30 to terminate the Bluetooth pairing. Alternatively or additionally, if bed status data received by wall module 32 from bed 30 indicates that casters 82 of bed 30 have been released or unbraked, then the wireless pairing termination signal is sent by Bluetooth transceiver 122 of wall module 32 to Bluetooth transceiver 106 of bed 30 to terminate the Bluetooth pairing. In some embodiments, both unplugging of power cord 144 from wall module 32 and releasing of the caster brakes of bed 30 is required before the pairing termination signal is sent by wall module 32 to bed 30. This manner of control of wireless pairing termination is the opposite arrangement of that described in U.S. Pat. No. 10,085,905 in which a controller of the bed determines when a disconnect signal should be sent to a wall unit to terminate the pairing therebetween. However, in alternative embodiments contemplated by the present disclosure, bed 30 initiates unpairing from wall module 32 based on the unpairing criteria discussed above.

Optionally, the wireless pairing termination signal is not sent by Bluetooth transceiver 122 until a threshold amount of time elapses (e.g., 10 seconds or 30 seconds just to give a couple arbitrary examples). Thus, if a caregiver has released the casters 82 in order to reposition bed 30 by a small amount in the patient room, or if the power plug 180 is inadvertently removed from receptacle 136 of wall module 32, then the bed 30 and wall module 32 remain paired if the casters are braked or the power plug 180 is plugged back into receptacle 136, respectively, during the threshold amount of time. After the wireless pairing between bed 30 and wall module 32 is terminated, no more wireless data and/or messages are transmitted from Bluetooth transceiver 106 of bed 30 over wireless communications link 34. However, in some embodiments, data and/or messages are still able to be transmitted from WiFi transceiver 100 of bed 30 via wireless communications link 56 to one or more WAP's 52 of system 20. Such WiFi data and/or messages may be transmitted from bed 30 while bed 30 is being moved from one location in healthcare facility 22 to another. A battery onboard bed 30 is used to provide the power to MCB 92 and WiFi transceiver 100 to allow for such wireless communications in such embodiments.

Figure 7:
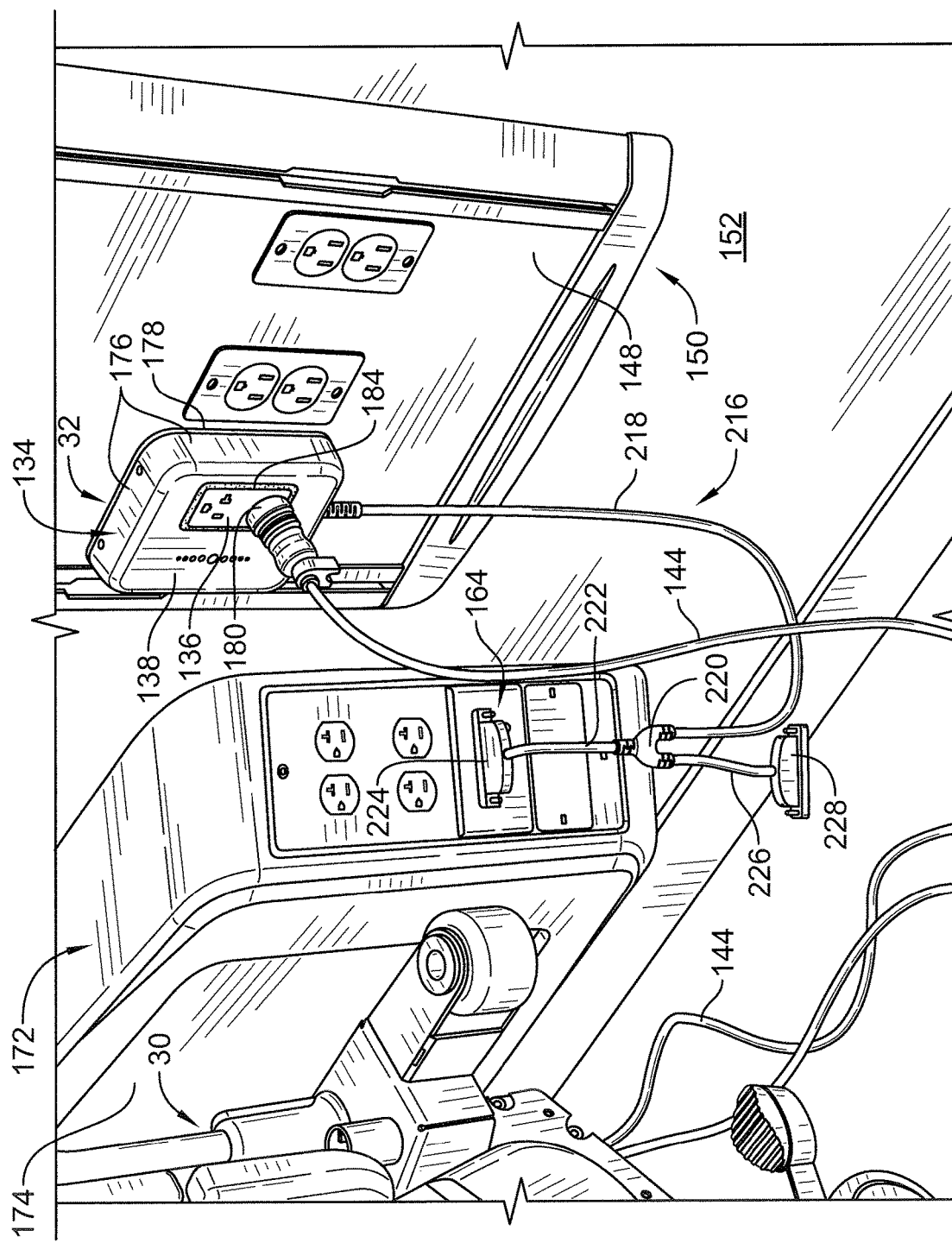
FIG. 7 is a perspective view, similar to FIG. 5, but showing a Y-cable extending from a bottom of the wall module, the Y-cable having a first nurse call connector coupled to the nurse call port of the ASBC and the Y-cable having a second nurse call connector that is configured for coupling to a mating nurse call connector at an end of a nurse call cable extending from the patient bed.
Figure 8:
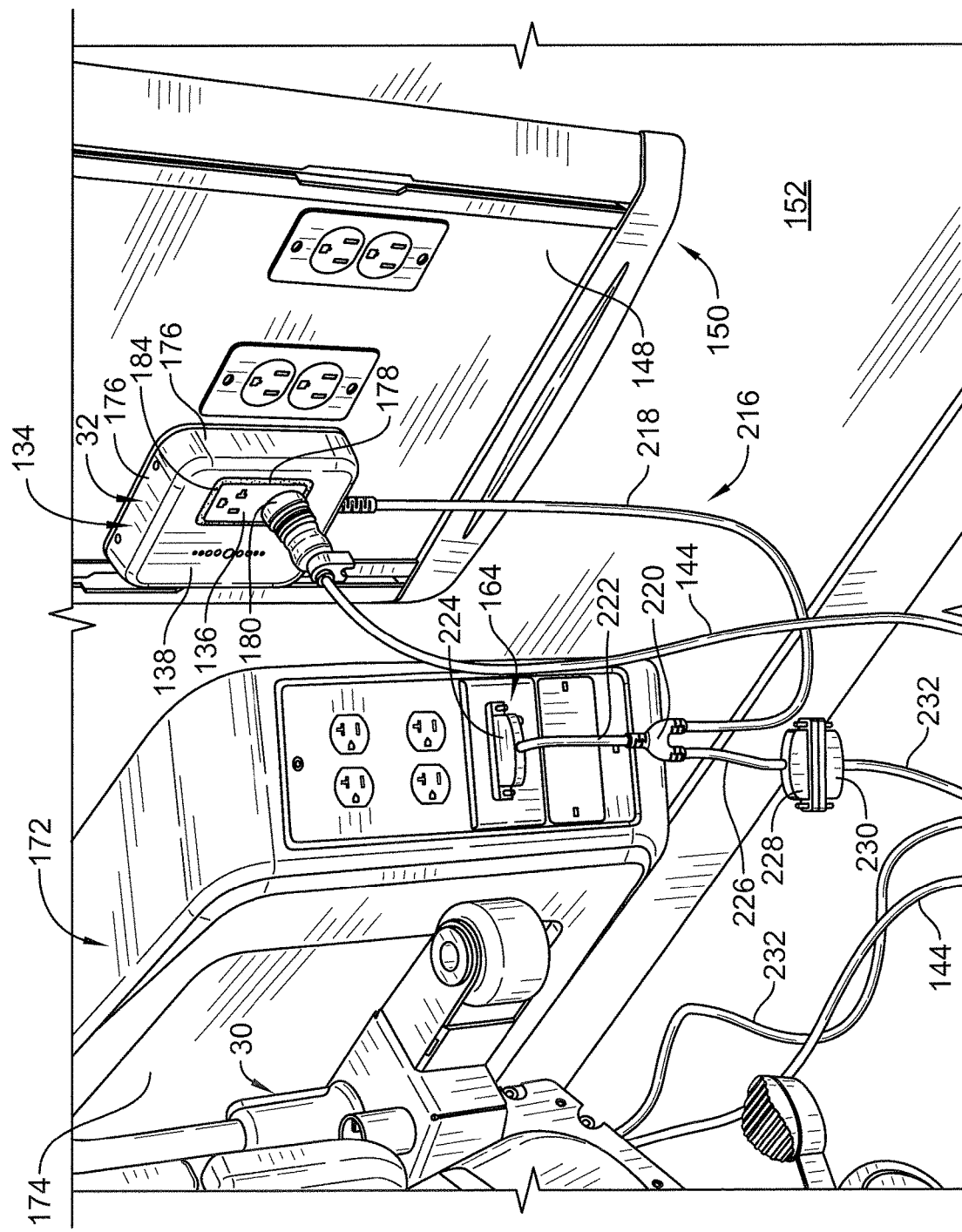
FIG. 8 is a perspective view, similar to FIG. 7, in which the second nurse call connector of the Y-cable is connected to the nurse call able extending from the patient bed such that wired data communication is established between the patient bed and the wall module and such that wired data communication is established between the patient bed and the ASBC.

Referring now to FIG. 7, an embodiment of wall module 32 is shown in which a Y-cable 216 extends from a bottom of wall module 32 in lieu of cable 44. Y-cable 216 includes a main branch or segment 218 extending between wall module 32 and a Y-junction 220 of cable 216, a first auxiliary branch or segment 222 extending from Y-junction 220 and terminating at a first nurse call connector 224 which is configured to couple to nurse call port 126 of ASBC 164, and a second auxiliary branch or segment 226 extending from Y-junction 220 and terminating at a second nurse call connector 228. Second nurse call connector 228 is configured to couple to a third nurse call connector 230 located at an end of a nurse call cable 232 that extends from bed 30 as shown in FIG. 8. Thus, connector 228 at the end of auxiliary branch 226 of Y-cable 216 allows for wired connection of communication board 94 of bed 30 to both ASBC 164 and wall module 32 when nurse call connector 230 is coupled to nurse call connector 228.

In some embodiments, when connector 228 of Y-cable 216 is coupled to connector 230 of cable 232, Bluetooth communications between wall module 32 and bed 30 are not established or, if already established, are suspended. Thus, wired communications over cable 216 between bed 30 and wall module 32 takes precedence over the wireless communications between bed 30 and wall module 32 over wireless communications link 34. As noted above, wireless WiFi communications between WiFi transceiver 120 of wall module 32 and one or more WAP's 52 via wireless communications link 54 are still enabled even when wall module 32 has a wired communication link, such as via cable 216, with bed 30.

Figure 9:
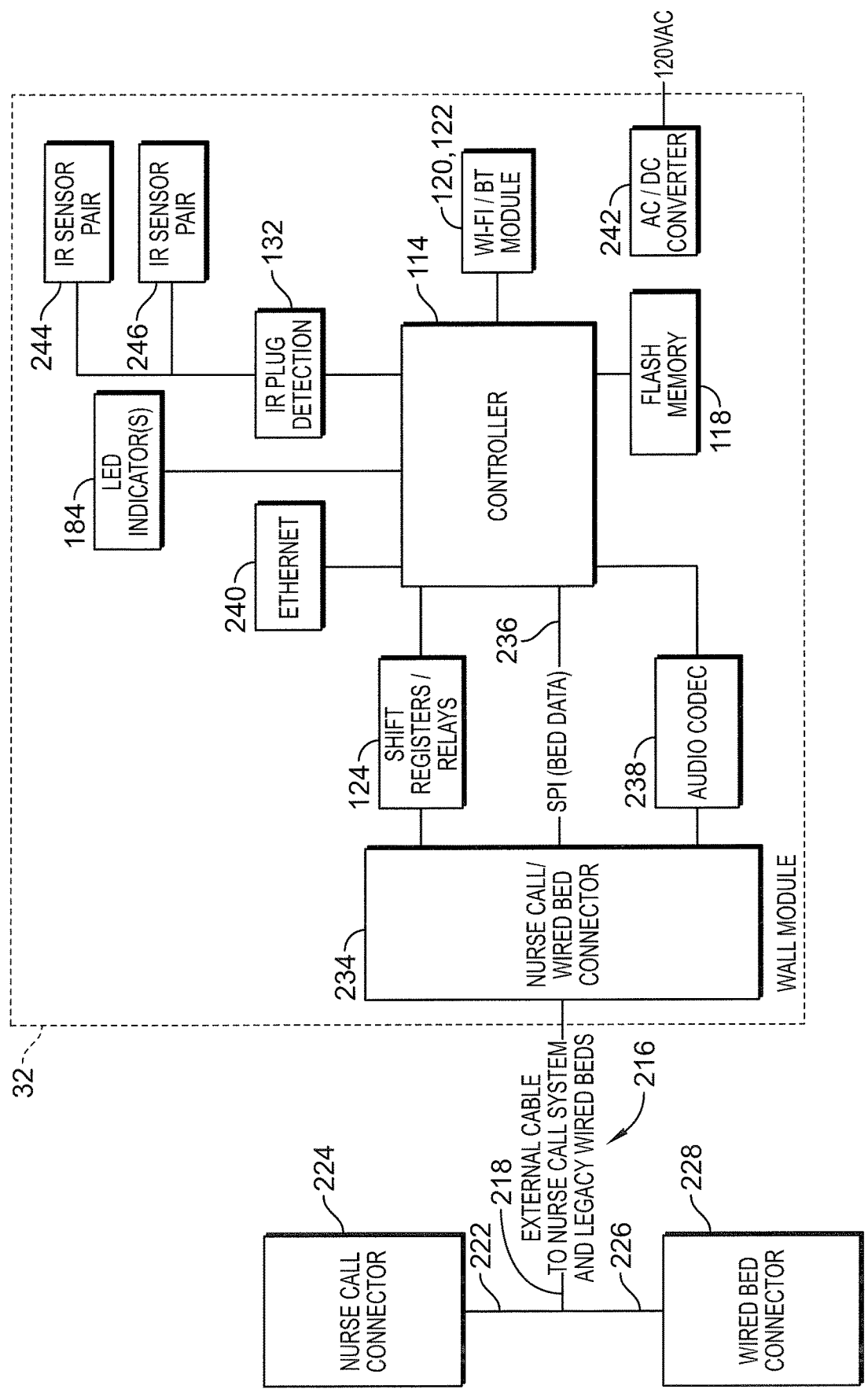
FIG. 9 is a diagrammatic view showing electrical componentry of the wall module and showing the Y-cable extending from the wall module, the electrical componentry including shift registers and/or relays, a Serial Peripheral Interface (SPI) line, and an audio codec that interconnect a controller of the wall unit with a nurse call/wired bed connector of the wall module.

Referring now to FIG. 9, a block diagram is provided and shows that an end of main branch 218 of Y-cable 216 is coupled to a nurse call/wired bed connector 234 within an interior region of wall module 32. Portions of SOM 114 of FIG. 2 are shown as separate blocks in FIG. 9. For example, a controller 114 in FIG. 9 includes the microprocessor 116 of SOM 114 whereas flash memory 118 and WiFi/BT module 120, 122 are shown as separate blocks. In other words, the memory 118 of SOM 114 is flash memory in some embodiments. Furthermore, the WiFi transceiver 120 and Bluetooth transceiver 122 are included in a single WiFi/BT module (labeled as WI-FI/BT MODULE 120, 122 in FIG. 9) in some embodiments. The single module 120, 122 includes, for example, a single antenna that is used for both WiFi and Bluetooth communications. Controller 114 determines whether the transmissions from module 120, 122 are WiFi communications or Bluetooth communications in such embodiments.

Still referring to FIG. 9, a shift registers/relays block 124, a Serial Peripheral Interface (SPI) line 236, and an audio coder-decoder (codec) block 238 interconnect controller 114 and the nurse call/wired bed connector 234. In some embodiments, connector 234 is a 37-pin connector similar to those described elsewhere herein. Thus, the on/off state of some pins of the 37-pin connector 234 are determined by the states of relays and some are determined by the states of shift registers. That is, not all pins of the 37-pin connector have a corresponding relay coupled thereto. SPI line 236 connects to multiple pins of the 37-pin connector in some embodiments. For example, SPI line 236 includes three wires or conductors connected to corresponding pins of connector 234 including a SPI clock wire, a SPI data out wire, and a SPI data in wire. Audio codec 238 includes various wires or conductors associated with audio signals originating from microphone 112 of bed 30 and audio signals being sent to speaker 110 of bed 30 from some other device such as nurse call master station 50.

In the illustrative FIG. 9 embodiment of wall module 32, an Ethernet port 240 is coupled to controller 114 and provides wall module 32 with the capability of being coupled to the facility network 60 by an Ethernet cable. Thus, Ethernet port 240 comprises an RJ-45 port in some embodiments. If an Ethernet cable is coupled to port 240 to provide a wired communications link with network 60, then WiFi communications via wireless communications link 54 are suspended or disabled. Thus, the wired connection to network 60 via Ethernet port 240 of wall module 32 takes precedence over the wireless communications link 54 with network 60.

As also shown in FIG. 9, wall module 32 includes an alternating current/direct current (AC/DC) converter 242 that receives 120 Volt AC (VAC) power via prongs 154 and/or prongs 158 of wall module 32 from outlet 156 and/or outlet 160, respectively, of duplex AC receptacle 146. AC/DC converter converts the 120 VAC power into one or more DC voltage levels (e.g. 5 V DC, 12 V DC, etc.) needed to power the various components of wall module 32. Plug detector 132 of FIG. 9 is labeled as infrared (IR) plug detection 132 and is coupled to a first IR sensor pair 244 and a second IR sensor pair 246. IR sensor pairs 244, 246 are discussed in further detail below in connection with FIG. 14.

Figure 10:
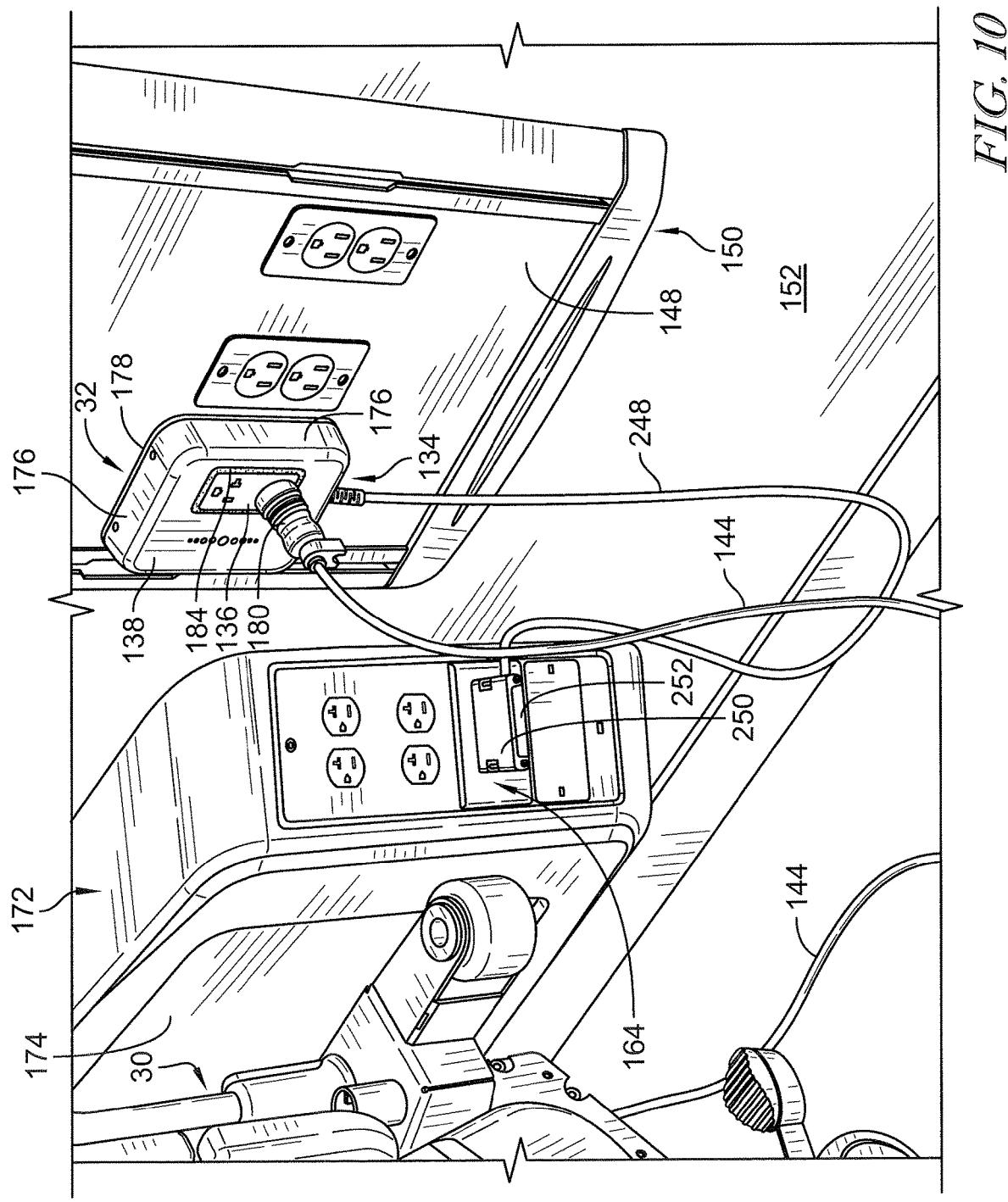
FIG. 10 is a perspective view, similar to FIG. 8, showing an alternative embodiment cable extending from a bottom of the wall module, the alternative embodiment cable terminating at a dual coupler nurse call connector, a first coupler of the dual coupler nurse call connector being configured to mate with the nurse call port of the ASBC, and a second coupler of the dual nurse call connector being configured to mate with the connector at the end of the nurse call cable (not shown in FIG. 10) extending from the bed.

Referring now to FIG. 10, an embodiment of wall module 32 is shown in which a T-cable 248 extends from a bottom of wall module 32 in lieu of cable 44 and in lieu of cable 216.

Figure 11:
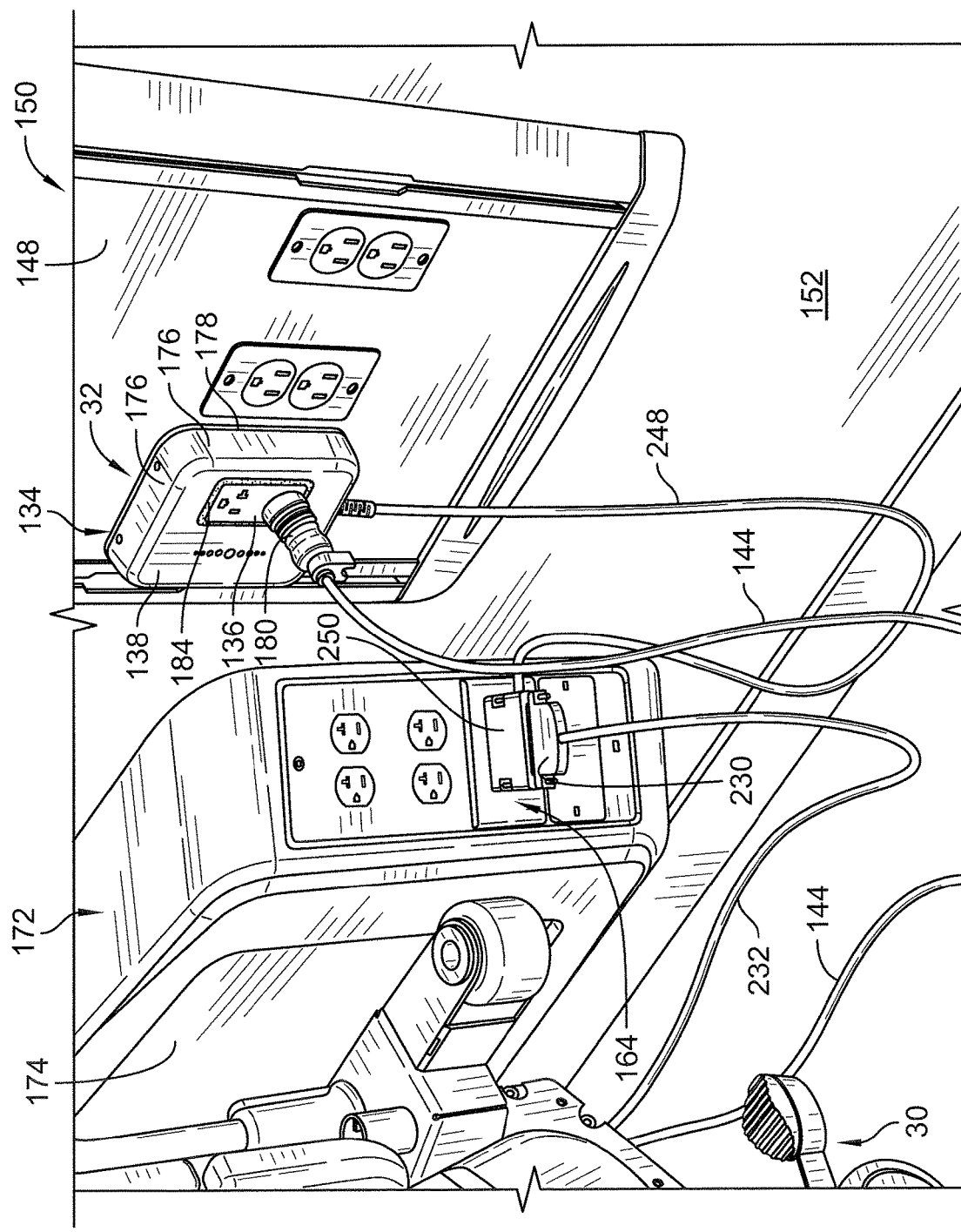
FIG. 11 is a perspective view, similar to FIG. 10, showing the connector at the end of the nurse call cable extending from the bed coupled to the second coupler of the dual nurse call connector, thereby to provide wired connectivity between the patient bed and the nurse call system.

T-cable 248 terminates at a connector body 250 having a first nurse call connector configured to couple to nurse call outlet 126 of ASBC 164 as shown in FIGS. 10 and 11 and having a second nurse call connector 252, shown in FIG. 10, configured to couple to nurse call connector 230 at the end of nurse call cable 232 extending from bed 30 as shown in FIG. 11. One end of T-cable 248 enters into a side of connector body 250 and the conductors or wires within cable 248 are routed to the respective pins of the first and second connectors of connector body 250. An opposite end of cable 248 couples to nurse call/wired bed connector 234 within the interior region of housing 134 of wall module 32 in the same manner that main branch 218 of cable 216 couples to connector 234 as discussed above. Thus, each of cables 216, 248 is configured for wired connection to both ASBC 164 and nurse call cable 232 of bed 30. However, instead of having separate auxiliary branches 222, 226 with respective nurse call connectors 224, 228 like Y-cable 216, connector body 250 of T-cable 248 provides a dual coupler nurse call connector configured to couple to nurse call port 126 of ASBC 164 and nurse call connector 230 of cable 232 of bed 30.

In some embodiments, when connector 252 of connector body 250 of T-cable 248 is coupled to connector 230 of cable 232, Bluetooth communications between wall module 32 and bed 30 are not established or, if already established, are suspended. Thus, wired communications over cable 248 between bed 30 and wall module 32 takes precedence over the wireless communications between bed 30 and wall module 32 over wireless communications link 34. As noted above, wireless WiFi communications between WiFi transceiver 120 of wall module 32 and one or more WAP's 52 via wireless communications link 54 are still enabled even when wall module 32 has a wired communication link, such as via cable 248, with bed 30.

Figure 12:
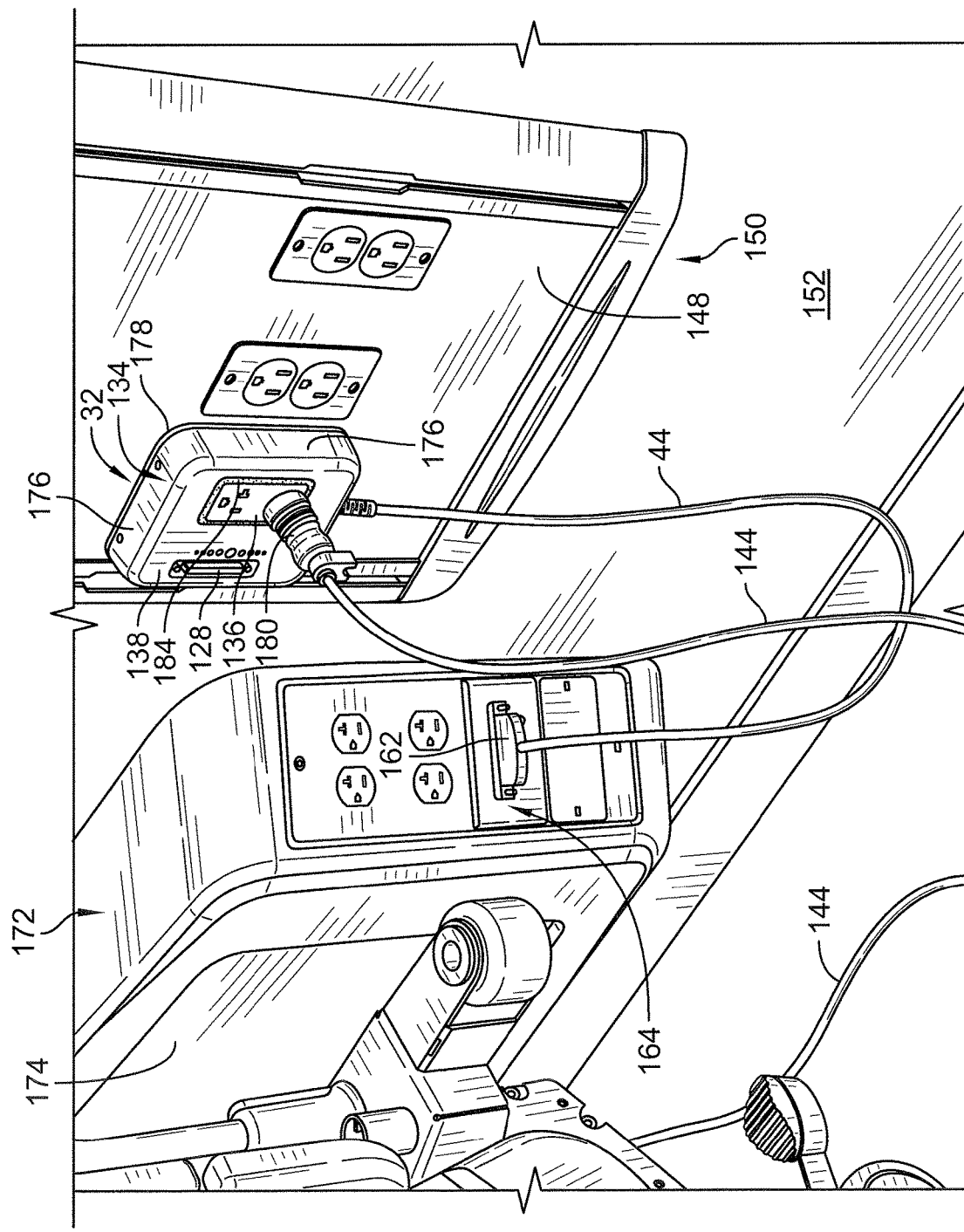
FIG. 12 is a perspective view, similar to FIG. 5, showing an alternative embodiment wall module having a nurse call connection port next to the duplex pair of AC outlets of the wall module, the nurse call connection port of the wall module being configured to mate with the connector at the end of the nurse call cable (not shown in FIG. 12) extending from the bed.
Figure 13:
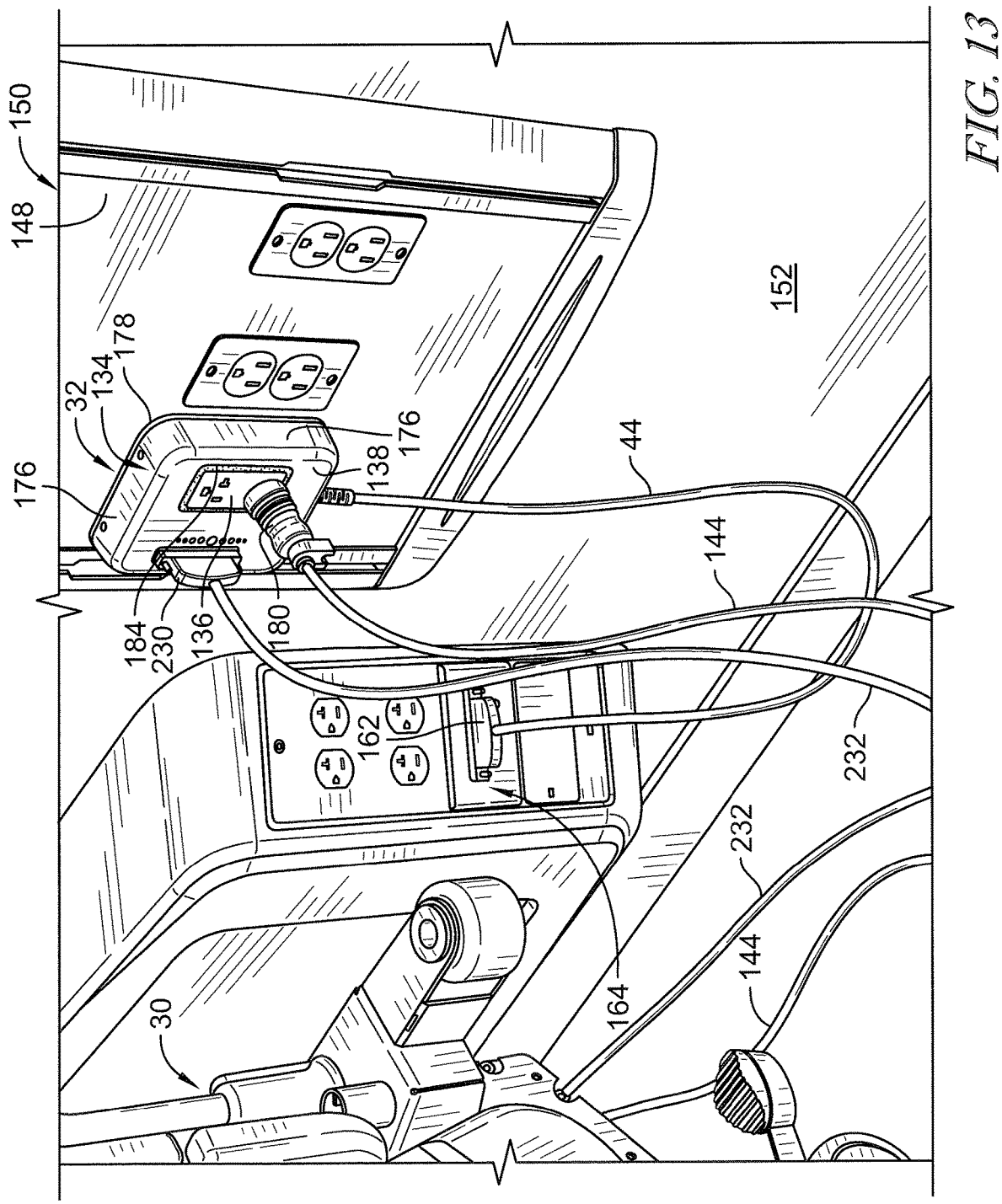
FIG. 13 is a perspective view, similar to FIG. 12, showing the connector at the end of the nurse call cable extending from the bed coupled to the nurse call connection port of the wall module, thereby to provide wired connectivity between the patient bed and the nurse call system via the wall module.

Referring now to FIG. 12, an embodiment of wall module 32 is shown in which nurse call connection port 128 is accessible on the front wall 138 of housing 134 next to the duplex AC outlet 136. Port 128 was discussed above in connection with FIG. 2. By way of recap, port 128 of module 32 allows for wired connectivity with bed 30. In particular, nurse call connection port 128 of wall module 32 is configured to mate with the connector 230 at the end of the nurse call cable 232 extending from the bed 30 as shown in FIG. 13. In the illustrative example, port 128 is a 37-pin connector having its long dimension oriented generally vertically.

As noted above, when cable 232 is coupled to port 128 of wall module 32, such as with connector 230 as shown in FIG. 13, Bluetooth communications between wall module 32 and bed 30 are not established or, if already established, are suspended. Thus, wired communications over cable 232 between bed 30 and wall module 32 takes precedence over the wireless communications between bed 30 and wall module 32 over wireless communications link 34. As noted above, wireless WiFi communications between WiFi transceiver 120 of wall module 32 and one or more WAP's 52 via wireless communications link 54 are still enabled even when wall module 32 has a wired communication link, such as via cable 232, with bed 30.

Figure 14:
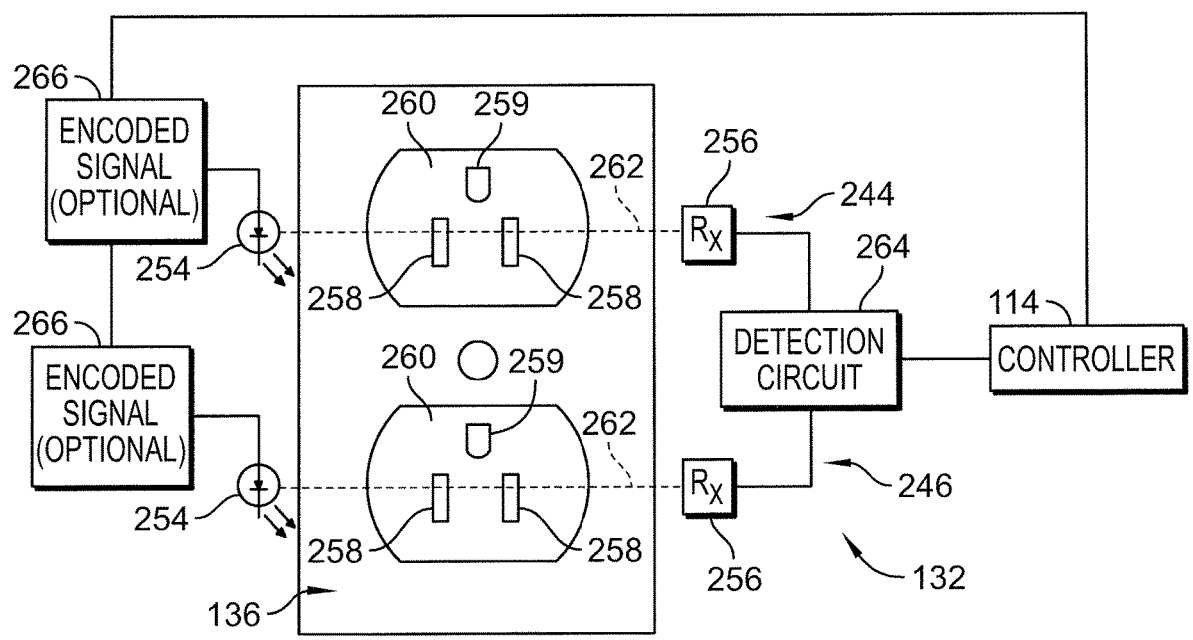
FIG. 14 is a diagrammatic view of a first embodiment of a plug detector for use in the wall module, the first embodiment of the plug detector including photo emitter/photo detector pairs that are generally horizontally aligned with power prong receivers of the respective outlets of the duplex AC outlet of the wall module.

Referring now to FIG. 14, a first embodiment of plug detector 132 for use in wall module 32 is shown. Plug detector 132 of FIG. 14 includes the IR sensor pairs 244, 246 referred to above in connection with FIG. 9. In particular, each IR sensor pair 244, 246 of the first embodiment of plug detector 132 includes a photo emitter 254 and a photo detector or receiver 256. The photo emitter 254 and photo detector 256 of each sensor pair 244, 246 are generally horizontally aligned with power prong receivers or openings 258 of the respective outlet 260 of the duplex AC outlet 136 of wall module 32. When power plug 180 of bed 30, or really any power plug for that matter, is not connected to either of outlets 260, an IR light beam 262 emitted by each photo emitter 254 is received by the respective horizontally aligned photo detector 256 as indicated diagrammatically in FIG. 14.

When power prongs 182 of power plug 180 are received in openings 258 of the upper or lower outlet 260 of receptacle 136, the light beam 262 of the respective sensor pair 244, 246 is blocked from reaching the respective photo receiver 256. The absence of the receipt of light beam 262 by either of photo receivers 256 is detected by a detection circuit 264 of plug detector 132. In some embodiments, detection circuit 264 includes one or more logic gates (e.g., OR gate, AND gate, etc.) having signals from photo detectors 256 as inputs and having an output coupled to SOM or controller 114. Detection circuit 264 may further include one or more amplifiers, filters, transistors, resistors, and other circuit elements in some embodiments. Optionally, controller 114 provides encoded signals to photo emitters 254 in some embodiments as indicated by blocks 266 in FIG. 14. For example, encoded signals 266 may include patterned light signals that are turned on and off periodically as commanded by controller 114 so that photo emitters 254 are not continuously emitting IR light.

It is contemplated by the present disclosure that a device which is not programmed to wirelessly pair with wall module 32 (referred to herein as a "non-pairable device") may be plugged into one of the upper or lower outlets 260 of receptacle 136 prior to a pairable device (e.g., a device such as bed 30 that is programmed for time-based wireless pairing with wall module 32) being plugged into the other of the upper and lower outlets 260 of receptacle 136. In such situations, one of IR sensor pairs 244, 246 detects the non-pairable device being plugged in and wall module 32 proceeds to transmit BT scans 192 in an attempt to pair with the non-pairable device. However, the non-pairable device does not respond with any BT advertisements having uptimes and so wall module 32 does not pair with the non-pairable device. Subsequently, when the pairable device 30 is plugged into the remaining outlet 260 of receptacle 136, wall module 32 again transmits BT scans 192 and proceeds to successfully pair with the pairable device 30 according to process 200 of FIG. 6A.

If the pairable device 30 is plugged into one of outlets 260 of receptacle 136 of wall module 32 of FIG. 14 prior to any other devices being plugged into the other of outlets 260, then one of IR sensor pairs 244, 246 detects the pairable device being plugged in and wall module 32 proceeds to pair with the pairable device according to process 200. Thereafter, if another device is plugged into the remaining outlet 260, wall module 32 does not transmit any BT scans 192 and does not make any attempt to pair with the second device because the wall module 32 is already paired with the first, pairable device. This is true even if the second device is also a pairable device. In other words, wall module 32 only wirelessly pairs with one pairable device, such as bed 30, at a time.

Figure 15:
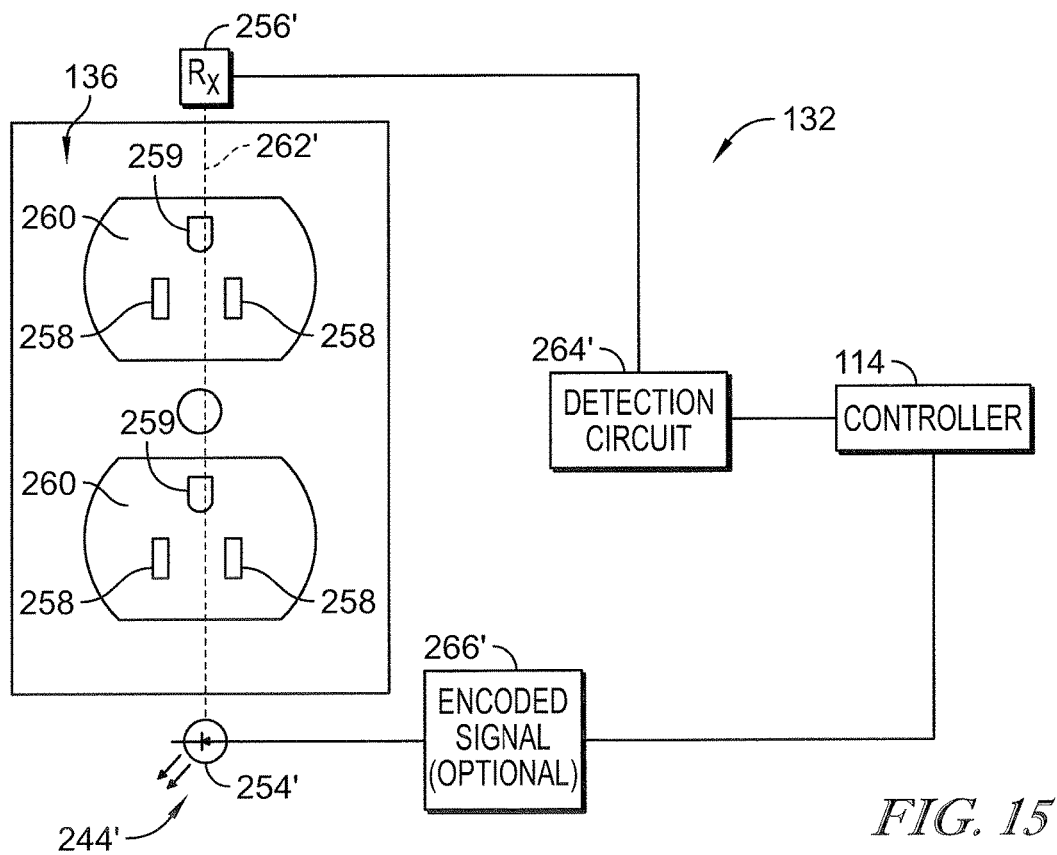
FIG. 15 is a diagrammatic view of a second embodiment of a plug detector for use in the wall module, the second embodiment of the plug detector including a photo emitter and a photo detector that are generally vertically aligned with ground prong receivers of the outlets of the duplex AC outlet of the wall module.

Referring now to FIG. 15, a second embodiment of plug detector 132 for use in wall module 32 is shown. Plug detector 132 of FIG. 15 includes a single IR sensor pair 244'. In particular, IR sensor pair 244' of the second embodiment of plug detector 132 includes a photo emitter 254' and a photo detector or receiver 256'. The photo emitter 254' and photo detector 256' of sensor pair 244' are generally vertically aligned with ground prong receivers or openings 259 of the respective outlet 260 of the duplex AC outlet 136 of wall module 32. When power plug 180 of bed 30, or really any power plug for that matter, is not connected to either of outlets 260, an IR light beam 262' emitted by photo emitter 254' is received by the vertically aligned photo detector 256' as indicated diagrammatically in FIG. 15.

When ground prong 182 of power plug 180 is received in either of openings 259 of the upper or lower outlet 260 of receptacle 136, the light beam 262' of the sensor pair 244' is blocked from reaching the photo receiver 256'. The absence of the receipt of light beam 262' by photo receiver 256' is detected by a detection circuit 264' of plug detector 132. In some embodiments, detection circuit 264' includes one or more amplifiers, filters, transistors, resistors, and other circuit elements. Optionally, controller 114 provides an encoded signal to photo emitter 254' in some embodiments as indicated by block 266' in FIG. 15. For example, encoded signal 266' may include a patterned light signal that is turned on and off periodically as commanded by controller 114 so that photo emitter 254' is not continuously emitting IR light.

As compared to plug detector 132 of FIG. 14 having two IR sensor pairs 244, 246, plug detector 132 of FIG. 15 has only one IR sensor pair 244' and therefore, has less circuit components which allows for reduced weight and reduced cost for wall module 32 as compared to the FIG. 14 embodiment. However, once light beam 262' is blocked by a ground prong of a first device being plugged into one of outlets 260 of receptacle 136, it is not possible for wall module 32 to detect a second device being plugged into the other of outlets 260 of receptacle 136 because light beam 262' has already been blocked by the ground prong of the first device being received in the corresponding ground opening 259. Thus, if wall module 32 has plug detector 132 of FIG. 15 included therein, then it is required that the pairable device, such as bed 30, be the first device that is plugged into wall module 32 in order for successful pairing between the pairable device 30 and the wall module 32 to occur. Thus, in response to light beam 262' becoming blocked due to a first device being plugged into receptacle 136, wall module 32 transmits BT scans 192 to begin the time-based wireless pairing process 200.

With regard to the embodiments of FIGS. 14 and 15, use of IR light beam 262, 262' can be replaced by other types of wireless signals between appropriate emitters and detectors in further embodiments. For example, other suitable source/detector pairs include use of radio frequency (RF) signals, including in the GHz region. In such embodiments an RF emitter and an RF detector is used. The presence of one or more of prongs 182 in the RF signal path interrupts the RF signal from reaching the RF detector.

With regard to the embodiment of FIG. 15, the housing 134 of wall module 32 containing the source/detector pairs 244' is configured so as to mitigate a number of exogenous environmental stimuli such as ambient room light and sunlight from a window by situating the source or emitter 254' on a bottom portion of front wall 138 which serves as an AC cover plate for receptacle 136, and emitting IR light beam 262' upwardly towards the detector 256' to eliminate the effects of ambient lighting and sunlight. If desired, the detector 256' may be recessed even further in a well provided at a top portion of front wall 138 to prevent reflections from the floor from entering the detector space and causing spurious indications.

This same approach may be used by physical location and configuration of the source/detector pair 244' to mitigate false triggering that may potentially be caused by objects such as bed sheets, cords, wires, tubes and any other obstructions that may reflect light into the signal path of light beam 262' between the source/detector pair 244' by recessing the signal path 262' into the interior region of wall module 32. In further embodiments, the light beam 262' may be angled with respect to the floor of the patient room (e.g., may be inclined with respect to horizontal and vertical) to further isolate the beam path from outside object reflections which might tend to interfere with the detection path and create a spurious connection indication. For example, in a variant FIG. 15 embodiment, light beam 262' or multiple light beams 262' are emitted diagonally across the AC receptacle 136 such that the beam(s) 262' cross through the left opening 258 of the upper outlet 260 and the right opening 258 of the lower outlet. Alternatively, such a diagonally emitted light beam 262' or light beams 262' cross through the right opening 258 of the upper outlet 260 and the left opening 258 of the lower outlet.

A similar approach using diagonal light beams 262 may be implemented in connection with variants of the FIG. 14 embodiment. For example, detector pairs 244 may have their emitters 254 and detectors 256 located so that light beams 262 cross through opening 259 and one of openings 258 of the respective upper and lower outlets 260. In such embodiments, having the emitter 254 of each pair 244, 246 lower in elevation than the detector 256, such that the emitters 254 emit light upwardly at an angle, will have a tendency to more adequately eliminate the effects of ambient lighting, sunlight, and light reflected by objects.

Use of IR detector pairs 244, 244', 246 in the embodiments of FIGS. 14 and 15, as the case may be, has the advantage of not putting any restrictions on the size or shape of the AC plug 180 and/or receptacle 136, which are not uniform throughout the medical industry even within the United States. Thus, the embodiments of FIGS. 14 and 15 allow for the detection of the insertion of any AC plug that will fit into the connection contacts of the corresponding receptacle without restricting the physical dimensions of the AC plug, thereby providing for reliable detection of AC plug connection.

Additionally, the light or signal frequency of light beams 262, 262' should be chosen such that the optical characteristics of the AC plug 180 and prongs 182 will not affect the operation of these embodiments of plug detectors 132. There are AC plugs that are optically transparent in the visible spectrum for humans, but the detection of the AC plug can still be guaranteed by proper design of the detection signal path electronics.

Another method of mitigating the effects of ambient light and other light in connection with the embodiments of FIGS. 14 and 15 is to provide encoded signals 266, 266' to the respective emitters 254, 254', such as by using a simple square wave, or an 8 bit number, or any other manner that is distinct from properties of ambient light, sunlight, and reflected light. In connection with such encoded signals 266, 266', it is desirable to avoid frequencies used by IR remote controls if an IR emitter 254, 254' is used in the respective pair 244, 244', 246.

Still with regard to the embodiments of FIGS. 14 and 15, in a further embodiment of these embodiments, the emitters 254, 254' and receivers 256, 256' of the respective embodiments, may be placed in front of the respective outlets 260, such as by being supported on protruding portions of housing 134 of wall module 32 or by having the outlets 260 recessed inwardly into a cavity formed in housing 134 of wall module and then placing the emitters 254, 254' and receivers 256, 256' on sidewall surfaces and/or top and bottom surfaces of the portions of housing 134 defining the cavity. In such alternative embodiments, the body of plug 180 blocks the respective light beam 262, 262'. In a variant embodiment, a hole is provided through housing 134 and the outlets 156, 160 (see FIG. 3) are accessible through the hole or within the hole of housing 134. In such a variant embodiment, the emitters 254, 254' and receivers 256, 256' are located on sidewall surfaces and/or top and bottom surfaces of the portions of housing 134 defining the hole therethrough. Further with regard to such a variant embodiment, outlet 136 is omitted from wall module 32 as are prongs 154, 158 since the plug 180 of bed 30 plugs into the existing outlets 156, 160 through the hole formed in housing 134.

Figure 16:
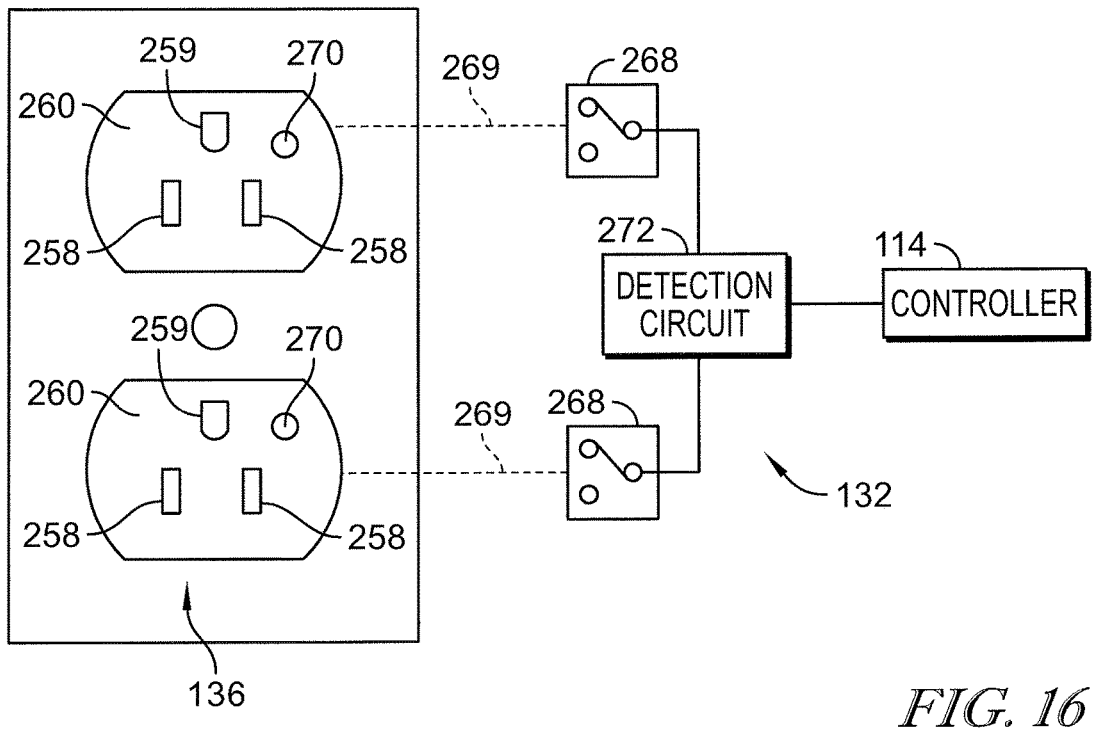
FIG. 16 is a diagrammatic view of a third embodiment of a plug detector for use in the wall module, the third embodiment of the plug detector including mechanical switches that change from an opened state to a closed state in response to a plug being inserted into the respective outlet of the duplex AC outlet of the wall module.

Referring now to FIG. 16, a third embodiment of plug detector 132 for use in wall module 32 is shown. Plug detector 132 of FIG. 16 includes mechanical switches 268 that change from an open state to a closed state in response to a plug, such as power plug 180, being inserted into the respective outlet 260 of the duplex AC receptacle 136 of the wall module 32. One of switches 268 is used with the upper outlet 260 and the other of switches 268 is used with the lower outlet 260 as indicated by dotted lines 269 in FIG. 16. In the illustrative example, switches 268 are plunger switches having a plunger 270 that extends outwardly from a front face of the respective outlet 260 (e.g., out of the plane of the paper with regard to FIG. 16). Plungers 270 are spring loaded outwardly to their respective open positions.

When a plug is plugged into either of outlets 260, the respective plunger 270 is moved inwardly further into the respective outlet 260 against the spring bias due to contact between a front surface of a plug body of the plug and a distal end of the corresponding plunger 270. Inward movement of either of plungers 270 into the corresponding outlets 260 changes the state of the respective switch 268 from the open position to the closed position. A detection circuit 272 detects the positions of switches 268. In some embodiments, detection circuit 264 includes one or more logic gates (e.g., OR gate, AND gate, etc.) having signals from switches 268 as inputs and having an output coupled to SOM or controller 114. Detection circuit 272 may further include one or more amplifiers, filters, transistors, resistors, and other circuit elements in some embodiments.

It is contemplated by the present disclosure that a non-pairable device may be plugged into one of the upper or lower outlets 260 of receptacle 136 of FIG. 16 prior to a pairable device 30 being plugged into the other of the upper and lower outlets 260 of receptacle 136 of FIG. 16. In such situations, one of switches 268 closes thereby to detect the non-pairable device being plugged in and wall module 32 proceeds to transmit BT scans 192 in an attempt to pair with the non-pairable device. However, the non-pairable device does not respond with any BT advertisements having uptimes and so wall module 32 does not pair with the non-pairable device. Subsequently, when the pairable device 30 is plugged into the remaining outlet 260 of receptacle 136 of FIG. 16, wall module 32 again transmits BT scans 192 and proceeds to successfully pair with the pairable device according to process 200 of FIG. 6A.

If the pairable device 30 is plugged into one of outlets 260 of receptacle 136 of wall module 32 of FIG. 16 prior to any other devices being plugged into the other of outlets 260, then one of switches 268 closes resulting in the detection of the pairable device 30 being plugged in and wall module 32 proceeds to pair with the pairable device 30 according to process 200. Thereafter, if another device is plugged into the remaining outlet 260 of FIG. 16, wall module 32 does not transmit any BT scans 192 and does not make any attempt to pair with the second device because the wall module 32 is already paired with the first, pairable device 30. This is true even if the second device is also a pairable device. In other words, wall module 32 only wirelessly pairs with one pairable device 30, such as bed 30, at a time.

In variant embodiments to the embodiment of FIG. 16, other types of sensors may be used in lieu of mechanical switches 268. For example, the presence of the AC plug 180 and its associated electrical characteristics could be used to sense the presence or absence of the plug 180 by utilizing the permeability and permittivity of the plastic or metal in the AC plug 180 to sense the presence of the plug. Accordingly, capacitive sensors may be provided in wall module 32 for use as plug detector 132 in lieu of mechanical switches 268 in some embodiments. In further variants, plug 180 carries a magnet and plug detector 132 of wall module 32 includes a magnet detector, such as a Hall Effect sensor, to detect the magnet when plug 180 is plugged into one of outlets 260 of receptacle 136. Alternatively, a motion detection sensor could be used in wall module 32 as the plug detector 132 by detecting motion in the area near the outlets 260 of receptacle 136 under the assumption that the motion is due to plug 180 being plugged into one of outlets 260 of receptacle 136.

Figure 17:
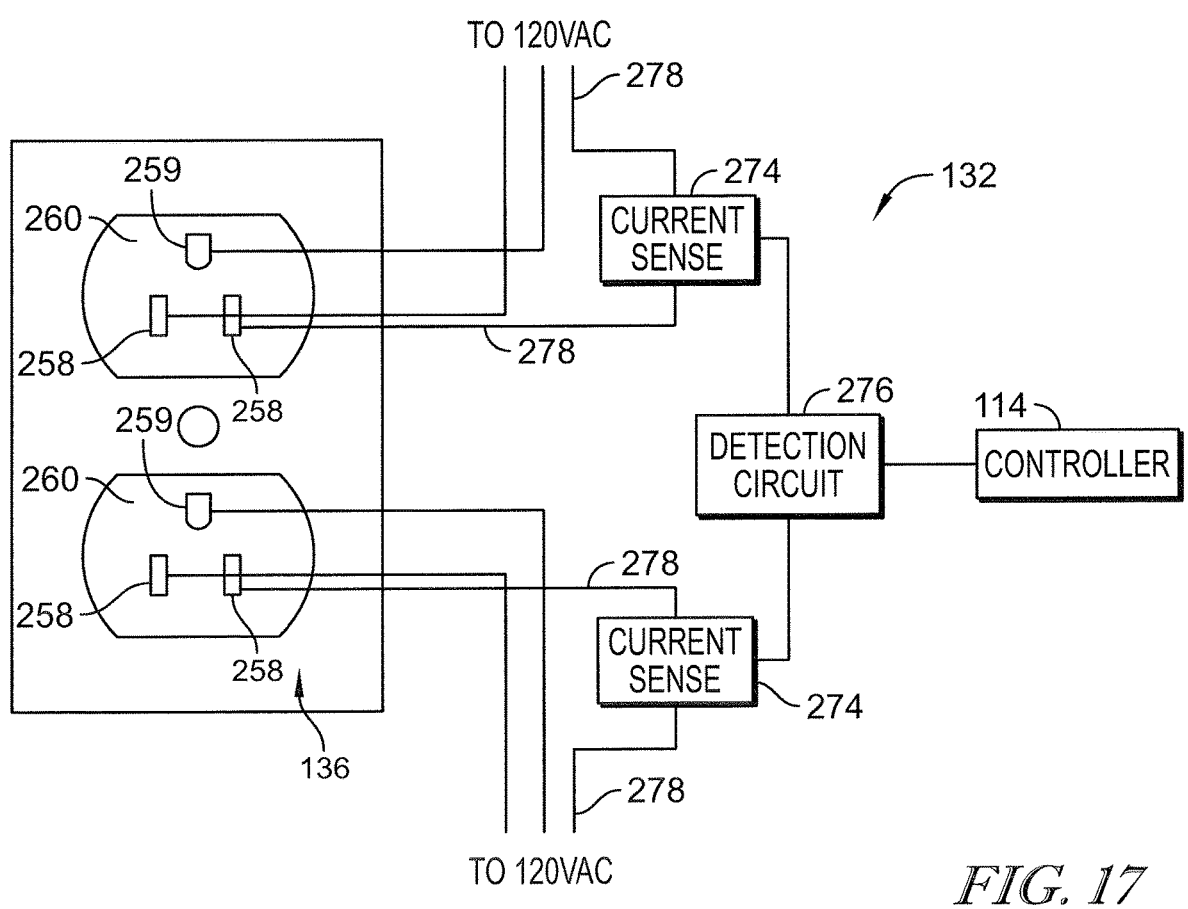
FIG. 17 is a diagrammatic view of fourth embodiment of a plug detector for use in the wall module, the fourth embodiment of the plug detector including current sensors coupled to a power prong of the respective outlets of the duplex AC outlet of the wall module.

Referring now to FIG. 17, a fourth embodiment of plug detector 132 for use in wall module 32 is shown. The fourth embodiment of plug detector 132 includes current sensors, indicated by current sense blocks 274, that are coupled to one of the power prong openings 258 of the respective outlets 260 of the duplex AC receptacle 136 of wall module 32. Current sensors 274 are configured to sense the flow of current that occurs when a plug is plugged into the respective outlet 260. The sensing of current by sensors 274 is communicated to a detection circuit 276 which, in turn, signals controller 114 of wall module 32 that current has been detected. This current detection by sensors 274 corresponds to block 188 of the time-based wireless pairing process 200 of FIG. 6A.

In some embodiments, current sensors 274 include Hall effect sensors that each detect a magnetic field produced by the AC current flowing in a respective power line 278 that couples to an electrical contact provided in the opening 258 of the corresponding outlet 260. The detected magnetic field is converted to a voltage which, in some embodiments, is amplified by an amplifier of current sensor 274. The voltage from the Hall Effect sensor, or the amplified voltage, is provided to detection circuit 276. Similar to detection circuits 264, 264', 272 discussed above, detection circuit 276 includes one or more logic gates (e.g., OR gate, AND gate, etc.), but having signals from current sensors 274 as inputs, and having an output coupled to SOM or controller 114. Detection circuit 276 may further include one or more amplifiers, filters, transistors, resistors, and other circuit elements in some embodiments. In some embodiments, bed 30 also includes current sensors and detection circuitry that are substantially the same as current sensors 274 and detection circuit 276 of wall module 32. Signals from such current sensors on bed 30 are used to start the timer of MCB 92 as discussed above.

It is contemplated by the present disclosure that a non-pairable device may be plugged into one of the upper or lower outlets 260 of receptacle 136 of FIG. 17 prior to a pairable device 30 being plugged into the other of the upper and lower outlets 260 of receptacle 136 of FIG. 17. In such situations, one of current sensors 274 detects the non-pairable device being plugged in and wall module 32 proceeds to transmit BT scans 192 in an attempt to pair with the non-pairable device. However, the non-pairable device does not respond with any BT advertisements having uptimes and so wall module 32 does not pair with the non-pairable device. Subsequently, when the pairable device 30 is plugged into the remaining outlet 260 of receptacle 136 of FIG. 17, wall module 32 again transmits BT scans 192 and proceeds to successfully pair with the pairable device according to process 200 of FIG. 6A.

If the pairable device 30 is plugged into one of outlets 260 of receptacle 136 of wall module 32 of FIG. 17 prior to any other devices being plugged into the other of outlets 260, then one of current sensors 274 detects the current flow resulting from the pairable device 30 being plugged in and wall module 32 proceeds to pair with the pairable device 30 according to process 200. Thereafter, if another device is plugged into the remaining outlet 260 of FIG. 17, wall module 32 does not transmit any BT scans 192 and does not make any attempt to pair with the second device because the wall module 32 is already paired with the first, pairable device 30. This is true even if the second device is also a pairable device. In other words, wall module 32 only wirelessly pairs with one pairable device 30, such as bed 30, at a time.

Figure 18:
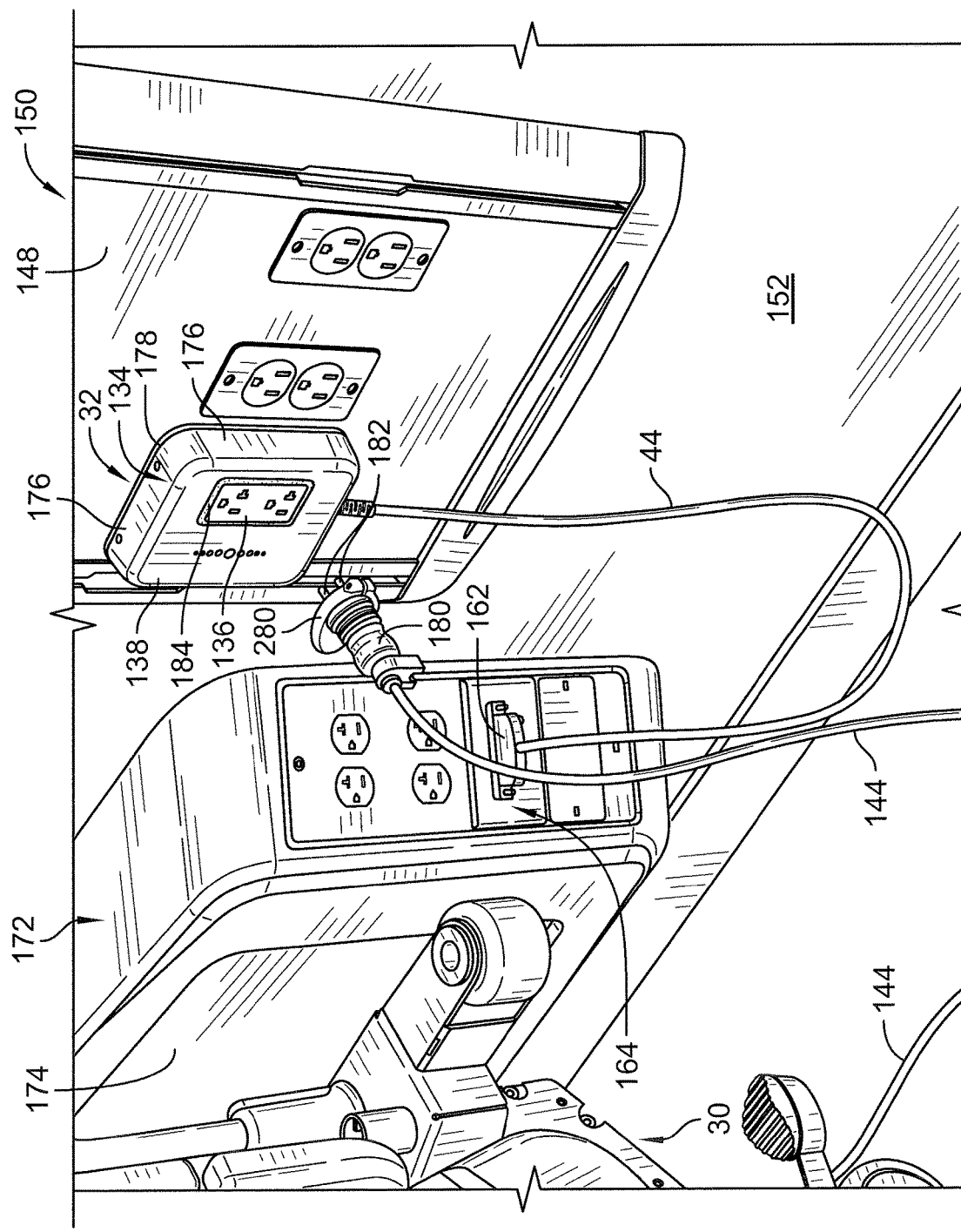
FIG. 18 is a perspective view, similar to FIG. 4, showing a transponder tag attached to the power plug at the end of the power plug extending from the patient bed.
Figure 19:
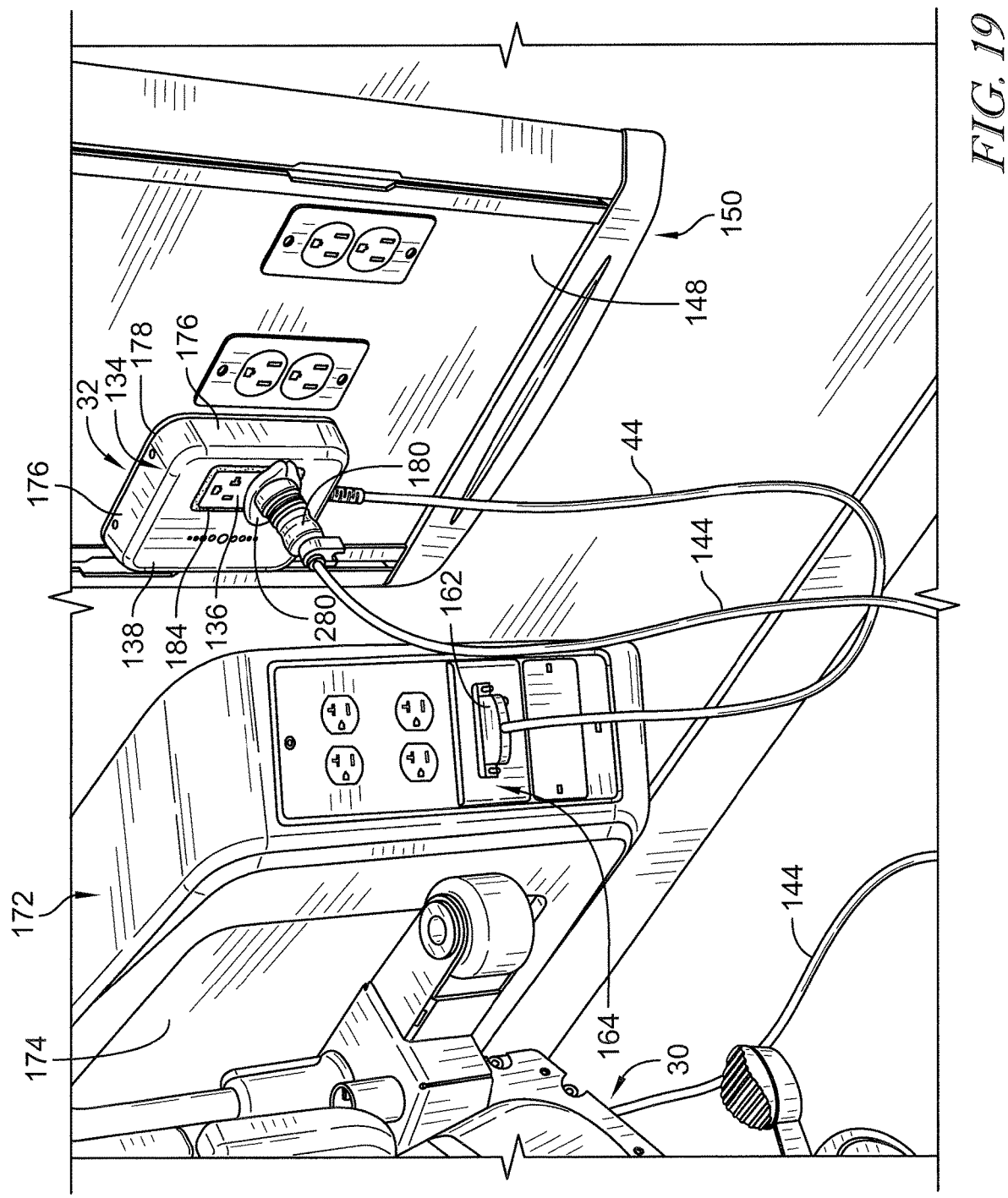
FIG. 19 is a perspective view, similar to FIG. 18, showing the plug with the transponder tag plugged into one of the outlets of the duplex AC outlet of the wall module so that a reader within the wall module can sense a transponder of the transponder tag and begin the timer of the wall module as part of the time-based wireless pairing operation.

Referring now to FIGS. 18 and 19, an embodiment of wall module 32 is shown in which plug detector 132 is configured as a tag reader. Otherwise, wall module 32 of FIGS. 18 and 19 is substantially the same as wall module 32 of FIGS. 4 and 5. Thus, like reference numbers are used in FIGS. 18 and 19 to denote portions that are the same as those of FIGS. 4 and 5, respectively. Accordingly, the discussion above of FIGS. 4 and 5 is equally applicable to FIGS. 18 and 19, respectively, unless specifically noted otherwise. In particular, in the illustrative example of FIGS. 18 and 19, a short range transponder tag 280, such as a near field communication (NFC) tag, is attached to power plug 180 of power cord 144 that extends from bed 30. In the illustrative example, transponder tag 280 is mounted to the plug body of plug 180 closely adjacent to the end of the plug body from which prongs 182 extend. Thus, when plug 180 is plugged into one of the outlets of receptacle 136, transponder tag 280 is situated right next to front wall 138 of housing 134 of wall module 32 as shown in FIG. 19.

When plug 180 is plugged into receptacle 136, transponder tag 280 is within the reception range of the reader 132 located in the interior region of wall module 32. In response to reading tag 280, wall module 32 initiates the wireless pairing process 200 of FIG. 6A, although the timer of wall module 32 is started at block 188 in response to reader 132 detecting tag 280 rather than in response to any current being sensed. In some embodiments, reader 132 periodically emits an interrogation signal to determine if any transponder tag 280 is present within the reception range of reader 132. If the transponder contained within or on tag 280 is an NFC transponder, then the reception range is one the order of about 4 inches to about 10 inches. The transponder is a passive transponder in some embodiments such that the signal emitted by reader 132 is reflected by the transponder tag back to the reader 132 along with a transponder ID. In other embodiments, an active transponder (e.g., a battery powered transponder) is provide within or on tag 280. In such embodiments, a response signal is transmitted from the active transponder of tag 280 back to reader 132 in response to receipt of the interrogation signal.

Figure 20:
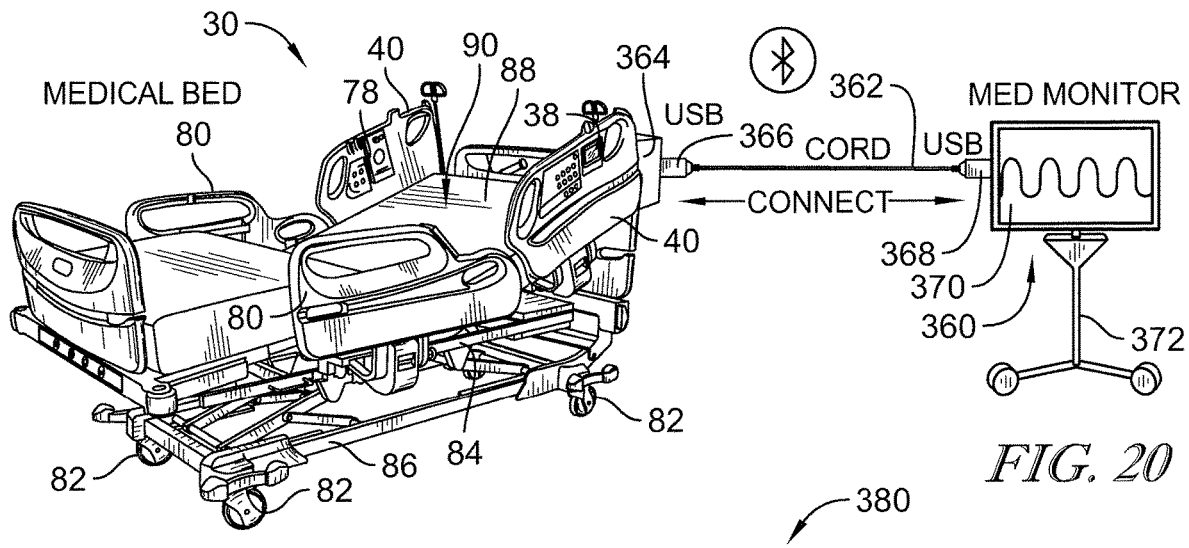
FIG. 20 is a perspective view showing a medical bed connecting to a medical monitor with a Universal Serial Bus (USB) cord to initiate a wireless pairing operation between the bed and the monitor.
Figure 23:
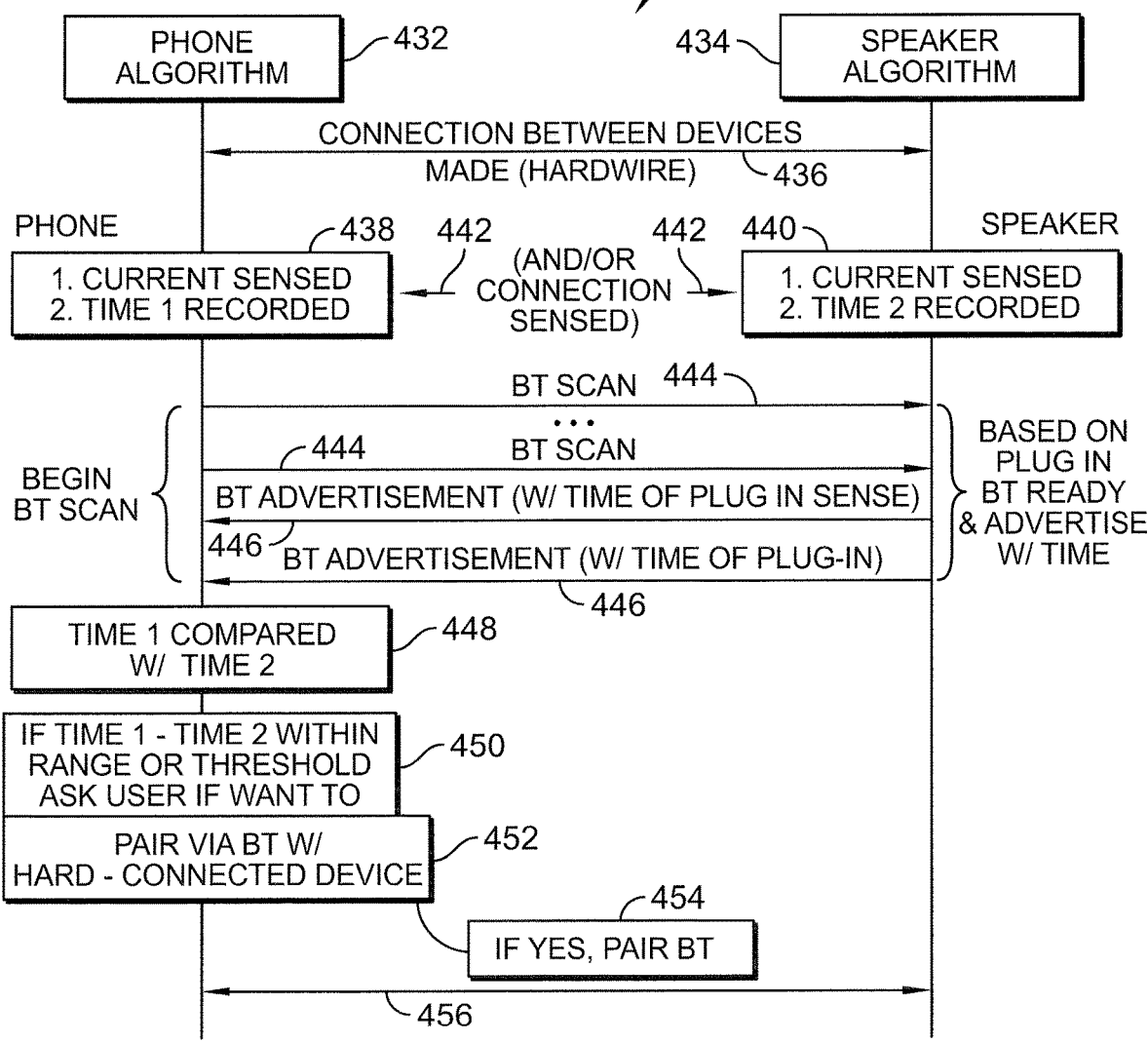
FIG. 23 is a swim lane diagram showing steps of the wireless pairing operation between the phone and the speaker unit of FIG. 22.

It should be noted that the manner in which transponder tag 280 is used in the embodiment of FIGS. 18 and 19 of the present disclosure is different than the use of a transponder tag or RFID tag in the embodiments of FIGS. 20, 23 and 24 of U.S. Pat. No. 9,830,424. In those embodiments, a tag ID is received by wall circuitry, which may include Bluetooth circuitry, and then the tag ID is transmitted back to the bed along with a wall circuitry ID. If the bed confirms that the proper tag ID was transmitted back to the bed, then wireless pairing is implemented. Thus, the pairing processes disclosed in U.S. Pat. No. 9,830,424 are not time-based. In the embodiment of FIGS. 18 and 19 of the present disclosure, the detection of transponder tag 280 by reader 132 is used to start the time-based wireless pairing process 200 and no tag ID is ever transmitted back to bed 30 by the wall module. Accordingly, the tag ID of transponder tag 280 does not need to be programmed into memory 98 or memory 104 of bed 30.

By using wall module 32 according to any of the embodiments disclosed herein for wireless communications with bed 30 via wireless data link 34, the traditional nurse call cable between bed 30 and nurse call port 126 can be eliminated. As such, only power plug 180 of power cord 144 of bed 30 needs to be plugged into wall module 32 when bed 30 is used to support a patient in a patient room. When the bed 30 is to be moved to a new location, only the power plug 180 needs to be unplugged from wall module 32. Even if bed 30 is moved away from the room wall 152 while plug 180 is still plugged in, the plug 180 will easily be pulled out of receptacle 136 of wall module 32 with a very low probability of any damage to wall module 32 or plug 180. However, when used with beds that do not have wireless communication capability, such as Bluetooth communication capability, provision is made in various embodiments of wall unit 32 for wired communication with bed 30 using a traditional nurse call cable 232. It is also conceivable, although not desired, that such wired communications between bed 30 having wireless communication capability and wall module 32 can be implemented using the traditional nurse call cable 232.

Some beds do not have any microphone 112, but may have a speaker 110, and some beds do not have any speaker 110 or microphone 112. Accordingly, the present disclosure contemplates that some embodiments of wall module 32 include a microphone and/or speaker that are substantially similar to speaker 110 and microphone 112 of bed 30. Embodiments in which a combination speaker/microphone is provided in wall module 32 are also within the scope of the present disclosure. In such embodiments, one or more command messages may be sent to wall module 32 via wireless communications link 54 or via nurse call cable 44 to disable the speaker and/or microphone of wall module 32 if it is determined by one or more of servers 46, 62, 70, for example, that bed 30 having a speaker and/or microphone is in communication with wall module 32 via wireless communications link 34 or via nurse call cable 232. Similarly, if a pillow speaker having a speaker and microphone is coupled to port 166 of ASBC 164, for example, then one or more command messages may be sent to wall module 32 via wireless communications link 54 or via nurse call cable 44 to disable the speaker and/or microphone of wall module 32.

Based on the foregoing, the present disclosure contemplates system 20 for use in healthcare facility 22 and system 20 includes network 60 and nurse call system 43. System 20 also includes medical device 30 having first wireless transceiver 106, a first timer (e.g., implemented in software stored in memory 98 and executed by microprocessor 96), and a power cord 144 that terminates at a power plug 180. The medical device 30 has a first sensor (e.g., similar to current sensors 274 of FIG. 17) to determine that the medical device 30 is receiving power via the power plug 180 and power cord 144. The system 20 further has a wall unit 32 that is mounted at a fixed location in a patient room of the healthcare facility 22. The wall unit 32 has a second wireless transceiver 122 and a second timer (e.g., implemented in software stored in memory 118 and executed by microprocessor 116). The wall unit 32 is plugged into a first alternating current (AC) outlet 146 of the healthcare facility 22. The wall unit 32 has a second AC outlet 136 into which the power plug 180 of the medical device 30 is coupleable. The wall unit 32 has an AC plug sensor 132 that senses the power plug 180 being plugged into the second AC outlet 136. The first timer is started to measure a first uptime in response to the first sensor sensing that the medical device 30 is receiving power via the power plug 180 and the power cord 144. The second timer is started to measure a second uptime in response to the power plug 180 being plugged into the second AC outlet 136 of the wall unit 32. The medical device 30 is configured to transmit to the wall unit 32 from the first wireless transceiver 106 an advertisement including the first uptime. The wall unit 32 compares the first uptime with the second uptime and, if the first uptime is within a predetermined tolerance range of the second uptime, the wall unit 32 sends a pairing message 214 to the medical device 30 which results in the wall unit 32 and medical device 30 becoming automatically paired for subsequent wireless communications.

In some embodiments, the system 20 further includes a nurse call cord 44, 216, 248 extending from the wall unit 32. The nurse call cord 44, 216, 248 terminates at a first nurse call connector 162, 224, 250 that is configured for connection to a nurse call port 126 of the nurse call system 43. Optionally, the nurse call cord 216 may include an auxiliary cord branch 226 that may terminate at a second nurse call connector 228. In such embodiments, the second nurse call connector 228 is coupleable to a third nurse call connector 230 at an end of a device nurse call cord 232 that extends from the medical device 30. Further optionally, the first nurse call connector 250 is provided in a connector body of the nurse call cord 248. In such embodiments, the connector body 250 has a second nurse call connector 252 that is configured to couple to the third nurse call connector 230 at the end of the device nurse call cord 232 that extends from the medical device 30. Still further optionally, the wall unit 32 includes a first nurse call connector 128 that is configured to couple to a second nurse call connector 230 at an end of the device nurse call cord 232 that extends from the medical device 30.

It is contemplated by the present disclosure that the medical device 30 further includes a first wireless fidelity (WiFi) transceiver 100 that is configured to send WiFi messages to, and receive WiFi messages from, at least one wireless access point 52 of the network 60. If desired, the first wireless transceiver 106 includes a first Bluetooth transceiver 106 that is mounted to a first circuit board 94 of the medical device 30 and the first WiFi transceiver 100 is mounted to a second circuit board 92 of the medical device 30. Optionally, the wall unit 32 includes a second WiFi transceiver 120 that is configured to send WiFi messages to, and receive WiFi messages from, the at least one wireless access point 52 of the network 60.

In some embodiments, the second wireless transceiver 122 includes a second Bluetooth transceiver 122 and the system 20 further includes a first set of switches 108 on the first circuit board 94 to provide first contact closures that are indicative of a plurality of states of the medical device 30 and a second set of switches 124 in the wall unit 32. The second set of switches 124 have second contact closures that are controlled by a controller 114 of the wall unit 32 to match the plurality of states of the first contact closures based on data that contained in Bluetooth messages received by the second Bluetooth transceiver 122 from the first Bluetooth transceiver 106.

Optionally, at least one of the second contact closures changes state (e.g., changes from an open state to a closed state, or vice versa) to control a television 76 in the patient room. Alternatively or additionally, at least one of the second contact closures changes state to turn on a light 74 in the patient room. Further alternatively or additionally, the medical device 30 includes patient bed 30 and at least one of the second contact closures changes state to indicate an alarm state of a bed exit system of the patient bed 30. Still further alternatively or additionally, the medical device 30 includes patient bed 30 and at least one of the second contact closures changes state to indicate that a siderail 40, 80 of the patient bed 30 has been moved to a lowered position. Yet further alternatively or additionally, the medical device 30 includes patient bed 30 and at least one of the second contact closures changes state to indicate that brakes of casters 82 of the patient bed 30 are in a released state or condition. Alternatively or additionally, the medical device 30 includes patient bed 30 and at least one of the second contact closures changes state to indicate that an upper frame 84 of the patient bed 30 has been raised out of its lowest position. Further alternatively or additionally, the medical device 30 includes patient bed 30 and at least one of the second contact closures changes state to indicate that a nurse call button (e.g., one of the buttons of control panel 78) of the patient bed 30 has been pressed.

Optionally, the medical device 30 includes a speaker 110 and a microphone 112 and the first and second wireless transceivers 106, 122 are configured for transmission and receipt of audio messages after the medical device 30 and the wall unit 32 are paired. Further optionally, the wall unit 32 includes a light 184 that is illuminated to indicate a pairing state between the medical device 30 and the wall unit 32. For example, the light 184 surrounds a perimeter of the second AC outlet 136.

In some embodiments, the wall unit 32 determines whether to initiate unpairing from the medical device 30 based on device data received by the second wireless transceiver 122 from the first wireless transceiver 106 of the medical device 30. For example, the medical device 30 includes a frame 86 and casters 82 that are coupled to the frame 86 and the wall unit 32 initiates unpairing based on the device data indicating that brakes of the casters 82 are released. Alternatively or additionally, the wall unit 32 initiates unpairing based on the device data indicating that the power plug 180 of the medical device 30 has been unplugged. Further alternatively or additionally, the wall unit 32 determines whether to initiate unpairing from the medical device 30 in response to the AC plug sensor 132 sensing that the power plug 180 has been unplugged from the second AC outlet 136.

If desired, the AC plug sensor 132 of the wall unit includes a photo emitter 254, 254' and a photo detector 256, 256' that cooperate to detect presence of at least one prong 182 of the power plug 180 of the medical device 30 being inserted into the second AC outlet 136 of the wall unit 32. For example, the photo emitter 254 emits infrared (IR) light 262 in a generally horizontal direction as a beam for detection by the photo detector 256 and the at least one prong 182 blocks the IR light 262 from reaching the photo detector 256 after the power plug 180 is plugged into the second AC outlet 136. Alternatively, the photo emitter 254' emits infrared (IR) light 262' in a generally vertical direction for detection by the photo detector 256' and the at least one prong 182 blocks the IR light 262' from reaching the photo detector 256' after the power plug 180 is plugged into the second AC outlet 136.

In some embodiments, the AC plug sensor 132 includes a mechanical switch 268 that moves from a first state to a second state in response to the power plug 180 of the medical device 30 being plugged into the second AC outlet 136 of the wall unit 32. For example, the mechanical switch 268 includes a plunger switch 268 that has a plunger 270 that is pressed inwardly by a plug body of the power plug 180 when the power plug 180 is plugged into the second AC outlet 136. Alternatively or additionally, the AC plug sensor 132 includes a current sensor 274 to sense current flowing to at least one prong 182 of the power plug 180 after the power plug 180 is plugged into the second AC outlet 136 of the wall unit 32.

The present disclosure further contemplates that the AC plug sensor 132 of the wall unit 32 includes a reader that detects a tag 280 coupled to the power plug 180. If desired, the tag 280 carries a transponder that is read by the reader. For example, the transponder includes a near field communication (NFC) transponder. If desired, the NFC transponder is included in an NFC integrated circuit chip. Optionally, the reader emits energy to power the transponder to enable the transponder to send a signal back to the reader.

In some embodiments, the medical device 30 is configured to transmit a device identification (ID) to the wall unit 32 and the wall unit is configured to transmit the device ID and a location ID to at least one server 46, 62, 64, 66 of the network 60 of the healthcare facility 22. The location ID is correlatable to a location at which the medical device 30 is located in the healthcare facility 22. If desired, the medical device 30 includes a graphical display screen 38 and the wall unit 32 is configured to transmit from the second wireless transceiver 122 to the first wireless transceiver 106 of the medical device 30 a smart text string 36 that is displayed on the graphical display screen 38. The smart text string 36 includes a name of the location at which the medical device 30 is located and is different than the location ID. In such embodiments, the medical device 30 does not receive the location ID from the wall unit 32 and does not retransmit the smart text string 36.

Further according to the present disclosure, wall unit 32 is configured for wireless communication with medical device 30. The wall unit 32 includes a housing 134 that is configured to be mounted at a fixed location in a patient room of the healthcare facility 22. Wireless transceiver 122 and a timer (e.g., implemented in software stored in memory 118 and executed by microprocessor 116) is carried by the housing 134. The wall unit 32 is configured to plug into a first alternating current (AC) outlet 146 of the healthcare facility 22. A second AC outlet 136 is carried by the housing 134 and into which a power plug 180 of the medical device 30 is coupleable. An AC plug sensor 132 is carried by the housing and is configured to sense power plug 180 of the medical device 30 being plugged into the second AC outlet 136. The timer is started to measure a first uptime in response to the power plug 180 being plugged into the second AC outlet 136 of the wall unit 32. The wireless transceiver 122 of the wall unit 32 is configured to receive at least one transmission from the medical device 30 that includes a second uptime. The wall unit 32 compares the first uptime with the second uptime and, if the first uptime is within a predetermined tolerance range of the second uptime, the wall unit sends a pairing message 214 to the medical device 30 which results in the wall unit 32 and medical device 30 becoming automatically paired for subsequent wireless communications.

In some embodiments, the wall unit 32 further includes a nurse call cord 44, 216, 248 that extends from the housing 134. The nurse call cord 44, 216, 248 terminates at a first nurse call connector 162, 224, 250 that is configured for connection to a nurse call port 126 of a nurse call system 43 of the healthcare facility 22. Optionally, the nurse call cord 216 includes an auxiliary cord branch 226 that terminates at a second nurse call connector 228. In such embodiments, the second nurse call connector 228 is coupleable to a third nurse call connector 230 that is at an end of a device nurse call cord 232 that extends from the medical device 30. Further optionally, the first nurse call connector 250 is provided in a connector body of the nurse call cord 248. In such embodiments, the connector body has a second nurse call connector 252 that is configured to couple to third nurse call connector 230 that is at the end of the device nurse call cord 232 that extends from the medical device 30. Still further optionally, the housing 134 of the wall unit 32 carries a first nurse call connector 128 that is configured to couple to a second nurse call connector 230 at an end of a device nurse call cord 232 that extends from the medical device 30.

It is contemplated by the present disclosure that the housing 134 of the wall unit 32 carries a first wireless fidelity (WiFi) transceiver 120 that is configured to send WiFi messages to, and receive WiFi messages from, at least one wireless access point 52 of a network 60 of the healthcare facility 22. If desired, the wireless transceiver 122 carried by the housing 134 of the wall unit 32 includes a Bluetooth transceiver 122.

In some embodiments, the wall unit 32 further includes a controller 114 and a set of switches 124 that are carried by the housing 134. The set of switches 124 are configured to provide contact closures that are indicative of a plurality of states of the medical device 30 based on data contained in Bluetooth messages received by the Bluetooth transceiver 122 from the medical device 30.

Optionally, at least one of the contact closures changes state to control a television 76 in the patient room. Alternatively or additionally, at least one of the contact closures changes state to turn on a light 74 in the patient room. Further alternatively or additionally, the medical device 30 includes patient bed 30 and at least one of the contact closures changes state to indicate an alarm state of a bed exit system of the patient bed 30. Still further alternatively or additionally, the medical device 30 includes a patient bed 30 and at least one of the contract closures changes state to indicate that a siderail 40, 80 of the patient bed 30 has been moved to a lowered position. Yet further alternatively or additionally, the medical device 30 includes patient bed 30 and at least one of the contact closures changes state to indicate that brakes of casters 82 of the patient bed 30 are in a released state or condition. Alternatively or additionally, the medical device 30 includes patient bed 30 and at least one of the contact closures changes state to indicate that an upper frame 84 of the patient bed 30 has been raised out of its lowest position. Further alternatively or additionally, the medical device 30 includes patient bed 30 and at least one of the second contact closures changes state to indicate that a nurse call button (e.g., one of the buttons of control panel 78) of the patient bed 30 has been pressed.

Optionally, the medical device 30 includes a speaker 110 and a microphone 112 and the wireless transceiver 122 is configured for transmission and receipt of audio messages after the medical device 30 and the wall unit 32 are paired. Further optionally, the housing 134 of the wall unit 32 carries a light 184 that is illuminated to indicate a pairing state between the medical device 30 and the wall unit 32. For example, the light 184 surrounds a perimeter of the second AC outlet 136.

In some embodiments, the wall unit 32 includes a controller 114 that is configured to determine whether to initiate unpairing from the medical device 30 based on device data received by the wireless transceiver 122 from the medical device 3. For example, the medical device 30 includes a frame 86 and casters 82 that are coupled to the frame 86 and the controller 114 initiates unpairing based on the device data indicating that brakes of the casters 82 are released. Alternatively or additionally, the controller 114 initiates unpairing based on the device data indicating that the power plug 180 of the medical device 30 has been unplugged. Further alternatively or additionally, the controller 114 determines whether to initiate unpairing from the medical device 30 in response to the AC plug sensor 132 sensing that the power plug 180 has been unplugged from the second AC outlet 136.

If desired, the AC plug sensor 132 includes a photo emitter 254, 254' and a photo detector 256, 256' that cooperate to detect presence of at least one prong 182 of the power plug 180 of the medical device 30 being inserted into the second AC outlet 136. For example, the photo emitter 254 emits infrared (IR) light 262 in a generally horizontal direction for detection by the photo detector 256 and the at least one prong 182 blocks the IR light 262 from reaching the photo detector 256 after the power plug 180 is plugged into the second AC outlet 136. Alternatively, the photo emitter 254' emits infrared (IR) light 262' in a generally vertical direction for detection by the photo detector 256' and the at least one prong 182 blocks the IR light 262' from reaching the photo detector 256' after the power plug 180 is plugged into the second AC outlet 136.

In some embodiments, the AC plug sensor 132 includes a mechanical switch 268 that moves from a first state to a second state in response to the power plug 180 of the medical device 30 being plugged into the second AC outlet 136. For example, the mechanical switch 268 includes a plunger switch 268 that has a plunger 270 that is pressed inwardly by a plug body of the power plug 180 when the power plug 180 is plugged into the second AC outlet 136. Alternatively or additionally, the AC plug sensor 132 includes a current sensor 274 to sense current flowing to at least one prong 182 of the power plug 180 after the power plug 180 is plugged into the second AC outlet 136.

The present disclosure further contemplates that the AC plug sensor 132 includes a reader that detects a tag 280 that is coupled to the power plug 180. If desired, the reader is configured to detect the tag 280 by reading a transponder that is carried by the tag 280. For example, the reader is configured to detect the tag 280 by reading a near field communication (NFC) transponder that is carried by the tag 280. Optionally, the reader emits energy to power the NFC transponder to enable the NFC transponder to send a signal back to the reader. The NFC transponder is provided by an NFC integrated circuit chip in some embodiments of tag 280.

Figure 21:
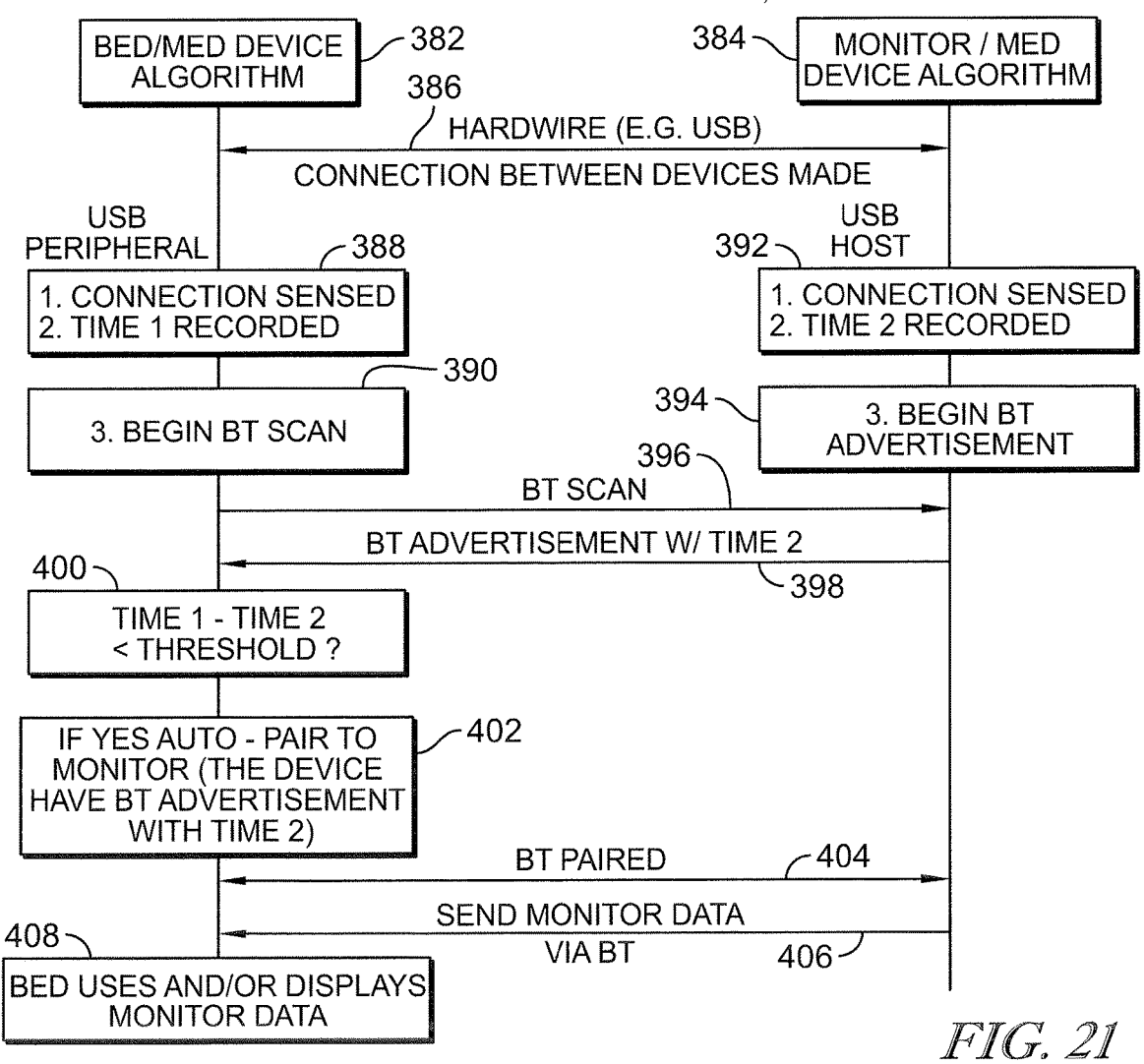
FIG. 21 is a swim lane diagram showing steps of the wireless pairing operation between the bed and the monitor of FIG. 20.

Referring now to FIG. 20, a first medical device, illustratively medical bed 30, connects to a second medical device, illustratively a medical monitor 360, with a Universal Serial Bus (USB) cord 362 to initiate a wireless pairing operation 380, shown in FIG. 21, between the bed 30 and the monitor 360. Thus, the wireless pairing scenarios contemplated above between bed 30 and wall unit 32 may similarly be implemented between bed 30 and other medical devices. Medical monitor 360 is another example of a communication unit according to the present disclosure.

Bed 30 of FIG. 20 is the same as bed 30 of FIG. 1 and so the same reference numerals are used for like components and the descriptions are not repeated. However, bed 30 of FIG. 20 has a USB port 364 to which a first USB connector 366 of cord 362 connects. Monitor 360 also has a USB port (not shown, but well known in the art) to which a second USB connector 368 of cord 362 connects. Illustratively, monitor 360 includes a display screen 370 on which patient physiological information is displayed. Monitor 360 is shown somewhat diagrammatically in FIG. 20 and represents devices such as electrocardiograms (EKG's), electroencephalograms (EEG's), respiration rate monitors, blood pressure monitors, pulse oximeters, and the like, including combinations of these. Illustrative monitor 360 is mounted to a wheeled stand 372 so as to be movable from room-to-room, as needed.

Referring now to FIG. 21, a swim lane diagram of steps of the wireless pairing operation 380 between the medical devices 30, 360 of FIG. 20 is shown. More particularly, the steps of operation 380 are carried out by a first algorithm as indicated by a block 382 labeled BED/MED DEVICE ALGORITHM and a second algorithm as indicated by a block 384 labeled MONITOR/MED DEVICE ALGORITHM. As the labels imply, block 382 represents an algorithm performed by bed 30 and block 384 represents an algorithm performed by monitor 360, or by other first and second medical devices in other embodiments.

Operation 380 begins in response to a hardwire connection being made between devices 30, 360, such as by the illustrative hardwire connection made in FIG. 20 by USB cord 362. This hardwire connection is depicted in FIG. 21 by a double-headed arrow 386 labeled HARDWIRE (E.G. USB) CONNECTION BETWEEN DEVICE MADE. After the hardwire connection is made, the bed 30, which serves as a USB peripheral, senses the connection and a first connection time is recorded (e.g., stored in memory of bed 30) as indicated at a block 388 labeled as 1. CONNECTION SENSED 2. TIME 1 RECORDED. Thereafter, bed 30 begins to make one or more BT scans as indicated at block 390 labeled 3. BEGIN BT SCAN. Substantially simultaneously (e.g., within a few seconds), the monitor 360, which serves as a USB host, senses the connection and a second connection time is recorded (e.g., stored in memory of monitor 360) as indicated at a block 392 labeled as 1. CONNECTION SENSED 2. TIME 2 RECORDED. Thereafter, monitor 360 begins to transmit one or more BT advertisements as indicated at block 394 labeled 3. BEGIN BT ADVERTISEMENT.

As shown in FIG. 21, the one or more BT scans made at block 390 is represented by an arrow 396 labeled BT SCAN and the one or more BT advertisements transmitted at block 394 are represented by an arrow 398 labeled BT ADVERTISEMENT W/TIME 2. Thus, the BT advertisements made by monitor 360 include time 2. After a scan 396 of bed 30 detects an advertisement 398 of monitor 360, bed 30 subtracts time 2 from time 1 and compares the difference to a threshold as indicated at a block 400 labeled TIME 1−TIME 2<THRESHOLD?. The threshold may be, for example, 2 or 3 seconds or less or some other larger threshold, at the discretion of the system designer. If the difference between time 2 and time 1 is less than the threshold, then bed 30 auto-pairs to monitor 360 or whatever device sent a BT advertisement with time 2 as indicated at a block 402 labeled IF YES AUTO-PAIR TO MONITOR (THE DEVICE HAVE BT ADVERTISEMENT WITH TIME 2).

The paired state between bed 30 and monitor 360 is represented in FIG. 21 by a double-headed arrow 404 labeled BT PAIRED. Either or both of devices 30, 360 have a visual or audible means of indicating that the wireless pairing has successfully been made and that the hardwire connection can be removed, such as by unplugging USB cord 362 from the respective USB ports. For example, a message may be displayed on GUI 38 of bed 30 and/or on display screen 370 of monitor 360 to indicate the successful pairing. Alternatively or additionally, a voice message announcing the successful wireless pairing between devices 30, 360 may be sounded by either of devices 30, 360.

After devices 30, 360 are wirelessly paired, cord 362 is able to be disconnected and the wireless pairing will remain as long as devices 30, 360 are within wireless communication range of each other. Thus, the location of monitor 360 relative to bed 30 is not limited by the length of cord 362, assuming that the wireless communication range is greater than the length of cord 362. Also, after devices 30, 360 are wirelessly paired, monitor 360 transmits monitor data, including the sensed patient physiological data, to bed 30 as indicated in FIG. 21 by an arrow 406 labeled SEND MONITOR DATA VIA BT. After bed 30 receives monitor data from monitor 360, the bed is able to use the monitor data and/or display the monitor data on GUI 38, for example, in accordance with the programming of bed 30, as indicated at a block 408 labeled BED USES AND/OR DISPLAYS MONITOR DATA.

In connection with block 408, bed 30 may initiate a therapy (e.g., lateral rotation therapy of mattress 88, alternating pressure therapy of mattress 88, or percussion and vibration (P&V) therapy of mattress 88), turn on a patient position monitoring or bed exit monitoring system of bed 30, send a message (e.g., informational message or alert/alarm message) to a nurse call system 43, or generate a local arm on bed 30 (e.g., display an alarm message on GUI 38 and/or sound an audible alarm using a sound producing device such a speaker or buzzer of bed 30). Bed 30 also may display on GUI 38 the physiological data (e.g., graphical trace and/or numeric data) sensed by monitor 360.

In one variant embodiment, the roles of the bed 30 and monitor 360 as USB peripheral and USB host are reversed such that the bed 30 serves as USB host and the monitor 360 serves as USB peripheral. In such a variant embodiment, the positions of blocks 382, 384 in operation 380 are reversed. In addition, block 408 is moved over to the right hand swim lane in FIG. 21 and direction of arrow 406 is reversed. In a further variant embodiment, data is transmitted over the hardwire connection (e.g., cord 362 in the illustrative example) to pair the two devices 30, 360. For example, the MAC addresses or manufacturer ID's or other device ID's or codes are exchanged between devices 30, 360 over the hardwire connection and then, after the hardwire connection is removed, devices 30, 360 communicate via BT using the exchanged ID's or codes. In still a further variant embodiment, the scans and advertisements by devices 30, 360 do not begin until ID's or codes are exchanged between devices 30, 360 over the hardwire connection. For example, either or both of devices 30, 360 may be programmed to only participate in a wireless pairing operation if the ID or code received over the hardwire connection matches an authorized ID or code stored in memory of the respective device 30, 360.

Figure 22:
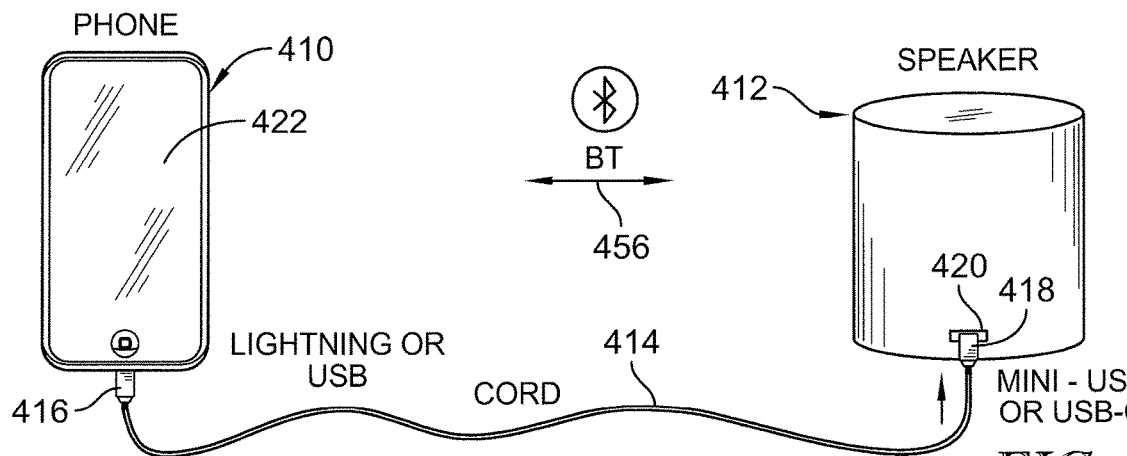
FIG. 22 is a perspective view of a mobile phone connecting to a speaker unit with a mini-USB cord or similar such cord to initiate a wireless pairing operation between the phone and the speaker unit.

Referring now to FIG. 22, a first device, such as a mobile phone 410, connects to a second device, such as a speaker unit 412, with a mini-USB cord 414 or similar such cord, to initiate a wireless pairing operation 430, shown in FIG. 23, between the phone 410 and the speaker unit 412. Thus, the wireless pairing scenarios contemplated above between medical devices 30, 360 may similarly be implemented between non-medical devices such as consumer devices. Mobile phone 410 and speaker unit 412 are each additional examples of communication units according to the present disclosure.

Cord 414 includes a first connector 416 such as a lightning connector of the type available from Apple Inc. of Cupertino, California or a USB connector. Mobile phone 410 includes a port (not shown, but well known in the art) configured to receive connector 416. At an opposite end of cord 414 is a second connector 418 such as a mini-USB connector or a USB-C connector that connects to a port 420 of device 412. Of course, other types of connectors 416, 418 of cord 414 are within the scope of the present disclosure as dictated by the given type of ports provided by the first and second devices with which the given cord is to interconnect.

As its name implies, speaker unit 412 includes one or more speakers (not shown) through which sound is played. In some embodiments, for example, speaker unit 412 is an AMAZON® ECHO® unit or an AMAZON® ALEXA® unit. Mobile phone 410 includes a display screen (e.g., a touchscreen) on which information regarding the wireless pairing status between devices 410, 412 is displayed.

Referring now to FIG. 23, a swim lane diagram of steps of the wireless pairing operation 430 between the devices 410, 412 of FIG. 22 is shown. More particularly, the steps of operation 430 are carried out by a first algorithm as indicated by a block 432 labeled PHONE ALGORITHM and a second algorithm as indicated by a block 434 labeled SPEAKER ALGORITHM. As the labels imply, block 432 represents an algorithm performed by phone 410 and block 434 represents an algorithm performed by speaker unit 412, or by other first and second devices in other embodiments.

Operation 430 begins in response to a hardwire connection being made between devices 410, 412, such as by the illustrative hardwire connection made in FIG. 22 by mini-USB cord 414. This hardwire connection is depicted in FIG. 23 by a double-headed arrow 436 labeled CONNECTION BETWEEN DEVICES MADE (HARDWIRE). After the hardwire connection is made, the phone 410 senses the connection via a current sensor and a first connection time is recorded (e.g., stored in memory of phone 410) as indicated at a block 438 labeled as 1. CURRENT SENSED 2. TIME 1 RECORDED. Substantially simultaneously (e.g., within a few seconds), the speaker unit 412 senses the connection via a current sensor and a second connection time is recorded (e.g., stored in memory of speaker unit 412) as indicated at a block 440 labeled as 1. CURRENT SENSED 2. TIME 2 RECORDED.

Alternatively, the connection of connectors 416, 418 of cord 414 to respective devices 410, 412 may be sensed in some other way than current sensing (e.g., limit switch, infrared beam obstruction, etc.) as indicated by a double headed arrow 442 labeled (AN/OR CONNECTION SENSED) and extending between blocks 438, 440.

After the steps of block 438 occur, phone 410 begins to make one or more BT scans as indicated by a series of arrows 444 labeled as BT SCAN. After the steps of block 440 occur, speaker unit begins to transmit one or more BT advertisements with the time at which plug-in of cord 414 was sensed as indicated by a series of arrows 446 labeled, in one instance, BT ADVERTISEMENT (W/TIME of PLUG IN SENSE), and labeled, in another instance, BT ADVERTISEMENT (W/TIME OF PLUG-IN). Thus, the BT advertisements made by speaker unit 412 include time 2. After a scan 444 of phone 410 detects an advertisement 446 of speaker unit 412, phone 410 compared time 1 with time 2 as indicated at a block 448 labeled TIME 1 COMPARED W/TIME 2.

After time 1 and time 2 are compared at block 448, operation 430 proceeds to determine if time 1 and time 2 are within a threshold amount of time of each other. This is accomplished by subtracting time 2 from time 1, for example. The threshold may be, for example, 2 or 3 seconds or less or some other larger threshold, at the discretion of the system designer. If the difference between time 1 and time 2 is within the threshold, then phone 410 displays a message on display screen 422 asking a user whether to pair the devices 410, 412 via Bluetooth as indicated by blocks 450, 452 with block 450 being labeled IF TIME 1–TIME 2 WITHIN RANGE OR THRESHOLD ASK USER IF WANT TO and block 452 being labeled PAIR VIA BT W/HARD-CONNECTED DEVICE. If the user indicates on display screen 422 of phone 410 that such a wireless pairing should be made, as indicated at a block 454 labeled IF YES, PAIR BT, then devices 410, 412 become wirelessly paired as indicated by double-headed arrow 456 shown in FIGS. 22 and 23.

According to this disclosure, either or both of devices 410, 412 have a visual or audible means of indicating that the wireless pairing has successfully been made and that the hardwire connection can be removed, such as by unplugging mini-USB cord 414 from the respective ports. For example, a message may be displayed on display screen 422 of phone 410 to indicate the successful pairing. Alternatively or additionally, a voice message announcing the successful wireless pairing between devices 410, 412 may be sounded by either of devices 410, 412.

After devices 410, 412 are wirelessly paired, cord 414 is able to be disconnected and the wireless pairing will remain as long as devices 410, 412 are within wireless communication range of each other. Thus, the location of speaker unit 412 relative to phone 410 is not limited by the length of cord 414, assuming that the wireless communication range is greater than the length of cord 414.

In one variant embodiment, the roles of the phone 410 and speaker unit 412 are reversed in operation 430. In such a variant embodiment, the positions of blocks 432, 434 in operation 430 and the positions of the headings PHONE and SPEAKER above blocks 438, 440 are reversed. In a further variant embodiment, data is transmitted over the hardwire connection (e.g., cord 414 in the illustrative example) to pair the two devices 410, 412. For example, the MAC addresses or manufacturer ID's or other device ID's or codes are exchanged between devices 410, 412 over the hardwire connection and then, after the hardware connection is removed, devices 410, 412 communicate via BT using the exchanged ID's or codes. In still a further variant embodiment, the scans and advertisements by devices 410, 412 do not begin until ID's or codes are exchanged between devices 410, 412 over the hardwire connection. For example, either or both of devices 410, 412 may be programmed to only participate in a wireless pairing operation if the ID or code received over the hardwire connection matches an authorized ID or code stored in memory of the respective device 410, 412.

Referring now to FIGS. 24 and 25, an alternative embodiment wall module 460 includes a housing 462 that carries an AC duplex outlet 464 having a first AC receptacle 466 and a second AC receptacle 468 beneath the first AC receptacle 466. Housing 462 is formed to include a front recess 470 in a front wall 472 thereof. Receptacles 466, 468 of duplex AC outlet 464 are accessible within recess 470. Housing 426 is generally box-shaped and includes a top wall 474, a bottom wall 476, and a pair of spaced apart sidewalls 478 extending between top and bottom walls 474, 476. Walls 474, 476, 478 join each other at rounded corners of housing 462 and also join with front wall 472 at rounded edges. In some embodiments, the dimensions of wall module 460 as defined by housing 462 are about 5 inches (12.7 centimeters (cm)) in width, about 5 inches (12.7 cm) in height, and about 1.25 inches (3.175 cm) in depth.

A label 480 is adhered to a central region of top wall 474 and includes a bed icon. Thus, a caregiver or other healthcare facility staff member viewing wall module 460 from above is notified by the bed indicia on label 480 that a patient bed, such as bed 30, should be plugged into one of receptacles 466, 468. Front wall 472 of housing 426 includes a generally rectangular informational zone 482 to the left of recess 470. Zone 482 includes an illuminateable wireless bed communication icon 484, an illuminateable nurse call icon 486, and an illuminateable caution icon 488 which is illuminated so as to be visible in FIG. 25, but is not illuminated and so is not visible in FIG. 24. Each of illuminateable icons 484, 486, 488 is a deadfront icon. The term "deadfront" refers to an image that, when backlit, can readily be seen but when not back lit cannot readily be seen or, stated another way, is substantially invisible. Thus, in FIG. 24, icons 484, 486 are backlit so as to be readily visible and icon 488 is deadfronted. In FIG. 25, all of icons 484, 486, 488 are backlit.

Wall module 460 includes a nurse call cable 490 extending downwardly from bottom 476 of housing 462. Only a portion of cable 490 can be seen in FIGS. 24 and 25. In response to wall module 462 successfully communicating wirelessly with bed 30 via Bluetooth, icon 484 is turned on so that icon 484 is visible. In some embodiments, the backlighting of icon 484 is green. During the wireless pairing process with bed 30, such as when wall module 460 is sending or receiving a Bluetooth advertisement, icon 484 flashes green, or more particularly, the green backlighting of icon 484 is turned on and off repeatedly.

In response to cable 490 being connected to ASBC 164 of nurse call system 43 and after wall module 460 has successfully been wirelessly paired with bed 30 for wireless Bluetooth communications, the illumination of icon 486 is turned on so that icon 486 is visible. In some embodiments, the backlighting of icon 486 is white in color. If no bed is plugged into either of receptacles 464, 468 such that no Bluetooth communication between wall module 460 and any bed 30 is occurring, then the backlighting of all of icons 484, 486, 488 is turned off such that all of icons 484, 486, 488 become deadfronted. Accordingly, the icon illumination scenarios shown in FIGS. 24 and 25 are provided only for discussion purposes, it being understood that the depicted illumination scenarios can only occur if a bed 30 is plugged into one of receptacles 466, 468. However, if bed 30 is hardwired to the nurse call system 43, such as via the use of Y-cable 216 or T-cable 248, then icon 486 is backlit and icon 484 remains unlit.

Caution icon 488 is only illuminated if an error occurs. In some embodiments, the backlighting of icon 488 is yellow or amber in color. One example of an error that may occur resulting in illumination of icon 488 is if nurse call cable 490 becomes disconnected from ASBC 164. In such a situation, nurse call icon 486 is turned off in addition to caution icon 488 being turned on. In some embodiments in which bed 30 includes GUI 38, then a message regarding the error is also displayed on GUI 38. Such a message may read, for example, "The Wall Module Cable has become disconnected from the wall." An image depicting the disconnected cable is be shown on the GUI 38 as well in some embodiments. Other errors resulting in illumination of caution icon 488 include those occurring in the internal circuitry of wall module 460. If bed 30 is hardwired to the nurse call system 43, such as via the use of Y-cable 216 or T-cable 248, when an error in the internal circuitry of wall module 460 occurs, then nurse call icon 486 remains illuminated along with the illumination of caution icon 488.

If a Y-cable 216 is being used with wall module 460 and the bed 30 becomes disconnected from nurse call connector 228 at the end of cord branch 226 (or if T-cable 248 is being used and bed 30 becomes disconnected from connector 250), then nurse call icon 486 is turned off. In this situation, if bed 30 includes a GUI 38, then a message appears on GUI 38 with instructions to either unplug bed 30 from wall module 460 and plug it back in to wall module 460 in order to initiate a new Bluetooth pairing process between bed 30 and wall module 460, or to reconnect the wired connection between bed 30 and Y-cable 216 (or T-cable 248). Such a message may read, for example, "Please unplug and replug bed power cord into Wall Module or use the wired Call Light Connection."

If bed 30 is paired wirelessly with wall module 460 and then the wireless pairing drops unexpectedly or an error occurs in the internal circuitry of wall module 460, then icons 484, 486 are turned off and caution icon 488 is illuminated. In this situation, if bed 30 includes a GUI 38, then a message appears on GUI 38 with instructions to either unplug bed 30 from wall module 460 and plug it back in to wall module 460 in order to initiate a new Bluetooth pairing process between bed 30 and wall module 460, or to reconnect the wired connection between bed 30 and the nurse call system 43. Such a message may read, for example, "Please unplug and replug bed power cord into Wall Module or use the wired Call Light Connection." So, basically, if a wired or wireless connection to the nurse call system 43 from bed 30 is dropped or lost, the message on GUI 38 advises the user to reestablish the connection to the nurse call system 43 either wirelessly or via a wired connection by appropriate action.

In a variant embodiment of wall module 460, duplex AC outlet receptacle 464 is oriented so that receptacles 466, 468 are in a side-by-side arrangement rather than in the above-below arrangement depicted in FIGS. 24 and 25. In such a variant embodiment, label 480 is attached to whichever of sidewalls 478 of housing 462 becomes the upwardly facing wall and icons 484, 486, 488 are rotated by 90 degrees within zone 482 so as to have the proper upright orientation. In such a variant embodiment of wall module 460, nurse call cable 490 can either remain extending from wall 476 of housing 462 (i.e., projecting sideways from housing 462) or be moved so as to extend downwardly from which of sidewalls 478 becomes the downwardly facing wall at the option of the module designer.

The variant embodiment of wall module 460 having receptacles 466, 468 in the side-by-side arrangement, basically results from rotating the illustrative wall module 460 by 90 degrees. Thus, it should be understood that the description below of wall module 460 having receptacles 466, 468 in the above-below arrangement is equally applicable to the variant embodiment of wall module 460 having receptacles 466, 468 in the side-by-side arrangement with the described structures simply being rotated by 90 degrees in the variant embodiment.

Still referring to FIGS. 24 and 25, recess 470 in the front wall 472 of housing 462 is defined by a recess top wall 492, a recess bottom wall 494, a pair of spaced apart recess sidewalls 496, and a recess back wall 498. Walls 492, 494, 496 extend forwardly from recess back wall 498 to a front wall surface 500 of front wall 472. Recess sidewalls 496 extend generally vertically between top and bottom walls 492, 494 and blend therewith at rounded corner regions. Sidewalls 496 taper by a slight amount inwardly from front wall surface 500 to recess back wall 498. Thus, in FIG. 25, portions of a first pair of apertures 502 formed in one of recess sidewalls 496 and portions of a second pair of apertures 504 formed in the other of recess sidewalls 496 can be seen.

A first infrared (IR) beam is provided in front of receptacle 466 between an upper set of apertures 502, 504 and a second IR beam is provided in front of receptacle 468 between a lower set of apertures 502, 504. If desired, a transparent lens or window 506 covers or fills one or more of openings 502, 504 as shown, for example, in FIG. 24 with regard to openings 502. When power plug 180 of bed 30 is plugged into receptacle 466 or receptacle 468, the respective IR beam is blocked or broken which results in the detection by the circuitry of wall module 460 that bed 30 has been plugged into wall module 460. In a variant embodiment of wall module 460, a single generally vertically oriented IR beam is provided between an aperture formed in recess top wall 492 and an aperture formed in recess bottom wall 494. Thus, when power plug 180 is plugged into either of receptacles 466, 468, the single IR beam is broken which results in the detection by the circuitry of wall module 460 that bed 30 has been plugged into wall module 460.

Figure 26:
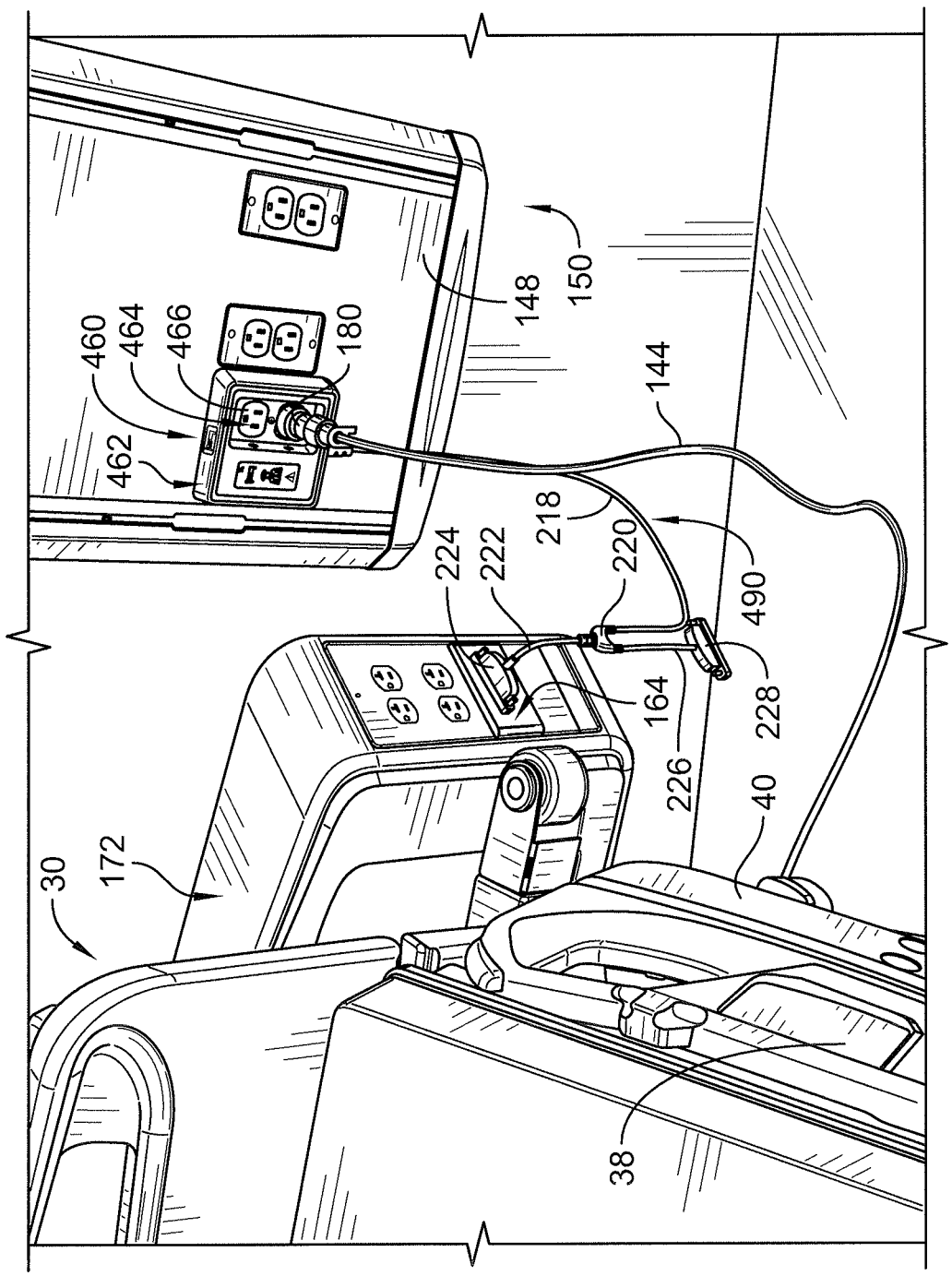
FIG. 26 is a perspective view, similar to FIG. 7, showing a Y-cable extending from a bottom of the wall module of FIGS. 24 and 25, the Y-cable having a first nurse call connector coupled to the nurse call port of an ASBC and the Y-cable having a second nurse call connector that is configured for coupling to a mating nurse call connector at an end of a nurse call cable that extends from the patient bed.

Referring now to FIG. 26, bed 30 has its power plug 180 at the end of power cord 144 plugged into wall module 460 which, illustratively, is mounted to panel 148 of service chase 150. In particular, plug 180 is plugged into the lower receptacle 468 of duplex AC outlet 464. Also in the FIG. 26 example, nurse call cable 490 is shown to be the same as Y-cable 216 of FIG. 7 and so the same reference numbers are used to denote portions of cable 490 that are the same as portions of cable 216. Other portions of FIG. 26 that are the same as FIG. 7 are also denoted with like reference numbers. Accordingly, the descriptions above the various portions of FIG. 26 having like reference numbers are equally applicable to FIG. 26 and so the descriptions are not repeated.

Wall module 460 uses breakbeam technology in connection with its AC plug sensor such that when the IR beam in front of either of receptacles 466, 468 is broken, wall module 460 the steps for wirelessly pairing wall module 460 and bed 30 occurs in the same manner as described above. Thus, the present disclosure contemplates that any of the wireless pairing algorithms discussed above in connection with FIGS. 6A-6D may be implemented by wall module 460 and bed 30 in various embodiments. Furthermore, the discussion above of the circuitry of wall module 32 in connection with FIG. 2 and FIG. 9 is equally applicable to wall module 460 unless specifically noted otherwise and so the description is not repeated.

Figure 27:
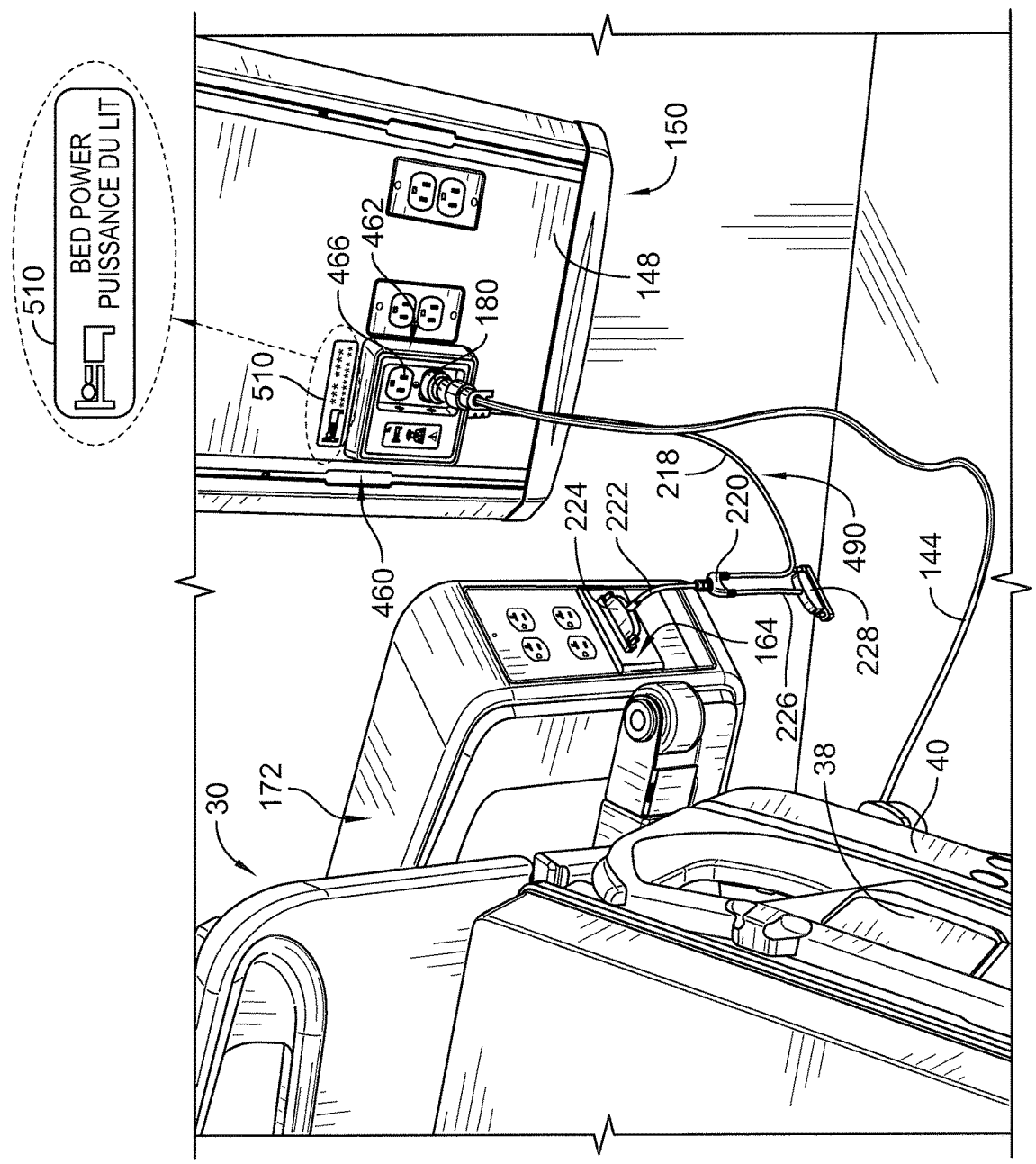
FIG. 27 is a perspective view, similar to FIG. 26, showing that the bed icon label is omitted from the top wall of the housing and replaced with a bed power label that is adhered to a vertical wall of a service chase above the wall module.

Referring now to FIG. 27, an embodiment of wall module 460 is shown in which bed icon label 480 is omitted from top wall 474 of housing 462 and is replaced with a bed power label 510. Label 510 is adhered to vertical wall or panel 148 of service chase 150 above wall module 460. In the illustrative example of label 510, the text "BED POWER" and "PUISSANCE DU LIT" appears next to a bed icon. Thus, English and French text is provided on illustrative label 510 to indicate, in two different languages, that power cord 144 of bed 30 should be plugged into either of receptacles 466, 468 of duplex AC outlet 464 of wall module 460. In other embodiments of label 510, text is provided in only one language. Embodiments of label 510 having two or more languages including at least one language other than English or other than French are contemplated by the present disclosure as well.

Figure 28:
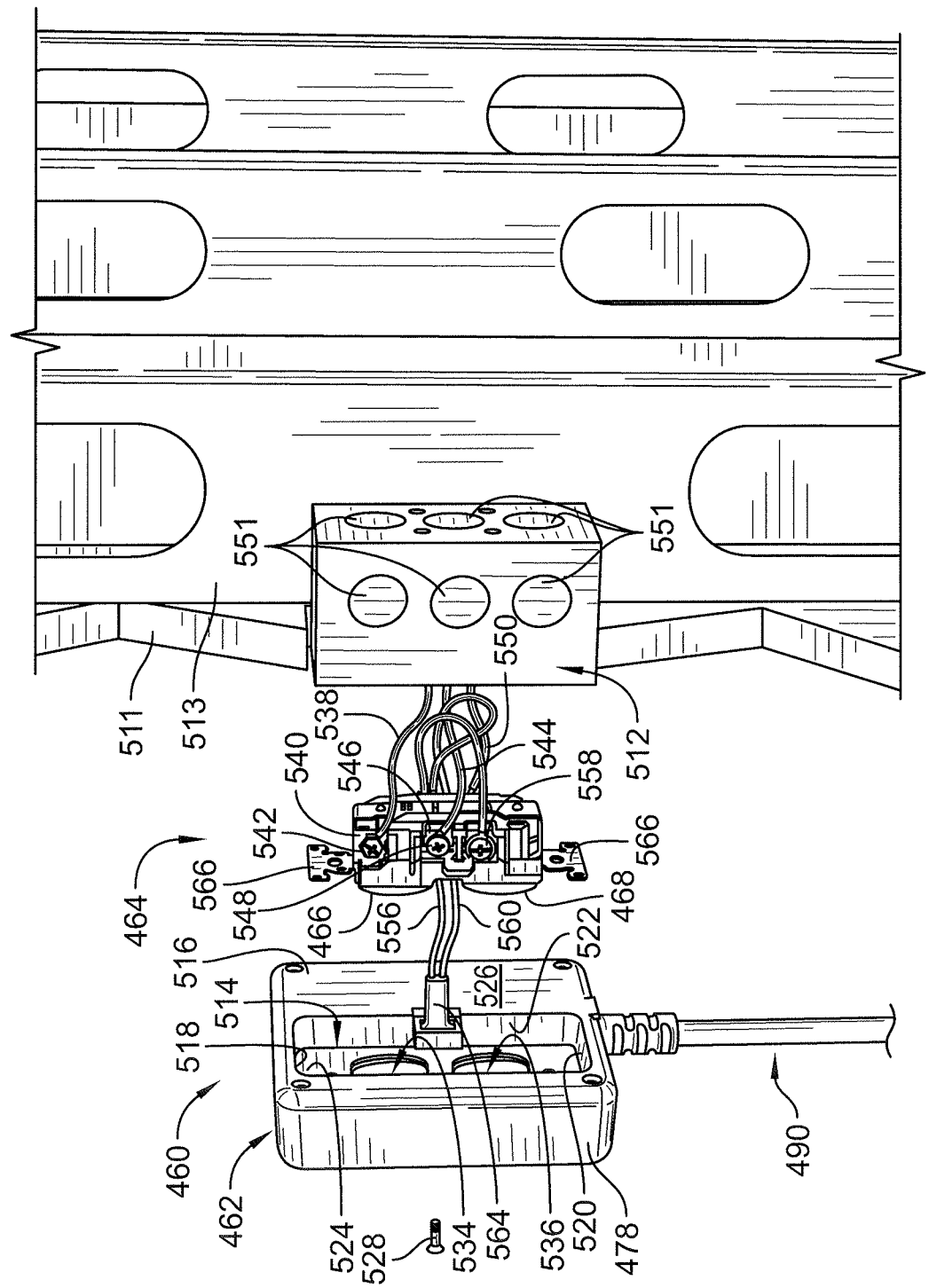
FIG. 28 is a perspective view of first steps of an installation process of the wall module of FIGS. 24 and 25 showing the healthcare facility duplex AC outlet detached from an electrical gang box of the healthcare facility and arranged for insertion into a recess formed in a back wall of the wall module, showing a short coupling screw in front of the wall module, and showing electrical wiring from the wall module attached by screws to a neutral bus and a hot bus at the sides of the healthcare facility duplex AC outlet.

Referring now to FIGS. 28-33, steps for installing wall module 460 in a healthcare facility are shown. In FIG. 28, duplex AC outlet 464 of a healthcare facility is detached from an electrical gang box 512 of the healthcare facility and is arranged for insertion into a rear recess 514 formed in a back wall 516 of housing 462 of wall module 460. Gang box 512 remains mounted to a wall 511 and/or to a stud 513 of the healthcare facility. Recess 514 formed in back wall 516 is about the same size as recess 470 formed in front wall 472 and these recesses 470, 514 are generally aligned. Recess 514 in the back wall 516 of housing 462 is defined by a recess top wall 518, a recess bottom wall 520, a pair of spaced apart recess sidewalls 522, and a recess front wall 524. Walls 518, 520, 522 extend rearwardly from recess front wall 524 to a back wall surface 526 of back wall 472. Recess sidewalls 522 extend generally vertically between top and bottom walls 518, 520 and blend therewith at rounded corner regions.

Figure 34:
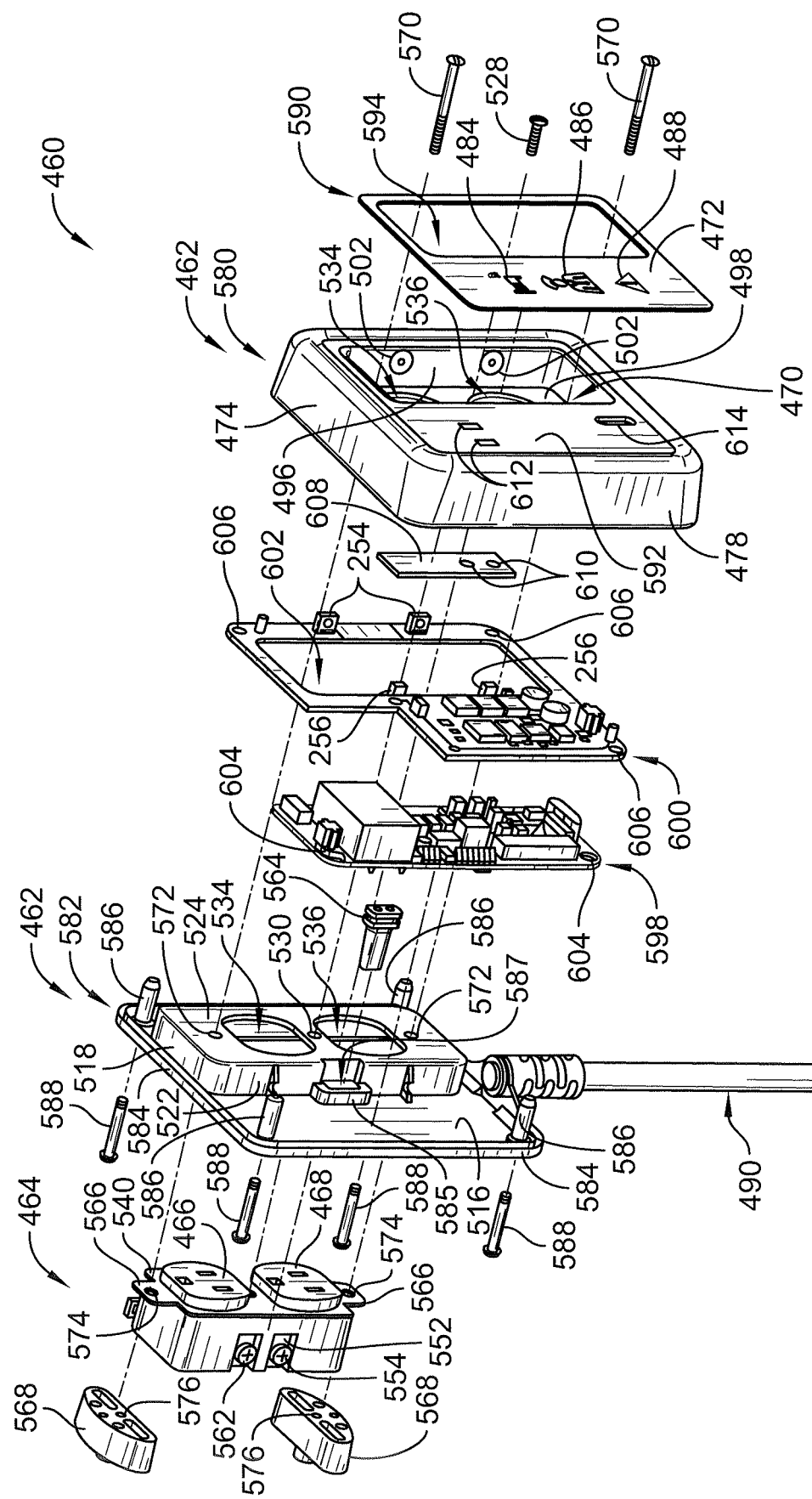
FIG. 34 is an exploded view of the wall module of FIGS. 24-33 showing, from left to right, the upper and lower spacers, the healthcare facility duplex AC outlet, four coupling screws, a molded back plate of the housing with the nurse call cable extending downwardly therefrom, a grommet for the electrical wiring of the wall module, a nurse call circuit board, a main circuit board having a rectangular opening for receipt of the AC outlets of the duplex AC outlet therethrough and having photo emitters and photodetectors supported on opposite sides of the rectangular opening, a WiFi/Bluetooth antenna, a molded front plate of the housing, a cosmetic overlay, and the long and short screws.
Figure 35:
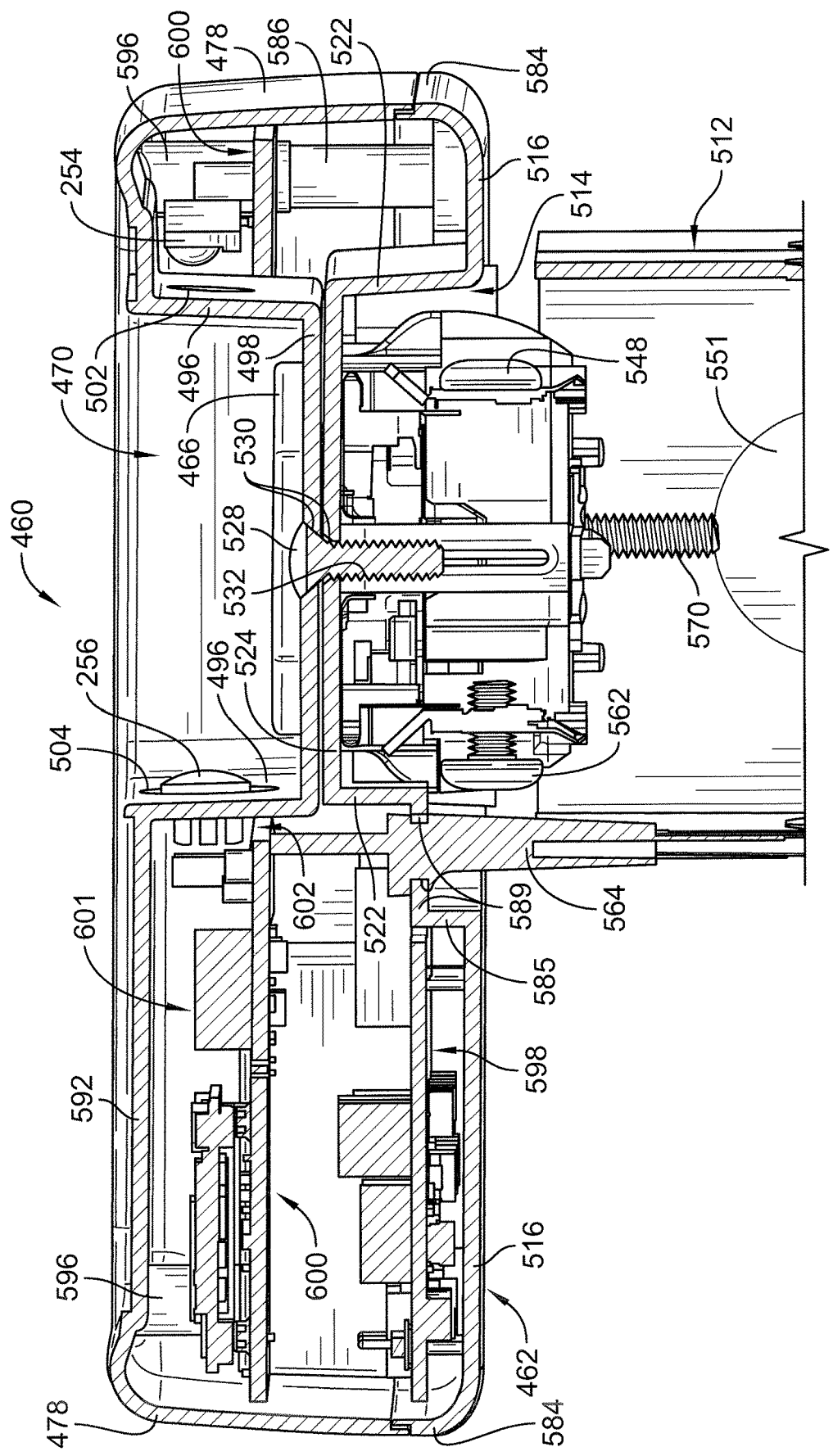
FIG. 35 is a cross sectional view of the wall module, taken along line 35-35 of FIG. 33, showing one of the photo emitters and one of the photodetectors being in optical communication through respective apertures formed in sidewalls of a portion of the front plate of the housing that defines the recess in the front wall of the housing and showing the nurse call circuit board and main circuit board being supported within an interior region of the housing of the wall module in spaced apart, parallel relation.

Still referring to FIG. 28, a short coupling screw 528 is shown in front of the wall module 460 and is arranged for insertion through screw-receiving apertures 530, shown in FIGS. 34 and 35, formed in recess back wall 498 and recess front wall 524 for threaded engagement with a thread bore 532 of duplex AC outlet 464. Threaded bore 532 is situated between the first and second AC receptacles 466, 468 of AC outlet 464. Each of recess back wall 498 and recess front wall 514 are formed to include an upper opening 534 shaped to receive upper AC receptacle 466 therethrough and a lower opening 536 shaped to receive lower AC receptacle 468 therethrough. Housing 462 is configured to that recess back wall 498 is positioned against recess front wall 514 either in abutting relation or with minimal spacing, such as on the order of about 0.1 mm to about 1.0 mm, therebetween. Apertures 530 of walls 498, 514 are generally aligned (e.g., within manufacturing tolerances) and in registry with each other, openings 534 of walls 498, 514 are aligned and in registry with each other, and openings 536 of walls 498, 514 are aligned and in registry with each other.

When duplex AC outlet 464 is removed from gang box 512, the power conductors or wires of the healthcare facility are left attached to the duplex AC outlet as shown in FIG. 28. In particular, a ground wire 538 remains electrically coupled to a ground frame 540 of outlet 464 by use of a screw 542 that clamps an exposed portion of wire 538 to ground frame 540, a neutral wire 544 remains electrically coupled to a neutral bus 546 of outlet 464 by use of a screw 548 that clamps an exposed portion of wire 544 to neutral bus 546, and a hot wire 550 remains electrically coupled to a hot bus 552 (see FIG. 34) of outlet 464 by use of a screw 554 that clamps an exposed portion of wire 550 to hot bus 552. Wires 538, 544, 550 are routed into gang box 512 from suitable AC power cabling (not shown) of the healthcare facility. For example, wires 538, 544, 550 extend into gang box 512 through a hole formed by removing one of circular punch outs 551 from a side of gang box 512 that faces stud 513.

After duplex AC outlet 464 is removed from gang box 512, electrical wiring from wall module 460 is electrically coupled to neutral bus 546 and hot bus 552. In particular, a neutral wire 556 extends from back wall 516 of housing 462 and has an exposed portion clamped to neutral bus 546 by use of a screw 558. Similarly, a hot wire 560 extends from back wall 516 of housing 462 and has an exposed portion clamped to hot bus 552 by use of a screw 562 (see FIG. 34). Thus, the circuitry of wall module 460 receives its power from the healthcare facility via electrical wiring 544, 550, 556, 560 and buses 546, 552 of duplex AC outlet 464. Wall module 460 includes a grommet and strain relief 564 at the interface between wires 556, 560 and back wall 516 of housing 462. Wires 556, 560 are press fit through respective passages formed in grommet and strain relief 564 and couple to the circuitry of wall module 460 in the interior region thereof.

Figure 29:
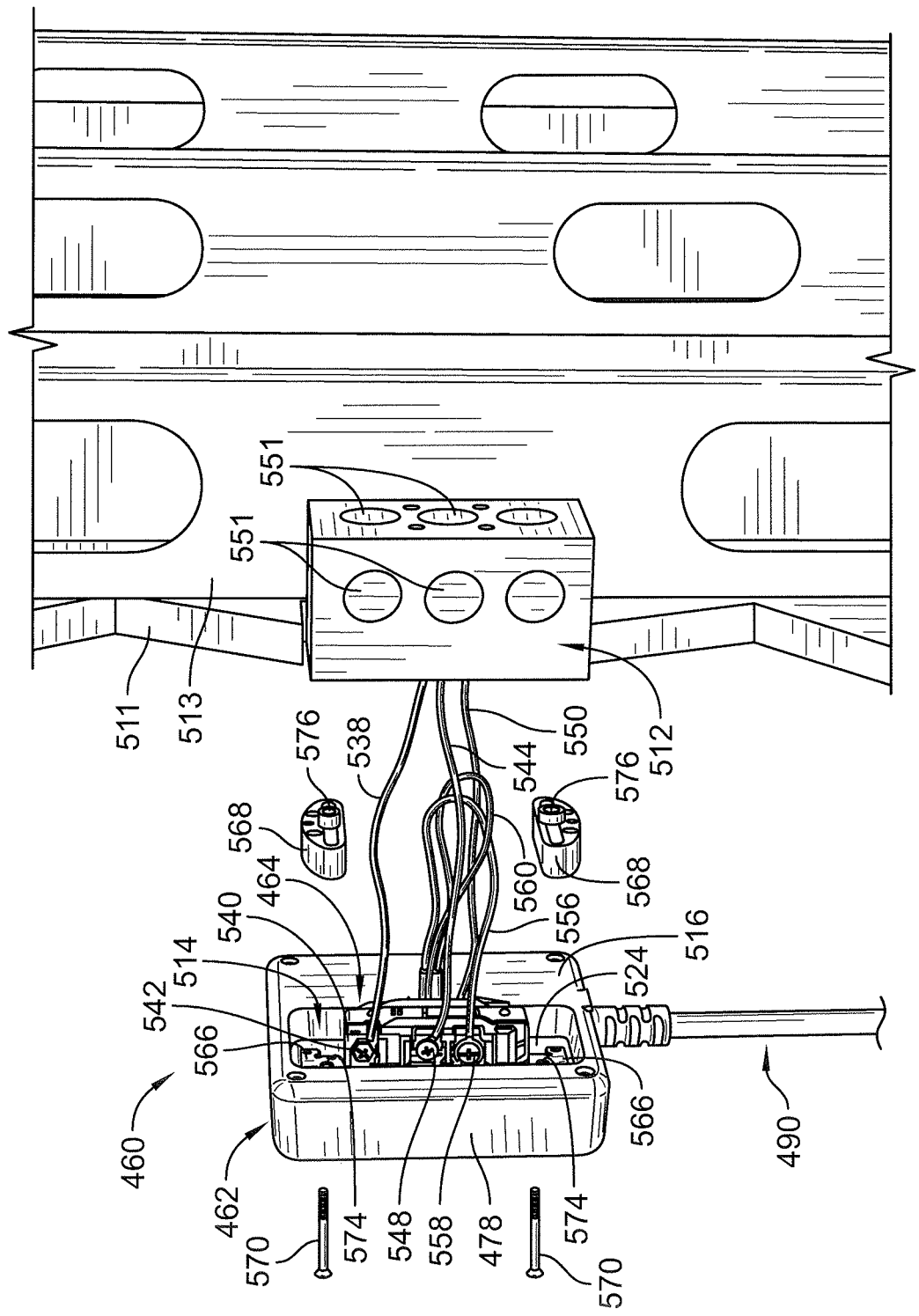
FIG. 29 is a perspective view, similar to FIG. 28, of further steps of the installation process showing the duplex AC outlet received in the recess of the back wall of the wall module, an upper and lower spacer arranged for insertion into the recess of the back wall of the wall module and aligned with respective upper and lower flanges of a ground frame of the duplex AC outlet, and showing upper and lower long screws arranged for insertion through the front and rear walls of the wall module, through apertures in the respective upper and lower flanges of the ground frame, and through the respective upper and lower spacers for receipt in threaded receivers of the gang box.

Referring now to FIG. 29, further steps of the process for installing wall module 460 are shown in which the duplex AC outlet 464 has been inserted into recess 514 of back wall 516 of wall module 460. When placed in recess 514, upper and lower flanges 566 of ground frame 540 abut recess front wall 524. Furthermore, front regions of outlets 466, 468 project through openings 534, 536 of recess front wall 524 and recess back wall 498 such that a slight amount of front regions of outlets 466, 468, such as on the order of about 0.1 mm to about 2 mm, extend beyond recess back wall 498 into recess 470.

Also in FIG. 29, upper and lower spacers 568 are shown arranged for insertion into recess 514 of back wall 516 of wall module 460 and are aligned with respective upper and lower flanges 566 of ground frame 540 of duplex AC outlet 464. Additionally, upper and lower long screws 570 are shown in FIG. 29 arranged for insertion through apertures 572 in the recess back and front walls 498, 524 of wall module 460. Apertures 572 in recess back wall 498 cannot be seen but they are substantially the same as aperture 530 in recess back wall 498 shown in FIG. 35. Upper and lower long screws 570 also are arranged in FIG. 29 to extend through apertures 574 in the respective upper and lower flanges 566 of ground frame 540 and through passages 576 formed in the respective upper and lower spacers 568 for receipt in threaded receivers (not shown, but well known in the art) of gang box 512.

Figure 30:
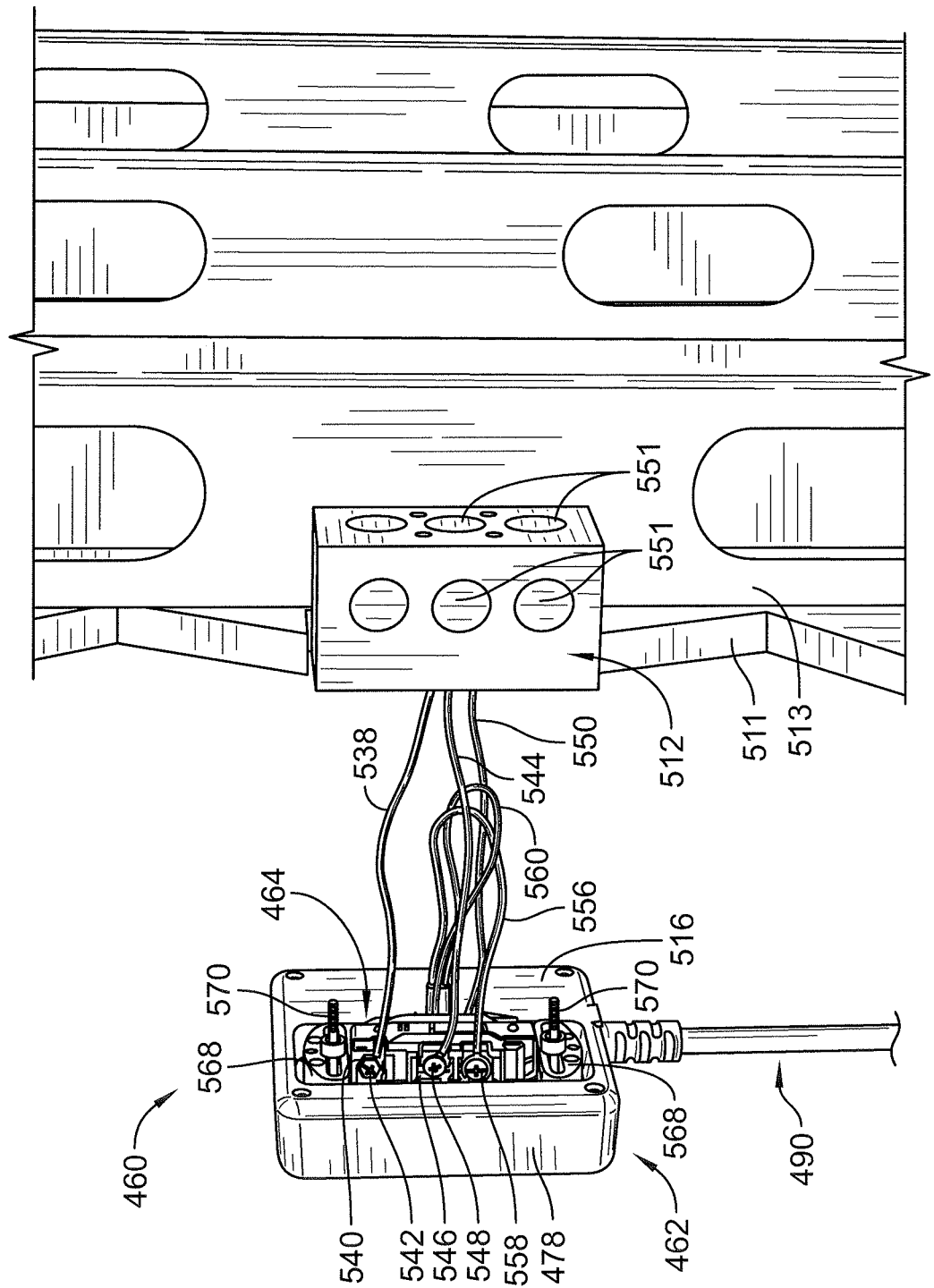
FIG. 30 is a perspective view, similar to FIG. 29, of still further steps of the installation process showing the upper and lower spacers received in the recess of the back wall of the wall module and showing threaded portions of the long screws projecting from the upper and lower spacers toward the junction box.
Figure 31:
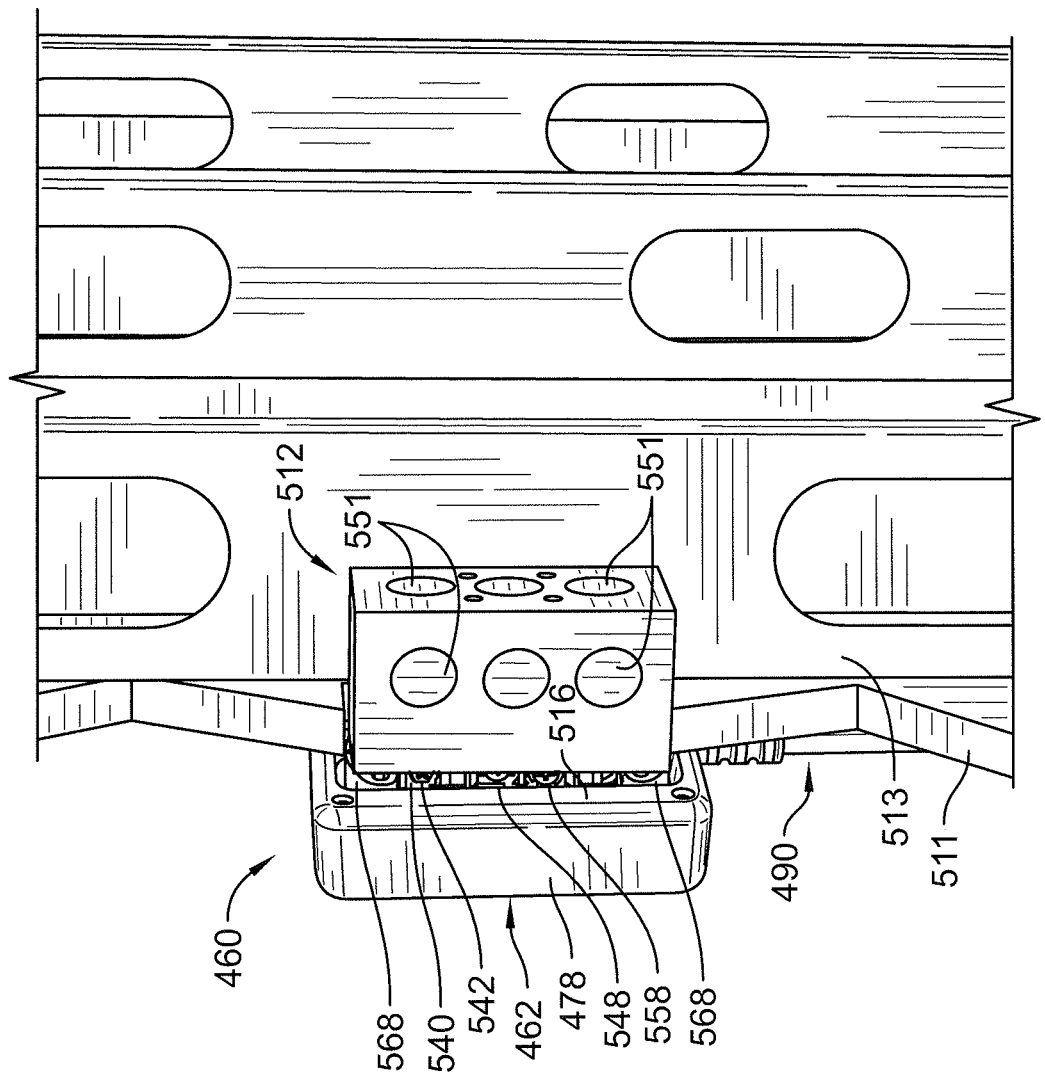
FIG. 31 is a perspective view, similar to FIG. 30 of the yet further steps of the installation process showing the wall module fastened to the junction box.

Referring now to FIG. 30, still further steps of the process for installing wall module 460 in the healthcare facility are shown in which the upper and lower spacers 566 have been inserted into recess 514 of back wall 516 of wall module 460 and in which long screws 570 have been inserted through apertures 572 and passages 576 such that threaded portions of the long screws 570 project from the upper and lower spacers 568 toward the gang box 512. When inserted into recess 514, spacers 568 fill the space in recess 514 between flanges 566 and the back surface 526 of wall module 460 provided by back wall 516 around the opening into recess 514. FIG. 31 shows wall module 460 fastened to gang box 512. When wall module 460 is fastened to gang box 512, screws 570 are threaded into the threaded apertures of gang box 512 until back wall 516 of housing 462 of wall module 464 abuts wall 511 of the healthcare facility. The present disclosure contemplates that fasteners other than screws 528, 570 may be used in wall module 464 if desired. Such other fasteners may include for example, rivets, snaps, snap fingers, barbed couplers, dowels, biscuits, straps, ties, cam locks, adhesive, magnets, clamps, clasps, and similar such devices.

Figure 32:
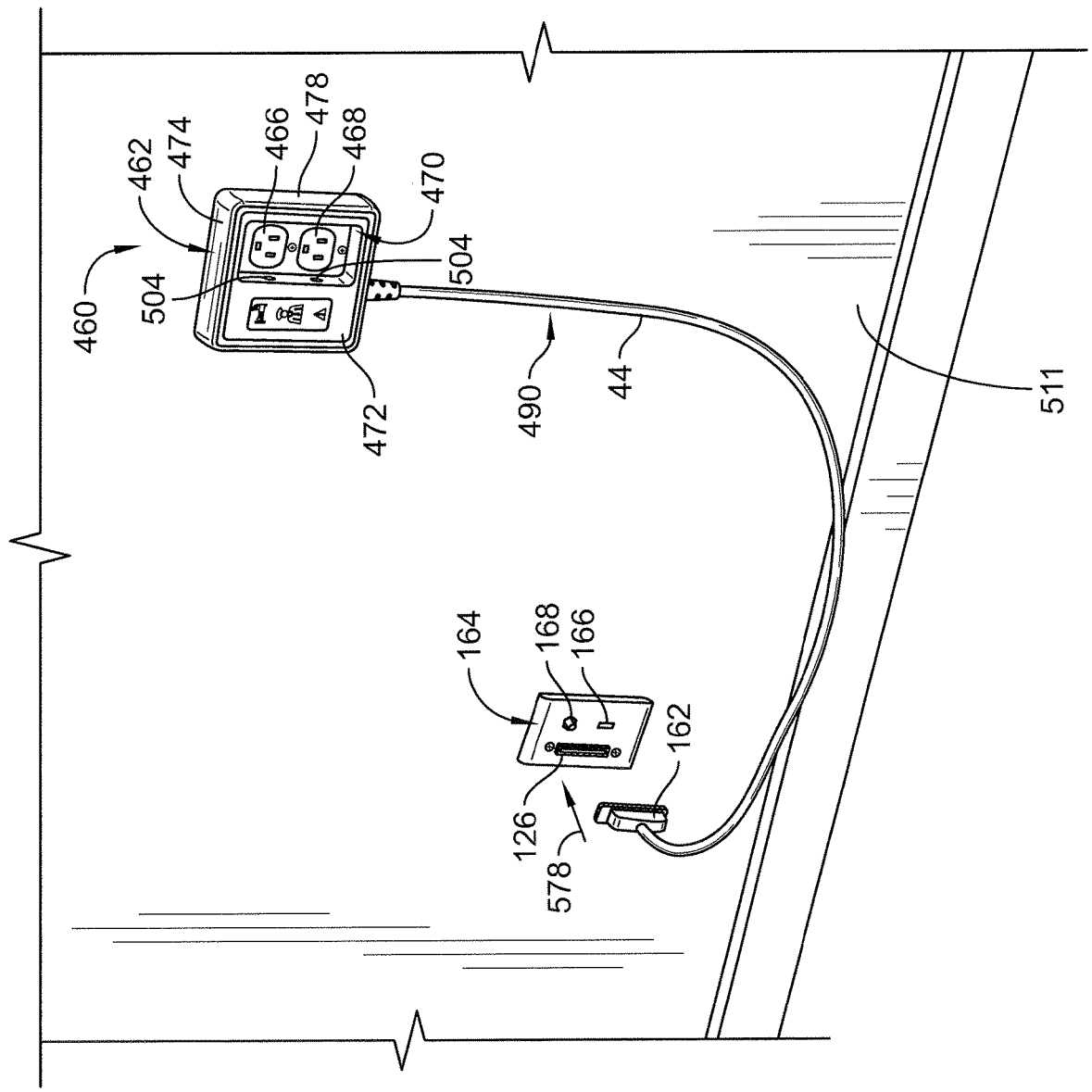
FIG. 32 is a perspective view of the wall module of FIGS. 24-31 showing a variant nurse call cable extending from a bottom of the wall module and terminating at a nurse call connector arranged for coupling to a nurse call port of an audio station bed connector (ASBC) mounted to a room wall of the patient room.
Figure 33:
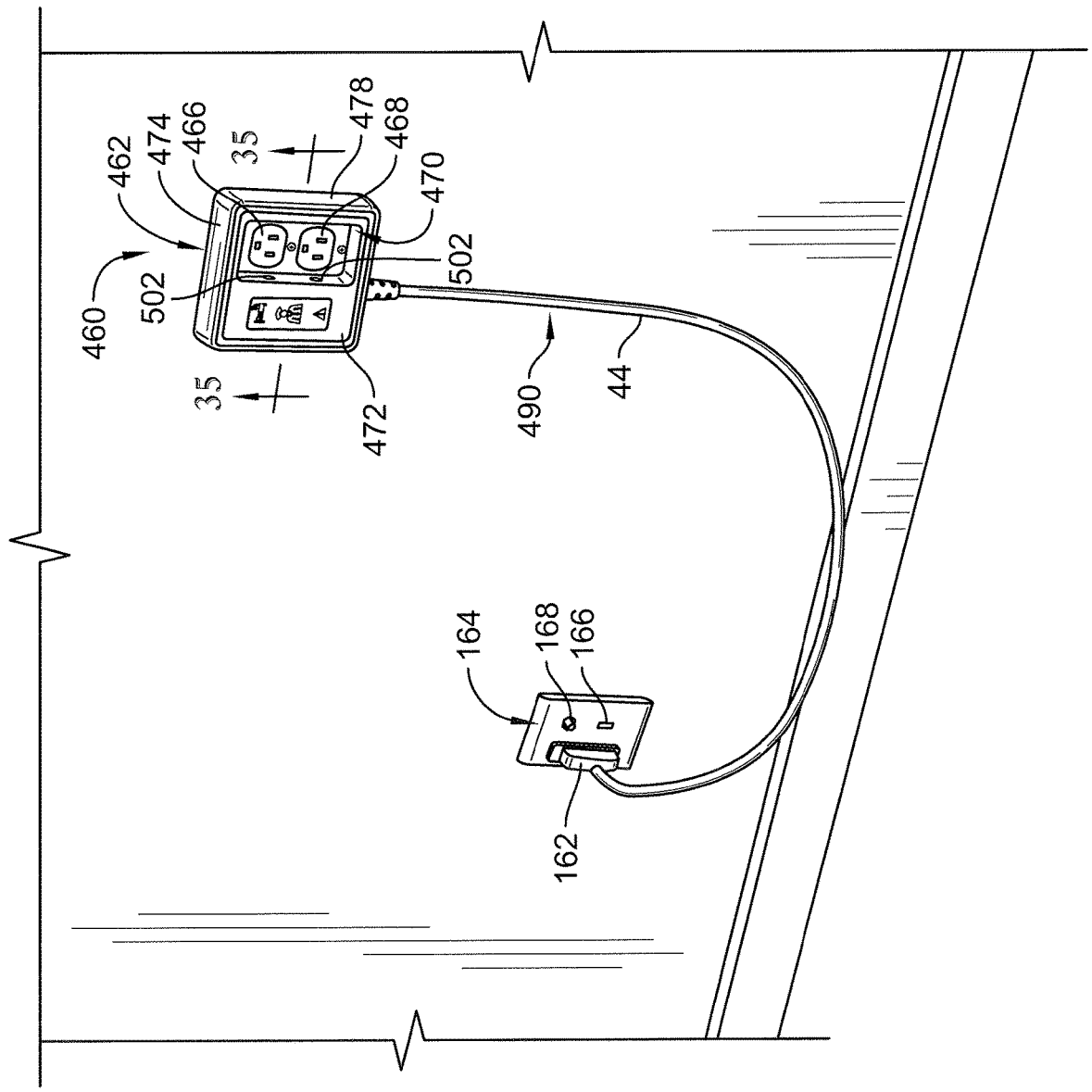
FIG. 33 is a perspective view, similar to FIG. 32, showing the nurse call connector of the variant nurse call cable coupled to the nurse call port of the ASBC to complete the installation process of the wall module of FIGS. 24-32.

Referring now to FIG. 32, the depicted wall module 460 is shown with nurse call cable 490 being 37-pin nurse call cable 44 that terminates at nurse call connector 162. Thus, the description above of cable 44 and connector used with wall module 32 is equally applicable to wall module 460 and the description is not repeated. In FIG. 32, connector 162 is arranged for coupling to nurse call port 126 of ASBC 164 which is mounted to room wall 511 of the respective patient room. Nurse call connector 162 is movable in the direction of arrow 578 to couple to nurse call port 126 of ASBC 164. The discussion above of ASBC 164, nurse call port 126, speaker pillow port 166, and jack receptacle 168 in connection with FIGS. 3 and 4 is equally applicable to FIG. 32 and the description is not repeated. As shown in FIG. 33, nurse call connector 162 of nurse call cable 44 is coupled to nurse call port 126 of ASBC 164 which completes the installation process of wall module 460 in the respective patient room.

Referring now to FIG. 34, an exploded view of wall module 460 is shown. Several of the components of wall module 460 and the associated features were discussed above and the descriptions of these are not repeated. As shown in FIG. 34, housing 462 of wall module 460 includes a molded front plate 580 and a molded back plate 582. Molded front plate 580 includes walls 474, 476, 478, 492, 494, 496 and a main wall 592. Front wall 472 and front surface 500 of housing 462 actually are provided by an overlay 590 that adheres to main wall 592 of molded front plate 580. A central region of wall 592 is recessed inwardly from an outer peripheral region of wall 592 by an amount that is about the same as the thickness of overlay 590 such as on the order of about 0.5 mm to about 2 mm. Overlay 590 includes a rectangular opening 594 through which recess 470 is accessible.

Molded back plate 582 includes walls 516, 518, 520, 522, 524. Molded back plate 582 also includes a rim or ridge 584 that extends by a slight amount (e.g., about 2 to about 3 mm) from the periphery of back wall 516 toward molded front plate 580. Molded back plate 582 includes a passage wall 585 adjacent to recess sidewall 522 that forms an opening 587 for receipt of strain relief and grommet 564. A groove provided in the grommet portion of strain relief and grommet 564 receives a lip 589 of wall 585 therein as shown best in FIG. 35. A portion of lip 589 projects from recess sidewall 522 as also shown in FIG. 35.

Molded back plate 582 further includes four tubular standoffs 586 in the corner regions thereof as shown in FIG. 34. Wall module 460 includes four coupling screws 588 that extend through standoffs 586 and are threaded into threaded bosses 596, two of which are shown in FIG. 35, that are molded into the corner regions of molded front plate 580 in the interior region thereof. Thus, when molded back plate 582 is attached to molded front plate 580 with screws 588, ridge 584 abuts walls 474, 476, 478. Other fasteners (see above) may be used to connect plates 580, 582 together in other embodiments. Molded front and back plates 580, 582 are made from a plastics material having suitable strength characteristics or from a metal material, such as powdered or sintered metal like aluminum, for example.

Referring again to FIG. 34, wall module 460 includes a nurse call circuit board 598 and a main circuit board 600 having a rectangular opening 602 for receipt of AC outlets 466, 468 of duplex AC outlet 464 therethrough. Nurse call circuit board 598 includes components associated with the nurse call functionality of wall module 460 such as including, for example, shift registers and/or relays 124, port 128, and audio codec 238 shown in FIGS. 2 and 9. Main circuit board 600 includes circuit components associated with other functions of wall module 460 such as including, for example, SUM 114 with microprocessor 116, memory 118, WiFi module 120, and Bluetooth module 122 also shown in FIGS. 2 and 9. Furthermore, main circuit board 600 has two photo emitters 254 and two photodetectors 256 supported on opposite sides of rectangular opening 602. As shown in FIG. 35, nurse call circuit board 598 and main circuit board 600 are supported within an interior region 601 of housing 462 of wall module 460 in spaced apart, parallel relation.

Photo emitters 254 of wall module 460 are aligned with respective holes 502 formed in one of recess sidewalls 496 and photodetectors 256 of wall module 460 are aligned with respective holes 504 formed in the other of recess sidewalls 496 as shown best in FIG. 35. Main circuit board 600, therefore, also includes detection circuit 264 shown in FIG. 14. As alluded to above in connection with the discussion of FIGS. 14 and 15, beams of IR light 262, 262' are provided in front of receptacles or outlets 260 in some contemplated variant embodiments. Illustrative wall module 460 is such a modified embodiment, similar to FIG. 14, in which beams of IR light 262 between photo emitters 254 and photodetectors 256 are provided in front of receptacles 466, 468. As noted above, one of these beams of IR light are broken or interrupted when plug 180 from bed 30 is plugged into receptacle 466 or receptacle 468. In another variant embodiment of wall module 460, similar to FIG. 15, a single beam of IR light 262' between photo emitter 254' and photodetector 256' is provided in front of both receptacles 466, 468 and is broken in response to plug 180 being plugged into either of receptacles 466, 468.

Circuit board 598 includes apertures 604 formed in two of the corner regions thereof. Circuit board 600 includes apertures 606 formed in three of the corner regions thereof. Tubular standoffs 586 and/or bosses 596, as the case may be, extend through the respective apertures 604, 606 of circuit boards 598, 600 to hold the circuit boards 598, 600 in place in the interior region of housing 462. As shown in FIG. 34, wall module includes a WiFi/Bluetooth antenna 608. Antenna 608 is rectangular in shape and has a pair of apertures 610 in a bottom region thereof for connection to the electric circuitry of board 600. A pair of apertures 612 are formed in main wall 592 of molded front plate 580 for receipt of a pair of clips (not shown) that are used to attach antenna 608 behind main wall 592. LED's 184 shown diagrammatically in FIG. 9 are built into the overlay 590 behind the respective icons 484, 486, 488. An aperture 614 is formed in main wall 592 of molded front plate 580 and a ribbon cable (not shown) extending from overlay 590 is routed through aperture 614 for connection to main circuit board 600. The ribbon cable includes the conductors that used for turning the LED's 184 of overlay 590 on and off.

Figure 36:
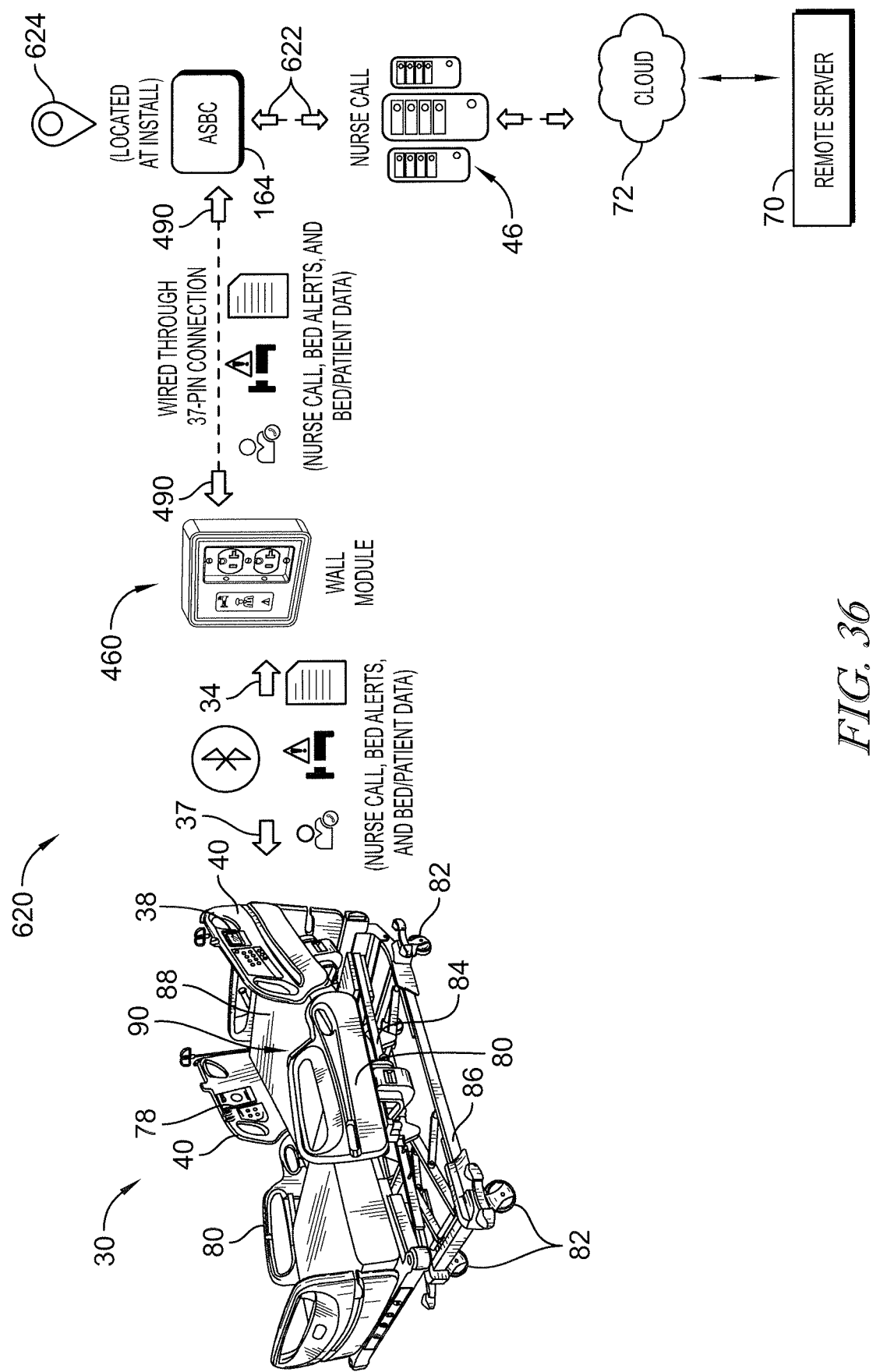
FIG. 36 is a diagrammatic view showing a first system architecture in which the wall module of FIGS. 24-35 communicates wirelessly with a bed and communicates via wired communication links with an ASBC and a nurse call server that, in turn, communicates with a remote server via the Internet (aka the cloud) and in which the bed, the wall module, the ASBC, and nurse call software on the nurse call server are provided by the same manufacturer.

Referring now to FIG. 36, an alternative embodiment system 620 is shown. System 620 has some components and features that are substantially the same as system 20 discussed above and therefore, the same reference numbers are used to denote such components and features of system 620 without repeating the descriptions. Thus, the descriptions above of such features and components of system 20 are equally applicable to system 620 unless specifically noted otherwise. System 620 has an architecture in which wall module 460 of FIGS. 24-35 communicates wirelessly with bed 30 via communication links 34, 37. Wall module 460 also communicates via a wired communication link, such as cable 490, with ASBC 164 and via a wired communication link 622 with one or more nurse call servers 46 that, in turn, communicates with remote server 70 via the Internet (aka the cloud) 72.

In the embodiment of system 620 of FIG. 36, bed 30, wall module 460, ASBC 164, remote server 70, and the nurse call software on the one or more nurse call servers 46 are provided by the same manufacturer. Thus, communications from bed 30 over wireless link 34 includes nurse calls, bed alerts, bed status data, and patient data occurring on, or detected by, bed 30 and that are formatted in a manner that is compatible for handling by the other hardware components of system 620. With regard to systems 20, 620, nurse calls are generated in response to the patient on bed 30 pressing a nurse call button on control panel 78 of bed 30 or on a controller housing supported by an arm of bed 30 that overlies the patient or on a patient control pendant, control pod, or pillow speaker unit that is wired to the circuitry of bed 30 by a cable or the like. In this regard, see U.S. Patent Application Publication No. 2018/0333317 A1 (see particularly, the discussion of nurse call button 558 at paragraphs 116-118), U.S. Pat. No. 10,363,182 (see particularly, nurse call button 100 in FIG. 2 and the discussion thereof at col. 6, lines 28-30), U.S. Pat. No. 8,104,117 (see particularly, FIG. 4 and the discussion of user inputs including a button 46 for nurse call at col. 6, lines 12-20), and U.S. Pat. No. 7,520,006 (see particularly FIGS. 68-73) and the discussion of nurse call button 1528 at col. 56, lines 46-48), each of which is hereby incorporated by reference herein in its entirety to the extent not inconsistent with the present disclosure which shall control as to any inconsistencies.

Further with regard to system 20 of FIG. 1 and system 620 of FIG. 36 (and the other systems of FIGS. 37-42 described below), examples of bed alerts include one or more of the following: (i) bed exit alerts indicating that a patient has exited from bed 30 or has shifted sufficient weight (e.g., 30 lbs.) off of bed 30 just prior to actually leaving the bed completely, (ii) patient position alerts indicating that the patient has sat up in bed 30 or has moved toward a side of bed 30 beyond a threshold amount, (iii) siderail down alerts indicating that one or more of siderails 40, 80 have been moved to a lowered position, (iv) caster brake alerts indicating that caster brakes of bed 30 have been released or unbraked, (v) bed not down alerts indicating that upper frame 84 of bed 30 has been moved out of its lowest position relative to base frame 86 of bed 30, (vi) head-of-bed (HOB) angle alarms indicating that a head section of bed 30 has been lowered below a threshold angle (e.g., about 30 degrees, about 45 degrees, or about 60 degrees), and (vii) air mattress alerts indicating that a malfunction in an air mattress or related pneumatic system has occurred. This list is not intended to be exhaustive and so other bed alerts may be transmitted by bed 30 to wall modules 32, 460 via respective wireless links 34 in other embodiments.

Still further with regard to system 20 of FIG. 1 and system 620 of FIG. 36 (and the other systems of FIGS. 37-42 described below), examples of bed status data include data indicating one or more of the following: (i) whether the bed brakes are set or braked, (ii) whether upper frame 84 is in its lowest position relative to base frame 86, (iii) whether siderails 40, 80 are in the respective raised positions, (iv) an HOB angle value, (v) motor lockout status (e.g., data indicating whether lift system motors are locked out, whether any of the mattress support deck articulation motors are locked, or that all bed movement motors are locked out), (vi) whether a cardiopulmonary resuscitation (CPR) release handle has been pulled to rapidly lower a head section of the mattress support deck, to move thigh and foot sections of the mattress support deck into positions substantially coplanar with the head section, and to move the upper frame 84 of bed 30 into a Trendelenburg position, (vii) whether the mattress support deck and upper frame 84 have been moved into a chair egress position, (viii) whether a patient has been detected by a weigh scale system of bed 30, (ix) whether a therapy surface 90 on bed 30 has been turned on (mattress 90 is sometimes referred to herein as a surface, as is known in the art), (x) whether a turn assist mode of surface 90 has been activated (i.e., turned on), (xi) whether a maximum inflation mode of surface 90 has been activated, (xii) whether a surface therapy of surface 90 has been activated (e.g., percussion therapy, vibration therapy, rotation therapy, or an opti-rest therapy in which mattress zones such as head, seat, thigh, and foot zones of surface 90 are sequentially deflated partially and then re-inflated), (xiii) whether a percussion/vibration module is present on bed 30 for embodiments of bed 30 in which a percussion/vibration module is used with the pneumatic system of bed 30, (xiv) whether a rotation module is present on bed 30 for embodiments of bed 30 in which a percussion/vibration module is used with the pneumatic system of bed 30, (xv) whether a bed weigh scale is installed on bed 30, (xvi) whether a bed exit alarm is installed on bed 30, (xvii) whether a powered air surface 90 is installed on bed 30, (xviii) bed ID, (xix) bed type, and (xx) whether service is required for bed 30. This list is not intended to be exhaustive and so other bed status data may be transmitted by bed 30 to wall modules 32, 460 via respective wireless links 34 in other embodiments.

Yet further with regard to system 20 of FIG. 1 and system 620 of FIG. 36 (and the other systems of FIGS. 37-42 described below), patient data transmitted from bed 30 includes, for example, one or more of the following: patient weight as measured by the weigh scale system of bed 30, heart rate measured by one or more heart rate sensors provided on some embodiments of bed 30, and respiration rate measured by one or more respiration sensors provided on some embodiments of bed 30. In some embodiments, the same sensor or sensors that measure heart rate on bed 30 also are used to measure respiration rate. Other embodiments of bed 30 may include one or more sensors to measure other physiological characteristics of the patient supported on bed 30, such as blood pressure, pulse oximetry, and temperature, just to name a few. Bed 30 may also read and/or store patient ID (e.g., a medical record number MRN) of the patient for transmission as patient data in some embodiments. These examples of patient data are not intended to be exhaustive and so other patient data may be transmitted by bed 30 to wall modules 32, 460 via respective wireless links 34 in other embodiments.

In FIG. 36, a diagrammatic location icon 624 is shown above ASBC 164 to indicate that a location ID is programmed into ASBC 164 in connection with the installation of ASBC 164 in the healthcare facility. The location ID in ASBC 164 corresponds to the room in which bed 30 and the respective wall module 32, 460, as the case may be, are located. In some embodiments, a computer coupled to nurse call server 46, such as a master nurse station computer, is used to assign the location ID's to the various ASBC's 164 installed in the healthcare facility. In some embodiments, nurse call server 46 associates the bed ID of bed 30 with the location ID of the room, as stored in ASBC 164, in response the bed ID and location ID being transmitted over communication link 622 to server 46. In the embodiment of system 620 shown in FIG. 36, the location ID is not transmitted to wall module 460 or to bed 30.

In some embodiments of system 620, the functionality of local bed data server 62 of FIG. 1 is also included on one or more of nurse call servers 46. If desired, therefore, the bed alerts, bed status data, and patient data received by one or more servers 46 from bed 30 (really, from multiple beds 30 of the healthcare facility) are transmitted to one or more EMR servers 64, one or more ADT servers 66, and one or more other servers 68 (e.g., on or more RTLS servers), as well as to remote server 70 via the cloud 72. Furthermore, a status board 48 is communicatively coupled to one or more nurse call servers 46 for display of some or all of the bed alerts, bed status data, and patient data in some embodiments of system 620.

Figure 37:
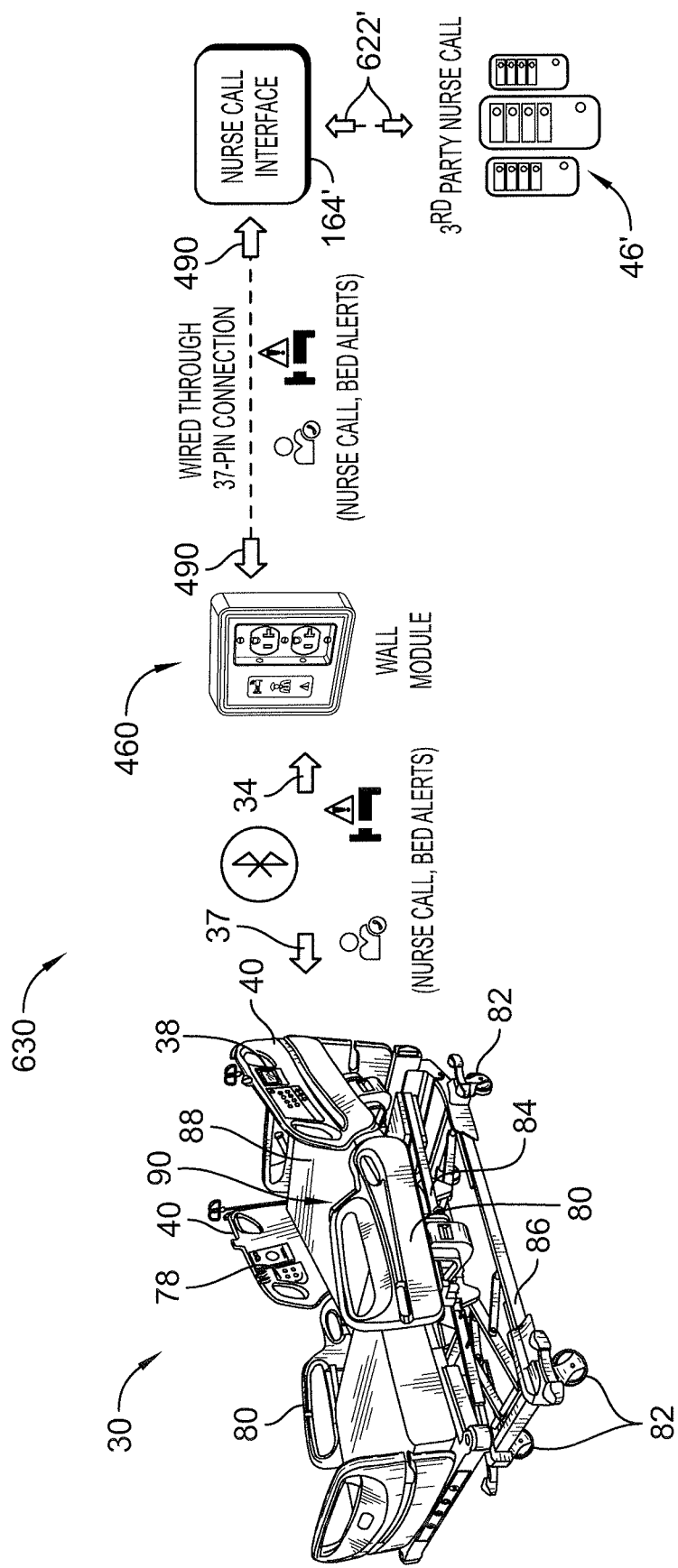
FIG. 37 is a diagrammatic view, similar to FIG. 36, showing a second system architecture in which the wall module of FIGS. 24-35 communicates wirelessly with the bed and communicates via wired communication links with a nurse call interface and a nurse call server and in which the nurse call interface and nurse call software on the nurse call server are provided by a different manufacturer than the manufacturer of the bed and the wall module.

Referring now to FIG. 37, another alternative embodiment system 630 is shown. System 630 has some components and features that are substantially the same as systems 20, 620 discussed above and therefore, the same reference numbers are used to denote such components and features of system 630 without repeating the descriptions. Thus, the descriptions above of such features and components of systems 20, 620 are equally applicable to system 630 unless specifically noted otherwise. System 630 has an architecture in which wall module 460 of FIGS. 24-35 communicates wirelessly with bed 30 via communication links 34, 37. However, in system 630, bed 30 only sends nurse calls and bed alerts to wall module 460. Thus, bed status data and patent data is not sent from bed 30 to wall module 460 in system 630. All bed alerts are sent as priority alerts in some embodiments of system 630. Wall module 460 communicates via wired communication link 490 with a nurse call interface 164' and via a wired communication link 622' with one or more nurse call servers 46'.

In the embodiment of system 630 of FIG. 37, bed 30 and wall module 460 are provided by a first manufacturer but ASBC 164' and the nurse call software on the one or more nurse call servers 46' are provided by a different third party manufacturer (i.e., not the first manufacturer and not the healthcare facility). Thus, prime symbols ("'") are used to denote portions of system 630 that are not provided by the first manufacturer. Basically, system 630 is illustrated herein to show that wall module 460 is able to be used with a third party nurse call system, if desired, as long as the third party nurse call system is equipped with a 37-pin connector on interface 164' for connection to nurse call cable 490 extending from wall module 460. It is within the present disclosure for the one or more nurse call servers 46' of system 630 to be communicatively coupled to other computer devices but these are not shown in FIG. 37 because such additional system architecture is at the discretion of the healthcare facility.

Figure 38:
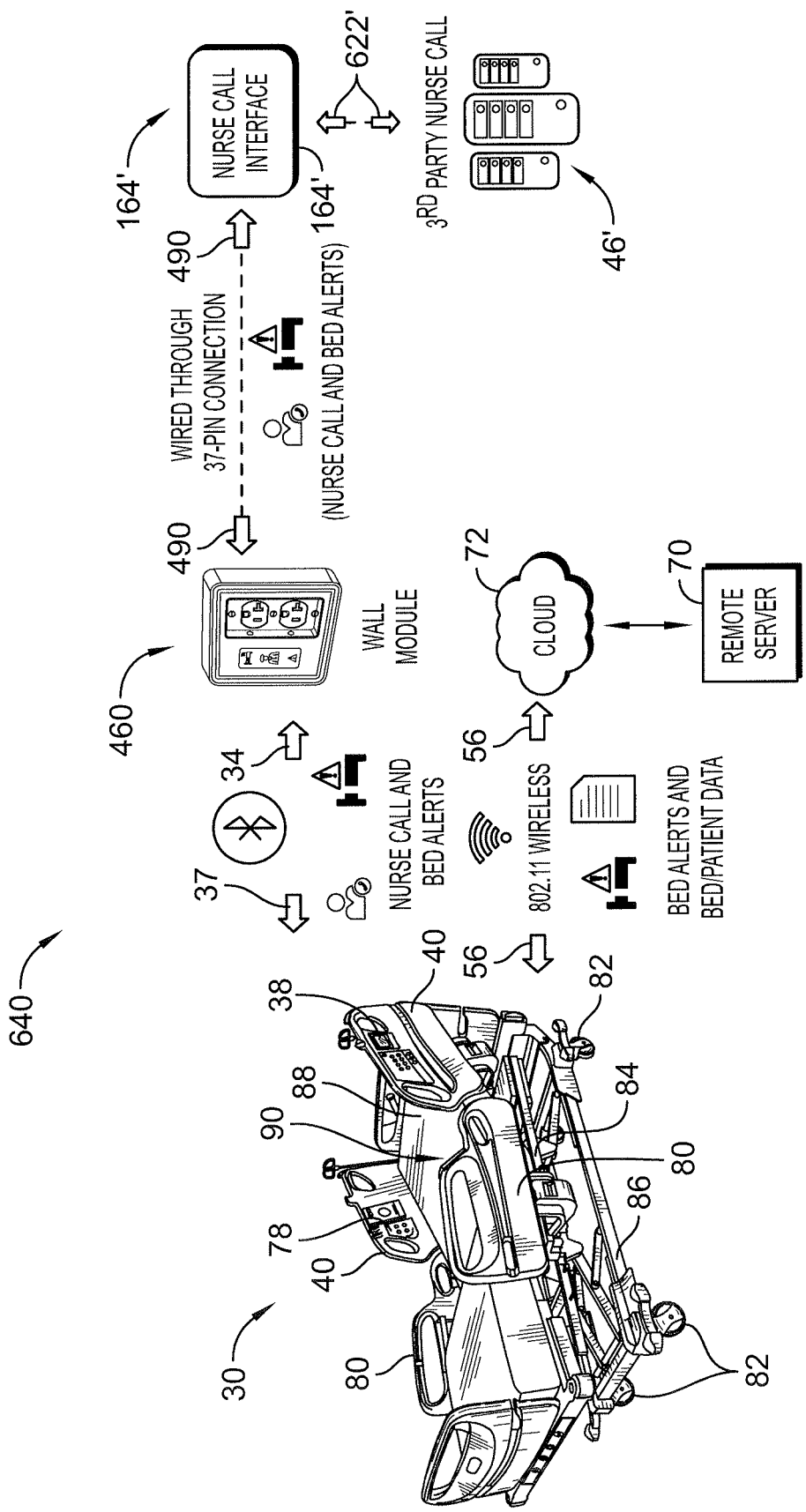
FIG. 38 is a diagrammatic view, similar to FIG. 37, showing a third system architecture in which the bed is configured to communicate wirelessly with a remote server via the Internet (aka the cloud)

Referring now to FIG. 38, yet another alternative embodiment system 640 is shown. System 640 has some components and features that are substantially the same as systems 20, 620, 630 discussed above and therefore, the same reference numbers are used to denote such components and features of system 640 without repeating the descriptions. Thus, the descriptions above of such features and components of systems 20, 620, 630 are equally applicable to system 640 unless specifically noted otherwise. System 640 has an architecture in which wall module 460 of FIGS. 24-35 communicates wirelessly with bed 30 via communication links 34, 37. Wall module 460 also communicates with nurse call interface 164' via cable or communication link 490, and interface 164', in turn, communicates with third party nurse call server 46' via communication link 622'. This portion of system 640 is the same as system 630 described above. However, in system 640, bed 30 is also equipped with WiFi communication capability, indicated by the 802.11 Wireless text and WiFi icon, in FIG. 38. In particular, bed 30 communicates with the cloud 72 via wireless communication link 56 in system 640. WAP 52 and facility network 60, shown in FIG. 1 for example, are not shown in FIG. 38 but are present in system 640 in some embodiments. Thus, in system 640, nurse calls and bed alerts are sent to one or more servers 46' from bed 30 via wall module 460, whereas bed alerts, bed status data, and patient data are sent to the remote server 70 from bed 30 via the Internet or cloud 72.

In some embodiments, the remote server 70 of systems 620, 640 is configured to transmit bed alerts and bed status data back to other computer devices of the healthcare facility. For example, the bed alerts and bed status data are transmitted by server 70 as health level seven (HL7) messages to an EMR server 64 of the healthcare facility in some embodiments of systems 620, 640. Server 70 is also connected to a computer having a display screen for display of a dashboard that includes the bed alerts and bed status data in some embodiments of systems 620, 640. In some embodiments of systems 620, 640, remote server 70 receives room location information (e.g., location ID) corresponding to the room location of bed(s) 30 of the healthcare facility and transmits the location information back to the respective bed(s) 30 via the cloud 72 and wireless communication link 56. GUI(s) 38 of bed(s) 30, in turn, display(s) the location information. The location information may be transmitted to remote server 70 from one or more ADT servers 64 of the healthcare facility, for example.

Figure 39:
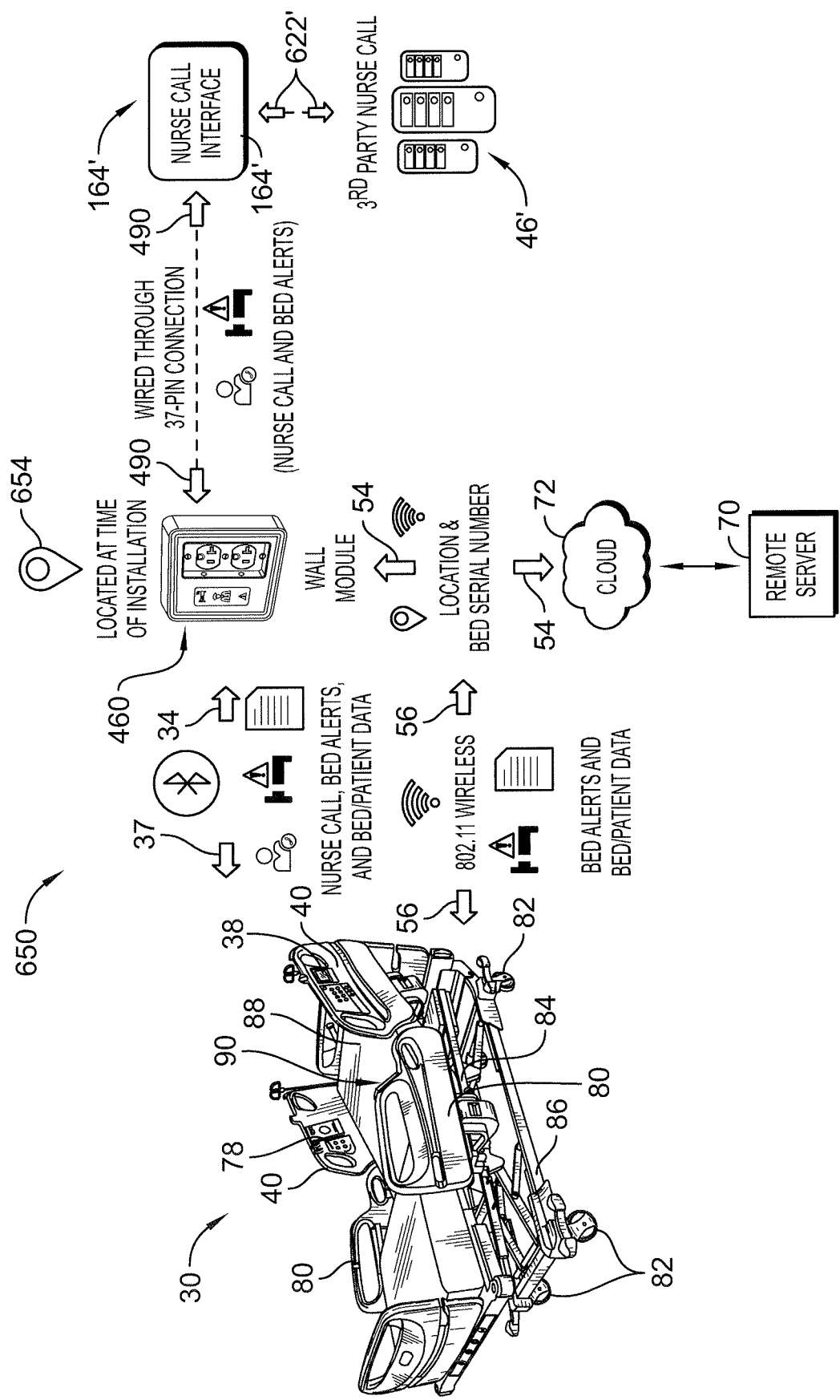
FIG. 39 is a diagrammatic view, similar to FIG. 38, showing a fourth system architecture in which the bed and the wall module are each configured to communicate wirelessly with a remote server via the Internet (aka the cloud)

Referring now to FIG. 39, still a further alternative embodiment system 650 is shown. System 650 is basically the same as system 640 of FIG. 38 except that in system 650, in addition to communication with bed 30, wall module 460 also communicates with remote server 70 via wireless communication link 54 and the cloud 72. Like system 640, system 650 includes WAP 52 and facility network 60 although these components are not shown in FIG. 39. Thus, wall module 460 communicates with WAP 52 via wireless communication link 54 that, in turn, communicates with cloud 72 via the network 60 of the healthcare facility. Furthermore, in system 650, bed 30 communicates bed status data and patient data, in addition to nurse calls and bed alerts, to wall module 460.

In FIG. 39, a diagrammatic location icon 654 is shown above wall module 460 to indicate that a location ID is programmed into wall module 460 in connection with the installation of wall module 460 in the healthcare facility. The location ID in wall module 460 corresponds to the room in which bed 30 and wall module 460 are located. In some embodiments, the location ID is communicated to wall module 460 from ADT server 66 via network 60 and one of WAP's 52. In other embodiments, an RTLS server 68 communicates the location ID to wall module 460 via network 60 and one of WAP's 52. In still other embodiments, the location ID is programmed into wall module 460 locally via a wired connection of a computer device (e.g., laptop computer, tablet computer, or other hand held electronic device) to an electrical port (e.g., a USB port or a JTAG connector) on the back or wall module 460 or internally of wall module 460. If the electrical port for programming the location ID into wall module 460 is in the interior region 601 of wall module 460, then molded back plate 582 is disconnected from molded front plate 480 to gain access to the electrical port in some embodiments. Alternatively, an openable or removable access door may be provided as part of back wall 516 for accessing the electrical port.

Still referring to FIG. 39, wall module 460 of system 650 transmits the location ID and the bed ID (e.g., bed serial number) via the cloud 72 to remote server 70. Bed 30 transmits bed alerts, bed status data which includes the bed ID, and patient data to remote server 70 via the cloud 72. Of course, these transmissions from wall module 460 and bed 30 also involve the use of one or more WAP's and infrastructure of facility network 60 as noted above. Because the bed ID is common to the transmissions from wall module 460 and from bed 30, remote server 70 is able to associate the bed alerts, bed status, and patient data to the room location corresponding to the location ID. In some embodiments, nurse call server 46 associates the bed ID of bed 30 with the location ID of the room, as stored in ASBC 164, in response the bed ID and location ID being transmitted over communication link 622 to server 46. In the embodiment of system 620 shown in FIG. 36, the location ID is not transmitted to wall module 460 or to bed 30.

Figure 40:
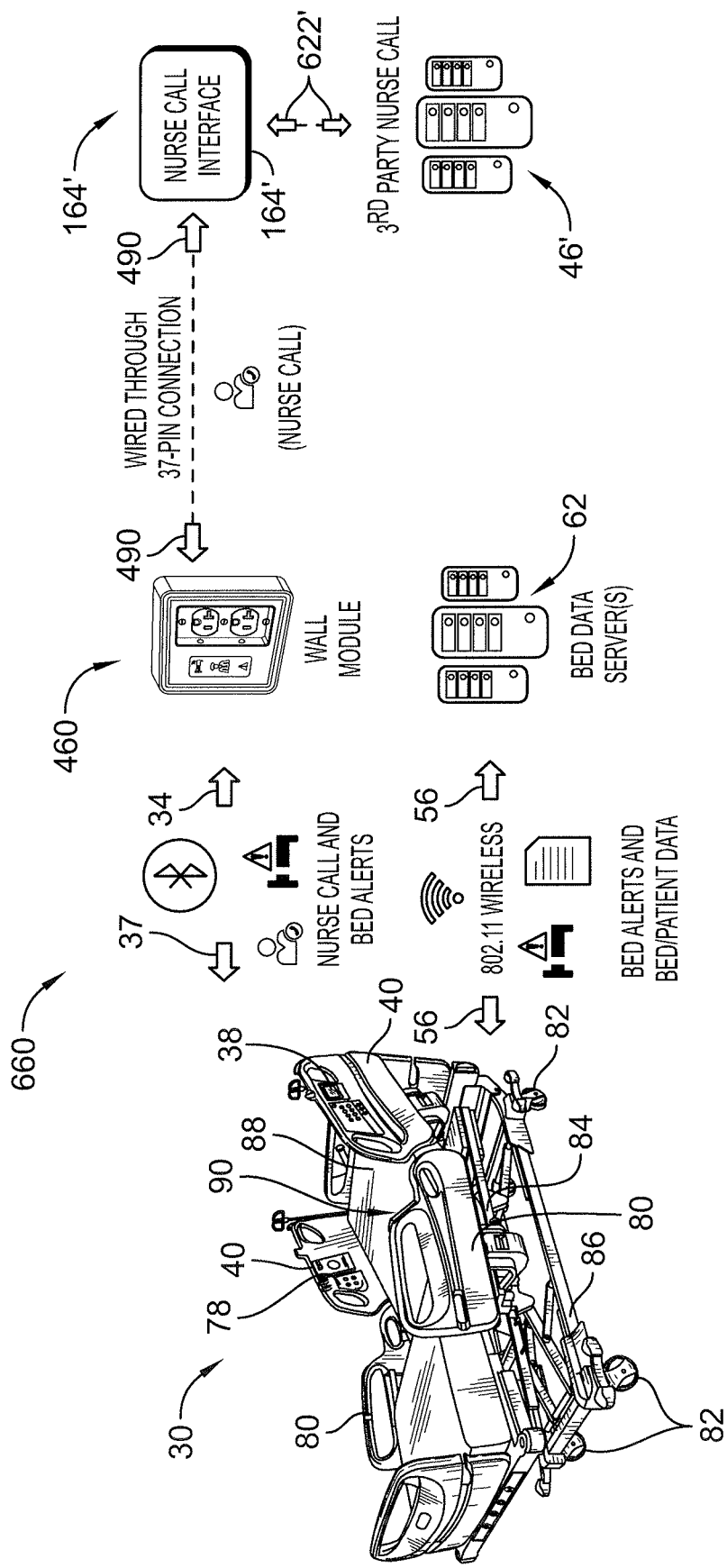
FIG. 40 is a diagrammatic view, similar to FIG. 38, showing a fifth system architecture in which the bed is configured to communicate wirelessly with one or more bed data servers of the healthcare facility.

Referring now to FIG. 40, yet still another alternative embodiment system 660 is shown. System 660 is basically the same as system 640 of FIG. 38 except that in system 660, in addition to Bluetooth communication with wall module 460, bed 30 also communicates using WiFi technology one or more bed data servers 62 of the healthcare facility via wireless communication link 56. Like system 640, system 660 includes one or more WAP's 52 and facility network 60 although these components are not shown in FIG. 40. Thus, bed 30 communicates with one of WAP's 52 via wireless communication link 56 that, in turn, communicates with one or more of servers 62 via the network 60 of the healthcare facility. Furthermore, in system 660, bed 30 communicates bed alerts, bed status data, and patient data to bed data server(s) 62. Also, like in system 640, bed 30 in system 660 communicates nurse calls and bed alerts to wall module 460 via wireless communications link 34. It is within the present disclosure for the one or more bed data servers 62 of system 660 to be communicatively coupled to other computer devices but these are not shown in FIG. 40 because such additional system architecture is at the discretion of the healthcare facility.

In some embodiments of system 660, a status board 48 is coupled to one or more of bed data servers 62, either directly, or via infrastructure of facility network 60 and/or components of nurse call system 43 so that some or all of the bed alerts, bed status data, and patient data from bed 30 can be displayed on the status board 48. Further, in some embodiments of system 660, an RTLS server 68 communicates with bed data server(s) 62 to provide location information (e.g., location ID) of bed 30 which, in turn, enables the bed location to also be displayed on status board 48. In this regard, server(s) 62 of system 660 include(s) software, such as SMARTSYNC™ software available from Hill-Rom Company, Inc., to effectuate associating the location ID with the bed alerts, bed status data, and patient data. For example, in some embodiments, bed 30 has an RFID tag attached thereto for communication with transmitters, receivers, and/or transceivers that are located throughout the healthcare facility and that communicate with the RTLS server 68. Such RFID tags communicate with the transmitters, receivers, and/or transceivers using one or more wireless communication technologies such as radio frequency (RF), infrared (IR), or ultrasound communication technologies as is known in the art. In some embodiments, the bed data server(s) 62 of system 660 is configured to transmit bed alerts, bed status data, and patient data to other computer devices of the healthcare facility. For example, the bed alerts, bed status data, and patient data are transmitted by server(s) 62 as HL7 messages to an EMR server 64 of the healthcare facility in some embodiments of system 660.

Figure 41:
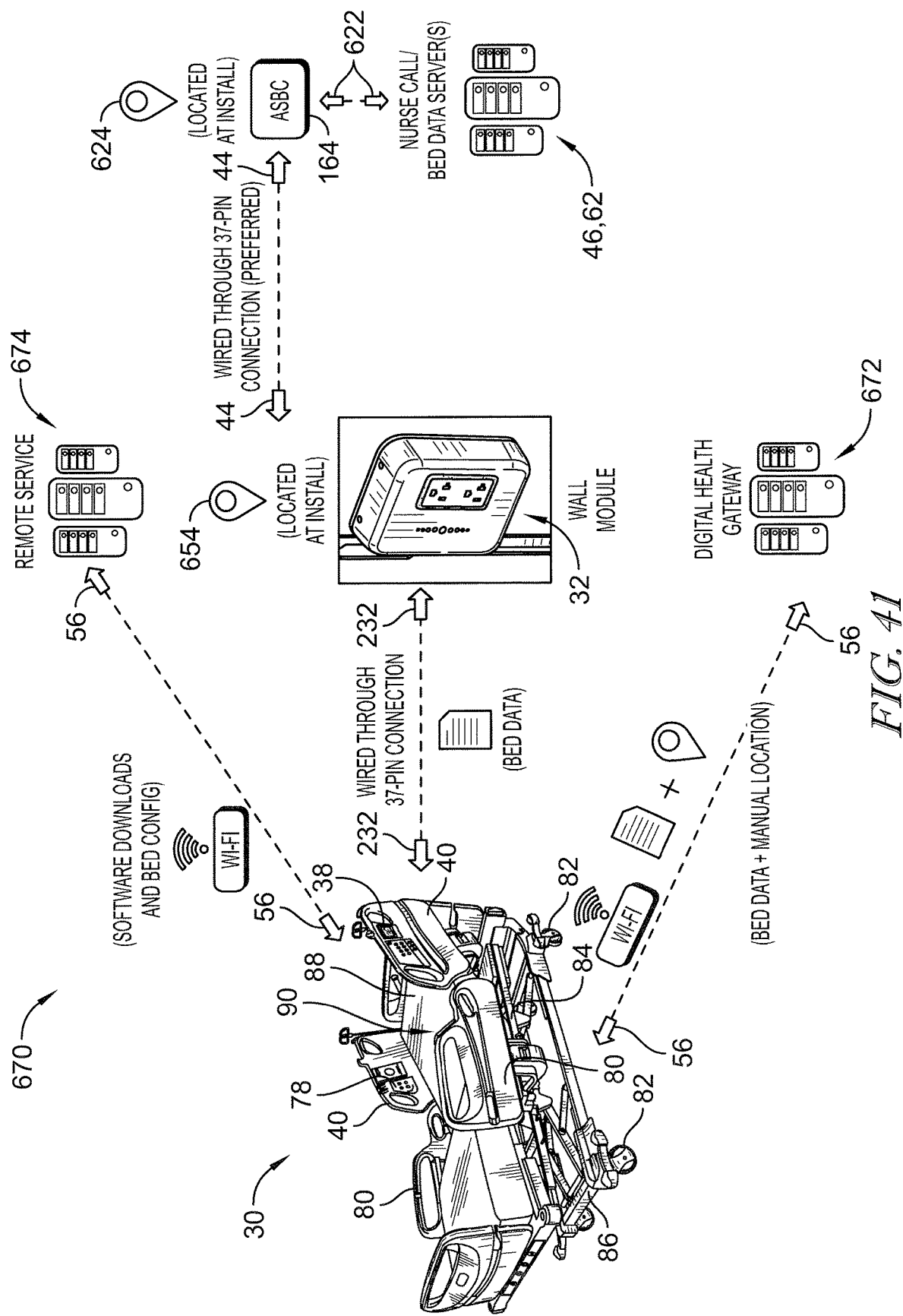
FIG. 41 is a diagrammatic view of a sixth system architecture in which the bed is coupled to the wall module via a wired connection, the wall module is coupled via wired communications links with an ASBC and with one or more bed data servers, and in which the bed is configured to communicate wirelessly with one or more remote service servers and one or more digital health gateway servers.

Referring now FIG. 41, yet still a further alternative embodiment system 670 is shown. System 670 has bed 30 connected to wall module 32 via nurse call 232 that extends from bed 30. Thus, in system 670, cable 232 connects to Y-cable 214, T-cable 248, or nurse call port 128 of wall module 32, as the case may be. Wall module 32, in turn, is coupled to ASBC 164 via wired communication link 44 and ASBC 164 is coupled to one or more nurse call servers 46 and/or bed data servers 62 via wired communication link 622 as shown diagrammatically in FIG. 41. As noted above in connection with system 20, the software that provides the nurse call functionality and the bed status data handling functionality of servers 46, 62, are stored and run by the same server. Thus, like system 20, in some embodiments of system 670, the software that implements functions of the local bed data server 62 is SMARTSYNC™ software available from Hill-Rom Company, Inc. and the software that implements functions of nurse call server 46 is NAVICARE® nurse call software, also available from Hill-Rom Company, Inc., which software is stored and run by the same server.

As also shown in FIG. 41, bed 30 communicates via wireless communication link 56 with one or more digital health gateway servers 672. More particularly, bed 30 communicates with one of WAP's 52 via wireless communication link 56 that, in turn, communicates with one or more of servers 672 via the network 60 of the healthcare facility. The present disclosure contemplates that digital health gateway servers 672 are located within the healthcare facilities' computer network (e.g., Ethernet) in some embodiments and are located remotely in other embodiments. Thus, if digital health gateway servers 672 are located remotely from the healthcare facility, then the facility network 60 communicates through the Internet or cloud 72 with the one or more digital health gateway servers 672.

The one or more digital health gateway servers 672 of system 670 receive a more robust set of bed data (and bed alerts and patient data in some embodiments of system 670) than the bed data that is received by the one or more nurse call servers 46 and bed data servers 62 via ASBC 164. Furthermore, in the illustrative embodiment, bed 30 is configured to permit a caregiver or other user to manually enter location data (e.g., room number) using GUI 38 of bed 30. The manually entered location data is stored in memory 96 and/or memory 104 of bed for transmission via WiFi module 100 over wireless data link 56 to the one or more digital health gateway servers 672 along with the bed data. Additional details of manual entry of location data on a patient bed can be found in U.S. Pat. No. 11,011,267 (see particularly, FIGS. 5-11 and the related discussion at col. 19, line 51—col. 22, line 25) and U.S. Patent Application Publication No. 2020/0345568 A1 (see particularly, FIGS. 4A, 4B, and 7-9 and the related discussion at paragraphs 80-97 and 113-120), each of which is hereby incorporated by reference herein in its entirety to the extent not inconsistent with the present disclosure which shall control as to any inconsistencies.

Still referring to FIG. 41, location icon 624 is shown above ASBC 164 and location icon 654 is shown above wall module 32. Thus, the discussion above in connection programming ASBC 164 with location information in connection with system 620 of FIG. 36 and programming wall module 460 with location information in connection with system 650 of FIG. 39 is equally applicable to ASBC 164 and wall module 32 of system 670 of FIG. 41 and so the descriptions are not repeated. It should be noted that both ASBC 164 and wall module 32 are programmed with location information because bed 30 is able to connect via wired connection 232 to either of these devices. Accordingly, if nurse call cable 232 from bed 30 is directly into ASBC 164 of system 670, wall module 32 is bypassed and so, the one or more nurse call servers 46 and/or bed data servers 62 rely only on the location data from ASBC 164 to determine the location of bed 30.

As further shown in FIG. 41, bed 30 of system 670 communicates via wireless communication link 56 with one or more remote service servers 674. More particularly, bed 30 communicates with one of WAP's 52 via wireless communication link 56 that, in turn, communicates with one or more of servers 674 via the network 60 of the healthcare facility. The present disclosure contemplates that remote service servers 674 are located within the healthcare facilities' computer network (e.g., Ethernet) in some embodiments and are located remotely in other embodiments. Thus, if remote service servers 674 are located remotely from the healthcare facility, then the facility network 60 communicates through the Internet or cloud 72 with the one or more remote service servers 672.

Remote service servers 672 receive bed configuration data from bed 30, including bed serial number, bed type, and software version numbers of the various software modules that are stored and run on bed 30 (e.g., weight scale software module, main control board software module, communication board software module, pneumatic system software module, and the like). Based on the software version(s) received by one or more remote service servers 674, updated software for the various software modules is downloaded wirelessly to bed 30 as needed if the software version on bed 30 is an outdated software version. In some embodiments of system 670, the various software modules are combined into a single software package for bed 30 such that only one software version number is included in the bed configuration data sent to one or more remote service servers 674. In such embodiments, the software downloads to bed 30 from the one or more remote service servers 674 include a single updated software package.

Figure 42:
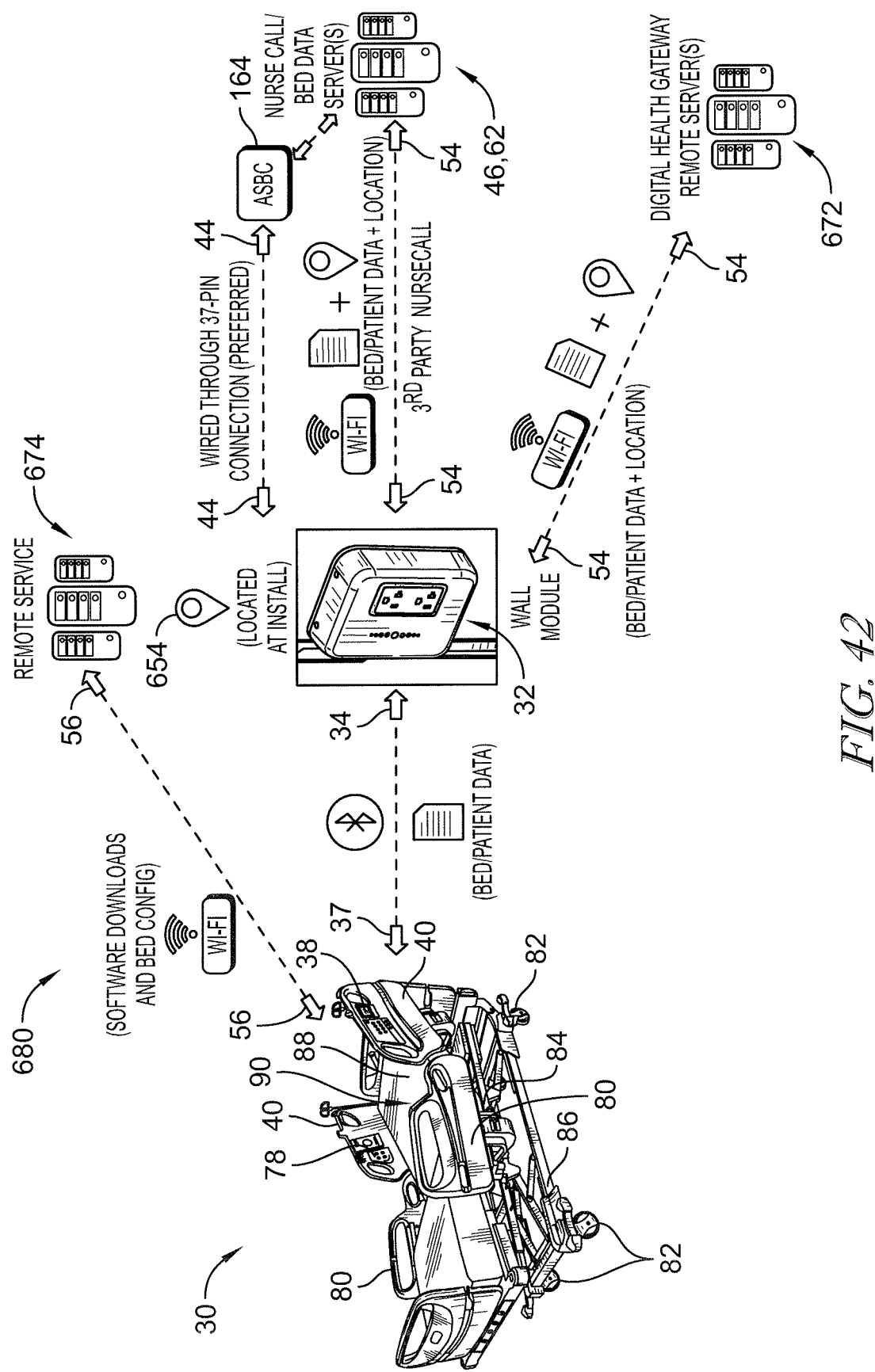
FIG. 42 is a diagrammatic view of a seventh system architecture in which the wall module communicates wirelessly with a bed and communicates via wired communication links with an ASBC and a nurse call server which also serves as a bed data server, the wall module also being configured to communicate wirelessly with the bed data server and with one or more digital health gateway servers and/or remote servers, and in which the bed is configured to communicate wireless with one or more remote service servers.

Referring now to FIG. 42, a further embodiment system 680 is shown. All of the components of system 680 have been described above in connection with other system embodiments and so, like reference numbers have been used to denote components of system 680 that have been discussed above in connection with the various other system embodiments. One of the differences in system 680 as compared to the previously discussed systems 20, 620, 630, 640, 650, 660, 670 is that wall module 32 communicates via wireless communication link 54 with one or more digital gateway servers 672. More particularly, wall module 32 communicates with one of WAP's 52 via wireless communication link 54 that, in turn, communicates with one or more of servers 672 via the network 60 of the healthcare facility. If digital health gateway servers 672 are located remotely from the healthcare facility, then the facility network 60 communicates through the Internet or cloud 72 with the one or more digital health gateway servers 672 as well.

Still referring to FIG. 42, wall module 32 of system 680 also communicates wirelessly with bed 30 via communication links 34, 37. In FIG. 42, bed status data and patient data is shown being communicated from bed 30 to wall module 32, but bed alerts are also communicated to wall module 32 in system 680 according to this disclosure. Bed 30 of system 680 further communicates wirelessly with one or more remote service servers 674 via wireless communication link 56 to send bed configuration data and receive software downloads in the same manner as described above in connection with system 670.

In system 680, wall module 32 is able to communicate with one or more nurse call servers 46 and/or one or more bed data servers 62 via wired communication link 44 and ASBC 164 and via wireless communication link 54. Thus, some bed status data and alerts are sent to one or more servers 46, 62 from wall module 32 via a first communication path including wired communication link 44 and ASBC 164 and some bed status data, patient data, and location information is sent to one or more servers 46, 62 from wall module 32 via a second path including wireless communication link 54. Some or all of the data sent via the first, wired path may also be sent via the second, wireless path. As noted above, the nurse call and bed data handling functionality of servers 46, 62 reside on a single server in some embodiments.

In system 680, location information is programmed into wall module 32 in the same manner as described above. It should be appreciated that the programming of wall module 32 dictates which data is sent to one or more servers 46, 62 along each of the first (wired) and second (wireless) paths. This is in contrast to the systems disclosed in U.S. Pat. No. 10,500,401 in which a controller on a patient bed determines whether to send data from the bed along two different wireless paths, one that includes a wireless access point and one that does not. Wall module 32 of system 680 also determines which bed status data, patient data, and location data is transmitted via wireless communication link 54 to one or more digital health gateway servers 672. Thus, in system 680, wall module 32 is configured to transmit data via a wired communication link to a local server, transmit data via a wireless communication link to the same local server, and transmit data via a wireless communication link to a remote server. As also indicated in FIG. 42, the data sent wirelessly from wall module 32 via wireless communication link 54 in system 680 may be destined for a third party nurse call system or server. In such embodiments, one or more nurse call servers 46 run nurse call software that is provided by the third party and that is capable of receiving the data transmitted wirelessly from wall module 32.

In the discussion above of FIGS. 1 and 36-42, systems 20, 670, 680 having wall modules 32 may just as well have wall modules 460 in lieu of the illustrative wall modules 32 in other embodiments. Similarly, systems 620, 630, 640, 650, 660 having wall modules 460 may just as well have wall modules 32 in lieu of the illustrative wall modules 460 in other embodiments. Each of systems 20, 620, 630, 640, 650, 660, 670, 680 may include the variants of wall modules 32, 460 discussed throughout the present disclosure in other embodiments.

As is apparent in the above discussion, wall units or modules 32, 460 are versatile in that they can be used in a wide variety of system architectures in a healthcare facility. In some architectures, wall modules 32, 460 do not have WiFi communication capability or, at least, do not have the WiFi communication capability enabled, if present. Similarly, in some architectures, bed(s) 30 do not have WiFi communication capability or, at least, do not have the WiFi communication capability enabled, if present. Thus, the present disclosure contemplates that, in some architectures, bed 30 and the corresponding wall module 32, 460 both have WiFi communication capability enabled for communication of various types of data as described above. However, in the disclosed embodiments, bed 30 and the corresponding wall module 32, 460 are configured to communicate wirelessly with each other after wireless pairing as also described above. Some beds 30 may not have the ability to communicate with wall modules 32, 460 or may have such capability disabled. In such beds 30, wall modules 32, 460 are configured for direct wired connection to cables 232 that extend from beds 30 using, for example, Y-cables 214, T-cables 248, or nurse call ports 128 provided on wall modules 32 (and on wall modules 460 in alternative embodiments).

Figure 43:
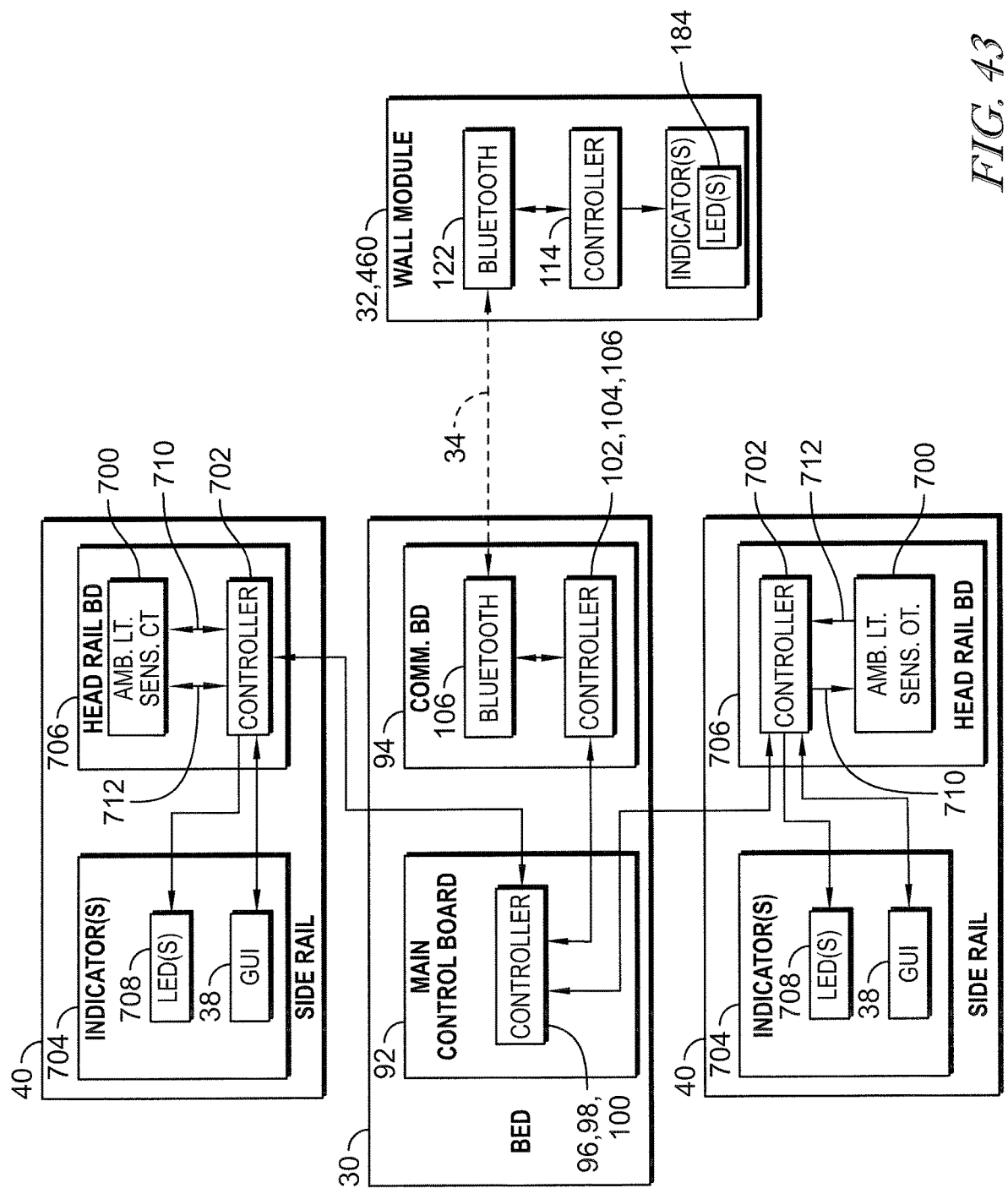
FIG. 43 is a diagrammatic view showing a patient bed having ambient light sensor circuits in siderails of the patient bed for use by a respective controller in controlling a brightness at which light emitting diodes (LED's) and a graphical user interface (GUI) are illuminated and showing a wall unit having indicators and a controller of the wall unit which is configured to control a brightness of the wall unit indicators based on information transmitted wirelessly from the patient bed pertaining to the ambient light detected by the ambient light sensor circuits.

Referring now to FIG. 43, an embodiment of patient bed 30 is shown in which an ambient light sensor circuit 700 is coupled to each of head end siderails 40 (aka head rails 40) of the patient bed for use by a respective controller 702 in controlling a brightness at which illuminable indicators 704 on the head rails 40 are operated. In the illustrative example, ambient light sensor circuits 700 and controllers 702 are included as part of respective head rail printed circuit boards 706, referred to herein as head rail boards 706, that are contained in the interior regions of siderails 40. Also in the illustrative embodiment, indicators 704 on each of head rails 40 includes one or more light emitting diodes (LED's) 708. In other embodiments, only one of head rails 40 includes GUI 38 and in still other embodiments, GUI's 38 are omitted from both head rails 40.

It is within the scope of the present disclosure for any one or more of ambient light sensor circuits 700, controller 702, one or more GUI's 38 and one or more LED's 708 to be located elsewhere on bed 30 in addition to, or in lieu of, being included on siderails 40. For example, other barriers on patient bed 30 such as siderails 80, a head board, and/or a foot board may contain these. Alternatively or additionally, any one or more of circuits 700, controllers 702, GUI 38, and LED's 708 are included on base frame 86 and/or upper frame 84, such as on a foot end frame member of a foot section of bed 30, for example, at the discretion of the bed designer. Embodiments in which only one ambient light sensor circuit 700 and one controller 702 are included in patient bed 30 are also contemplated by the present disclosure.

In the illustrative example of FIG. 43, controller 702 of each head rail board 706 is communicatively coupled to controller 96, 98, 100 of main control board 82 of bed 30. The controller block in FIG. 43 is intended to represent the microprocessor 96, memory 98, and WiFi module 100 shown in FIG. 2, for example, and so all of these reference numbers are use in connection with the controller block in FIG. 43. Controllers 702 also include a microprocessor and memory, for example. To reduce the clutter in FIG. 43, blocks representing these separate portions of controller 96, 98, 100 and controllers 702 are omitted.

Figure 44:
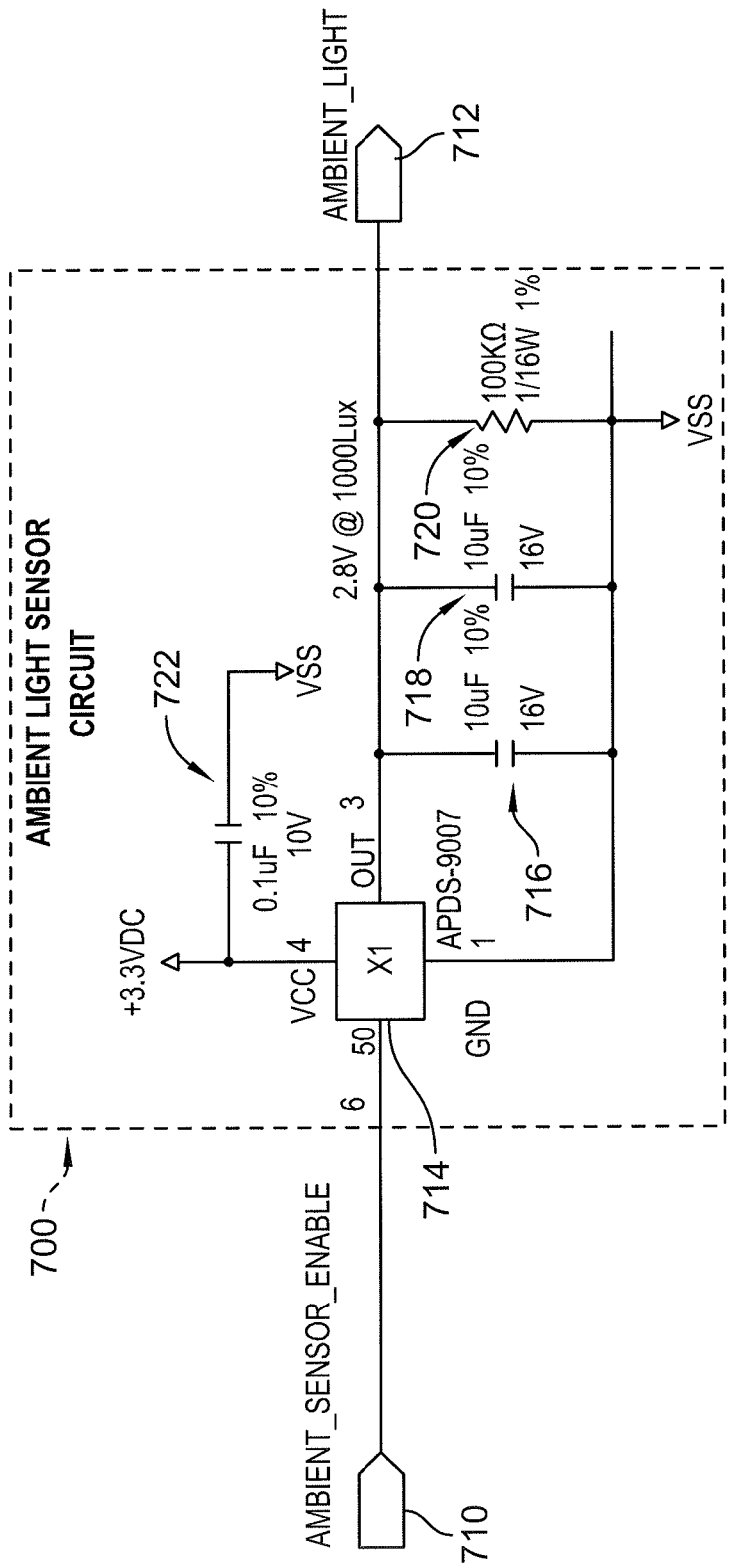
FIG. 44 is an electric circuit schematic of one of the ambient light sensor circuits, the other ambient light sensor circuit being the same.

Controllers 702 each provide an ambient light sensor enable signal 710 to the respective ambient light sensor circuit 700 to enable (aka turn on or activate) circuit 700 to sense ambient light as shown in FIGS. 43 and 44. Controllers 702 each receive an ambient light output signal 712 that is indicative of the ambient light sensed by an ambient light sensor 714, shown in FIG. 44, of circuit 700. In the illustrative embodiment, ambient light sensor 714 is a model no. APDS-9007 ambient light photo sensor with logarithmic current output available from Broadcom Limited of San Jose, California, USA. As shown in FIG. 44, ground pin 1 of sensor 714 is coupled to ground (aka $V_{SS}$). Ground pin 1 is also coupled to an output line from out pin 3 of sensor 714 via a parallel combination of first and second 10 microfarad (μF) capacitors 716, 718 and a 100 kilo ohm (kΩ) resistor 720. Capacitors 716, 718 serve as a low-pass filter to filter out AC noise (e.g., 50/60 Hertz (Hz) and 100 Hz) generated by light sources such a fluorescent lamps or incandescent lamps and resistor 720 serves as a load resistor that determines the amount of current-to-voltage conversion in the circuit 700. The ambient light output signal is provided from out pin 3 of sensor. VCC pin 4 of sensor 714 is coupled to a +3.3 Volt DC (VDC) power supply and to $V_{SS}$ through a 0.1 μF capacitor 722. Pins 2 and 5 of sensor 714 are "no connect" pins that do not connect to any other circuit elements.

As indicated in FIG. 44, the ambient light output signal has a voltage of about 2.8 Volts (V) at 1000 Lux. Any Lux value between 401 Lux and 1000 Lux is generally considered normal lighting for indoor environments. Any Lux value of 400 and below is considered dim (201 Lux to 400 Lux) or dark (51 Lux to 200 Lux) or very dark (11 Lux to 50 Lux) lighting conditions for indoor environments. The APDS-9007 ambient light photo sensor has a dynamic range of 3 Lux to 70,000 Lux, but that full dynamic range is not needed in circuit 700. An ambient light output signal 712 of about 0.5 V corresponds to roughly 10 Lux in some embodiments.

In the illustrative example of FIGS. 43 and 44, the ambient light output signal 712 is analyzed by the respective controller 702 to determine whether the ambient light has a first brightness above a threshold value or a second brightness below the threshold value. At the discretion of the system designer, the threshold value may be 400 Lux, 200 Lux, or 50 Lux which corresponds to the breakpoints between normal lighting, dim lighting, dark lighting, or very dark lighting discussed above. In other embodiments, a different threshold value for determining the dividing line between "light" brightness conditions and "dark" brightness conditions is used. In still other embodiments, controllers 702 are programmed with multiple threshold values so that more than two brightness conditions are determinable (e.g., high, medium, and low brightness conditions). Further granularity such as four brightness conditions, five brightness conditions, etc. are within the scope of the present disclosure.

In the illustrative embodiment, controllers 702 output pulse width modulated (PWM) signals to the one or more LED's 708 to control the brightness at which the one or more LED's 708 are illuminated. For example, if the ambient light is above the threshold value such that controller 702 determines the room in which patient bed 30 is located has "light" brightness conditions, then a PWM signal of a first duty cycle (e.g., 75%, 80%, 85%, or 90%, just to give a few arbitrary examples) is applied by controller 702 to the one or more LED's 708. On the other hand, if the ambient light is below the threshold value such that controller 702 determines the room in which patient bed 30 is located has "dark" brightness conditions, then a PWM signal of a second duty cycle (e.g., 25%, 30%, 35%, 40%, 45% or 50%, just to give a few arbitrary examples) is applied by controller 702 to the one or more LED's 708. The actual value of the PWM signals for "light" and "dark" brightness conditions is at the discretion of the system designer.

As alluded to above, in other embodiments, controllers 702 are configured to determine more than two brightness levels based on respective ambient light output signals 712 (e.g., three brightness levels, four brightness levels, etc.). In such other embodiments, PWM signals corresponding to the number of brightness levels being determined by controllers 702 are applied to the respective one or more LED's 708. Of course, the higher the PWM duty cycle, the brighter the one or more LED's 708 will illuminate. Thus, for three brightness levels, the PWM duty cycles may be, for example, 33%, 50%, and 67% just to give an arbitrary example. For four brightness levels, the PWM duty cycles may be, for example, 20%, 40%, 60%, and 80%, again, just to give an arbitrary example.

With regard to brightness control of GUI's 38 on bed 30, it should be appreciated that GUI's 38 have their own control circuits (e.g., controllers with microprocessors, memory, and I/O ports) and so it is not necessary for PWM signals to be provided to GUI's 38 by respective controllers 702, although that is not to rule out the possibility that PWM signals from controllers 702 could be used for brightness control of GUI's 38 in some embodiments. In some embodiments, however, controllers 702 send multi-bit messages to GUI's 38 with at least one bit of the multi-bit message being allocated for brightness control (e.g., 0 for "dark" brightness control and 1 for "light" brightness control, or vice versa).

In embodiments in which brightness of GUI's 38 are controlled at more than two brightness levels, then two bits of the multi-bit message are allocated for brightness control to give up to four levels of brightness control (e.g., 00, 01, 10, or 11 for the allocated two bits, as appropriate). If more than four levels of brightness control of GUI's 38 are desired by the system designer, then an appropriate number of bits (e.g., three bits) are allocated in the multi-bit messages from controllers 702 to respective GUI's 38. Thus, controllers 702 each include analog-to-digital (A/D) converters, which are included in a microcontroller integrated circuit chip (e.g., DART or Variscite chips disclosed herein) that convert the analog ambient light output signals 712 into digital data that is includes in the multi-bit messages sent from controllers 702 to respective GUI's 38.

Controller 96, 98, 100 (referred to hereinafter as simply controller 96) receives an ambient light results signal from each of controllers 702. In some embodiments, the ambient light results signal is embedded in a multi-bit digital message from each of controllers 702. As such, the multi-bit digital message from controllers 702 to controller 96 has at least one bit allocated for brightness control and more than one bit, depending upon the number of levels of brightness control. For example, the digital data related to detected ambient light can be the same as discussed above in connection with control of the brightness of GUI's 38. In other embodiments, controller 96 receives PWM signals from controllers 702 having the same duty cycles as the PWM signal provided from controllers 702 to LED's 708.

Controller 96 processes the incoming multi-bit messages or PWM signals, as the case may be, from controllers 702 and provides a combined results signal to controller 102, 104, 106 (referred to hereinafter as simply controller 102) pertaining to the ambient light detected by sensors 714 of circuits 700. Of course, if patient bed 30 has only one ambient light sensor circuit 700 and one controller 702 for brightness control of indicators 704, then the combined results signal relating to brightness control will be the same as the results signal received by controller 96 from the single controller 702 in some embodiments. The combined results signal is encoded digitally in an allocated bit, or in allocated bits, in a multi-bit message at the discretion of the system designer, although this not to rule out the possibility that the combined results signal from controller 96 to controller 102 could be a PWM signal.

The bits allocated for brightness control information in the multi-bit message that includes the combined results signal may or may not be the same bits as the multi-bit messages sent by controllers 702 to controller 96. For example, the number of bits in the messages between controllers 702 and controller 96 may be different than the number of bits in the messages between controller 96 and controller 102, for example. Thus, the positions of the bits pertaining to be brightness control in the messages from controller 96 to controller 102 may be different than those of the messages from controllers 702 to controller 96 in some embodiments, or they may be at the same positions in the multi-bit messages in other embodiments.

In some instances, it is possible that the results signals from controllers 702 to controller 96 do not match. For example, in a light/dark two level brightness control situation, one of controllers 702 may indicate that "light" ambient lighting was detected by the corresponding ambient light sensor circuit 700 and the other of controllers 702 may indicate that "dark" ambient lighting was detected by the corresponding ambient light sensor circuit 700. Such a situation may occur, for example, if patient bed 30 is situated in a patient room with one of siderails 40 adjacent a wall of the patient room and the other of the siderails exposed to open space in the patient room. Presumably, but not necessarily, the ambient light sensor circuit 700 in the siderail 40 adjacent the room wall may detect dark ambient lighting conditions and the other ambient light sensor circuit 700 in the other siderail 40 may detect light ambient lighting conditions. The present disclosure contemplates that controller 96 is configured to give precedence to the results signal indicating light ambient lighting conditions and generates the combined results signal accordingly so that indicators 184 of the corresponding wall module 32, 460 are controlled to be illuminated brightly rather than dimly.

In some embodiments in which the light/dark two level brightness control scheme is implemented, if there is a conflict between the results signals from controllers 702 to controller 96, controller 96 provides a feedback signal to whichever of controllers 702 has its corresponding circuit 700 detecting a dark level of ambient lighting. The feedback signal is used by the respective controller 702 to override the dark ambient lighting condition detected by the associated circuit 700 such that the corresponding indicators are controlled by the respective controller 702 to shine or illuminate at the light (e.g., high) brightness level rather than the dim (e.g., low) brightness level.

At the discretion of the system designer, the results signals from controllers 702 to controller 96 may include digital values of the Lux values corresponding to the voltages of the ambient light output signals 712, or the voltage values of signals 712 themselves. In such embodiments, controller 96 is configured to average the digital values in the results signals from controllers 702 and then provide averaged results signals back to controllers 702 which, in turn, use the averaged values indicated in the averaged results signals for determination of the level at which indicators 704 are to be illuminated. Such an averaging approach may be used in systems implementing two, three, four, or more levels of brightness control for indicators 704. Controllers 702 simply compare the averaged values to the one or more brightness level thresholds to determine the brightness level at which indicators 704 are to be controlled. A similar averaging approach can be used if the results signals to controller 96 from controllers 702 are PWM signals. For example, if one controller 702 provides a 60% duty cycle PWM signal to controller 96 and the other controller 702 provides a 40% duty cycle PWM signal to controller, then the averaged results signals sent from controller 96 back to controllers 702 is a 50% duty cycle PWM signal.

In some embodiments having more than two brightness levels for illuminating indicators 704 on patient bed 30, if the results signals from controllers 702 are in conflict, controller 96 may pick an intermediate brightness level at which to operate the indicators 704 if the conflicting signals are two levels apart, otherwise the higher brightness level is chosen. For example, in a three brightness level scenario having high, medium, and low brightness levels, if one of the results signals indicates that indicators 704 on one of siderails 40 should be operated at a high brightness level and the other of the results signals indicates that indicators 704 on the other of siderails 40 should be operated at a low brightness level, then controller 96 provides feedback signals to both of controllers 702 indicating that the indicators 704 on both siderails 40 should be operated at the medium brightness level. In a four brightness level scenario, a similar intermediate level approach is implemented by controller 96 if there is only one intermediate level between the results signals from controllers 702. If there are two intermediate levels between the results signals from controllers 702, then controller 96 is configured to pick the brightest level from among the two intermediate levels in some embodiments.

Regardless of which method described above is used for controlling the brightness of indicators 704, controller 96 provides the combined results signal to controller 102 of communication board 94 as either part of a multi-bit message or as a PWM signal as described above. If a PWM signal is provided to controller 102 from controller 96, then controller 102 converts the PWM signal to one or more bits of a multi-bit message that is output to Bluetooth transceiver 106 of patient bed 30. If the combined results signal is already embedded digitally in the multi-bit message received by controller 102 from controller 96, then the digital combined results information pertaining to indicator brightness control does not need to be converted into digital form. In any event, the multi-bit message including the combined results signal information is transmitted wirelessly from Bluetooth transceiver 106 of patient bed 30 to Bluetooth module 122 of wall module 32 or wall module 460, as the case may be, via wireless communication link 34. Controller 114 of wall module 32, 460 then determines the brightness level at which the indicator(s), embodied as one or more LED's 184 in the illustrative embodiments, are to be controlled.

In some embodiments, a single bit in the multi-bit message communicated via wireless communications link 34 from transceiver 106 to transceiver 122 is allocated for brightness control. Thus, the one or more LED's 184 of wall module 32, 460 are controlled so as to be illuminated at the "light" (e.g., high) brightness level or the "dark" (e.g., low or dim) brightness level. In this regard, the controller 114 of wall module 32, 460 provides a PWM signal to each of the LED's 184 corresponding to the brightness level at which the one or more LED's 184 are to be controlled. The discussion above of PWM signal control of LED's 704 by controllers 702 on patient bed 30 is equally applicable to PWM signal control of LED's 184 for wall module 32, 460 and so, is not repeated. In other embodiments, one or more LED's 184 of wall module 32, 460 are controlled at more than two brightness levels by controller 114 in the same manner as discussed above with regard to the manner in which controllers 702 control the brightness levels of LED's 708.

Based on the foregoing, it should be appreciated that the brightness level at which LED's 184 of wall module 32, 460 are illuminated is controlled based on the amount of ambient light sensed by ambient light sensors 714 included in circuits 700 of bed 30. Accordingly, wall module 43, 460 does not need to include its own ambient light sensor or associated ambient light sensor circuit. Furthermore, it is contemplated that the brightness at which LED's 184 of wall module 32, 460 are illuminated substantially matches the brightness at which LED's 708 of patient bed 30 are illuminated. When the patient room in which bed 30 and module 32, 460 are located is dark, it is desirable for the indicators 184, 704 to be dimmed so as not to potentially interfere with the patient's ability to sleep. However, when the ambient light in the patient room is high, it is desirable for the indicators 184, 704 to be illuminated more brightly so as to be more easily discernable in the light.

The present disclosure further contemplates that wall module 32, 460 similarly controls the brightness of the one or more LED's 184 of wall module 32, 460 when the bed 30 has a wired connection to wall module 32, 460 such as via any one or more of cables 216, 232, 248 discussed above in connection with FIGS. 2, 8, 9, 11, 13, 26, and via cable 490 having branch 226 and connector 228 as discussed above in connection with FIG. 41, for example. In such configurations, controller 114 of wall module 32, 460 processes the multi-bit messages received via the wired connections with regard to brightness control in the same manner as described above with regard to wireless multi-bit messages. Furthermore, it should be understood that the indicator brightness control aspects described herein in connection with FIGS. 43 and 44 can be implemented in the various systems described herein with regard to FIGS. 1-42 and the variants thereof.

Although, use of one or more ambient light sensors 714 on patient bed 30 to sense ambient light which is, in turn, used to control brightness of one or more indicators 704 of patient bed 30 and also one or more indicators 184 of wall module 30, or wall module 460, as the case may be, is described above, it is within the scope of the present disclosure for a similar ambient light sensing and indicator brightness control scheme to be used between first and second devices of various types, such as between the following: (i) bed 30 and medical monitor 360 shown in FIG. 20 and (ii) mobile phone 410 and speaker unit 412 shown in FIG. 22, just to give a couple of additional examples. Additional types of devices that may implement the contemplated ambient light sensing and indicator brightness control scheme between them include any of the other types of devices mentioned herein above, such as medical devices that may include but are not limited to, for example, physiological monitors such as electrocardiographs (EKG's), electroencephalographs (EEG's), pulse oximeters, blood pressure monitors, heart rate monitors, respiration rate monitors, and temperature monitors; other patient care equipment including intravenous (IV) pumps, drug infusion pumps, respiratory therapy devices, ventilators, sequential compression devices (SCD's) for preventing deep vein thrombosis (DVT), and passive motion machines; as well as other types of patient support apparatuses such as stretchers, chairs, wheelchairs, surgical tables, patient lifts, and examination tables, just to name a few.

It should be appreciated, therefore, that having one or more ambient light sensors on a first device to control brightness of indicators on a second device by encoding ambient light control data in a wireless message from the first device to the second device is the broad concept contemplated by the present disclosure. Such an arrangement allows the second device to be made smaller and less expensively due to the absence of the ambient light sensor in the second device. Furthermore, by controlling brightness of indicators on two devices (e.g., indicators 184, 704 in the illustrative example of FIG. 43) in the same manner by using the same ambient light control data, the indicators on the two devices will be dimmed or made brighter, as the case may be, substantially simultaneously (e.g., within the time needed for signal processing and transmission by the circuitry of the two devices, such as on the order of 5 seconds or less).

Figure 45A:
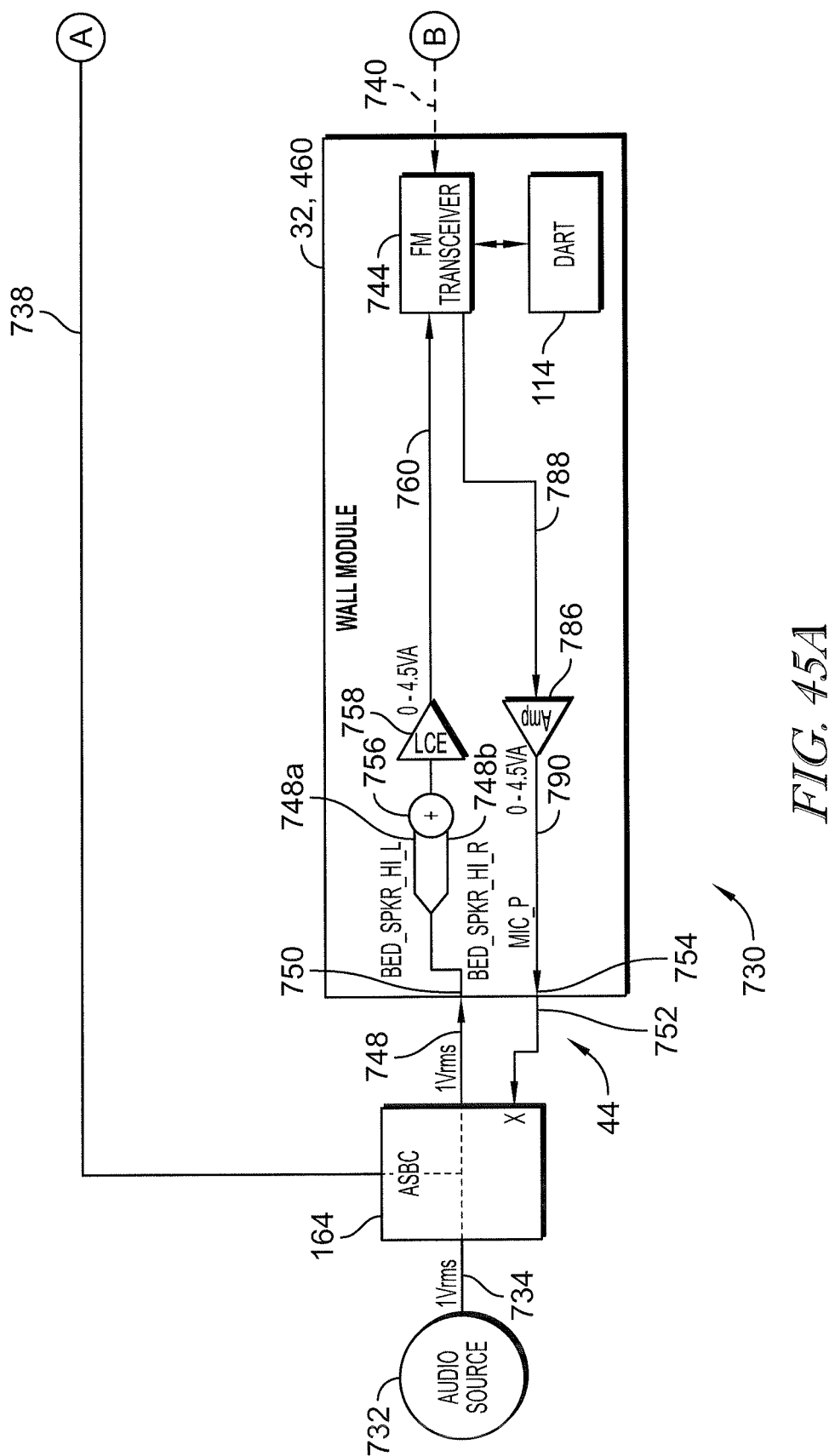
FIGS. 45A and 45B make up a block diagram of a system in which a wall module and a patient bed communicate data via Bluetooth transceivers and also communicate audio via frequency modulation (FM) transceivers.
Figure 45B:
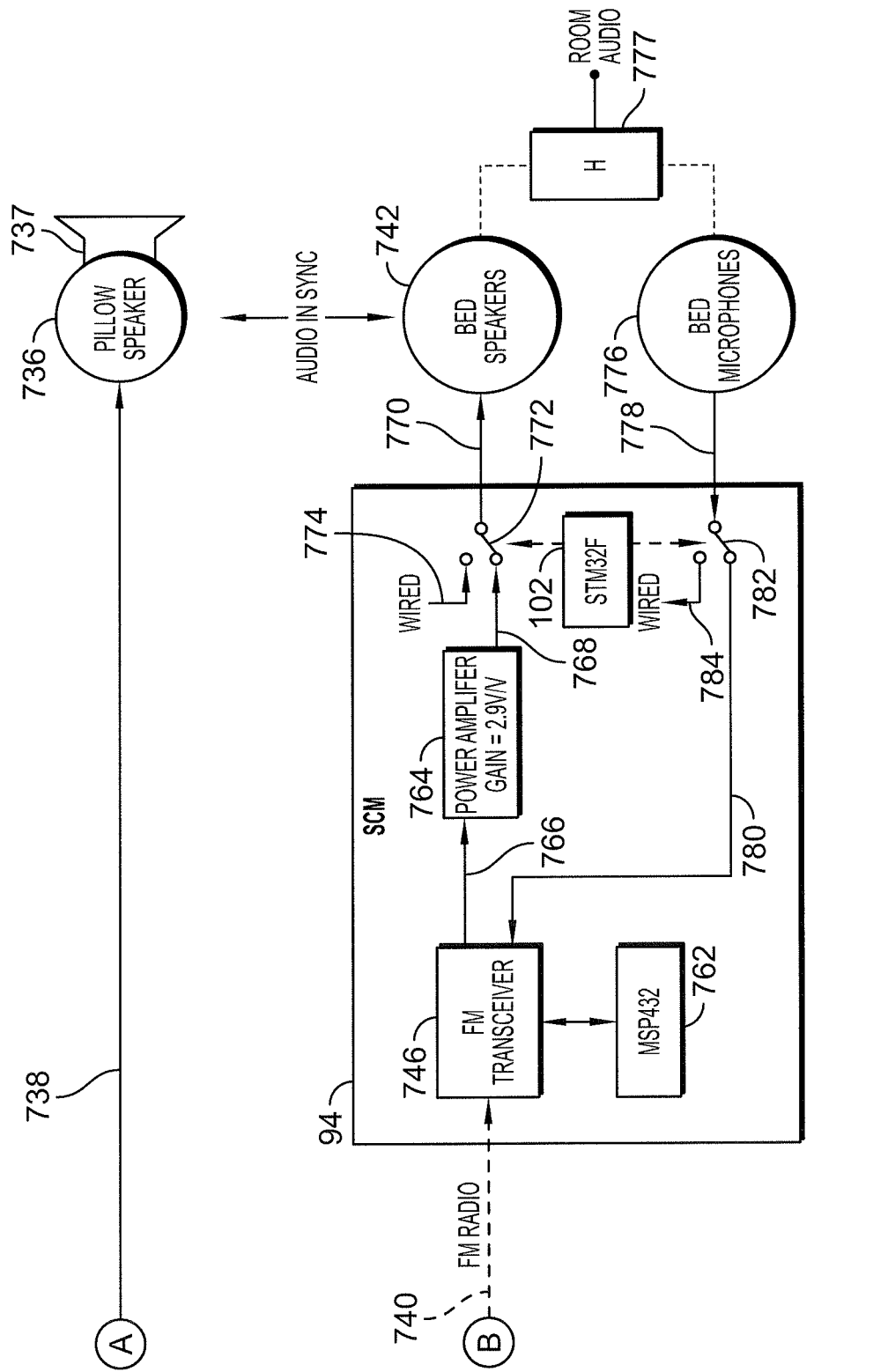

Referring now to FIGS. 45A and 45B, a system 730 includes bed 30 and wall module 32 or wall module 460 (both reference numbers are used to denote the illustrated wall module). System 730 further includes ASBC 164 which is coupled to an audio source 732 via a hardwire connection 734. ASBC 164 of system 730 is also coupled to a pillow speaker unit 736 via a hardwire connection 738. Bed 30, wall modules 32, 460, and ASBC 164 were all discussed above in connection with FIGS. 1-19 and 24-44 and that discussion is equally applicable to these same elements in system 730 of FIGS. 45A and 45B. The discussion below focusses on aspects of the communication between wall module 32, 460, as the case may be, and bed 30 and in particular, the discussion below relates to handling of audio in and between wall module 32, 460 and bed 30.

In system 730, audio signals 740 are transmitted wirelessly between wall module 32, 460 and bed 30. The audio signals 740 are separate from the Bluetooth communications over Bluetooth communications link 34 discussed above. This is because it has been found that sending audio packets via Bluetooth between wall module 32, 460 and bed 30 introduces a delay or communication latency that is unacceptable under certain scenarios. In particular, it has been found that because audio source 732 is connected to ASBC 164 via hardwire connection 734, and because ASBC 164 is connected to pillow speaker unit 736 via hardwire connection 738, the audio originating from audio source 732 is played almost instantly (aka in real time) by a pillow speaker 737 of pillow speaker unit 736, assuming the pillow speaker 737 is not muted and is turned on (i.e., the volume of the pillow speaker unit 736 is not all the way off). However, it has been found that due to communication latency over Bluetooth communication link 34, any audio originating from audio source 732 that were to be transmitted over link 34 as audio packets is not played through one or more speakers 742 of bed 30 until about 100 milliseconds-about 200 milliseconds later than it is played through the pillow speaker 737 of pillow speaker unit 736. It has been found that this produces a delay or echo effect that is undesirable.

To alleviate the undesirable echo effect of the audio between speaker 737 and speaker(s) 742 according to some illustrative embodiments, audio transmission 740 is made from wall module 32, 460 to bed 30 by components having a low communication latency. Low communication latency according to the present disclosure means that the audio played through speaker(s) 742 is less than 50 milliseconds delayed from the audio played through pillow speaker 737. As long as the audio played through speakers 737, 742 is less than 50 milliseconds delayed, it has been found that listeners perceive the audio as being played substantially simultaneously. In the illustrative embodiment, bed 30 has two speakers 742, one on a first of siderails 40 and another on a second of siderails 40. In other embodiments, bed 30 has only one speaker 742. In still further embodiments, bed 30 has more than two speakers 742.

In the illustrative example of system 730 of FIGS. 45A and 45B, wall module 32, 460 includes a frequency modulation (FM) transceiver 744 and bed 30 includes an FM transceiver 746. Audio is communicated bidirectionally between transceivers 744, 746. However, other radio transceivers (e.g., amplitude modulation (AM) transceivers or short wave radio transceivers) that are capable of modulating an analog audio signal may be used in wall module 32, 460 and bed 30 in lieu of FM transceivers 744, 746, if desired in other embodiments. Wireless communication between transceivers 744, 746 over communications link 740 has low latency such that the audio played by speakers 737, 742 is perceived as occurring substantially simultaneously (e.g., less than 50 milliseconds delay).

Transceiver 744 is coupled electrically to controller 114 of wall module 32, 460 for bidirectional wired communication. Some aspects of the operation of transceiver 744 is controlled by commands sent from controller 114. Controller 114 communicates information to controller 114 for use in decision making, as well. For example, communication link 740 between transceivers 744, 746 is not established until wall module 32, 460 is paired with bed 30, such as any of the methods described hereinabove in which a time-based pairing operation is implemented. After wall module 32, 460 and bed 30 are paired for communications over wireless communications link 34, controller 114 signals transceiver 744 to establish communication link 740 with bed 30 as will be described in further detail below.

With reference to FIG. 45A, among the electrical conductors of nurse call cable 44 are one or more analog audio input lines 748 that are coupled to an analog audio input 70 of wall module 32, 460 and one or more analog audio output lines 752 that are coupled to an analog audio output 754 of wall module 32, 460. Thus, analog audio input line(s) 748 and analog audio output line(s) are hardwire connections between ASBC 164 and wall module 32, 460. In the illustrative example, lines 748 include a left bed speaker line 748a, labeled as BED_SPKR_HI_L in FIG. 45A, and a right bed speaker line 748b, labeled as BED_SPKR_HI_R in FIG. 45A. This is because the 37-pin connector 126 of ASBC 164 has connectors allocated for left and right bed speakers when bed 30 is connected directly to 37-pin connector 126 via a standard 37-pin nurse call cable. As indicated in FIG. 45A, the analog audio signals on lines 748a, 748b are 1 Volt root mean square (Vrms) signals. In other embodiments, lines 748, 742 are included in other cables disclosed herein, such as cables 216 (particularly portions 218, 222), 248, 490 depending upon the embodiment, in lieu of cable 44.

Wall module includes a summer 756 that combines the analog audio signals communicated on lines 748a, 748b into a single audio signal that is input into a limiter/compressor/expander (LCE) 758. The LCE 758 is an analog circuit that applies varying gain based on the input voltage level of the signal coming into the LCE 758. If the input level is too high, the LCE 758 will limit the output voltage so that the output voltage does not overdrive a line input 760 to the FM transceiver 744. If the input level is too low, the LCE 758 will expand the output voltage, which counterintuitively means that the output voltage will be attenuated because the input signal to the LCE 758 is too low to be real audio and therefore, is considered to be noise. Thus, for low input levels, the LCE 758 serves as a noise gate. If the input level is in between the thresholds or levels that are too high and too low, then the LCE 758 operates within a compression region in which some level of gain is applied to the audio signal, or not, depending upon the configuration of the LCE 758. Compression generally means that the quieter and louder audio levels are made to be closer to each other to limit the dynamic range of the audio signal. As indicated in FIG. 45A, the analog audio signal output by LCE 758 on line 460 in the illustrative example is 0-4.5 Volts-Ampere (VA).

The analog audio signal on line 460 is provided to FM transceiver 744 which, in turn, converts the analog audio signal into wireless FM audio signal 740 for transmission from transceiver 744 of wall module 32, 460 to transceiver 746 of bed 30. Transceiver 746 is included on siderail communication (SCM or SideComm) board 94 in the illustrative example. The operation of FM transceiver 746 is controlled by software resident on a microprocessor or microcontroller 762 of SCM board 94. In the illustrative embodiment, microcontroller 762 is a model no. MSP432 microcontroller available from Texas Instruments of Dallas, Texas. In other embodiments, FM transceiver 746 is controlled by software resident in memory 104 and executed by microprocessor 102 (see FIG. 2).

Transceiver 746 converts the incoming wireless FM audio signal 740 into a wired audio signal that is provided to a power amplifier 764 on a line 766. As indicated in FIG. 45B, in the illustrative example power amplifier 764 applies a 2.94 V/V gain to the audio signal on line 766 and outputs the amplified audio signal to the bed speaker(s) 742 on first and second lines 768, 770 that are interconnected by a switch 772. When bed 30 is communicating wirelessly with wall module 32, 460, including via transceivers 744, 746, switch 772 is in the illustrative position in which lines 768, 770 are electrically interconnected. However, if bed 30 is plugged into ASBC 164 directly with a 37-pin nurse call cable, then switch 772 is moved to a second position disconnecting line 768 from line 770 and connecting bed speaker(s) 742 to a line 774 that carries the hardwire audio signal provided to bed 30 from audio source 732 via ASBC 164 and the 37-pin nurse call cable. In essence, if the bed 30 is hardwire connected to audio source 732, then wall module 32, 460 is bypassed such that the FM audio signal 740 from transceiver 744 to transceiver 746 is not necessary in order for bed 30 to play the audio originating from audio source 732.

In the illustrative embodiment, the position of switch 772 is controlled by microprocessor 102 of bed 30 as indicated diagrammatically in FIG. 45B by a dotted arrow. In the illustrative example, microprocessor 102 is included in a model no. STM32F microcontroller available from STMicroelectronics of Geneva, Switzerland. Thus, the term "microcontroller 102" is sometimes used herein and is shorthand for both microprocessor 102 and memory 104. In other embodiments, the functions carried out by microcontroller 102 and microcontroller 762 are carried out by a single microcontroller such that one or the other of microcontrollers 102, 762 are omitted from SCM board 94.

As further shown in FIG. 45B, bed 30 includes one or more microphones 776 that communicate with FM transceiver 746 via first and second lines 778, 780 that are interconnected by a switch 782. In some embodiments, bed 30 has a first microphone 776 on one of siderails 40 and a second microphone on the other of siderails 40. Similar to switch 772, if bed 30 is plugged into ASBC 164 directly with a 37-pin nurse call cable, then switch 782 is moved to a second position disconnecting line 778 from line 780 and connecting microphone(s) 776 to a line 784 that carries the hardwire audio signal from microphone(s) 776 of bed 30 via the 37-pin nurse call cable and ASBC 164 to a destination audio receiver that is communicatively coupled to ASBC 164. The destination audio receiver includes, for example, a speaker at a master nurse station computer, a speaker of a room station or staff station, a speaker of a wireless communication device carried by a caregiver, and the like. Thus, if the bed 30 is hardwire connected to ASBC 164, then wall module 32, 460 is bypassed such that the FM audio signal 740 from transceiver 746 to transceiver 744 is not necessary in order for bed 30 to transmit the audio detected by microphone(s) 776 of bed 30.

Similar to switch 772, the position of switch 782 is also controlled by microcontroller 102 as shown diagrammatically in FIG. 45B by a dotted line arrow. In other embodiments, microcontroller 762 is used to control the positions of switches 772, 782. Furthermore, in FIG. 45B, a transfer function, H, block 777 is shown and is intended to represent the ambient noise within the patient room that is picked up by microphone 776. The ambient noise includes audio from speakers 737, 742 as well as other noises such as people talking, equipment beeps, wheel noise from equipment being transported in the room or hallway, bed motor and pump noises, etc. Speaker(s) 742 and microphone(s) 776 shown in FIG. 45B are essentially the same as speaker 110 and microphone 112 shown in FIG. 2. However, different reference numbers are used in FIG. 45B that in FIG. 2 due to the diagrammatic circles indicating the plural (i.e., "speakers" and "microphones") of these elements whereas FIG. 2 depicts only one of each.

Assuming bed 30 is not connected directly to ASBC 164 by a 37-pin nurse call cable such that switch 782 is in the position shown in FIG. 45B interconnecting lines 778, 780, then the analog audio signal on line 780 from microphone(s) 776 is provided to FM transceiver 746 which, in turn, converts the analog audio signal into wireless FM audio signal 740 for transmission from transceiver 746 of bed 30 to FM transceiver 744 of wall module 32, 460. Transceiver 744 converts the incoming wireless FM audio signal 740 into a wired audio signal that is provided to an amplifier 786 on a line 788. As indicated in FIG. 45A, amplifier 786 outputs a 0-4.5 VA analog audio signal on a line 790 that is connected to analog audio output 754 of wall module 32, 460 which, as noted above, is connected to ASBC 164 via line 752 of cable 44. In FIG. 45A, line 752 is shown terminating as an "X" of ASBC 164 because the destination audio receiver is established during use and depends upon which device has opened up a communication channel with bed 30 to receive audio back from bed microphones 776.

It should be appreciated that, in a real world healthcare facility environment, multiple beds 30 and multiple wall modules 32, 460 may be within FM reception range of each other. Thus, it is desirable to select transmission and reception frequencies between transceivers 744, 746 between each wall module 32, 460 and its associated paired bed 30 that are not the same as any of the transmission and reception frequencies of other wall modules 32, 460 and other beds 30. To accomplish this, transceiver 744 of wall module 32, 460 scans the frequency spectrum of interest (e.g., FM frequencies in the illustrative example) and determines which frequencies are in use by other devices and stores those frequencies in memory, such as memory 118 of controller 114, as unavailable frequencies.

Once the frequency spectrum is scanned, controller 114 selects an available transmission frequency and an available reception frequency and tunes transceiver 744 to those selected available frequencies. Controller 114 also sends a notification via Bluetooth communications link 34 from transceiver 122 of wall module 32, 460 to transceiver 106 of bed 30 to notify controller 102 and/or controller 762 of bed 30 of the selected available transmission and reception frequencies. Controller 102 or controller 762 of bed 30, as the case may be, then tunes transceiver 746 to the selected available frequencies. It should be understood that the selected available transmission and receptions frequencies for audio signals 740 are frequencies that are not currently in use by other devices within reception range of transceivers 744, 746. Furthermore, it should be understood that because wall module 32, 460 is communicating the selected available transmission and reception frequencies to bed 30 over Bluetooth communications link 34, such communication only occurs after the wall module 32, 460 and bed 30 have become paired using any of the time-based Bluetooth pairing operations described above.

In one contemplated embodiment, transceiver 744 scans the FM spectrum channels by scanning at even frequencies in 200 kilohertz (kHz) steps from a minimum frequency of 76.0 megahertz (MHz) to a maximum frequency of 108.0 MHz so as to avoid commercial FM radio frequencies that broadcast at odd frequencies in 200 kHz steps from a minimum commercial radio frequency of 76.1 MHz to a maximum commercial radio frequency 108.1 MHz. Thus, the selected available FM transmission frequency and FM reception frequency will be even frequencies, such as 76.0 MHz, 76.2 MHz, 88.4 MHz, 90.6 MHz, 91.8 MHz, 93.0 MHz, 107.8 MHz, 108.0 MHz, just to give several random examples. The FM transmission frequency is different than the FM reception frequency in the contemplated embodiments. Furthermore, the transmission frequency of transceiver 744 is the reception frequency of transceiver 746 and the transmission frequency of transceiver 746 is the reception frequency of transceiver 744.

When scanning the frequency spectrum of interest, the transceiver 744 tunes to a particular reception frequency and determines if whether an audio signal above a threshold signal strength is received at that frequency (e.g., by determining a received signal strength indicator (RSSI)). If the audio signal is above the RSSI threshold, then the particular frequency is designated as unavailable. Transceiver 744 is then tuned to the next particular reception frequency and a similar determination made. This process repeats until the full spectrum of interest is scanned and all of the unavailable frequencies determined. The remaining frequencies (i.e., the one that are not unavailable) are the possible available frequencies from which to select. Any manner of selection from among the available frequencies are within the scope of the present disclosure. For example, selection of the two lowest available frequencies or the two highest available frequencies are contemplated. Alternatively, selection of two available frequencies that are roughly midway between the two unavailable frequencies that are furthest apart is another contemplated possibility. In any event, once wall module 32, 460 selects the transmission and reception frequencies for communications link 740 between transceivers 744, 746, the frequency scanning operation is terminated in some embodiments.

In some embodiments, even if bed 30 has a wired connection to ASBC 164 to receive/transmit audio on lines 774, 784, respectively, transceiver 744 still operates to scan the frequency spectrum of interest to determine the unavailable frequencies and, in some embodiments, to also make a selection of an available transmission frequency and an available reception frequency for audio communications link 740. Thus, if the wired connection between bed 30 and ASBC 164 is lost, wall module 32, 460 is able to notify bed 30 of the selected transmission and reception frequencies as quickly as possible after pairing and begin the audio signal transmission over audio communications link 740.

The present disclosure also contemplates embodiments in which wall module 32, 460 make Bluetooth broadcasts or transmissions to devices other than the paired bed 30 to notify the other devices of the transmission and reception frequencies selected by wall module 32, 460 during the frequency spectrum scanning process. Alternatively or additionally, the other devices identify the transmission and reception frequencies as unavailable in response to those frequencies being used in communications link 740 between transceivers 744,746. In either case, this permits the other such devices to store those transmission and reception frequencies in respective memory as unavailable frequencies. As noted above, pairing between wall module 32, 460 and patient bed 30 includes an exchange of unique identifiers between the Bluetooth transceiver 122 of wall module 32, 460 and the Bluetooth transceiver 106 of patient bed 30. In some embodiments, patient bed 30 and wall module 32, 460 communicate using a side channel to verify that the respective unique identifier from the other of patient bed 30 and wall module 32, 460 is present to confirm the audio transmission 740 received by the corresponding wireless transceiver 744, 746 originates from an expected source. For example, the side channel is another selected available frequency from those that are scanned by transceiver 744 during the frequency scanning process.

Figure 46:
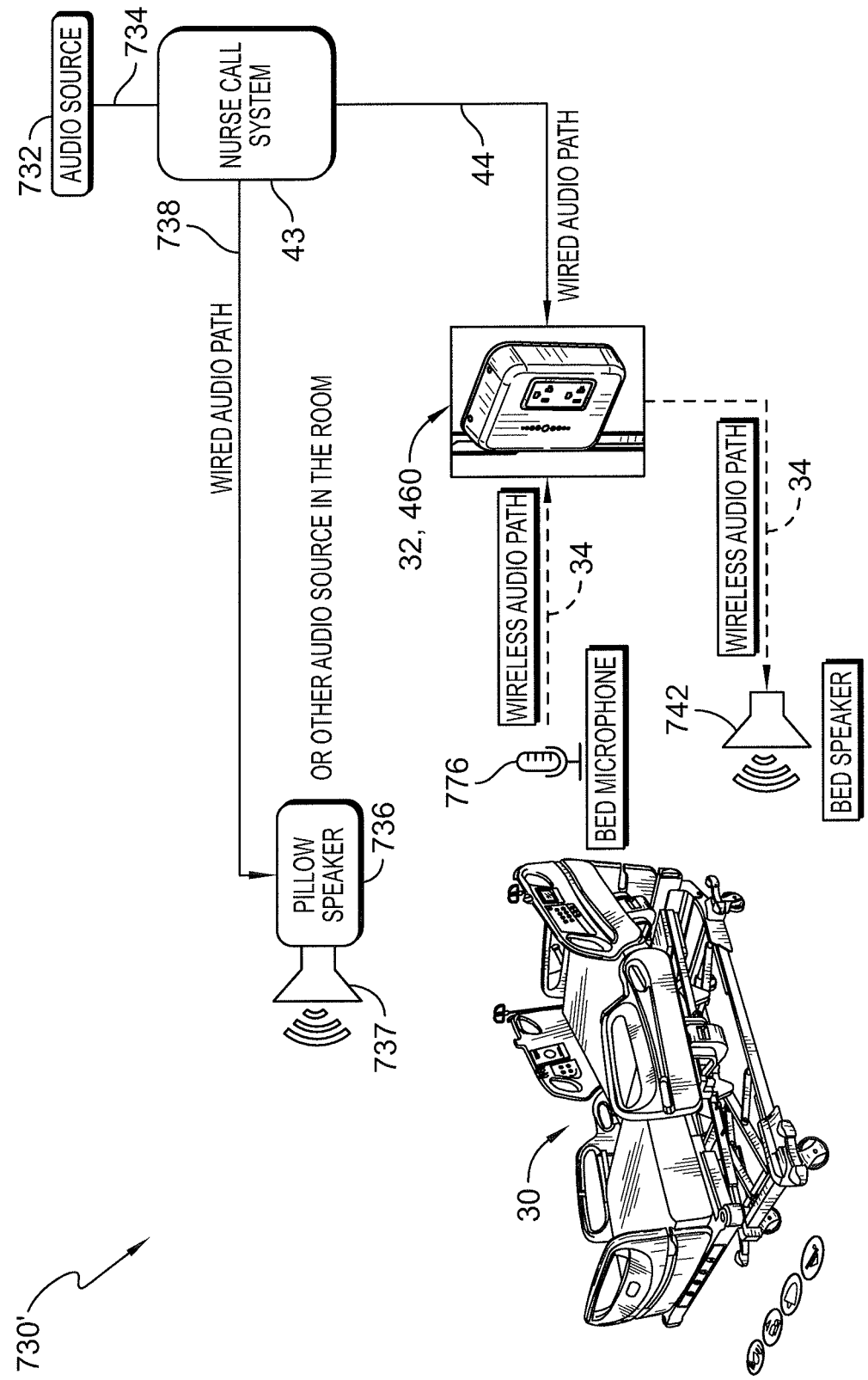
FIG. 46 is a block diagram of a system in which a wall module and a patient bed communicate wirelessly and in which the wall module includes a correlator to determine a correlation parameter by comparing an incoming wired audio signal to incoming wireless audio data and to mute one or more speakers of the patient bed if the correlation parameter violates a threshold condition.

Referring now to FIG. 46, a system 730' is shown with pillow speaker unit 736 coupled generically to nurse call system 43 via cable 738. Thus, system 730' of FIG. 46 is illustrative of the situation in which pillow speaker unit 736 couples to port 166 of ASBC 164 but is also illustrative of other situations in which pillow speaker unit 736 does not couple to port 166 of ASBC 164 but instead couples to nurse call system 43 via some other port or some other nurse call system infrastructure 42. Furthermore, system 730' illustrates audio source 732 coupled generically via hardware connection 734 to nurse call system 43. Thus, audio source 732 may be coupled to nurse call system 43 via infrastructure 42 other than ASBC 164 but that is not to rule out the possibility that the audio source is coupled to ASBC 164 in system 730'.

System 730' of FIG. 46 differs from system 730 of FIGS. 45A and 45B in that transceiver 744 is omitted from wall module 32, 460 and transceiver 746 is omitted from bed 30. Instead of using low latency transceivers 744, 746 for communication of audio signals between wall module 32, 460 and bed 30, a correlator is implemented in the software of wall module 32, 460 to compare the audio signal from audio source 732 that is fed to wall module 32, 460 via wired data link 44 in the illustrative example, and the wireless audio signal that is picked up by microphone 776 of bed 30 and transmitted from Bluetooth transceiver 106 of bed 30 to Bluetooth transceiver 122 of wall module 32, 460 via wireless data link 34. More particularly, controller 114 of wall module 32, 460 calculates a correlation parameter, such as a correlation coefficient, based on the comparison between the audio signal of wireless data link 34 and wired data link 44 (or wired data links 216, 248, 490 in other embodiments). Thus, in system 730', connector 234 of wall module 32, 460 serves as a first audio input that receives a first audio signal on cable 44 or portions 218, 222 of cable 216 (see FIG. 9) or cable 248 or cable 490, as the case may be, and Bluetooth transceiver 122 of wall module 32, 460 serves as a second audio input that receives a second audio signal as part of the data transmitted over wireless communications link 34.

If the correlation parameter determined by controller 114 is above a threshold, then wall module 32, 460 either stops sending audio data originating from the audio source 732 and/or sends a command signal to bed 30 to turn off speaker(s) 742 (e.g., to disable speaker(s) 742 from playing any audio). In essence, microphone 776 of bed 30 detects the audio being played by speaker(s) 742 of bed 30 as well as other ambient audio 777 in the room, including audio being played by speaker 737 of pillow speaker unit 736, assuming speaker 737 is not turned off. A high correlation parameter value is indicative that bed speaker(s) 742 and pillow speaker 737 are both playing the audio originating from audio source 732 such that an undesirable echo or delay is occurring. The echo is produced because the real time audio signal fed to wall module 32, 460 via hardwire connection of cable 44, 216, 248, 490, depending upon the embodiment, is played substantially instantaneously through pillow speaker 737, while the same audio is also played by speaker(s) 742 of bed 30 after a delay period (e.g., more than 50 milliseconds) due to the communication latency of the wireless communication link 34 from wall module 32, 460 to bed 30. In that situation, therefore, wall module 32, 460 either commands bed 30 to turn off speaker(s) 742 so that the audio is played only by speaker 737 of pillow speaker unit 736 or wall module 32, 460 stops sending audio packets to bed 30. In either case, the echo is eliminated.

If the correlation parameter is below the threshold value, then the one or more speakers 742 of bed 30 are left on because the low correlation parameter is indicative that audio is not also being played through speaker 737 of pillow speaker unit 736. Another situation in which the correlation parameter may be below the threshold value is if the sound from the pillow speaker 237 is muffled, such as by being placed underneath bedding (e.g., sheets and/or blankets) or being placed at a position relatively far away (e.g., three or four feet or more) from microphone 776 of bed 30. A further situation in which the correlation parameter may be below the threshold value is if the sound from the pillow speaker 237 is turned down significantly such that the sound emanating from speaker(s) 742 of bed 30 dominates or drowns out the sound emanating from pillow speaker 237.

Even after wall module 32, 460 operates to turn off speaker(s) 742 of bed, either by ceasing to send audio packets or by sending a mute command to bed 30, wall module 32, 460 continues to receive audio packets corresponding to sound picked up by microphone 776 of bed 30 for comparison to the incoming hardwire audio signal received at the first audio input. Thus, wall module 32, 460 continues to determine the value of the correlation parameter and compare it to the threshold to determine whether the speaker(s) 742 of bed 30 should be turned back on, such as by re-enabling Bluetooth transceiver 122 to start sending audio packets over data link 34 or by sending an unmute command to bed 30 via data link 34. Thus, the present disclosure contemplates that wall module 32, 460 of system 730' calculates the correlation parameter value on an ongoing basis, which may be continuous or at discrete intervals, and dynamically operates to turn speaker(s) 742 of bed 30 on and off based on whether the correlation parameter value is above or below the threshold value.

Prophetically, it is believed that the correlation parameter threshold will be a correlation coefficient that has an absolute value somewhere in the range of about 0.4-about 0.9. More particularly, the present disclosure contemplates that a Pearson correlation coefficient is calculated by controller 114 of wall module 32, 460, but that is not to rule out the possibility of using other types of correlation coefficients (e.g., Spearman's correlation coefficient or polychoric correlation coefficient) in other embodiments. In still other embodiments, the correlation parameter comprises some other variable such as covariance and/or standard deviation just to name a couple.

The Pearson correlation coefficient value can vary mathematically between −1 and +1, but the correlator of wall module 32, 460 evaluates the absolute value of the correlation coefficient value. From a practical standpoint, the audio signal from audio source 732 will always be played first through speaker 737 and then, after the latency delay period, will play through speaker(s) 742 (assuming speaker(s) is turned on), such that the correlation coefficient value calculated by the correlator of controller 112 of wall module 32, 460 will have an absolute value between 0 and +1. There are a number of available software packages or modules that have a correlation coefficient calculator. Such software includes MATLAB software available from The MathWorks, Inc. of Natick, Massachusetts and GNU Octave software available from Octave of San Francisco, California, for example, just to name a couple.

Figure 47:
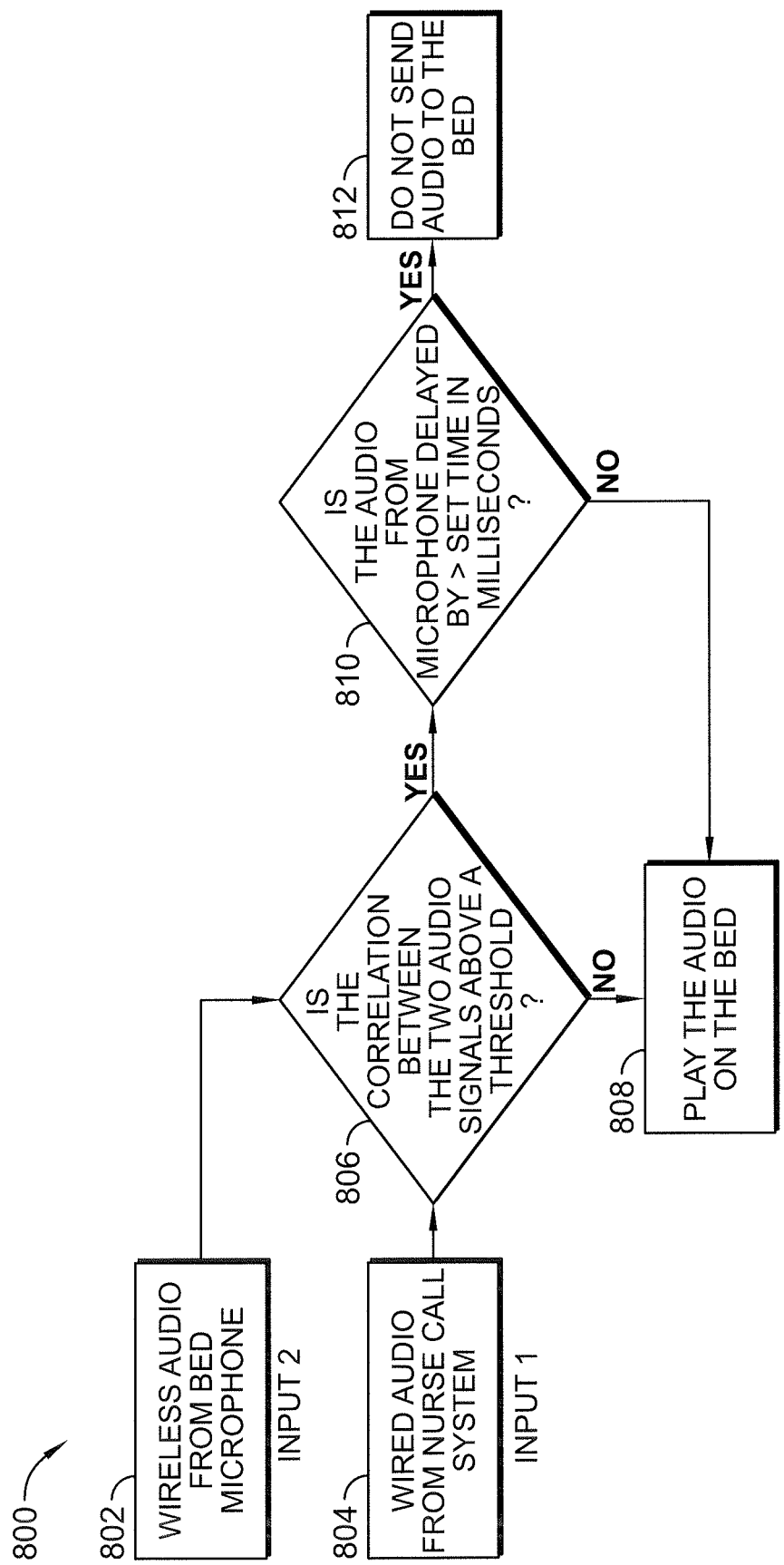
FIG. 47 is an algorithm implemented by the wall module of FIG. 46 to determine whether to mute the one or more speakers of the patient bed.

Referring now to FIG. 47, an algorithm 800 implemented by wall module 32, 460 to determine whether to mute the one or more speakers 742 of the patient bed 30 is shown. Algorithm 800 is illustrative of one possible algorithm contemplated above in connection with the discussion of FIG. 46. Those skilled in the art will understand how algorithm 800 may be modified to achieve the other embodiments and scenarios discuss above in connection with FIG. 46.

As indicated at block 804 of algorithm 800, wired audio from nurse call system 43 is provided to wall module 32, 460 as a first audio input signal which is labeled as "Input 1" in FIG. 47. At block 802 of algorithm 800, wireless audio 802 from bed microphone 776 is also provided to wall module 32, 460 as a second audio input signal (particularly, audio packets) which is labeled as "Input 2" in FIG. 47. Wall module 32, 460 then compares Input 1 and Input 2 to determine a correlation coefficient value between the inputs. At block 806, controller 114 of wall module 32, 460 determines whether the calculated correlation value (referred to in block 806 as simply a "correlation") is above a threshold value (referred to in block 806 as simply a "threshold").

As indicated at block 808, if the correlation determined at block 806 is not above the threshold, then wall module 32, 460 continues to operate to play the audio on bed 30 through speaker(s) 742. As indicated at block 810, if the correlation determined at block 806 is above the threshold, then wall module 32, 460 proceeds to determine whether the audio from microphone 776 of bed 30 is delayed by greater than a set time (e.g., a time delay threshold) as compared to the wired audio signal from the nurse call system 43. If at block 810 the set time is less than the time delay threshold, then wall module 32, 460 continues to operate to play the audio on bed 30 through speaker(s) 742 as indicated at block 808. If at block 810 the set time is greater than the time delay threshold, then wall module 32, 460 ceases to send any audio packets to bed 30 over wireless communications link 34 as indicated at block 812.

In some embodiments, the delay between the wired and wireless audio signals (e.g., Input 1 and Input 2) is determined by calculating a cross-correlation or autocorrelation between the two signals. The MATLAB and GNU Octave software mentioned above have the capability to calculate a cross-correlation value and an autocorrelation value, for example. Another way to determine a time delay is to plot a power spectrum of the two signals, determine peaks of the two signals in the plot, and determine a time difference between the occurrences of the two peaks. In any event, the present disclosure contemplates that a time delay of 50 milliseconds or less between the two audio signals (e.g., Input 1 and Input 2) is acceptable, as noted above, but other time delay thresholds can be used if desired. For example, the time delay threshold implemented at block 810 is 25 milliseconds in some embodiments. Thus, time delay thresholds between about 25 milliseconds and about 50 milliseconds are within the scope of the present disclosure.

While the systems 730, 730' described above are contemplated as being used for handling of wired and wireless audio between bed 30 and wall unit 32, 460, the present disclosure contemplates that FM transceivers 744, 746 and the associated circuitry discussed above in connection with FIGS. 45A and 45B and the correlator discussed above in connection with FIGS. 46 and 47 may just as well be used in other combinations of devices for the same respective purposes. Such other combinations of devices may include, for example, medical device 360 in combination with bed 30 as discussed above in connection with FIGS. 20 and 21 and may include, for example, mobile phone 410 in combination with speaker unit 412 as discussed above in connection with FIGS. 22 and 23.

According to another embodiment contemplated by the present disclosure, bed speaker 742 is muted or unmuted by a service technician as part of the configuration of wall module 32, 460 that occurs in connection with the installation of one or more wall modules 32, 460 in a healthcare facility. Other aspects of wall module 32, 460 are also configured in connection with the installation as well, as will now be described below in connection with FIGS. 48-52.

Referring now to FIG. 48, a landing page 820 appears on a display screen of a service technician's mobile device such as, for example, a mobile phone, a tablet computer, or a laptop computer in response to a wall module configuration application being launched by the service technician on their mobile device. For example, the service technician may select a wall module configuration tile that appears on the display screen of their mobile device. The wall module configuration application is used by the service technician after one or more wall modules 32, 460 are installed in a healthcare facility and prior to use with a medical device such as hospital bed 30 in order to configure the one or more wall modules for subsequent operation. In some embodiments, the service technician blocks an IR light beam such as one of light beams 262, 262' or one those in front of receptacles 466, 468, to initiate a scanning process from the wall unit 32, 460 that results in linking with the service technician's mobile device by the wall units 32, 460 within communication distance of the mobile device of the service technician.

Landing page 820 includes a field 822 with a text string 824 stating "Not Connected" which indicates that the service technician's mobile device is not in wireless communication with any wall unit 32, 460. In some embodiments, the service technician's mobile device is configured to wirelessly communicate with wall module 32, 460 via Bluetooth communications. Thus, the service technician's mobile device is configured to communicate with Bluetooth transceiver 122 of wall module 32, 460. In response to selection of field 822 or text string 824 by the service technician, such as by touching or tapping filed 822 or text string 824, as the case may be, a devices page 826 appears on the display of the mobile device of the service technician as shown, for example, in FIG. 49. Thus, in some embodiments, field 822 serves as a selectable button or icon that the service technician uses to navigate to devices page 826 and, in other embodiments, the service technician selects just text string 824 to navigate to page 826. The terms "button" and "icon" are used interchangeably herein.

Devices page 826 of FIG. 49 includes a list 828 of the one or more wall modules 32, 460 that are within Bluetooth communication range of the service technician's mobile device. In the illustrative example, list 828 contains module ID's for three wall modules 32, 460. The module ID's, which illustratively are MAC addresses for the three wall modules 32, 460, appear in rows 830a, 830b, 830c of list 828. Each of rows 830a, 830b, 830c has a Connect button 832 which is selectable to designate which wall module 32, 460 from among the three listed wall modules 32, 460 the technician's mobile device is to pair and communicate for configuration.

In response to selection of button 832 of one of rows 830a, 830b, 830c of list 828 on page 826, a configuration home page 834 appears on the display screen of the service technician's mobile device. Icon 838 is highlighted on page 834 so the service technician knows which page is being displayed on their mobile device. In the illustrative example, the service technician has chosen to connect with the wall module 32, 460 associated with row 830a of list 828 of page 826 for configuration purposes as indicated by the module ID (illustratively, 00:00:00:00:00) which appeared in row 830a also appearing near the top of page 834 in FIG. 50. At the bottom of page 834, a menu 836 appears with a home icon or button 838, a setup icon or button 840, and a maintenance icon or button 842. On page 834, home icon 838 is highlighted to indicate that the service technician is viewing the configuration home page 834.

Figure 50:
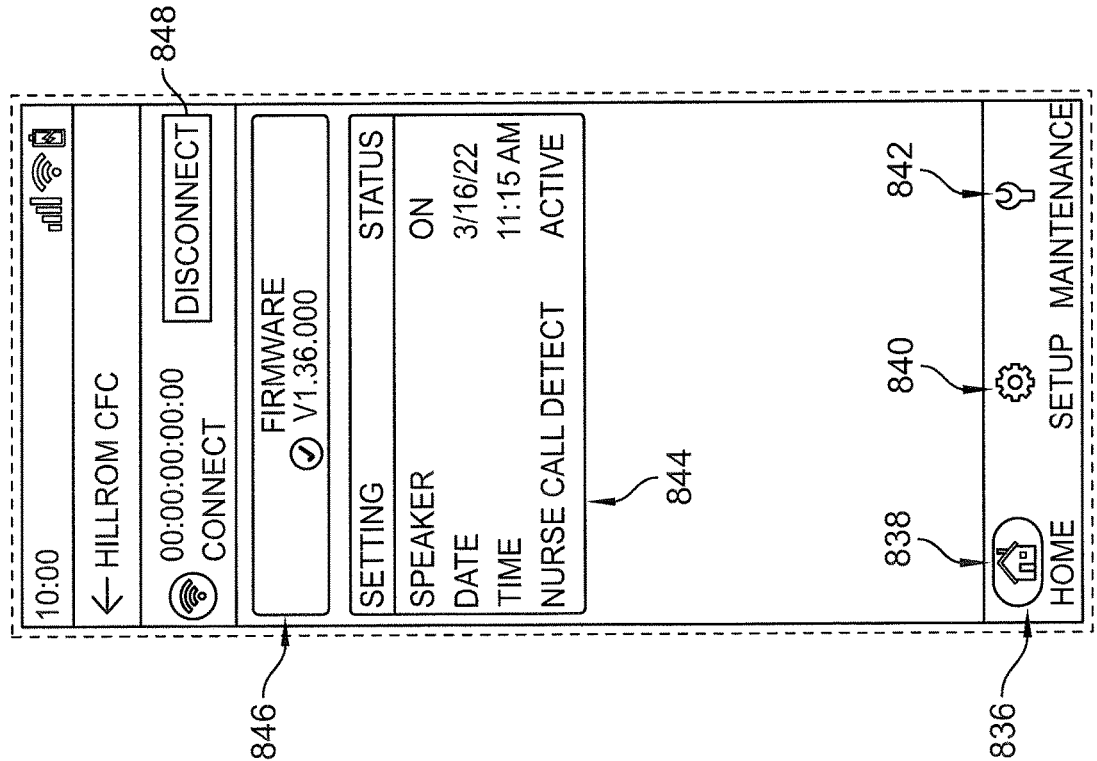
FIG. 50 is a screen shot of an example of a configuration home page that appears on the service technician's mobile device in response to selection of a connect button on the devices page that appears adjacent the module ID of the wireless module with which the service technician desires to connect for configuration purposes.

Illustrative page 834 of FIG. 50 includes an informational table 844 and a firmware field 846 above table 844. In the given example, table 844 has five rows with the first row including a Setting heading and a Status heading. The second through fifth rows of table 844 include information pertaining to the current configuration of the wall module 32, 460 with which the mobile device of the service technician is connected. In the illustrative example of table 844, the second row indicates that a Speaker setting has an On status, the third row indicates that a Date setting is Mar. 16, 2022, the fourth row indicates that a Time setting is 11:15 AM, and the fifth row indicates that a Nurse Call Detect setting has an Active status.

Still referring to FIG. 50, the illustrative firmware field 846 of page 834 indicates that the wall module 32, 460 with which the mobile device of the service technician is connected is operating according to firmware version v1.36.000. Page 834 also includes a Disconnect button or icon 848 that is selectable to disconnect the mobile device of the service technician from the wall module 32, 460 with which the mobile device is currently communicating. In some embodiments, selection of button 848 returns the user from page 834 to page 826 of FIG. 49 so that another wall module 32, 460 can be chosen for configuration, if desired.

Figure 51:
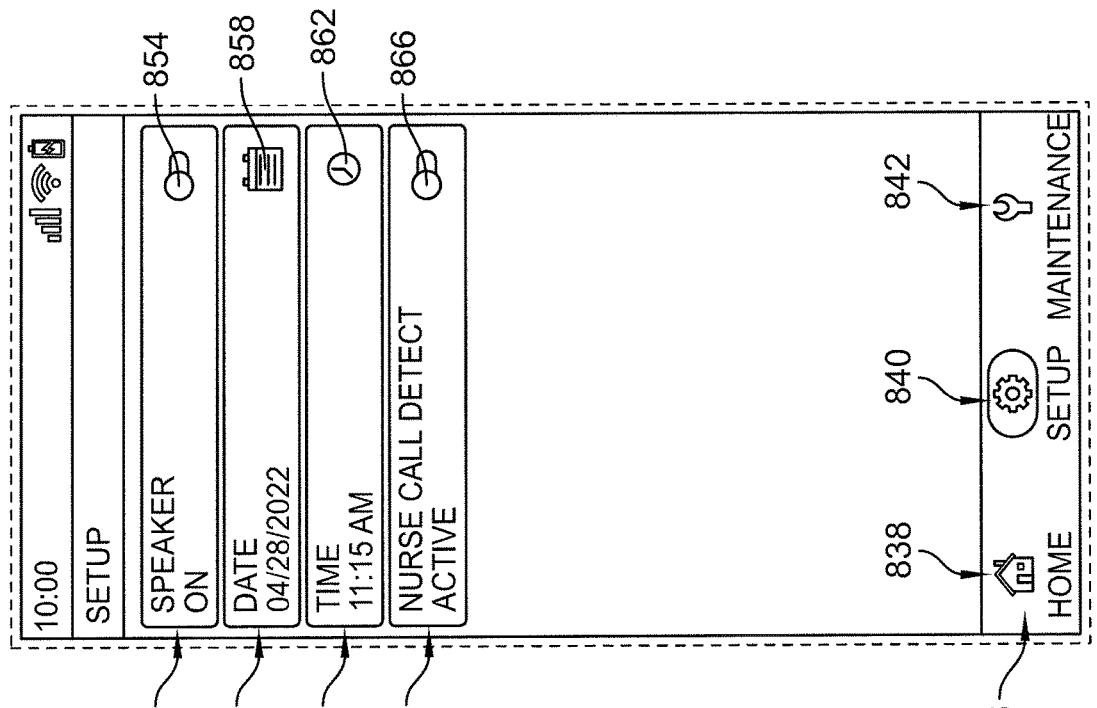
FIG. 51 is a screen shot of an example of a setup page that appears on the service technician's mobile device in response to a setup icon being selected on the home page of FIG. 50, the setup page including a speaker slider that can be slid between on and off positions to unmute and mute, respectively, a speaker of a bed that pairs with the selected wall module in the future or that is currently paired with the wall module, the setup page further having date and time fields that are selectable for adjustment of date and time, and the setup page still further having a nurse call slider that is movable between active and non-active positions.

In response to selection of setup icon 840 on page 834, a setup page 850 appears on the service technician's mobile device as shown, for example, in FIG. 51. Icon 840 is highlighted on page 850 so the service technician knows which page is being displayed on their mobile device. Setup page 850 includes a Speaker field 852 that, in turn, includes a speaker slider 854 that can be slid between on and off positions to unmute and mute, respectively, speaker 742 of a bed, such as bed 30, that pairs with the selected wall module 32, 460 in the future or that is currently paired with the wall module 32, 460. That is, the service technician can use their mobile device not only to configure wall modules 32, 460 after initial installation, but also to change the configuration of wall modules 32, 460 after they have initially been configured.

In the illustrative example of FIG. 51, slider 854 is in the on position such that speaker 742 of any bed 30 that pairs with the selected wall module 32, 460 will be unmuted. Thus, as a result of slider 854 being in the on position, any audio feed to wall module 32, 460, be it a digital audio feed such as, for example, from a voice over Internet protocol (VoIP) server, or an analog audio feed such as, for example, an analog audio feed from a television, will be transmitted as digital audio data (e.g., audio packets containing 1's and 0's) from Bluetooth transceiver 122 of wall module 32, 460 to Bluetooth transceiver 106 of bed 30 for playing through speaker 742. If desired, the service technician viewing page 850 can select slider 854 and move it to the right from the illustrative on position to the off position to mute speaker 742 of bed 30. To move slider 854 between the on and off positions, a touch-and-drag operation is performed with the user's finger, for example.

Field 852 includes the text "On" beneath a Speaker heading when slider 854 is in the on position shown in FIG. 51 and, in response to moving slider 854 to the off position, the text "Off" appears beneath the Speaker heading. As a result of slider 854 being in the off position, any audio feed to wall module 32, 460, be it a digital audio feed or an analog audio feed, will be changed by the circuitry (e.g., controller 114 of wall module 32, 460) to digital audio data that corresponds to silence (e.g., audio packets containing all 0's). The audio packets containing all 0's are still transmitted from Bluetooth transceiver 122 of wall module 32, 460 to Bluetooth transceiver 106 of bed 30 and is actually played through speaker 742 as silence. In other words, in some embodiments, speaker 742 of bed 30 is always turned on, but when muted, is playing silence. Regardless of the position of slider 854, non-audio data packets continue to be transmitted between bed 30 and wall unit 32, 460 in the normal manner.

In embodiments in which slider 854 of page 850 of the configuration application of wall module 32, 460 is used to mute and unmute speaker of bed 30, the audio packets are sent via Bluetooth over communications link 34 such that FM transceivers 744, 746 discussed above in connection with FIGS. 45A and 45B are not needed and can be omitted. Furthermore, the use of slider 854 of page 850 of the configuration application of wall module 32, 460 to mute and unmute speaker 742 of bed 30 may done in lieu of or in addition to the use of the correlator discussed above in connection with FIGS. 46 and 47. From a practical standpoint, slider 854 is moved to the off position to mute speaker 742 of bed 30 when sound from various sound sources such as a master nurse station, television, mobile phone carried by a caregiver, a graphical audio station in another room, etc., are going to be played through a speaker of a pillow speaker unit or similar such speaker unit that has a wired connection to the network 60 of the healthcare facility. By muting speaker 742 of bed 30 with slider 854, the echo or stadium effect that may be produced as a result of sound delay when speaker 742 and another speaker in the room both play the same sound, is eliminated. If no pillow speaker unit or similar unit is present in the room, then slider 854 is moved to the on position so that speaker 742 of bed 30 plays the audio in an audible manner.

Still referring to FIG. 51, page 850 further includes a Date field 856 having a calendar icon or button 858 that, when selected, allows a date to be changed. The selected date in field 856 in the illustrative example is Apr. 28, 2022 and appears beneath a Date heading. Page 850 also includes a Time field 860 having a clock icon or button 862 that, when selected, allows a time to be changed. The selected time in field 860 in the illustrative example is 11:15 AM and appears beneath a Time heading. Page 850 still further includes a Nurse Call Detect field 864 which, in turn, includes a nurse call slider 866 that is movable between active and non-active positions. In the illustrative example of FIG. 51, slider 866 is in the active position and the word "Active" appears beneath the heading Nurse Call Detect.

If desired, the service technician viewing page 850 can select slider 866 and move it to the right using a touch-and-drag operation thereby moving slider 866 from the illustrative active position to the non-active position in which case the word "Non-active" appears beneath the Nurse Call Detect heading. In general, slider 866 is moved to the non-active position when wall module 32, 460 is interfacing with a third party nurse call system. This configures wall module 32, 460 to avoid providing an alert that the nurse call system is not detected (e.g., has become disconnected from the wall unit 32, 460) when, in fact, the third party nurse call system is still connected to wall module 32, 460. When slider 866 is in the active position, wall module 32, 460 is configured to detect a connection to the nurse call system 43 and issue an alert if the nurse call system 43 becomes disconnected, such as by disconnection of nurse call cable 44, 216, 248, 490, as the case may be.

When wall module 32, 460 is configured in the active nurse call detect mode by having slider 866 in the active position, then an alert condition caused by disconnection of the respective nurse call cable 44, 216, 248, 490 from nurse call system 43 results in two actions by wall module 32, 460. One action is that caution icon 488 is illuminated solid (i.e., does not flash) on the wall module 32, 460. The other action is that an alert message is transmitted to bed 30 from wall module 32, 460 and the bed 30, in turn, provide both an audible alert and visual alert (e.g., provide a message on GUI 38) to indicate that the respective nurse call cable 44, 216, 248, 490 has become disconnected from the nurse call system 43. When wall module 32, 460 is configured in the non-active nurse call detect mode by having slider 866 in the non-active position, then wall module 32, 460 and bed 30 will not issue any alerts with regard to disconnection of the respective nurse call cable.

Figure 52:
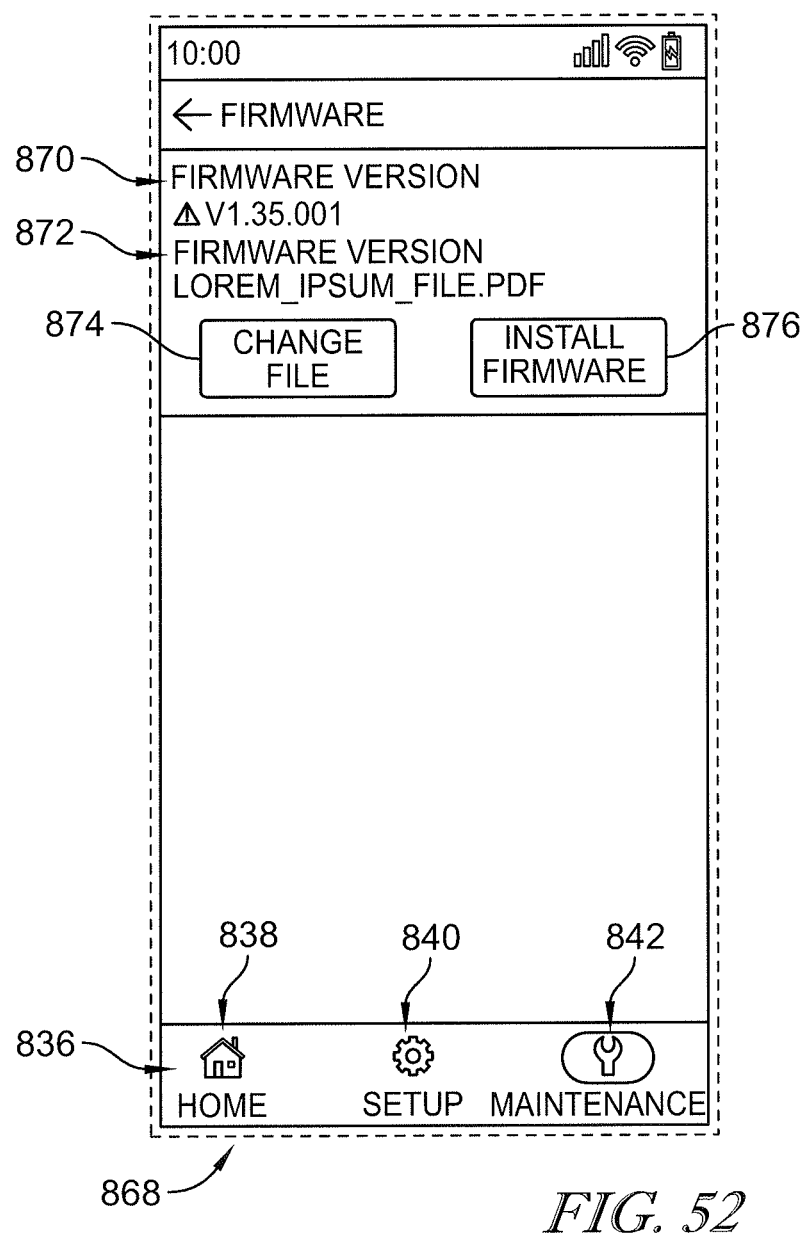
FIG. 52 is a screen shot of an example of a maintenance page that appears on the service technician's mobile device in response to a maintenance icon being selected on the home page of FIG. 50 or the setup page of FIG. 51, the maintenance page including a firmware version field that indicates a version of firmware for the wall module that is stored on the service technician's mobile device designated for upload to the wall module, a change file button that is selectable to pick designate a different firmware version from the service technician's mobile device for upload to the wall module, and an install firmware button that is selectable to initiate the upload of the designated firmware version to the selected wall module.

In response to selection of maintenance icon 842 on page 834 of FIG. 50 or page 850 of FIG. 51, a maintenance page 868 appears on the service technician's mobile device as shown, for example, in FIG. 52. Icon 842 is highlighted on page 868 so the service technician knows which page is being displayed on their mobile device. Maintenance page 868 of FIG. 52 includes a firmware version field 870 that indicates a version of the firmware for wall module 32, 460 that is stored on the service technician's mobile device and designated for upload to the wall module 32, 460. Page 868 also has a firmware file field 872 that contains the name of the file in which the firmware associated with the firmware version listed in field 870 is stored.

Still referring to FIG. 52, page 868 further includes a Change File button or icon 874 that is selectable to pick a different firmware version and file from the service technician's mobile device for upload to the wall module 32, 460. Thus, the service technician's mobile device may store multiple firmware files for possible upload to wall modules 32, 460. Page 868 also has an Install Firm icon or button 876 that is selectable to initiate the upload of the designated firmware version and file to the selected wall module 32, 460.

After the various wall module configurations are made using pages 850, 868, the service technician navigates back to home page 834 by selection of home icon 838 on page 850 or page 868 as the case may be, and then selecting disconnect button 848. The service technician can then pick another wall module 32, 460 from list 828 to configure or simply exit out of the configuration application altogether. It should be appreciated that the various configuration parameters (e.g., positions of sliders 854, 866, date, and time) and uploaded firmware file are stored in memory 118 such as, for example, a non-volatile memory portion of memory 118 of wall module 32, 460 for subsequent use.

The present disclosure contemplates that after wall module 32, 460 is configured by the service technician to operate in a manner that mutes or unmutes speaker 742 of the bed 30 that communicates with wall module 32, 460, circumstances may change in the future such that it may be desirable to change the mute/unmute configuration. For example, initially when wall module 32, 460 is configured, a pillow speaker unit may be present in the room such that it is desirable to mute speaker 742 of bed 30 during initial setup. Subsequently, however, the pillow speaker unit may be removed from the room for any of number of reasons such as for repair, replacement, or disinfection, just to name a few. On the other hand, during initial configuration of wall module 32, 460, no pillow speaker or other similar speaker may be present in the room such that it is desirable to unmute speaker 742 of bed 30 during initial setup. Accordingly, in some embodiments, bed 30 is configured to permit a user, such as a caregiver, to change the mute/unmute stetting of wall module 32, 460 using GUI 38 of bed 30 as will now be described in connection with FIGS. 53-56.

Figure 53:
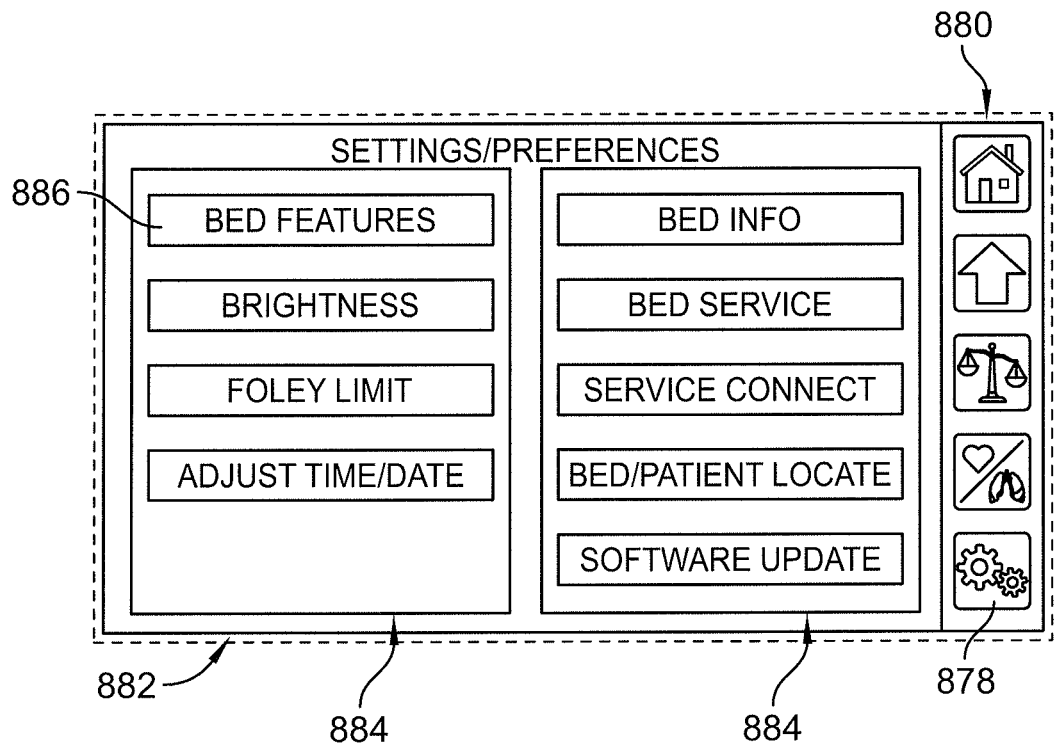
FIG. 53 is a screen shot of an example of a settings/preferences page that appears on a graphical user interface (GUI) of the patient bed as part of configuring audio for the bed.
Figure 54:
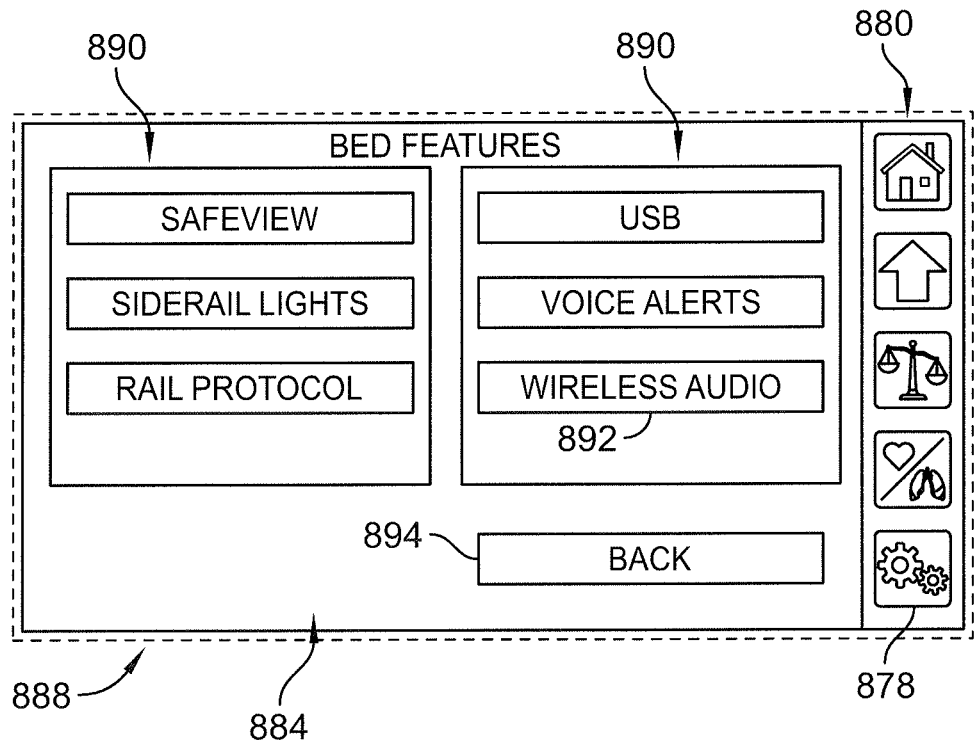
FIG. 54 is a screen shot of an example of a bed features page that appears on the GUI in response to a bed features button being selected on the settings/preferences page of FIG. 53.

In response to selection by the user of a settings/preferences button or icon 878 on a main menu 880 that appears on GUI 38, a Settings/Preferences page 882 appears on GUI 38 of patient bed 30 as shown in FIG. 53. Page 882 includes a two-column menu 884 of icons or buttons for selection by the user. For purposes of configuring audio for bed 30, the relevant button is a Bed Features button 886 which appears at the top of the left hand column of menu 884. In response to selection of icon 886 on page 882, a Bed Features page 888 appears on GUI 38 as shown in FIG. 54. Page 882 includes another two-column menu 890 of icons or buttons for selection by the user. For purposes of configuring audio for bed 30, the relevant button is a Wireless Audio button 892 which appears at the bottom of the right hand column of menu 890. Page 888 also displays a Back button 894 which, in response to selection by the user, returns the user to page 882 of FIG. 53.

Figure 55:
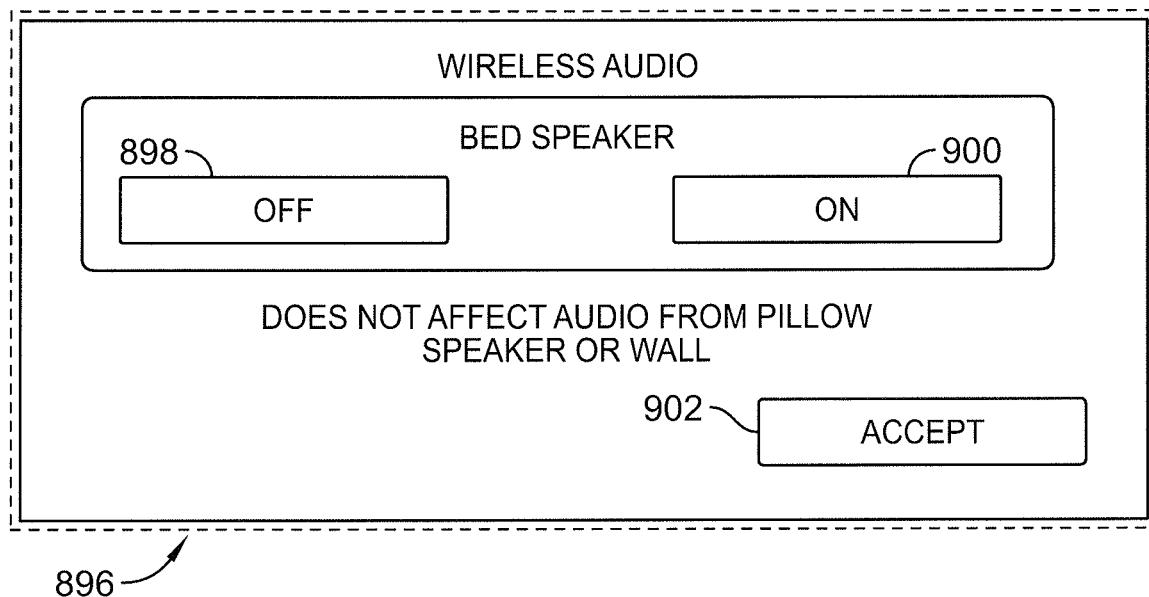
FIG. 55 is a screen shot of an example of a wireless audio page that appears on the GUI in response to a wireless audio button being selected on the bed features page of FIG. 54, the wireless audio page including an off button that is selectable to mute the bed speaker and an on button that is selectable to unmute the bed speaker.

In response to selection of Wireless Audio icon 892 on page 888 of FIG. 54, a Wireless Audio page 896 appears on GUI 38 of bed 30 as shown in FIG. 55. Wireless Audio page includes an Off button 898 that is selectable by the user to mute bed speaker 742 of the associated bed 30 and an On button 900 that is selectable by the user to unmute bed speaker 742 of the associated bed 30. Page 896 further displays the text string, "Does not affect audio from pillow speaker or wall," to notify the user that it is only bed speaker(s) 742 that is/are muted or umuted by the use of buttons 898, 900, respectively. Page 896 further displays an Accept button or icon 902 that is selectable by the user to initiate the transmission of an associated command message from bed 30 to the corresponding wall module 32, 460 to either operate in a manner that mutes the bed speaker(s) 742, if the Off button 898 is selected on page 896, or to operate in a manner that unmutes the bed speaker(s) 742, if the On button 900 is selected on page 896.

Based on the foregoing, it should be appreciated that, from the perspective of the wall module 32, 460, the use of bed GUI 38 to mute or unmute the bed speaker(s) 742 of bed 30 by use of buttons 898, 900 on page 896 is basically the same as the use of slider 854 on page 850 of the service technician's mobile device to mute and unmute the bed speaker(s) of bed 30. Thus, selection of Off button 898 on page 896 of GUI 38 of bed 30 causes the same result as moving slider 854 to the off position on page 850 of the service technician's mobile device. Similarly, selection of On button 900 on page 896 of GUI 38 of bed 30 causes the same result as moving slider 854 to the on position on page 850 of the service technician's mobile device.

Figure 56:
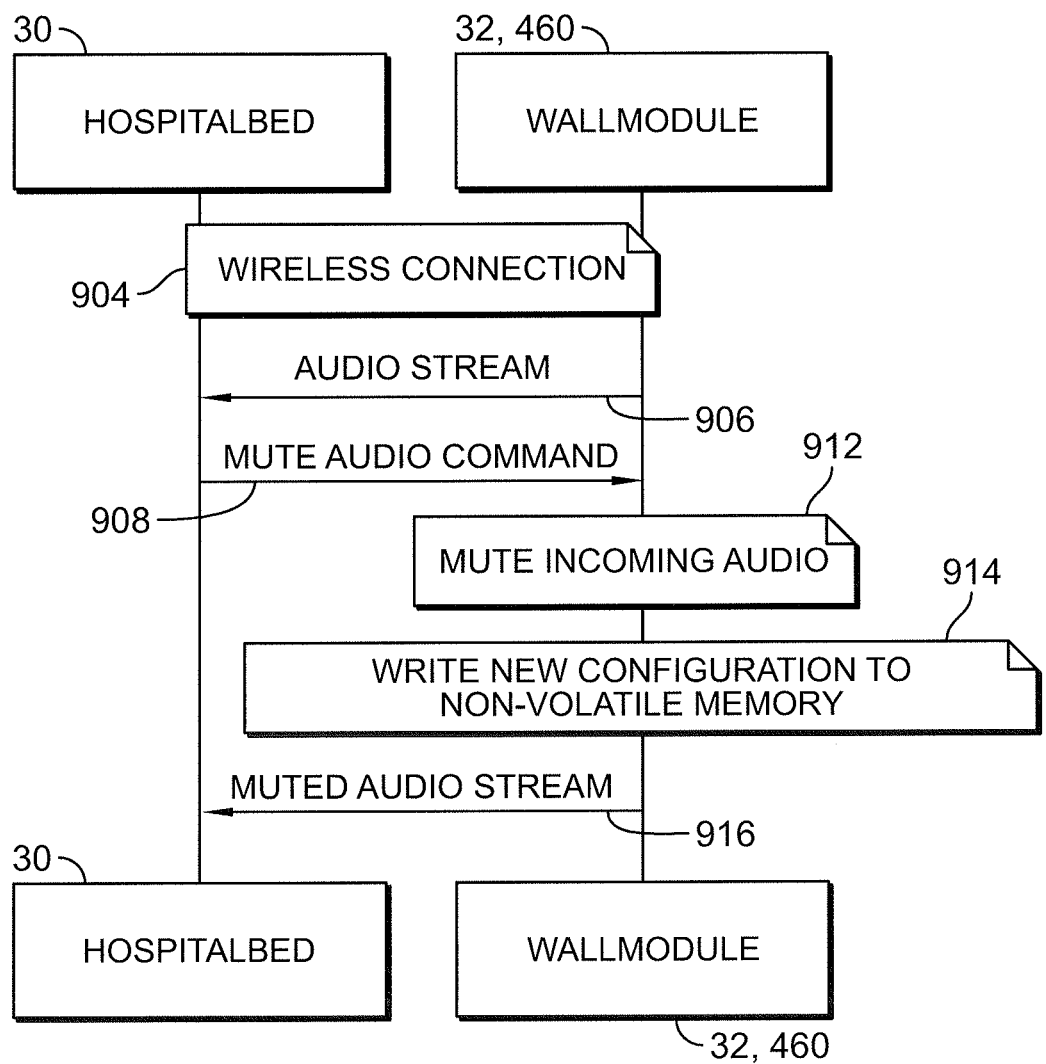
FIG. 56 is a swim lane diagram showing steps of the wireless audio configuration operation between the bed and the wall module when the bed is used to mute the bed audio.

Referring now to FIG. 56, a swim lane diagram is provided showing steps of a wireless audio configuration operation 910 between bed 30 and wall module 32, 460 in the situation when bed 30 is initially playing audio received from wall module 32, 460 through bed speaker(s) 742 and then bed 30 is used to mute the bed audio. As indicated at block 904 of operation 910, bed 30 and wall module 32, 460 are paired so as to have a wireless connection for wireless communication via datalink 34. Accordingly, wall module 32, 460 sends an audio stream to bed 30 as indicated by arrow 906. Audio stream 906 is unmuted such that audio packets sent from wall module 32, 460 to bed 30 have 1's and 0's corresponding to the audio feed received by wall module 32, 460 from an audio source (e.g., television, master nurse station, graphical room station (GRS) of another room, caregiver mobile phone, etc.) thereby causing bed speaker(s) 742 to produce audible sound.

Still referring to FIG. 56, bed 30 sends a Mute Audio Command to wall module 32, 460 as indicated by arrow 908. For example, the Mute Audio Command 908 is transmitted in response to Off button 898 being selected on page 896 on GUI 38 of bed 30, as shown in FIG. 55, and then Accept button 902 of page 896 being selected. In response to receipt of the Mute Audio Command 908 at wall module 32, 460, wall module 32, 460 operates to mute the incoming audio feed as indicated at block 912 and wot write the new audio configuration to the non-volatile memory portion of memory 118 of wall module 32, 460 as indicated at block 914. Thereafter, wall module 32, 460 transmits a muted audio stream 916 to bed 30. As discussed above, the muted audio stream 916 consists of audio packets having all 0's which corresponds to a transmission of silence.

Figure 57A:
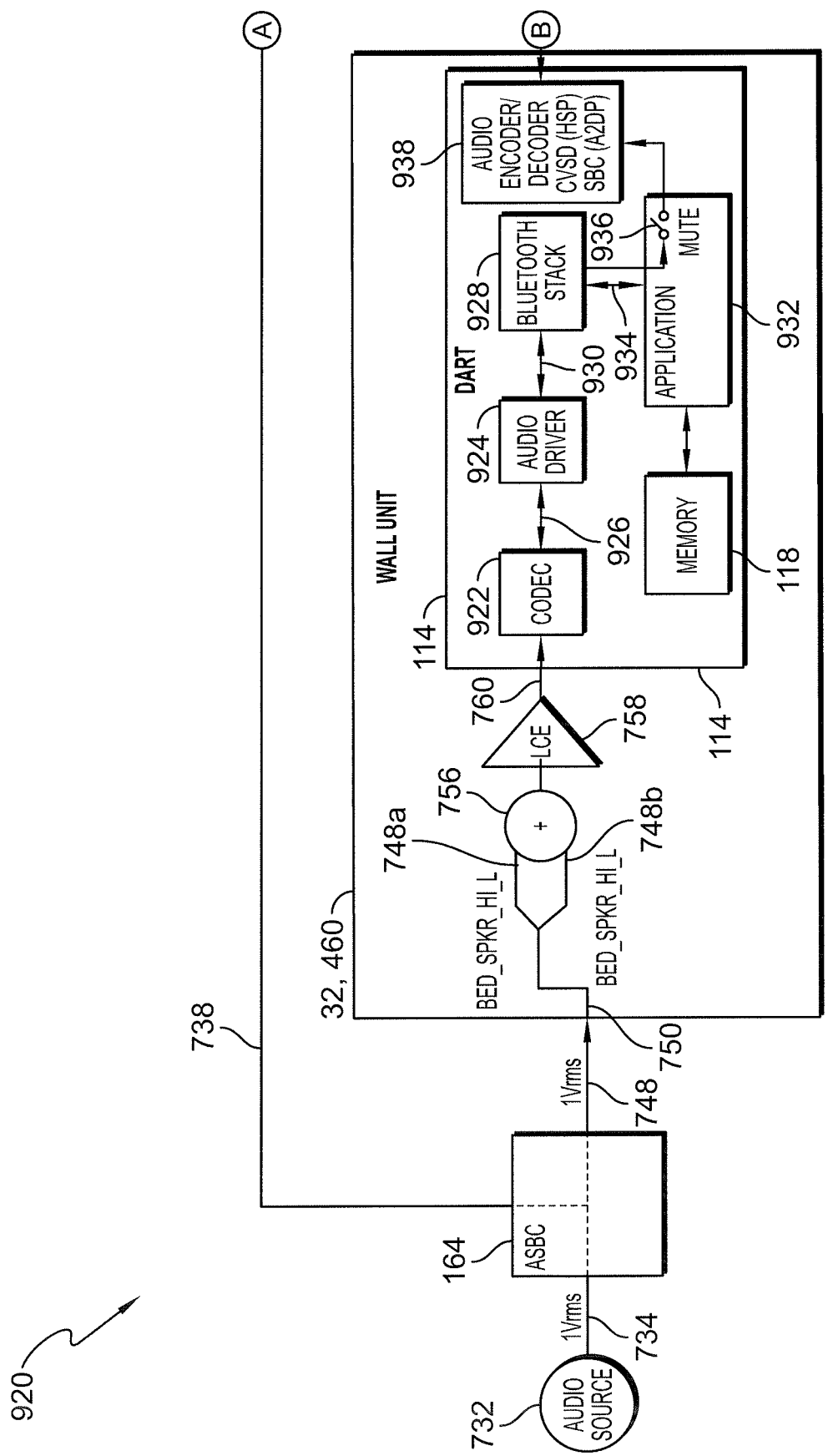
FIGS. 57A and 57B make up a block diagram of a system in which a wall module and a patient bed communicate data and audio via Bluetooth transceivers and also allow for muting of the audio.
Figure 57B:
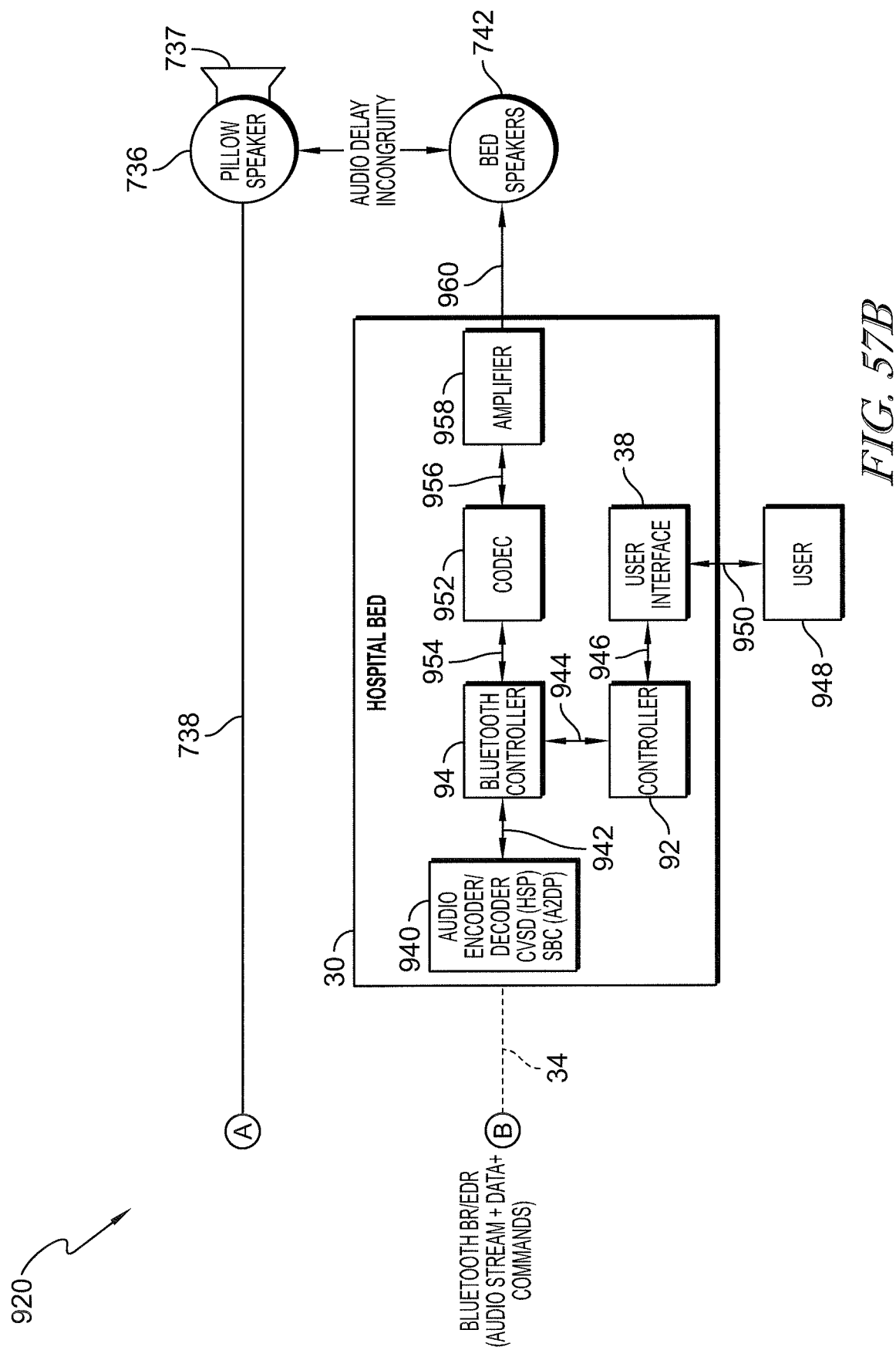

Referring now to FIGS. 57A and 57B, a block diagram is provided of a system 920 in which wall module 32, 460 and patient bed 30 communicate data and audio via Bluetooth transceivers and also allow for muting of the audio. The block diagram of FIGS. 57A and 57B is similar, in some respects, to the block diagram of FIGS. 45A and 45B. Accordingly, for common components between system 730 of FIGS. 45A and 45B and system 920 of FIGS. 57A and 57B, the same reference numbers are used and the descriptions are not repeated for the sake of brevity. One of the key differences between system 730 and system 900 is that the FM transceivers 744, 746 of system 730 are omitted in system 900. Other portions of system 920 of FIGS. 57A and 57B that are the same as components found in the block diagrams of FIGS. 2 and 9 are denoted with like reference numbers and the descriptions are not repeated.

As shown in FIG. 57A, line input 760 from LCE 758 of wall module 32, 460 is coupled to a coder/decoder 922 of SOM 114 which, in the illustrative example, is a model no. DART 6UL available from Variscite Ltd. of Lod, Israel. Codec 922 is, in turn, coupled to an audio driver 924 via one or more signal lines 926. Audio driver 924 is coupled to a Bluetooth stack 928 of SOM 114 by signal lines 930. A block 932 in FIG. 57A represents an application that handles the transmission of data and commands to and from Bluetooth stack 928 as indicated by a double headed arrow 934 and that determines whether the bed speaker(s) 742 is/are to be muted as indicated by diagrammatically by a mute switch 936. In the illustrative example, mute switch 936 is in the open position which means SOM 114 operates to transmit audio packets having only 0's regardless of what audio feed is received by wall module 32, 460 on line 748 from audio source 732. The application 932 may be stored in memory 118 of SOM 114, for example, and the mute switch may correspond to a flag (e.g., a 0 or 1 bit, or a multi-bit code) in memory 118 which determines whether the bed speakers(s) 742 is/are to be muted or unmuted.

Still referring to FIG. 57A, application 932 interfaces with an audio encoder/decoder 938 which sends and receives wireless communications to and from bed 30, respectively, via communications link 34. In the illustrative example, communications link 34 comprises Bluetooth BR/EDR communications which includes an audio stream, data, and commands. Furthermore, in the illustrative example, audio encoder/decoder 938 is configured to implement a continuously variable slope delta (CVSD) modulation scheme compatible with headset profile (HSP) operation and/or an advanced audio distribution profile (A2DP) with sub-band coding (SBC). Other audio encoder/decoder devices may be used in other embodiments.

Referring now to FIG. 57B, bed 30 includes an audio encoder/decoder 940 which sends and receives wireless communications to and from wall unit 32, 460, respectively, via communications link 34. In the illustrative embodiment, audio encoder/decoder 940 of bed 30 is the same as audio encoder/decoder 938 of wall module 32, 460 and so the discussion in the preceding paragraph also is applicable to audio encoder/decoder 940. Audio encoder/decoder 940 is coupled to Bluetooth controller 94 via communication lines 942. Controller 94, in turn, is coupled to the main controller 92 of bed 30 via communication lines 944. Controller 94 is in electrical communication with GUI 38 as indicated by double headed arrow 946 in FIG. 57B. The user of GUI 38 is represented diagrammatically in FIG. 57B by block 948. The user's interaction with GUI 38 is represented diagrammatically in FIG. 57B with a double headed arrow 950.

Bluetooth controller 94 is also coupled to a coder-decoder (codec) 952 via communication lines 954 as shown in FIG. 57B. An output 956 from codec 952 is input into an amplifier 958 and an output 960 from amplifier 958, in turn, is coupled to bed speaker(s) 742. FIG. 57B also includes the text, "Audio Delay Incongruity," which indicates that if both pillow speaker unit 736 is playing audio through speaker 737 while bed speaker(s) 742 are also playing audio originating from the same audio source 732, then an audio delay will occur due to the transmission delay of wireless audio over communications link 34 between wall module 32, 460 and bed 30. Of course, the audio delay incongruity is eliminated if wall module 32, 460 is configured to mute the bed speaker(s) 742 in one of the manners described above.

Figure 58:
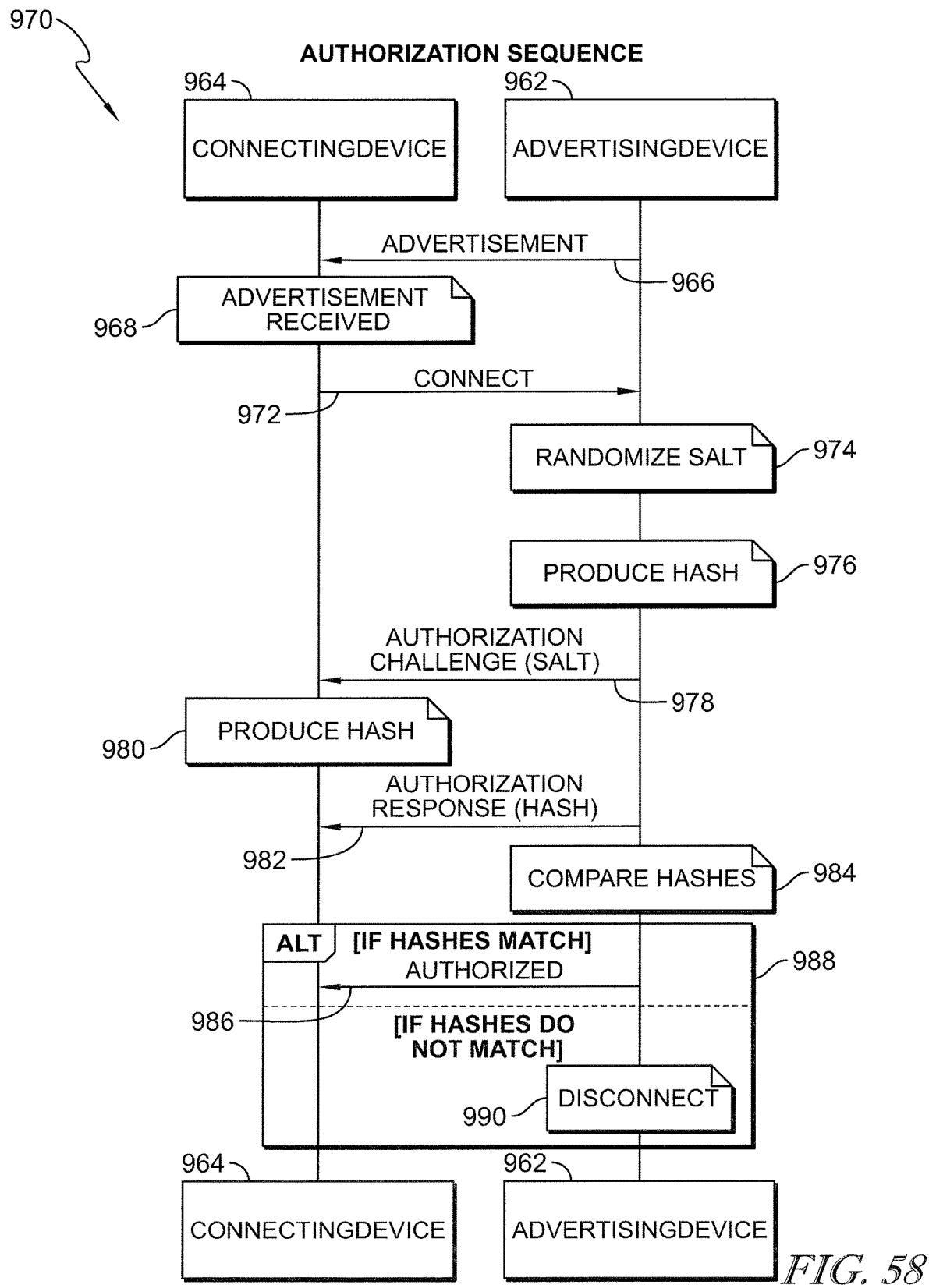
FIG. 58 is a swim lane diagram showing steps of an authorization operation in which an authorization challenge is issued by an advertising device to determine devices to eliminate from the possibility of Bluetooth pairing with the advertising device.

Referring now to FIG. 58, a swim lane diagram is provided showing steps of an authorization operation 970 between an advertising device 962 and a connecting device 964. Wall module 32,460 is an example of advertising device 962 and bed 30 is an example of connecting device 964 according to the present disclosure. However, the present disclosure contemplates that authorization operation 970 may be implemented between other types of advertising devices 962 and connecting devices 964 and so the description below is provided at this generic level. Furthermore, before describing operation 970 of FIG. 58 in detail, some background is provided.

When wireless devices advertise themselves as available for connection to a particular device, other third-party devices (such as personal mobile devices) may also receive these advertisements and may attempt a connection with the advertising device 962. To ensure connection by the advertising device 962 only with one or more desired connecting devices 964, the present disclosure contemplates that an authorization scheme 970, which includes a randomized authorization challenge and response, is used to disconnect from undesired or unauthorized devices before access is granted by the advertising device to retrieve data or execute commands from any connecting device. In any given patient room, it is possible that many third-party devices are present which could include other medical devices with wireless capability, caregiver cell phones, and patient wireless devices, just to name a few. There could also be a malicious actor in range that may try to actively hack into a wireless device that is advertising itself for connection.

According to the present disclosure, when the advertising device 962 receives a message corresponding to an attempted connection, it will send the connecting device 964 an authorization challenge. The authorization challenge contain randomized salt that the connecting device 964 uses in an algorithm to obtain the proper response. This response is then sent to advertising device 962. If correct, advertising device 962 authorizes connection with the connecting device 964 and allows data and command access to the connecting device 964. If incorrect, advertising device 962 immediately disconnects from the connecting device 964.

This authorization challenge/response operation 970 is at the application level. In other words, operation 970 occurs is in addition to any encryption or authentication methods that may be implemented by the underlying wireless protocol. In some instances, these wireless protocol authentication methods are public and well-known, whereas the particulars of this application-level operation 970 is not. Accordingly, in some embodiments, operation 970 is implemented in addition to the various time-based pairing operations described herein (e.g., operations 200, 300, 330, 350, 380, 430). Thus, in some embodiments, the requirements of the respective time-based pairing operation and the requirements of operation 970 must all be met before the advertising device 962 (e.g., wall module 32, 460) and the connecting device 964 (e.g., bed 30) successfully become paired. Requests for data and execution of commands are ignored by the advertising device 962 until a successful response to the authorization challenge is received by the advertising device 962 from the connecting device 964.

Both devices 962, 964 are programmed to implement the appropriate authorization challenge algorithm, which involves a hashing function for the randomized salt. Other devices that are not programmed with the authorization challenge algorithm will not be able to produce the correct response to the authorization challenge. The salt used for the authorization challenge is completely different on every connection to prevent brute-force attacks. Thus, the salt is a unique, cryptographic strength, randomized number of every connection attempt. Operation 970 is contemplated for use in environments, such as a medical facility, to obtain secure connections between particular devices while rejecting connections from all other devices.

According to operation 970, advertising device 962 issues an advertisement as indicated by arrow 966 in FIG. 58. Advertisement 966 is possibly received by multiple connecting device 964 within communication range of advertising device 962 but FIG. 58 only depicts one connecting device 964. As indicated at block 968, connecting device 964 receives advertisement 966 and, in response, connecting device transmits a connect message 972. In response to receiving connect message 972, advertising device 962 generates a randomized salt as indicated at block 974 and then performs a hash function on the generated randomized salt to generate a first hash value as indicated at block 976.

Advertising device 962 also transmits the randomized salt as an authorization challenge to connecting device 964 as indicated by arrow 978.

Still referring to FIG. 58, in response to receiving authorization challenge 978, connecting device 964 performs a hash function on the randomized salt contained in the authorization challenge as indicated at block 980, thereby to generate a second hash value. Connecting device 964 then transmits the second hash value as an authorization response to the advertising device as indicated by arrow 982. In response to receiving the authorization response 982 from connecting device 964, the advertising device compares the second hash value generated at block 980 with the first hash value generated at block 976 to determine if they match as indicated at block 984.

As indicated by arrow 986 in block 988 of FIG. 58, if the first and second hash values match, as determined at block 984, then advertising device 962 sends an authorized message to connecting device 964 which permits devices 962, 964 to become paired for subsequent wireless communications. On the other hand, if the first and second hash values do not match, as determined at block 984, then advertising device 962 disconnects from connecting device 964 as indicated at block 990. The hash functions or algorithms performed at blocks 976, 980 can be one of any of a number of types of cryptographic hashing functions, such as hashing algorithms known as MD5, SHA-1, SHA-2, NTLM, LANMAN, GOST, HAVAL, MD2, MD4, PANAMA, RadioGatun, RIPEMD, SHA-0, SHA-3, Tiger(2), and WHIRLPOOL; or cyclic redundancy checks (CRC's); or checksum operations; or any combination of these.

Figure 59:
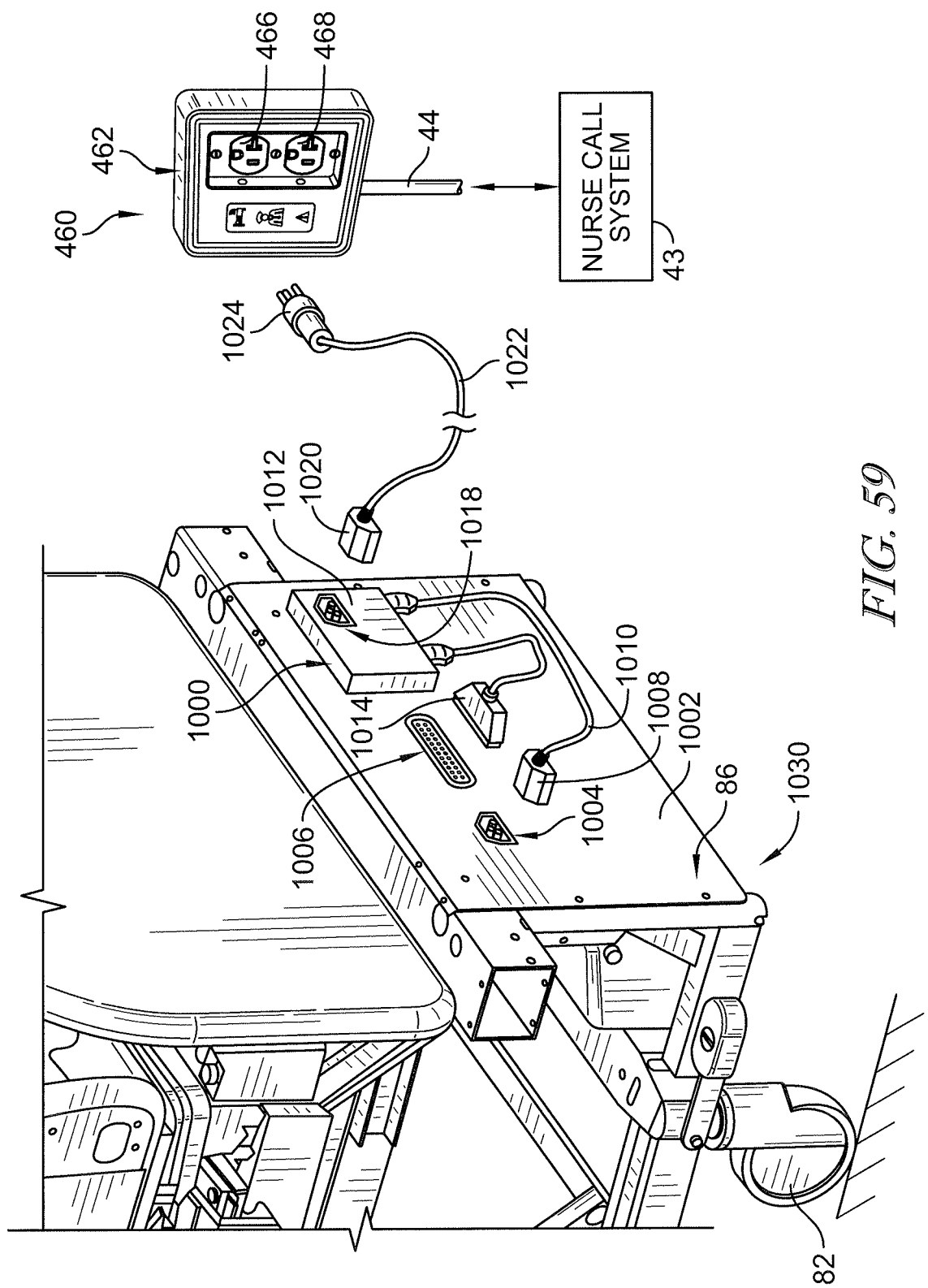
FIG. 59 is a perspective view of a portion of a head end of a legacy patient bed having a wireless adapter mounted to a base frame of the bed, the wireless adapter being configured to wirelessly pair with the wall module and communicate wirelessly with the wall module after pairing, the wireless adapter being configured to convert the legacy patient bed from one that is incapable of communicating wirelessly with the wall module to one that is.

Referring now to FIG. 59, a legacy patient bed 1030 is equipped with a wireless adapter 1000 that is configured for wireless communication with wall unit 460. Portions of bed 1030 that are substantially the same as like portions of bed 30 are denoted with like reference numbers. Thus, bed 1030 has a base frame 86 supported on a floor by a set of casters 82, only one of which can be seen in FIG. 59. Wireless adapter 1000 is mounted to a vertical panel 1002 of base frame 86 of bed 1030 in the illustrative example. Wireless adapter 1000 is configured to wirelessly pair with wall module 460 and communicate wirelessly with wall module 460 after pairing. In other embodiments, wireless adapter 1000 communicates with wall module 32. However, in the description that follows, reference will be made only to wall module 460.

In the absence of wireless adapter 1000, legacy bed 1030 is unable to communicate wirelessly with wall module 460. Thus, wireless adapter 1000 is configured to convert the legacy patient bed 1030 from one that is incapable of communicating wirelessly with wall module 460 to one that is. As such, wireless adapter 1000 retrofits to bed 1030 to add the wireless communication capability. While wireless adapter 1000 may be used with any of a variety of makes and models of beds, illustrative bed 1030 is a VERSACARE® bed available from Hill-Rom Company, Inc. Accordingly, adapter 1000 communicates with the wall units 32, 460 described above, and allows legacy or non-wireless beds, like bed 1030, to be upgraded to have wireless communication capability.

Still referring to FIG. 59, base frame 86 of bed 1030 includes an AC power port 1004 on vertical panel 1002. Port 1004 is normally used to connect bed 1030 to an AC power outlet using a standard AC power cord. Base frame 86 further includes a nurse call connector port 1006 on vertical panel 1002, illustratively a 37-pin connector port, that is normally used to connect bed 1030 to nurse call systems, such as nurse call system 43. Instead of connecting the ports 1004 and 1006 in their normal manner, ports 1004, 1006 are connected to the retrofit wireless adapter 1000. More specifically, in the illustrative embodiment, the AC power port 11004 is connected to a power connector 1008 at an end of a power cord 1010 that extends from a housing 1012 of the wireless adapter 1000. Similarly, the nurse call connector port 1006 is connected to a nurse call connector 1014 at an end of a nurse call cable 1016 that extends from housing 1012 of the wireless adapter 1000.

Wireless adapter 1000 includes an AC power port 1018 which is configured to couple to a power connector 1020 situated at one end of an AC power cord 1022 as suggested in FIG. 59. An AC plug 1024 is situated at an opposite end of AC power cord 1022 and is configured to plug into receptacle 466 or receptacle 468 of wireless module 460 in the same manner as power plug 180 described above. Thus, when plug 1024 is plugged into one of receptacles 466, 468, AC power is provided to wireless adapter 1000 and also to bed 1030 via cord 1010. In response to plug 1024 being plugged into one of receptacles 466, 468, the associated light beam in front of the respective receptacle 466, 468 is blocked by plug 1024 which initiates the time-based wireless pairing operation (e.g., one of operations 200, 300, 330, 350, as the case may be) described above and, in some embodiments, the authorization challenge operation 970.

After wireless adapter 1000 is installed on bed 1030 and pair with wall module 460, bed data and alerts, including nurse calls, are communicated to wireless module 1000 from port 1006 via cable 1010 and then are converted to wireless signals by wireless adapter 1000 for wireless transmission to wall module 460 via wireless data link 34. Wireless messages from wall module 460 are transmitted from wall module 1000 to wireless adapter 1000 and then provided to bed 1030 via cable 1010 and port 1006.

Figure 60:
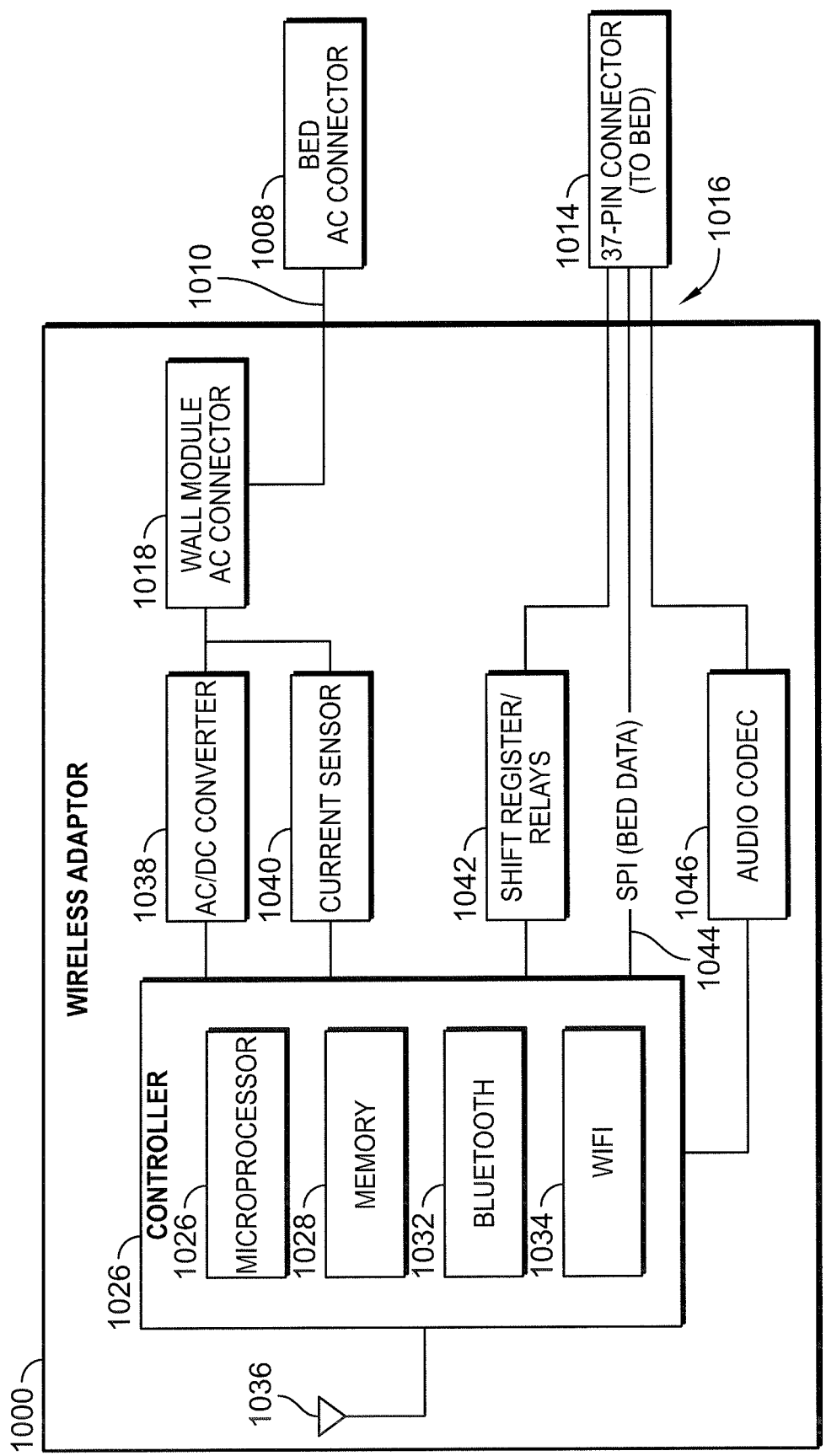
FIG. 60 is diagrammatic view of electrical componentry of the wireless adapter of FIG. 59.

Referring now to FIG. 60, the electrical componentry of the wireless adapter 1000 of FIG. 59 is shown diagrammatically. Wall module 1000 includes a controller 1026 having a microprocessor 1028 and memory 1032. Controller further includes a Bluetooth transceiver or radio 1032 and, optionally, a WiFi transceiver or radio 1034. That is, in some embodiments, WiFi transceiver 1034 is omitted from wireless adapter 1000. Controller may be, for example, a model no. VAR-SOM-MX6 System on Module (SoM) available from Variscite Ltd. of Lod, Israel in some embodiments or a model no. DART 6UL also available from Variscite Ltd. of Lod, Israel in other embodiments. Transceivers 1032, 1034 send and receive wireless signals through an antenna 1036 which is coupled to, or included in, controller 1026.

Still referring to FIG. 60, AC power port of 1018 of wireless adapter 1000 is coupled to controller 1026 by an AC/DC converter 1038 which converts the AC power received by adapter 1000 from power cord 1022 into DC power suitable for powering controller 1026. AC power port 1018 is also coupled to controller 1026 by a current sensor 1040 which senses when power connector or port 1018 is receiving AC power via cord 1022 and provides an output signal to controller 1040 to initiate a software timer of controller 1026 to start counting in connection with the wireless pairing process with wall module 460. As also shown in FIG. 60, AC connector 1018 of wireless adapter 1000 is also connected to cord 1010 and bed AC connector 1008 to feed AC power therethrough to bed 1030. Nurse call connector 1014 is coupled to controller 1026 by a set of shift registers and/or relays 1042, a serial peripheral interface (SPI) line 1044 for bed data, and an audio codec 1046 for audio.

Based on the foregoing, it will be appreciated that wireless adapter 1000 passes through AC power from the wall outlet 466, 468 to the AC port 1004 of the bed frame 86, but also uses the power to power Bluetooth and WiFi communication circuitry 1032, 1034 of controller 1026 in wireless adapter 1000. The wireless adapter 1000 is programmed with translation software that matches the make and model of the legacy bed 1030 to which it is connected. The translation software translates the signal flow from the nurse call port 1006 to Bluetooth and Wifi protocols. The Bluetooth signals are sent to wall unit 460 wirelessly and then used by wall module 460 as described above. One of the time-based pairing processes 200, 300, 330, 350 described above is programmed into the retrofit unit 1000 to conduct the pairing with wall unit 460 after port 1004 of bed 1030 is plugged into the wall unit 460 and after plug 1024 at the end of cord 1022 is plugged into one of the receptacles 466, 468 of wall unit 460. In some embodiments, retrofit unit 1000 is programmed with a variety of communication protocols for a variety of make, manufacturer, and models of beds, such as bed 1030, and automatically detects what protocol is being used by the bed and also uses an appropriate translation protocol for translating the signals to and from the bed into Bluetooth and/or Wifi signals for wireless transmission.

Figure 61:
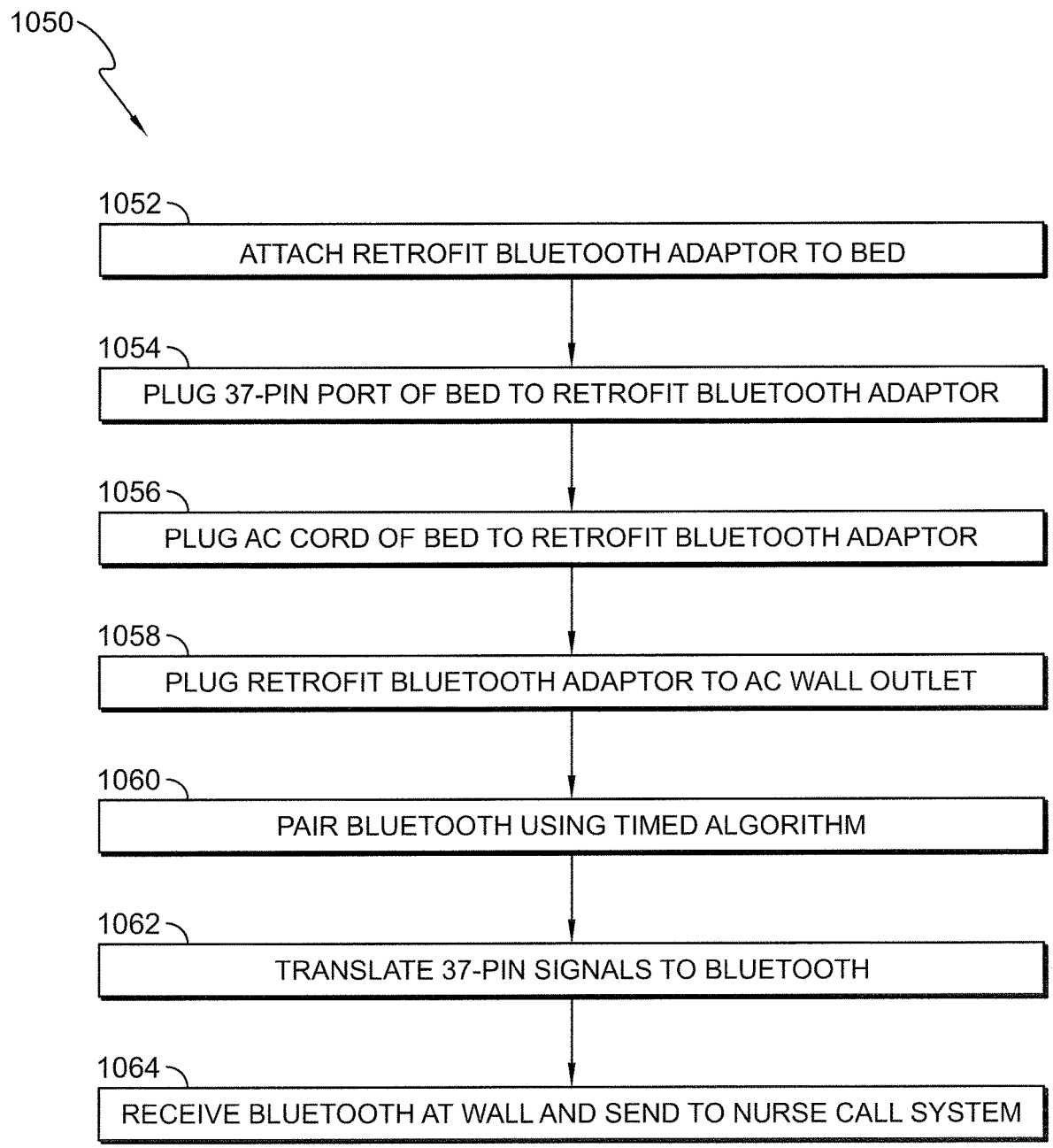
FIG. 61 is a flow chart showing steps to retrofit the wireless adapter of FIGS. 59 and 60 to the legacy patient bed to enable wireless communication between the legacy patient bed and the wall module.

Referring now to FIG. 61, a flow chart shows a process 1050 for retrofitting the wireless adapter 1000 of FIGS. 59 and 60 to the legacy patient bed 1030 to enable wireless communication between legacy patient bed 1030 and wall module 460. In the illustrative example of process 1050, retrofit wireless adapter 1000 is attached to the non-wireless or legacy bed 1030 as indicated at block 1052. Then, the 37-pin port 1006 of bed 1030 is connected to the retrofit adapter 1000 by inserting nurse call connector 1014 at the end of cord 1016 into nurse call port 1006 as indicated at block 1054. Furthermore, AC connector 1008 at the end of AC cord 1010 is plugged into AC port 1004 of frame 86 of bed 1030 as indicated at block 1056. The power outlet 1024 at the end of power cord 1022 of retrofit wireless adapter 1000 is plugged into one of AC outlets 466, 468 of wall unit 460 as indicated at block 1058.

Still referring to FIG. 61, a pairing process, such as one of the time-based pairing processes 200, 300, 330, 350 described above, is then used to pair wall unit 460 to the retrofit adapter 1000 as indicated at block 1060. After pairing, the retrofit adapter 1000 then translates the signals of the bed 1030 to which it is attached to Bluetooth signals as indicated at block 1062 and wirelessly transmits these. The transmitted Bluetooth signals are received by wall unit 460 and communicated to the nurse call system 43 to which the wall unit 460 is attached as indicated at block 1064.

Figure 62:
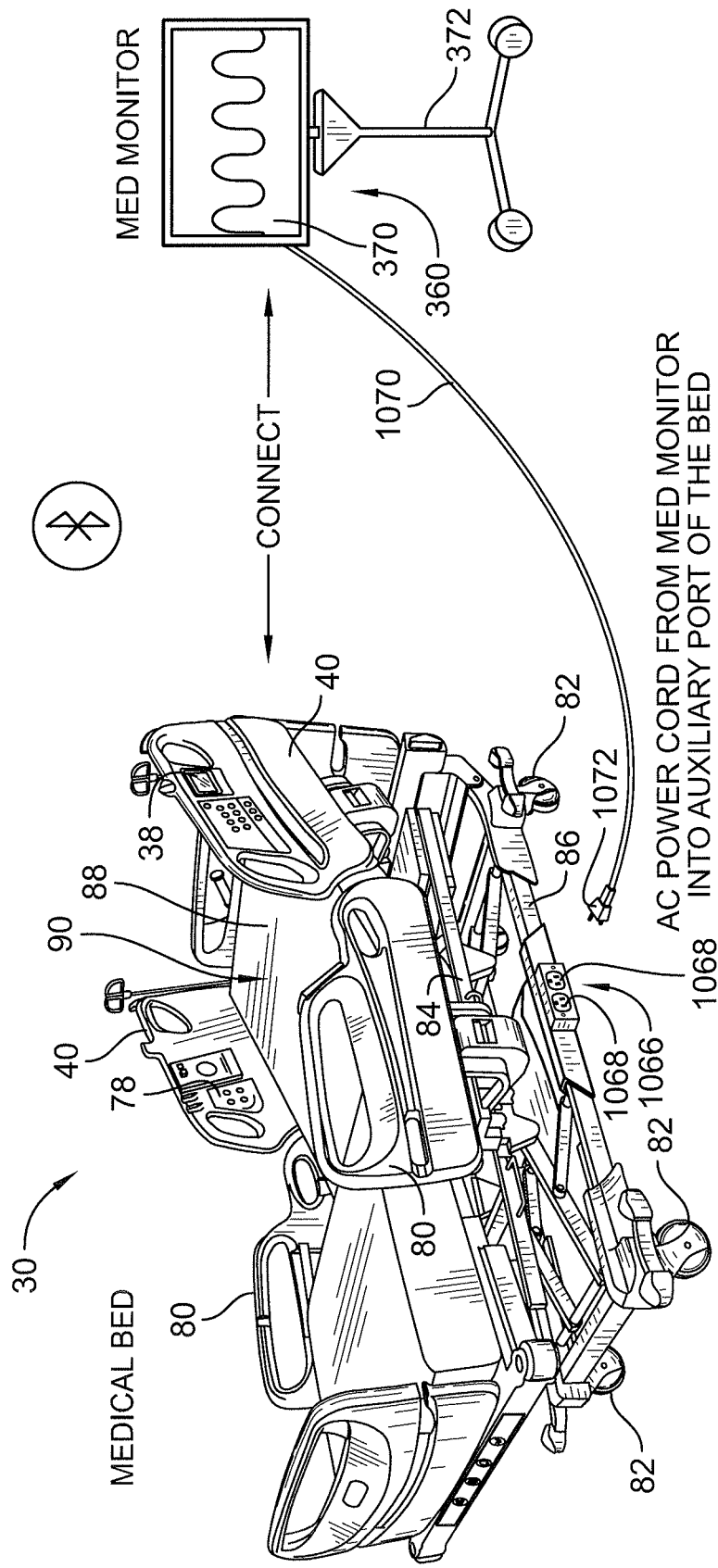
FIG. 62 is a perspective view showing a power plug at an end of a power cord of a medical monitor arranged for connection to an AC receptacle mounted to a frame of a medical bed to initiate a wireless pairing operation between the medical bed and the medical monitor.

Referring now to FIG. 62, a first medical device, illustratively medical bed 30, has an auxiliary power outlet 1066 which, in the illustrative example includes two AC receptacles 1068 but in other embodiments has only one AC receptacle 1068 or has more than two AC receptacles 1068. Auxiliary power outlet 1066 is coupled to base frame 86 in the depicted embodiment but may be coupled to some other portion of bed 30 in other embodiments. Other power outlets, similar to outlet 1066 are included in some versions of bed 30, such as being coupled to a head end portion of base frame 86 and/or to an opposite side of base frame 86. Thus, embodiments of bed 30 having two, four, six, or some other number of AC receptacles 1068 are contemplated by the present disclosure. The AC receptacles 1068 of bed 30 receive AC power through conductors (e.g., wires and cables) routed through bed 30 and AC power circuitry (e.g., fuses, transformers, voltage controllers, etc.) that are coupled to the main power cord 144 of bed 30. Thus, the healthcare facility's power infrastructure ultimately provides AC power to receptacles 1068 once power cord 144 of bed 30 is plugged into a facility AC outlet or those provided on wall module 32 or wall module 460.

A second medical device, illustratively a medical monitor 360, includes a power cord 1070 that terminates at a power plug 1072. In response to plugging power plug 1072 into one of AC receptacles 1068 of bed 30, a time-based wireless pairing operation is implemented between first and second medical devices 30, 360. Thus, according to the present disclosure, auxiliary power outlet 1066 includes any of the plug detectors discussed above in connection FIGS. 14-19 and/or as discussed above in connection with wall units 32, 460. Thus, the system depicted in FIG. 62 is similar to the system shown in FIG. 20 but instead of initiating the wireless pairing operation based on connection of Universal Serial Bus (USB) cord 362 between bed 30 and monitor 360, the wireless pairing operation is initiated by plugging cord 1070 of monitor 360 into one of AC receptacles 1068 of auxiliary power outlet 1066 of bed 30.

Based on the foregoing, it should be appreciated that the wireless pairing scenarios contemplated above between bed 30 and wall unit 32, or wall unit 460, as the case may be, similarly may be implemented between bed 30 and other medical devices, such as medical monitor 360, that are plugged into receptacles 1068 of bed 30. To accomplish the wireless pairing with other medical devices, bed 30 includes one or more wireless transceivers, such as Bluetooth transceivers like transceiver 106 described above in connection with FIG. 2. In some embodiments, transceiver 106 of bed 30 is used in connection with wirelessly pairing bed 30 to the various medical devices, like monitor 360, which plug into auxiliary AC receptacles 1068 in addition to being used in connection with wirelessly pairing bed to wall unit 32 or wall unit 460. In other embodiments, bed includes multiple transceivers 106 for use in wirelessly pairing bed 30 with other devices. For example, bed 30 may include a transceiver 106 for each power outlet 1066 provided on bed 30 in some embodiments. Additional circuitry like that discussed above in connection with FIGS. 2 and 9 (e.g., a controller and memory) may also be provided for each additional transceiver 106 on bed 30. It should be appreciated, therefore, that multiple medical devices 360 may be wirelessly paired with bed 30, with the number of receptacles 1068 provided on bed 30 dictating how many medical devices 360 may be wirelessly paired with bed 30.

Bed 30 of FIG. 62 is similar to bed 30 of FIG. 1, for example, and so the same reference numerals are used where appropriate for like components and the descriptions are not repeated. Similarly, medical monitor 360 of FIG. 62 is similar to medical monitor 360 of FIG. 20 and so the same reference numerals are used where appropriate for like components and the descriptions are not repeated. Illustratively, therefore, monitor 360 of FIG. 62 includes a display screen 370 on which patient physiological information is displayed. Monitor 360 is shown somewhat diagrammatically in FIG. 20 and represents devices such as electrocardiograms (EKG's), electroencephalograms (EEG's), respiration rate monitors, blood pressure monitors, pulse oximeters, temperature monitors, and the like, including combinations of these. Illustrative monitor 360 of FIG. 62 is mounted to wheeled stand 372 so as to be movable from room-to-room, as needed. Other medical devices that may plug into receptacles 1068 of bed 30 to initiate a wireless pairing operation with bed 30 include, for example, intravenous (IV) pumps, drug infusion pumps, respiratory therapy devices, ventilators, sequential compression devices (SCD's) for preventing deep vein thrombosis (DVT), hemodialysis equipment, renal therapy equipment, and passive motion machines, just to name a few.

Figure 63:
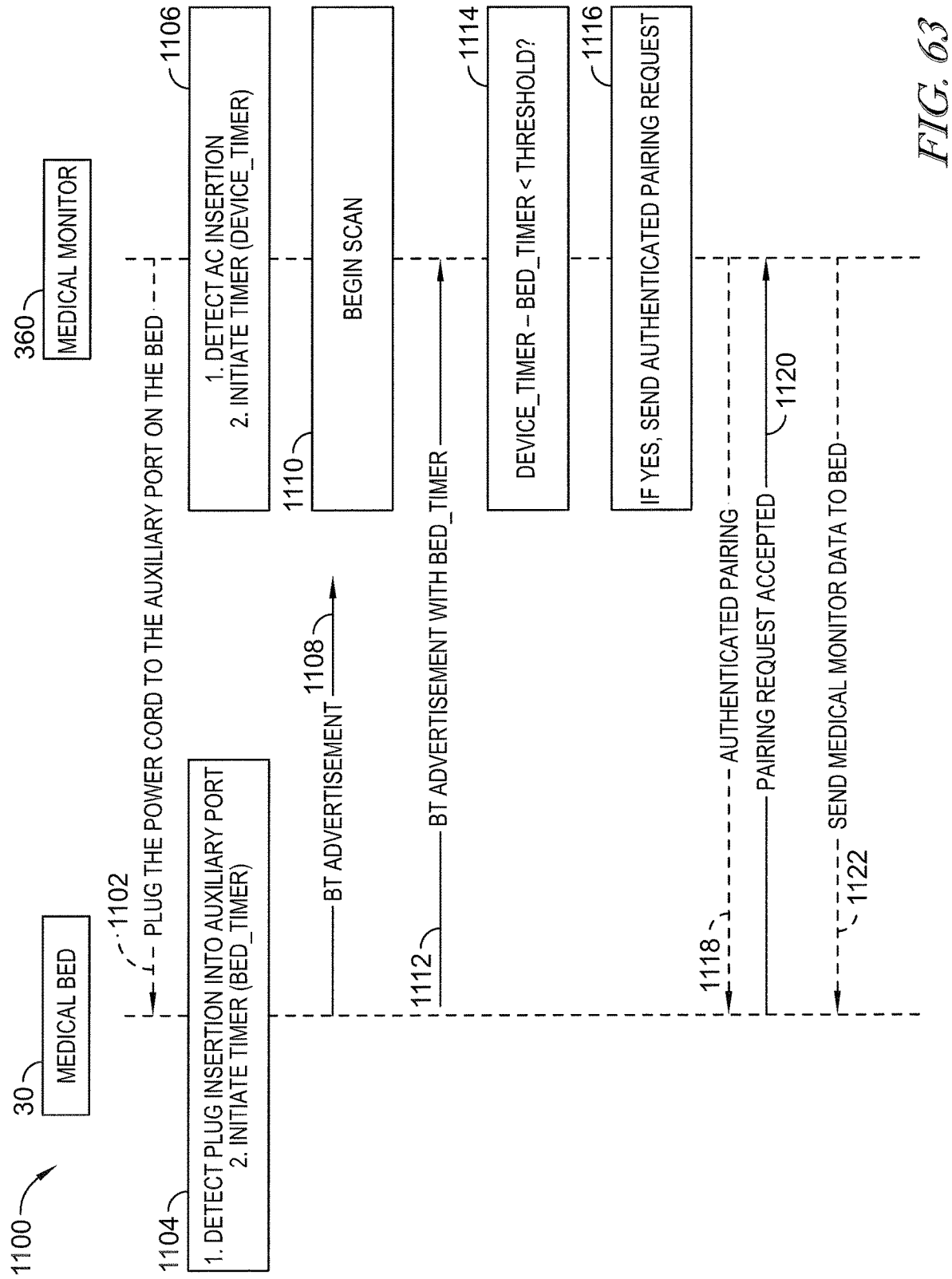
FIG. 63 is a swim lane diagram showing steps of a first embodiment of the wireless pairing operation between the medical bed and the medical monitor of FIG. 62.

Referring now to FIG. 63, a swim lane diagram of steps of one embodiment of a wireless pairing operation 1100 between the medical devices 30, 360 of FIG. 62 is shown. More particularly, the steps of operation 1100 are carried out by a first algorithm as indicated by a vertical dashed line extending downwardly from a block corresponding to medical bed 30 and a second algorithm as indicated by a vertical dashed line extending downwardly from a block corresponding to medical monitor 360. Thus, the dashed line extending downwardly from block 30 in FIG. 63 represents an algorithm performed by bed 30 and the dashed line extending downwardly from block 360 represents an algorithm performed by monitor 360, or by other first and second medical devices in other embodiments.

Operation 1100 begins in response to plug 1072 of power cord 1070 of medical monitor 360 being plugged into one of receptacles 1068 of bed 30 as indicated by a dashed arrow 1102 labeled PLUG THE POWER CORD TO THE AUXILIARY PORT ON THE BED. After power cord 1070 is plugged into one of receptacles 1068, bed 30 senses the connection and a bed timer is initiated as indicated at a block 1104 labeled as 1. DETECT PLUG INSERTION INTO AUXILIARY PORT 2. INITIATE TIMER (BED_TIMER). Substantially simultaneously (e.g., within a few seconds or less), medical monitor 360 senses the connection, such as with a current sensor, and a device timer is initiated as indicated at a block 1106 labeled as 1. DETECT AC INSERTION 2. INITIATE TIMER (DEVICE_TIMER).

Thereafter, bed 30 begins to transmit one or more BT advertisements as indicated by arrow 1108 which is labeled BT ADVERTISEMENT. Substantially simultaneously (e.g., within a few seconds or less), the monitor 360 begins making one or more scans to detect the BT advertisement(s) made by bed 30 as indicated at block 1110. Subsequently, after initial discovery of bed 30 and monitor 360 of each other, bed 30 begins to transmit one or more BT advertisements with the corresponding bed timer values at the time of each transmission as indicated by arrow 1112 which is labeled BT ADVERTISEMENT WITH BED_TIMER.

Still referring to operation 1100 of FIG. 63, after device 360 receives the BT advertisements with bed timer values 1112, monitor 360 subtracts the current device timer value from the received bed timer value to determine if the difference in timer values is less than a threshold as indicated at a block 1114 which is labeled DEVICE_TIMER–BED_TIMER<THRESHOLD?. The threshold may be, for example, 2 or 3 seconds or less or some other larger threshold, at the discretion of the system designer. If the difference between the device timer value and the bed timer value is less than the threshold, then monitor 360 concludes that an authenticated pairing request should be transmitted, as indicated at block 1116 which is labeled as IF YES, SEND AUTHENTICATED PAIRING REQUEST, followed by the actual transmission of the authenticated pairing request from monitor 360 to bed 30 as indicated by dashed arrow 1118 which is labeled AUTHENTICATED PAIRING.

In response to receipt of the authenticated pairing request 1118, bed 30 responds to medical monitor 360 to accept the pairing request as indicated by arrow 1120 which is labeled PAIRING REQUEST ACCEPTED. Subsequent to acceptance of the pairing request by bed 30, medical monitor 360 begins transmitting medical monitor data to bed 30 as indicated by dashed arrow 1122. In some embodiments, either or both of devices 30, 360 have a visual or audible means of indicating that the wireless pairing has successfully been made via operation 1100. For example, a message may be displayed on GUI 38 of bed 30 and/or on display screen 370 of monitor 360 to indicate the successful pairing. Alternatively or additionally, a voice message announcing the successful wireless pairing between devices 30, 360 may be sounded by either of devices 30, 360.

Figure 64:
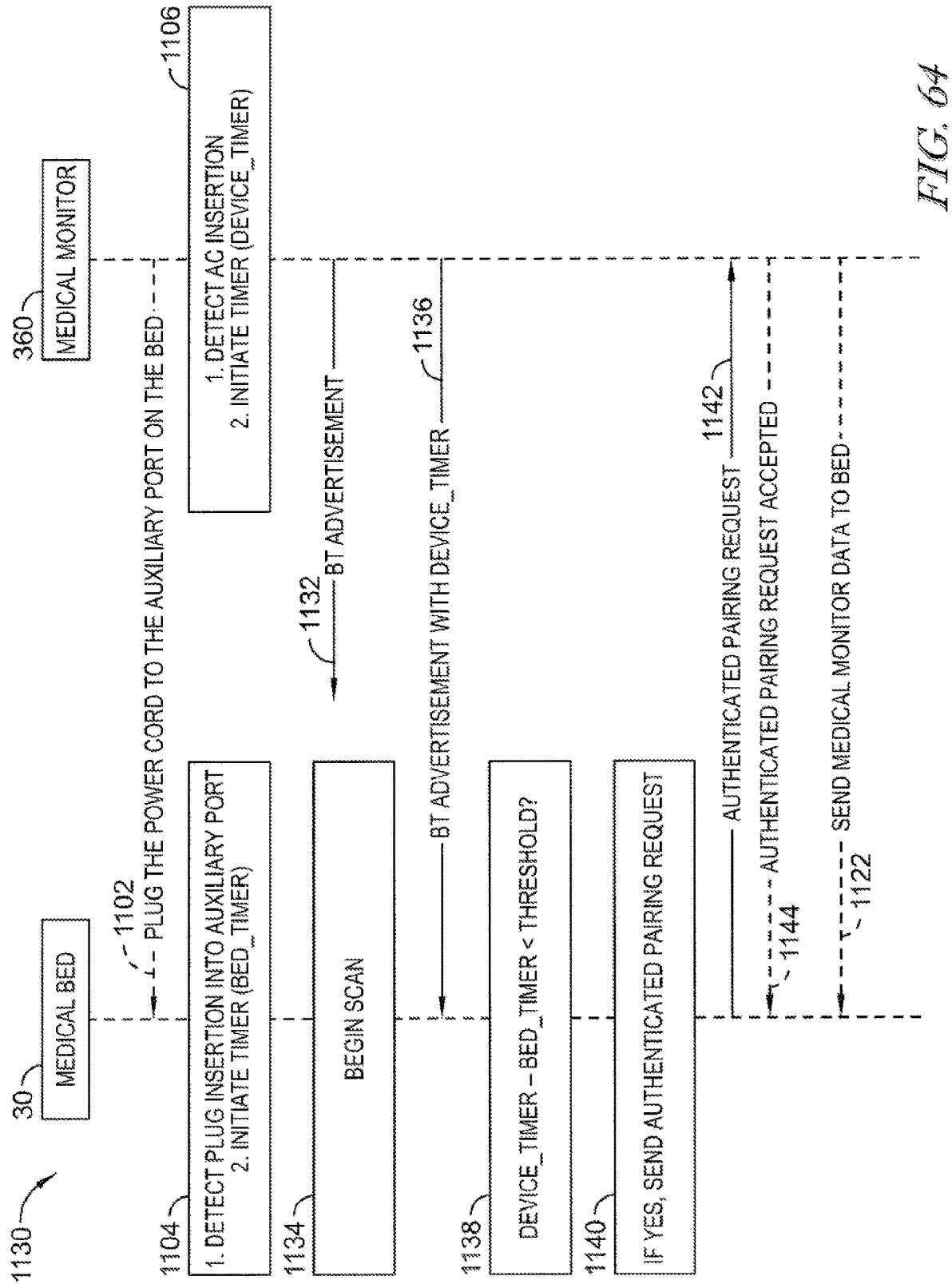
FIG. 64 is a swim lane diagram showing steps of a second embodiment of the wireless pairing operation between the medical bed and the medical monitor of FIG. 62.

In one variant embodiment shown in FIG. 64, the roles of the bed 30 and monitor 360 as BT advertiser and BT scanner are reversed. In such a variant embodiment, a wireless pairing operation 1130 is implemented between bed 30 and medical monitor 360. Similar to operation 1100, the steps of operation 1130 are carried out by a first algorithm as indicated by a vertical dashed line extending downwardly from a block corresponding to medical bed 30 and a second algorithm as indicated by a vertical dashed line extending downwardly from a block corresponding to medical monitor 360. Thus, the dashed line extending downwardly from block 30 in FIG. 64 represents an algorithm performed by bed 30 and the dashed line extending downwardly from block 360 in FIG. 64 represents an algorithm performed by monitor 360, or by other first and second medical devices in other embodiments.

Portions of operation 1130 that are the same as operation 1100 are denoted with like reference numbers. For example, like operation 1100, operation 1130 begins in response to plug 1072 of power cord 1070 of medical monitor 360 being plugged into one of receptacles 1068 of bed 30 as indicated by dashed arrow 1102 labeled PLUG THE POWER CORD TO THE AUXILIARY PORT ON THE BED. After power cord 1070 is plugged into one of receptacles 1068, bed 30 senses the connection and a bed timer is initiated as indicated at a block 1104 labeled as 1. DETECT PLUG INSERTION INTO AUXILIARY PORT 2. INITIATE TIMER (BED_TIMER) in FIG. 64. Substantially simultaneously (e.g., within a few seconds or less), medical monitor 360 senses the connection, such as with a current sensor, and a device timer is initiated as indicated at block 1106 labeled as 1. DETECT AC INSERTION 2. INITIATE TIMER (DEVICE_TIMER) in FIG. 64.

Thereafter, medical monitor 360 begins to transmit one or more BT advertisements as indicated by arrow 1132 which is labeled BT ADVERTISEMENT. Substantially simultaneously (e.g., within a few seconds or less), the bed 30 begins making one or more scans to detect the BT advertisement(s) made by medical monitor 360 as indicated at block 1134. Subsequently, after initial discovery of bed 30 and monitor 360 of each other, medical monitor 360 begins to transmit one or more BT advertisements with the corresponding device timer values at the time of each transmission as indicated by arrow 1136 which is labeled BT ADVERTISEMENT WITH DEVICE_TIMER.

Still referring to operation 1130 of FIG. 64, after bed 30 receives the BT advertisements with device timer values 1136, bed 30 subtracts the current device timer value from the received bed timer value to determine if the difference in timer values is less than a threshold as indicated at a block 1138 which is labeled DEVICE_TIMER–BED_TIMER<THRESHOLD?. The threshold may be, for example, 2 or 3 seconds or less or some other larger threshold, at the discretion of the system designer. If the difference between the device timer value and the bed timer value is less than the threshold, then bed 30 concludes that an authenticated pairing request should be transmitted, as indicated at block 1140 which is labeled as IF YES, SEND AUTHENTICATED PAIRING REQUEST, followed by the actual transmission of the authenticated pairing request from bed 30 to medical monitor 360 as indicated by arrow 1142 which is labeled AUTHENTICATED PAIRING REQUEST.

In response to receipt of the authenticated pairing request 1142, medical monitor 360 responds to bed 30 to accept the pairing request as indicated by dashed arrow 1144 which is labeled AUTHENTICATED PAIRING REQUEST ACCEPTED. Subsequent to acceptance of the pairing request by bed 30, medical monitor 360 begins transmitting medical monitor data to bed 30 as indicated by dashed arrow 1122 in FIG. 64. In some embodiments, either or both of devices 30, 360 have a visual or audible means of indicating that the wireless pairing has successfully been made via operation 1130. For example, a message may be displayed on GUI 38 of bed 30 and/or on display screen 370 of monitor 360 to indicate the successful pairing. Alternatively or additionally, a voice message announcing the successful wireless pairing between devices 30, 360 may be sounded by either of devices 30, 360.

After devices 30, 360 are wirelessly paired according to operation 1100 or operation 1130, power cord 1070 can be disconnected from the corresponding receptacle 1068 of bed 30, if desired, and the wireless pairing will remain as long as devices 30, 360 are within wireless communication range of each other. Of course, this assumes medical monitor 360 has an onboard battery or some other power source that provides sufficient power to continue to send and receive wireless communications to and from bed 30. For example, power cord 1070 can be unplugged from the associated receptacle 1068 of bed 30 and plugged into some other AC receptacle in the patient room with bed 30. Thus, the location of monitor 360 relative to bed 30 is not limited by the length of cord 1070, assuming that the wireless communication range is greater than the length of cord 1070.

The present disclosure further contemplates that, after devices 30, 360 are wirelessly paired, monitor 360 transmits monitor data, including sensed patient physiological data for example, to bed 30 as noted above in connection with dashed arrow 1122 of operation 1100 and operation 1130. After bed 30 receives monitor data from monitor 360, bed 30 is able to use the monitor data and/or display the monitor data on GUI 38, for example, in accordance with the programming of bed 30. It should also be appreciated that beds 30 equipped with one or more auxiliary power outlets 1066 are still able to be plugged into respective wall modules 32 or wall modules 460, as the case may be, and establish wireless pairing therebetween in any of the manners described above. That is, the wireless pairing between bed 30 and one or more medical monitors 360 initiated by plugging in corresponding power cords 1070 of medical monitors 360 to respective auxiliary power outlets 1066 of bed 30 is independent of the wireless pairing between bed 30 and a corresponding wall module 32, 460 initiated by plugging in a corresponding power cord 144 of bed 30 to a respective receptacle 260, 466, 468 of the associated wall module 32, 460.

In connection with receipt of medical monitor data as depicted diagrammatically by dashed arrow 1122 in FIGS. 63 and 64, bed 30 may initiate a therapy (e.g., lateral rotation therapy of mattress 88, alternating pressure therapy of mattress 88, or percussion and vibration (P&V) therapy of mattress 88), turn on a patient position monitoring or bed exit monitoring system of bed 30, send a message (e.g., informational message or alert/alarm message) to a nurse call system 43, or generate a local arm on bed 30 (e.g., display an alarm message on GUI 38 and/or sound an audible alarm using a sound producing device such a speaker or buzzer of bed 30). Bed 30 also may display on GUI 38 the physiological data (e.g., graphical trace and/or numeric data) sensed by monitor 360. Furthermore, in some embodiments, bed 30 of FIG. 62 is configured to transmit some or all of the medical monitor data received from the one or more medical monitors 360 to nurse call system 43 and/or network 60 for receipt by one or more servers 46, 62, 64, 66, 68 or other computer devices, such as via the wall module 32, 460 with which the bed 30 is wirelessly paired.

In variant embodiments of the systems described herein in which bed 30 and wall module 32 or wall module 460, as the case may be, wirelessly communicate after becoming wirelessly paired in any of the manners described herein, wall module 32, 460 is configured to detect the presence of pillow speaker unit 736 and, in response to detecting pillow speaker unit 736, wall module 32, 460 operates in a manner that mutes the speaker(s) 742 of patient bed 30 such as by sending audio packets containing all zeroes to the bed 30. For example, the circuitry of wall module 32, 460 is configured to detect the presence of the pillow speaker unit 736 by determining the presence of an echo due to the speaker 737 of pillow speaker unit 736 and the speaker 742 of patient bed 30 playing the same or similar audio with a delay therebetween as described above. Alternatively or additionally, the circuitry of wall module 32, 460 is configured to detect the presence of the pillow speaker unit 736 by receiving a signal from nurse call system 43 that a pillow speaker unit 736 is connected to the nurse call system 43 such as by being plugged into port 166 of ASBC 164 or being plugged into a port that is similar to port 166 but mounted to a room wall.

Plugging pillow speaker unit 736 into the nurse call system 43 is detectable, such as by detecting a current draw with a current sensor or detecting data received from the pillow speaker unit 736 or the like by a component of the nurse call system 43. In response, server 46 or nurse call master station 50 of nurse call system 43 then transmits a signal to wall unit 32, 460 indicating that pillow speaker unit 736 is present at the room location with the wall unit 32, 460. In response to pillow speaker unit 736 being unplugged wall unit 32, 460 operates in a manner to unmute the speaker(s) 742 of bed 30 so that audio of the audio feed received by wall unit 32, 460 is played through the speaker(s) 742 of the patient bed 30 that is wirelessly paired with the wall unit 32, 460.

When terms of degree such as "generally," "substantially," and "about" are used herein in connection with a numerical value or a qualitative term susceptible to a numerical measurement (e.g., vertical, horizontal, aligned), it is contemplated that an amount that is plus or minus 10 percent, and possibly up to plus or minus 20 percent, of the numerical value which is covered by such language, unless specifically noted otherwise. For example, "vertical" may be defined as 90 degrees from horizontal and so "substantially vertical" according to the present disclosure means 90 degrees plus or minus 9 degrees, and possibly up to plus or minus 18 degrees. The same tolerance range for "substantially horizontal" is also contemplated. Otherwise, a suitable definition for "generally," "substantially," and "about" is largely, but not necessarily wholly, the term specified.

Although certain illustrative embodiments have been described in detail above, variations and modifications exist within the scope and spirit of this disclosure as described and as defined in the following claims.

The invention claimed is:

1. A system comprising
   a wall module including a first wireless transceiver and first circuitry configured to receive an audio feed and a data feed,
   a patient bed including a second wireless transceiver, a speaker, and second circuitry coupled to the speaker and the second wireless transceiver, the second wireless transceiver being configurable for wireless communication with the first wireless transceiver, and
   a mobile device configured to link temporarily with the first wireless transceiver for wireless communication for configuration of the circuitry of the wall module, the mobile device being configured to receive a first user input to command the circuitry of the wall module to mute the speaker of the patient bed on a going-forward basis including after the link between the mobile device and the first wireless transceiver has been terminated,
   wherein in response to receipt of the first user input to mute the speaker of the patient bed, the circuitry of the wall module communicates with the second wireless transceiver via the first wireless transceiver in a first manner to place the patient bed in an on-going mute mode to prevent the audio feed from being audibly played through the speaker of the patient bed to thereby avoid an echo effect from occurring due to the audio feed being played through another nearby audio source.

2. The system of claim 1, wherein in response to receipt of the first user input to mute the speaker of the patient bed, the first circuitry commands the first wireless transceiver to transmit audio packets that correspond to silence.

3. The system of claim 2, wherein the audio packets that correspond to silence comprise all zeroes.

4. The system of claim 1, wherein the mobile device is configured to receive a second user input to unmute the speaker of the patient bed, wherein in response to receipt of the second user input to unmute the speaker of the patient bed, the first circuitry of the wall module communicates with the second wireless transceiver via the first wireless transceiver in a second manner that allows the audio feed to be audibly played through the speaker of the patient bed.

5. The system of claim 4, wherein the mobile device is configured to display a mute/unmute slider, the first user input corresponds to the mute/unmute slider being in a first position and the second user input corresponds to the mute/unmute slider being in a second position.

6. The system of claim 1, wherein the mobile device is configured to receive a firmware installation input from a user to upload firmware to the circuitry of the wall module via the first transceiver.

7. The system of claim 1, wherein the patient bed includes a graphical user interface (GUI) configured to receive inputs from a user to control functions of the patient bed, the GUI being configured to receive a third user input which results in a mute command being transmitted from the second wireless transceiver of the patient bed to the first wireless transceiver of the wall module to command the circuitry of the wall module to operate in the first manner to mute the speaker of the patient bed.

8. The system of claim 7, wherein the GUI is configured to receive a fourth user input which results in an unmute command being transmitted from the second wireless transceiver of the patient bed to the first wireless transceiver of the wall module to command the circuitry of the wall module to operate in a second manner that allows the audio feed to be audibly played through the speaker of the patient bed.

9. The system of any one of claim 1, wherein the first circuitry of the wall module and the second circuitry of the patient bed implement a time-based pairing operation to pair the patient bed with the wall module.

10. The system of claim 9, wherein the time-based pairing operation is initiated by plugging a power plug of the patient bed in to a power receptacle of the wall module.

11. The system claim 1, further comprising a nurse call cord extending from the wall module, the nurse call cord terminating at a first nurse call connector configured for connection to a nurse call port of a nurse call system.

12. The system of claim 11, wherein the nurse call cord includes an auxiliary cord branch terminating at a second nurse call connector, the second nurse call connector being coupleable to a third nurse call connector at an end of a bed nurse call cord extending from the patient bed.

13. The system of claim 1, wherein the patient bed includes a first WiFi transceiver and the wall module includes a second WiFi transceiver, the first and second WiFi transceivers each being configured to send WiFi messages to, and receive WiFi messages from, at least one wireless access point of a network.

14. A system comprising
   a wall module including a first wireless transceiver and first circuitry configured to receive an audio feed and a data feed,
   a patient bed including a second wireless transceiver, a speaker, and second circuitry coupled to the speaker and the second wireless transceiver, the second wireless transceiver being configurable for wireless communication with the first wireless transceiver, and
   a mobile device configured to link temporarily with the first wireless transceiver for wireless communication for configuration of the circuitry of the wall module, the mobile device being configured to receive a first user input to command the circuitry of the wall module to mute the speaker of the patient bed,
   wherein in response to receipt of the first user input to mute the speaker of the patient bed, the circuitry of the wall module communicates with the second wireless transceiver via the first wireless transceiver in a first manner that prevents the audio feed from being audibly played through the speaker of the patient bed,
   wherein the first circuitry of the wall module and the second circuitry of the patient bed implement a time-based pairing operation to pair the patient bed with the wall module,
   wherein the time-based pairing operation is initiated by plugging a power plug of the patient bed in to a power receptacle of the wall module,
   wherein plugging in the power cord to the power receptacle results in a first timer of the patient bed being started to measure a first uptime, wherein plugging in the power cord to the power receptacle results in a second timer of the wall module being started to measure a second uptime, wherein the wall module is configured to transmit to the patient bed from the first wireless transceiver an advertisement including the second uptime, wherein the patient bed compares the second uptime with the first uptime and, if the second uptime is within a predetermined tolerance range of the first uptime, the patient bed sends a pairing message to the wall module which results in the wall module and the patient bed becoming automatically paired for subsequent wireless communications.

15. A system comprising
a wall module including a first wireless transceiver and first circuitry configured to receive an audio feed and a data feed,
a patient bed including a second wireless transceiver, a speaker, and second circuitry coupled to the speaker and the second wireless transceiver, the second wireless transceiver being configurable for wireless communication with the first wireless transceiver, and
a mobile device configured to link temporarily with the first wireless transceiver for wireless communication for configuration of the circuitry of the wall module, the mobile device being configured to receive a first user input to command the circuitry of the wall module to mute the speaker of the patient bed,
wherein in response to receipt of the first user input to mute the speaker of the patient bed, the circuitry of the wall module communicates with the second wireless transceiver via the first wireless transceiver in a first manner that prevents the audio feed from being audibly played through the speaker of the patient bed,
wherein the first circuitry of the wall module and the second circuitry of the patient bed implement a time-based pairing operation to pair the patient bed with the wall module,
wherein the time-based pairing operation is initiated by plugging a power plug of the patient bed in to a power receptacle of the wall module,
wherein plugging in the power cord to the power receptacle results in a first timer of the patient bed being started to measure a first uptime, wherein plugging in the power cord to the power receptacle results in a second timer of the wall module being started to measure a second uptime, wherein the patient bed is configured to transmit to the wall module from the second wireless transceiver a message including the first uptime, wherein the wall module compares the first uptime with the second uptime and, if the first uptime is within a predetermined tolerance range of the second uptime, the wall module sends a pairing message to the patient bed which results in the wall module and the patient bed becoming automatically paired for subsequent wireless communications.

16. A system comprising
a wall module including a first wireless transceiver and first circuitry configured to send an audio feed, and
a patient bed including a second wireless transceiver, a speaker, and second circuitry coupled to the speaker and the second wireless transceiver, the second wireless transceiver being configurable for wireless communication with the first wireless transceiver,
wherein the first circuitry of the wall module is configured to detect the presence of a pillow speaker unit, the pillow speaker unit being separate from the patient bed and being handheld by a patient, and in response to the detection of the pillow speaker unit by the circuitry of the wall module, the wall module being configured to communicate with the second wireless transceiver via the first wireless transceiver in a first manner that prevents the audio feed from being audibly played through the speaker of the patient bed.

17. The system of claim 16, wherein in response to detection of the presence of the pillow speaker unit, the first circuitry commands the first wireless transceiver to transmit audio packets that correspond to silence.

18. The system of claim 17, wherein the audio packets that correspond to silence comprise all zeroes.

19. The system of claim 16, wherein the first circuitry of the wall module is further configured to detect absence of the pillow speaker unit, wherein in response to detection of the absence of the pillow speaker unit by the first circuitry, the wall module being configured to communicate with the second wireless transceiver via the first wireless transceiver in a second manner that allows the audio feed to be audibly played through the speaker of the patient bed.

20. The system of claim 16, wherein the patient bed includes a graphical user interface (GUI) configured to receive inputs from a user to control functions of the patient bed, the GUI being configured to receive a first user input which results in a mute command being transmitted from the second wireless transceiver of the patient bed to the first wireless transceiver of the wall module to command the first circuitry of the wall module to operate in the first manner to mute the speaker of the patient bed.

* * * * *